(12) United States Patent
Karp et al.

(10) Patent No.: US 11,369,607 B2
(45) Date of Patent: Jun. 28, 2022

(54) COMPOSITIONS, SYSTEMS, AND METHODS FOR GENERATING INNER EAR HAIR CELLS FOR TREATMENT OF HEARING LOSS

(71) Applicants: Massachusetts Institute of Technology, Cambridge, MA (US); The Brigham and Women's Hospital, Inc., Boston, MA (US)

(72) Inventors: Jeffrey M. Karp, Brookline, MA (US); Robert S. Langer, Newton, MA (US); Xiaolei Yin, Quincy, MA (US); Nitin Joshi, Boston, MA (US)

(73) Assignees: The Brigham and Women's Hospital, Inc., Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/752,256

(22) Filed: Jan. 24, 2020

(65) Prior Publication Data

US 2020/0323853 A1 Oct. 15, 2020

Related U.S. Application Data

(62) Division of application No. 14/845,263, filed on Sep. 3, 2015, now Pat. No. 10,568,883.

(60) Provisional application No. 62/051,003, filed on Sep. 16, 2014, provisional application No. 62/045,506, filed on Sep. 3, 2014.

(51) Int. Cl.

| | |
|---|---|
| *A61K 31/506* | (2006.01) |
| *C12N 5/0793* | (2010.01) |
| *A61K 35/36* | (2015.01) |
| *A61K 9/00* | (2006.01) |
| *A61K 31/167* | (2006.01) |
| *A61K 31/19* | (2006.01) |
| *A61K 31/422* | (2006.01) |
| *A61K 31/437* | (2006.01) |
| *A61K 31/4709* | (2006.01) |
| *A61K 31/5377* | (2006.01) |
| *A61K 31/55* | (2006.01) |
| *A61K 31/5517* | (2006.01) |
| *A61K 33/00* | (2006.01) |
| *C12N 5/071* | (2010.01) |

(52) U.S. Cl.
CPC .......... *A61K 31/506* (2013.01); *A61K 9/0046* (2013.01); *A61K 31/167* (2013.01); *A61K 31/19* (2013.01); *A61K 31/422* (2013.01); *A61K 31/437* (2013.01); *A61K 31/4709* (2013.01); *A61K 31/5377* (2013.01); *A61K 31/55* (2013.01); *A61K 31/5517* (2013.01); *A61K 33/00* (2013.01); *A61K 35/36* (2013.01); *C12N 5/062* (2013.01); *C12N 5/0627* (2013.01); *C12N 2501/105* (2013.01); *C12N 2501/11* (2013.01); *C12N 2501/115* (2013.01); *C12N 2501/415* (2013.01); *C12N 2501/42* (2013.01); *C12N 2501/727* (2013.01); *C12N 2501/999* (2013.01)

(58) Field of Classification Search
None
See application file for complete search history.

(56) References Cited

U.S. PATENT DOCUMENTS

| | | |
|---|---|---|
| 5,059,591 A | 10/1991 | Janoff et al. |
| 5,421,818 A | 6/1995 | Arenberg |
| 5,474,529 A | 12/1995 | Arenberg |
| 5,476,446 A | 12/1995 | Arenberg |
| 5,731,144 A | 3/1998 | Toothman et al. |
| 5,731,424 A | 3/1998 | Toothman et al. |
| 5,837,681 A | 11/1998 | Magal |
| 6,045,528 A | 4/2000 | Arenberg et al. |
| 6,124,449 A | 6/2000 | Gold et al. |
| 6,090,383 A | 7/2000 | Dasch et al. |
| 6,177,434 B1 | 1/2001 | Kopke et al. |
| 6,419,928 B1 | 7/2002 | Dasch et al. |
| 6,476,031 B1 | 11/2002 | Chakravarty et al. |
| 6,509,318 B1 | 1/2003 | Bhatnagar et al. |
| 6,593,290 B1 | 7/2003 | Gao |
| 6,943,191 B1 | 9/2005 | Narayanan et al. |
| 7,030,125 B2 | 4/2006 | Munchhof et al. |
| 7,087,626 B2 | 8/2006 | Beight et al. |
| 7,151,169 B2 | 12/2006 | Thompson et al. |
| 7,223,766 B2 | 5/2007 | Dugar et al. |
| 7,387,614 B2 | 6/2008 | Staecker |
| 7,498,031 B2 | 3/2009 | Fujioka et al. |

(Continued)

FOREIGN PATENT DOCUMENTS

| | | |
|---|---|---|
| CA | 2268331 A1 | 5/1998 |
| CA | 2984541 A1 | 11/2007 |

(Continued)

OTHER PUBLICATIONS

International Search Report and Written Opinion for Int'l Application No. PCT/US2015/048442, titled: "Compositions, Systems, and Methods for Generating Inner Ear Hair Cells for Treatment of Hearing Loss"; dated Jan. 29, 2016.

(Continued)

*Primary Examiner* — Samantha L Shterengarts
(74) *Attorney, Agent, or Firm* — Hamilton, Brook, Smith & Reynolds, P.C.

(57) ABSTRACT

Method and compositions for inducing the self-renewal of stem/progenitor supporting cells comprised by a cochlear cell population, including inducing the stem/progenitor cells to proliferate while maintaining, in the daughter cells, the capacity to differentiate into hair cells.

63 Claims, 31 Drawing Sheets
(26 of 31 Drawing Sheet(s) Filed in Color)
Specification includes a Sequence Listing.

(56) References Cited

U.S. PATENT DOCUMENTS

| | | |
|---|---|---|
| 7,514,445 B2 | 4/2009 | Freyne et al. |
| 7,723,486 B2 | 5/2010 | Ledbetter et al. |
| 8,071,591 B2 | 12/2011 | Nomura et al. |
| 8,207,216 B2 | 6/2012 | Kozikowski et al. |
| 8,298,825 B1 | 10/2012 | Hochedlinger et al. |
| 8,377,886 B2 | 2/2013 | Susztak et al. |
| 8,575,122 B2 | 11/2013 | Lichter et al. |
| 8,686,042 B2 | 4/2014 | Gil et al. |
| 8,771,754 B2 | 7/2014 | Hallahan |
| 8,852,626 B2 | 10/2014 | Lichter et al. |
| 9,333,171 B2 | 5/2016 | Lichter et al. |
| 9,347,042 B2 | 5/2016 | Shimmura et al. |
| 10,041,046 B2 | 8/2018 | Karp et al. |
| 10,041,047 B2 | 8/2018 | Karp et al. |
| 10,568,883 B2 | 2/2020 | Karp et al. |
| 10,954,490 B2 | 3/2021 | Karp et al. |
| 11,021,687 B2 | 6/2021 | Karp et al. |
| 2003/0028905 A1 | 2/2003 | Knaus et al. |
| 2004/0006030 A1 | 1/2004 | Monia et al. |
| 2004/0015781 A1 | 1/2004 | Brown et al. |
| 2004/0038856 A1 | 2/2004 | Chakravarty et al. |
| 2004/0138188 A1 | 7/2004 | Higgins et al. |
| 2004/0147574 A1 | 7/2004 | Munchhof |
| 2004/0204431 A1 | 10/2004 | Scarborough et al. |
| 2005/0032835 A1 | 2/2005 | Pandey et al. |
| 2005/0227936 A1 | 10/2005 | McSwiggen et al. |
| 2005/0245508 A1 | 11/2005 | Weller et al. |
| 2005/0245520 A1 | 11/2005 | Dodic et al. |
| 2005/0287127 A1 | 12/2005 | Li et al. |
| 2005/0287128 A1 | 12/2005 | Guerciolini et al. |
| 2006/0003929 A1 | 1/2006 | Bier et al. |
| 2006/0229266 A1 | 10/2006 | Kumar et al. |
| 2007/0066632 A1 | 3/2007 | Hart et al. |
| 2007/0088080 A1 | 4/2007 | Gordillo et al. |
| 2007/0155722 A1 | 7/2007 | Li et al. |
| 2007/0167918 A1 | 7/2007 | Reed et al. |
| 2008/0015161 A1 | 1/2008 | Vornlocher et al. |
| 2008/0108656 A1 | 5/2008 | Pandey et al. |
| 2009/0036382 A1 | 2/2009 | Bressan et al. |
| 2009/0270497 A1 | 10/2009 | Buggy |
| 2009/0325938 A1 | 12/2009 | Lichter et al. |
| 2010/0267141 A1 | 10/2010 | Shi et al. |
| 2010/0292205 A1 | 11/2010 | Lefker et al. |
| 2011/0135756 A1 | 6/2011 | Owens et al. |
| 2011/0166060 A1 | 7/2011 | Simons et al. |
| 2011/0305674 A1 | 12/2011 | Edge et al. |
| 2012/0059021 A1 | 3/2012 | Biechele et al. |
| 2012/0196312 A1 | 8/2012 | Sato et al. |
| 2013/0079329 A1 | 3/2013 | Hood et al. |
| 2013/0189327 A1 | 7/2013 | Ortega et al. |
| 2013/0324594 A1 | 12/2013 | Guthrie |
| 2014/0243227 A1 | 8/2014 | Clevers et al. |
| 2014/0248696 A1 | 9/2014 | Zhang et al. |
| 2016/0194604 A1 | 7/2016 | Karp et al. |
| 2017/0000728 A1 | 1/2017 | Lichter et al. |
| 2017/0071937 A1 | 3/2017 | Karp et al. |
| 2017/0226477 A1 | 8/2017 | Karp et al. |
| 2017/0349884 A1 | 12/2017 | Karp et al. |
| 2019/0017015 A1 | 1/2019 | Karp et al. |
| 2019/0350845 A1 | 11/2019 | Lichter et al. |
| 2021/0301254 A1 | 9/2021 | Karp et al. |
| 2021/0363491 A1 | 11/2021 | Karp et al. |

FOREIGN PATENT DOCUMENTS

| | | |
|---|---|---|
| CN | 1319968 C | 10/2005 |
| CN | 101341138 A | 1/2009 |
| CN | 103361300 A | 10/2013 |
| CN | 104726395 A | 6/2015 |
| EP | 0945464 A1 | 9/1999 |
| EP | 1739087 A1 | 1/2007 |
| EP | 1961748 A2 | 8/2008 |
| EP | 2636731 A1 | 9/2013 |
| EP | 2765188 A1 | 8/2014 |
| EP | 3277801 B1 | 10/2020 |
| WO | WO 96/40094 A1 | 12/1996 |
| WO | WO 98/19700 A1 | 5/1998 |
| WO | WO 99/58128 A1 | 11/1999 |
| WO | WO 00/12497 A2 | 3/2000 |
| WO | WO 00/31135 A1 | 6/2000 |
| WO | WO 00/59939 A1 | 10/2000 |
| WO | WO 01/85685 A1 | 11/2001 |
| WO | WO 02/094833 A1 | 11/2002 |
| WO | WO 03/037891 A1 | 5/2003 |
| WO | WO 03/097639 A1 | 11/2003 |
| WO | WO 2004/013135 A1 | 2/2004 |
| WO | WO 2004/021989 A2 | 3/2004 |
| WO | WO 2004/026307 A1 | 4/2004 |
| WO | WO 2004/026865 A1 | 4/2004 |
| WO | WO 2004/026871 A1 | 4/2004 |
| WO | WO 2004/067530 A1 | 8/2004 |
| WO | WO 2005/039570 A1 | 5/2005 |
| WO | WO 2006/018633 A1 | 2/2006 |
| WO | WO 2006/018967 A1 | 2/2006 |
| WO | WO 2006/100490 A1 | 9/2006 |
| WO | WO 2007/018818 A1 | 2/2007 |
| WO | 2007047509 A2 | 4/2007 |
| WO | WO 2007/048857 A1 | 5/2007 |
| WO | WO 2007/102770 A1 | 9/2007 |
| WO | WO 2008/010852 A2 | 1/2008 |
| WO | WO 2008/076556 A2 | 6/2008 |
| WO | WO 2008/077138 A1 | 6/2008 |
| WO | WO 2009/017453 A1 | 2/2009 |
| WO | WO 2009/017455 A1 | 2/2009 |
| WO | WO 2009/032667 A1 | 3/2009 |
| WO | WO 2009/132050 A9 | 10/2009 |
| WO | WO 2010/060088 A2 | 5/2010 |
| WO | WO 2010/068955 A2 | 6/2010 |
| WO | WO 2010/075551 A1 | 7/2010 |
| WO | 2010090513 A2 | 8/2010 |
| WO | WO 2010/104205 A1 | 9/2010 |
| WO | WO 2011/019957 A1 | 2/2011 |
| WO | 2011/050476 A1 | 5/2011 |
| WO | WO 2011/079841 A1 | 7/2011 |
| WO | WO 2011/089416 A1 | 7/2011 |
| WO | WO 2011/116930 A1 | 9/2011 |
| WO | 2011123572 A1 | 10/2011 |
| WO | WO 2011/143511 A2 | 11/2011 |
| WO | WO 2012/103012 A1 | 8/2012 |
| WO | 2012141471 A2 | 10/2012 |
| WO | WO 2013/051722 A1 | 4/2013 |
| WO | WO 2013/124413 A1 | 8/2013 |
| WO | WO 2014/003098 A1 | 1/2014 |
| WO | WO 2014/013255 A1 | 1/2014 |
| WO | WO 2014/039908 A1 | 3/2014 |
| WO | WO 2014/050779 A1 | 4/2014 |
| WO | WO 2014/059383 A1 | 4/2014 |
| WO | WO 2014/083132 A1 | 6/2014 |
| WO | WO 2014/159356 A1 | 10/2014 |
| WO | WO 2015/168149 A2 | 11/2015 |
| WO | WO 2015/175783 A1 | 11/2015 |
| WO | WO 2016/037016 A1 | 3/2016 |
| WO | 2017048193 A1 | 3/2017 |
| WO | 2017/120543 A1 | 7/2017 |
| WO | 2019183572 A1 | 9/2019 |

OTHER PUBLICATIONS

International Preliminary Report on Patentability for Int'l Application No. PCT/US2015/048442, titled: "Compositions, Systems, and Methods for Generating Inner Ear Hair Cells for Treatment of Hearing Loss"; dated Mar. 7, 2017.

Alford, et al., "American College of Medical Genetics and Genomics Guideline for the Clinical Evaluation and Etiologic Diagnosis of Hearing Loss," Genetics in Medicine: Official Journal of the American College of Medical Genetics, vol. 16, pp. 347-355, 2014.

Associação Brasileira de Otorrinolaringologia e Cirurgia Cérvico-facial et al., "Sensorineural Hearing Loss: Radiologic Diagnosis," Revista da Associacao Medica Brasileira, vol. 58, pp. 519-529, 2012.

Barker, et al., "Lgr5$^{+ve}$ stem cells drive self-renewal in the stomach and build long-lived gastric units in vitro," Cell Stem Cell, vol. 6, 25-36, 2010.

(56) References Cited

OTHER PUBLICATIONS

Barker, N., et al., "Identification of stem cells in small intestine and colon by marker gene Lgr5," Nature, 449, No. 25: 1003-1007 (Oct. 2007).

Borenstein, J. T., "Intracochlear Drug Delivery Systems," Expert Opinion on Drug Delivery, vol. 8, No. 9, pp. 1161-1174, Sep. 2011, published online May 26, 2011.

Bramhall, N. F. et al., "Lgr5-Positive Supporting Cells Generate New Hair Cells in the Postnatal Cochlea", Stem Cell Reports, 2(3): 311-322 (2014).

Brigande, J.V. and Heller, S., "Quo vadis, hair cell regeneration?" Nat. Neurosci., 12(6): 679-685 (2009).

Buczacki, S.J., et al., "Intestinal label-retaining cells are secretory precursors expressing Lgr5," Nature, 495: 65-72 (2013).

Butler et al., "Rational Design and Simple Chemistry Yield a Superior, Neuroprotective HDAC Inhibitor, Tubastatin A," J. Am. Chem. Soc., vol. 132: 10842-10846 (2010).

Byfield, et al., "SB-505124 Is a Selective Inhibitor of Transforming Growth Factor-β Type I Receptors ALK4, ALK5, and ALK7," Molecular Pharmacology, vol. 65, No. 3, pp. 744-752, Mar. 2004.

Callahan, et al., "Identification of Novel Inhibitors of the Transforming Growth Factor Beta1 (TGF-beta1) Type 1 Receptor (ALK5)," J. Med. Chem., vol. 45., No. 5, pp. 999-1001, Feb. 28, 2002.

Chai, R., et al., "Dynamic Expression of Lgr5, a Wnt Target Gene, in the Developing and Mature Mouse Cochlea", J. Assoc. Res. Otolaryngology, 12(4): 455-469 (2011).

Chai, R., et al., "Wnt signaling induces proliferation of sensory precursors in the postnatal mouse cochlea", Proc. Nat'l Acad. Sci. USA, 109(21): 8167-8172 (2012).

Chen, F-Q., et al., "Aminoglycoside-induced histone deacetylation and hair cell death in the mouse cochlea," J. Neurochem., 108(5): 1226-1236 (2009).

Cox, et al., "Spontaneous Hair Cell Regeneration in the Neonatal Mouse Cochlea in Vivo," Development, vol. 141, No. 4, pp. 816-829, Feb. 2014.

Crosnier, C., et al., "Organizing cell renewal in the intestine: stem cells, signals and combinatorial control.," Nature Reviews Genetics, 7: 349-359 (2006).

Dai, et al., "Human Serum and Glucocorticoid-Inducible Kinase-Like Kinase (SGKL) Phosphorylates Glycogen Syntheses Kinase 3 Beta (GSK-3beta) at Serine-9 Through Direct Interation," Biolchem. Biophys. Res. Commun., vol. 293, No. 4, pp. 1191-1196, May 17, 2002.

Davies, et al., "The Interaction Between β-Catenin, GSK3β and APC After Motogen Induced Cell-Cell Dissociation, and Their Involvement in Signal Transduction Pathways in Prostate Cancer," International Journal of Oncology, vol. 18, No. 4, pp. 843-847, Apr. 1, 2001.

Davis, et al, "Mesodermal Fate Decisions of a Stem Cell: the Wnt Switch," Cell Mol Life Sci., 65(17):2658-74 (2008) (abstract only).

Drottar, M., et al., "The Histone Deacetylase Inhibitor Sodium Butyrate Protects Against Cisplatin-Induced Hearing Loss in Guinea Pigs," Laryngoscope, 116(2): 292-296 (2006).

Dumont, et al., "Targeting the TGFβ Signaling Network in Human Neoplasia," Cancer Cell, vol. 3, No. 6, pp. 531-536, Jun. 2003.

Engleder, et al., "Preclinical Evaluation of Thermoreversible Triamcinolone Acetonide Hydrogels for Drug Delivery to the Inner Ear," International Journal of Pharmaceutics, vol. 471, No. 1-2, pp. 297-302, Aug. 25, 2014.

Espinoza, et al., "Phosphorylation by Glycogen Synthase Kinase-3β Down-Regulates Notch Activity, a Link for Notch and Wnt Pathways," Journal of Biological Chemistry, vol. 278, No. 34, pp. 32227-32235, Aug. 22, 2003.

Farin, H.F., et al., "Redundant sources of Wnt regulate intestinal stem cells and promote formation of Paneth cells," Gastroenterology, 143: 1518-1529 (2012).

Foltz, et al., "Glycogen Synthase Kinase-3β Modulates Notch Signaling and Stability," Current Biology, vol. 12, No. 12, pp. 1006-1011, Jun. 25, 2002.

Fu, et al., "SM16, an Orally Active TFG-β Type I Receptor Inhibitor Prevents Myofibroblast Induction and Vascular Fibrosis in the Rat Carotid Injury Model," Arteriosclerosis, Thrombosis and Vascular Biology, vol. 28, No. 4, pp. 665-671, Jan. 17, 2008.

Fuller, M.K., et al., "Intestinal crypts reproducibly expand in culture", J. Surg. Res., 178(1):48-54 (2012).

Garcia-Berrocal Jr., et al., "Alternatives to Systemic Steroid Therapy for Refractory Immune-Mediated Inner Ear Disease: A Physiopathologic Approach," Eur. Arch. Otorhinolarynqol, vol. 263, No. 11, pp. 977-982, Nov. 2006.

Gellibert, et al., "Identification of 1, 5-Naphthyridine Derivatives as a Novel Series of Potent and Selective TGF-Beta Type 1 Receptor Inhibitors," J. Med. Chem., vol. 47, No. 18, pp. 4494-4506, Aug. 26, 2004.

Haegebarth, et al., "Wnt Signaling, Lgr5, and Stem Cells in the Intestine and Skin," The American Jounral of Pathology, vol. 174, No. 3, pp. 715-721, Mar. 2009.

Haggarty, S.J., et al., "Domain-Selective Small-Molecule Inhibitor of Histone Deacetylase 6 (HDAC6)-Mediated Tubulin Deacetylation", Proc. Nat'l. Acad. Sci. USA, 100(8): 4389-4394 (2003).

Halder, et al., "A Specific Inhibitor of TGF-β Receptor Kinase, SB-431542, As a Potent Antitumor Agent for Human Cancers," Neoplasia, vol. 7, No. 5, pp. 509-521, May 2005.

Hong, et al., "Human Dynamin-Like Protein Interacts with the Glycogen Synthase Kinase 3β," Biochem. Biophys. Res. Commun., vol. 249, No. 3, pp. 697-703, Aug. 28, 1998.

Huang, et al., "Directed, Efficient, and Versatile Modifications of the Drosophila Genome by Genomic Engineering," PNAS, vol. 106, No. 20, pp. 8284-9290, May 19, 2009.

Huang, et al., "RAD18 Transmits DNA Damage Signaling to Elicit Homologous Recombination Repair," Nat. Cell. Biol., vol. 11, No. 5, pp. 592-603, May 2009.

Isaacson, et al., "Differential Diagnosis and Treatment of Hearing Loss," American Family Physician, vol. 18, pp. 1125-1132, 2003.

Itoh et al., "False HDAC inhibition by aurone compound;" Chemical and Pharmaceutical Bulletin, vol. 64 (2016); pp. 1124-1128.

Jeon, et al., "Notch Signaling Alters Sensory or Neuronal Cell Fate Specification of Inner Ear Stem Cells," Journal Neurosci, vol. 31, No. 23, pp. 8351-8358, Jun. 8, 2011.

Jung, P., et al., "Isolation and in vitro expansion of human colonic stem cells," Nat. Med., 17, 1225-1227 (2011).

Kanzaki, et al., "Novel in Vivo Imaging Analysis of an Inner Ear Drug Delivery System in Mice: Comparison of Inner Ear Drug Concentrations Over TimeAfter Transtympanic and Systemic Injections," PloS One, vol. 7:e48480, 2012.

Kawamoto, Tadafumi, "Use of a New Adhesive Film for the Preparation of Multi-Purpose Fresh-Frozen Sections from Hard Tissues, Whole-Animals, Insects and Plants," Arch Histol Cytol, vol. 66, No. 2, pp. 123-143, Apr. 2003.

Kazanjian, A., et al., "Atonal homolog 1 is required for growth and differentiation effects of notch/gamma-secretase inhibitors on normal and cancerous intestinal epithelial cells," Gastroenterology, 139: 918-928 (2010).

Koch, et al., "Stem cells living with a Notch," The Company of Biologists Ltd, Development, vol. 140, pp. 689-704, 2013.

Kujawa, et al., "Conditioning-Related Protection from Acoustic Injury: Effects of Chronic Deefferentation and Sham Surgery," J. Neurophysiol., vol. 78, pp. 3095-3106 (1997).

Lanford, et al., "Notch Signaling Pathway Mediates Hair Cell Development in Mammalian Cochlea," Nature Genetics, vol. 21, pp. 289-292, Mar. 1999.

Lasak, et al., "Hearing Loss: Diagnosis and Management," Primary Care, vol. 41, pp. 19-31, 2014.

Li, et al., "Interaction of Glycogen Synthase Kinase 3β with the DF3/MUC1 Carcinoma-Associated Antigen and β-Catenin," Molecular and Cellular Biology, vol. 18, No. 12, pp. 7216-7224, Dec. 1998.

Li, et al., "Retinoic Acid Stimulates Chondrocyte Differentiation and Enhances Bone Morphogenetic Protein Effects through Induction of Smad1 and Smad5," Endocrinology, vol. 144, No. 6, pp. 2514-2523, Feb. 3, 2003.

(56) References Cited

OTHER PUBLICATIONS

Liu, et al. "Identification of Stage-Specific Markers During Differentiation of Hair Cells From Mouse Inner Ear Stem Cells or Progenitor Cells in Vitro," Int. J. Biochem. Cell. Biol., vol. 60, pp. 99-111, Mar. 2015.

Liu, et al., "In vivo Notch reactivation in differentiating cochlear hair cells induces Sox2 and Prox1 expression but does not disrupt hair cell maturation," Dev Dyn., vol. 241, pp. 684-696, Apr. 2012.

Lu, Z., et al., "The Influence of Glycogen Synthase Kinase 3 in Limiting Cell Addition in the Mammalian Ear," pp. 1059-1075, published online in Wiley InterScience (www.interscience.wiley.com) May 9, 2008.

Lukacs, R.U., et al., "Isolation, cultivation and characterization of adult murine prostate stem cells," Nat. Protoc., 5(4):702-713 (2010).

Maisons et al., "Olivocochlear Innervation in the Mouse: Immunocytochemical Maps, Crossed Versus Uncrossed Contributions, and Transmitter Colocalization," J. Comp. Neurol., vol. 455, No. 3, pp. 406-416, Jan. 13, 2003.

Mak, et al., "The Tubcrin-Hamartin Complex Negatively Regulates β-Catenin Signaling Activity," The Journal of Biological Chemistry, vol. 278, No. 8, 5947-5951, Feb. 2003.

Martinez-Monedero, et al., "Differentiation of Inner Ear Stem Cells to Functional Sensory Neurons," Developmental Neurobiology, vol. 68, No. 5, pp. 669-684, Apr. 2008.

McCall, et al., "Drug Delivery for Treatment of Inner Ear Disease: Current State of Knowledge," Ear and Hearing, vol. 31, No. 2, pp. 156-165, Apr. 2010.

Meng, et al., "Gamma-Secretase Inhibitors Abrogate Oxaliplatin-Induced Activation of the Notch-1 Signaling Pathway in Colon Cancer Cells Resulting in Enhanced Chemosensitivity," Cancer Research, vol. 69, pp. 573-582, 2009.

Mikulec, et al., "Permeability of the Round Window Membrane is Influenced by the Composition of Applied Drug Solutions and by Common Surgical Procedures," Otol. Neurotol. vol. 29, No. 7, pp. 1020-1026, Oct. 2008.

Mimasu, et al., "Crystal structure of histone demethylase LSD1 and tranylcypromine at 2.25 A," Biochemical and Biophysical Research Communications, vol. 366, pp. 15-22, 2008.

Mizutari, et al., "Notch Inhibition Induces Cochlear Hair Cell Regeneration and Recovery of Hearing after Acoustic Trauma," Neuron, vol. 77, No. 1, pp. 58-69, Jan. 2013.

Mizutari, et al., "Spontaneous Recovery of Cochlear Fibrocytes After Severe Degeneration Caused by Acute Energy Failure," Frontiers in Pharmacology, vol. 5, No. 198, pp. 1-3, Aug. 26, 2014.

Nakamura, et al., "Axin, an Inhibitor of the Wnt Signalling Pathway, Interacts with β-Catenin, GSK-3β and APC and Reduces the β-Catenin Level," Genes Cells, vol. 3, No. 6, pp. 395-403, Jun. 1998.

Olsauskas-Kuprys, et al., "Gamma Secretase Inhibitors of Notch Signaling," OncoTargets and Therapy, vol. 6, pp. 943-955, 2013.

Peterson, et al., "Oral Administration of GW788388, An inhibitor of TGF-β Type 1 and II Receptor Kinases, Decreases Renal Fibrosis," Kidney International, vol. 73, pp. 705-715, (2008), published online Dec. 12, 2007.

Plontke, et al., "1D-and 3D-Computer Simulation for Experimental Planning and Interpretation of Pharmacokinetic Studies in the Inner Ear After Local Drug Delivery," Altex, vol. 21, Suppl 3, pp. 77-85, 2004.

Plontke, et al., "Cochlear Pharmacokinetics With Local Inner Ear Drug Delivery Using a Three-Dimensional Finite-Element Computer Model," Audiology & Neuro-Otology, vol. 12, pp. 37-48, 2007.

Plontke, et al., "Simulation of Application Strategies for Local Drug Delivery to the Inner Ear," ORL Journal for Oto-Rhino-Laryngology and Its Related Specialties, vol. 68, No. 6, pp. 386-392, Oct. 26, 2006.

Provenzano, M.J. and Domann, F.E., "A role for epigenetics in hearing: Establishment and maintenance of auditory specific gene expression patterns," Hearing Res., 233(1-2): 1-13 (2007).

Sage, et al., "Essential role of retinoblastoma protein in mammalian hair cell development and hearing," Proc. Natl. Acad. Sci. USA, vol. 103, pp. 7345-7350, May 2006.

Sage, et al., "Proliferation of Functional Hair Cells in Vivo in the Absence of the Retinoblastoma Protein," Science, vol. 307, pp. 1114-1118, Feb. 18, 2005.

Salt, et al., "Distribution of Dexamethasone and Preservation of Inner Ear Function Following Intratympanic Delivery of a Gel-Based Formulation," Audiology & Neuro-otology, vol. 16, pp. 323-335, 2011.

Salt, et al., "Local Inner Ear Drug Delivery and Pharmacokinetics," Drug. Discov. Today, vol. 10, No. 19, pp. 1299-1306, Oct. 1, 2005.

Salt, et al., "Principles of Local Drug Delivery to the Inner Ear," Audiol. Neurotol. vol. 14, No. 6, pp. 350-360, Nov. 16, 2009.

Salvi, et al., "Hair Cell Regeneration, Repair, and Protection," Springer Handbook of Auditory Research, vols. 1-33, 323 pages, 2008.

Sato, T., et al., "Long-term expansion of epithelial organoids from human colon, adenoma, adenocarcinoma, and Barrett's epithelium," Gastroenterology, 141: 1762-1772 (2011).

Sato, T., et al., "Paneth cells constitute the niche for Lgr5 stem cells in intestinal crypts," Nature, 469: 415-418 (2011).

Sawyer, et al., "Synthesis and Activity of New Aryl- and Heteroaryl-Substituted 5, 6-Dihiydro-4H-Pyrrolo[1,2-b]Pyrazole Inhibitors of the Transforming Growth Factor-Beta Type I Receptor Kinase Domain," Bioorg. Med. Chem. Lett., vol. 14, No. 13, pp. 3581-3584, Jul. 5, 2004.

Sawyer, et al., "Synthesis and Activity of New Aryl- and Heteroaryl-Substituted Pyrazole Inhibitors of the Transforming Growth Factor-Beta Type 1 Receptor Kinase Domain," J. Med. Chem., vol. 46, No. 19, pp. 3953-3956, Sep. 11, 2003.

Schwarz-Romond, et al., "The Ankyrin Repeat Protein Diversin Recruits Casein Kinase Iε to the β-Catenin Degradation Complex and Acts in Both Canonical Wnt and Wnt/JNK Signaling," Genes, Dev., vol. 16, No. 16, pp. 2073-2084, Jun. 2002.

Scoville, et al., "Current view: intestinal stem cells and signaling," Gastroenterology, 134(3): 849-864 (2008).

Seidman, M. D., "Glutamate Antagonists, Steroids, and Antioxidants as Therapeutic Options for Hearing Loss and Tinnitus and the Use of an Inner Ear Drug Delivery System," The International Tinnitus Journal, vol. 4, pp. 148-154, 1998.

Sekine, A., ct al., "Hath1 Up-Regulates Gastric Mucin Gene Expression in Gastric Cells", Biochem. Biophys. Res. Commun., 344(4): 1166-71 (2006).

Shariatmadari, M., et al., "Increased Wnt Levels in the Neural Tube Impair the Function of Adherens Junctions During Neurulation," Mol Cell Neurosci.,30(3): 437-51. Epub (2005) (abstract only).

Shi, et al., "Beta-Catenin Up-Regulates Atoh1 Expression in Neural Progenitor Cells by Interaction with an Atoh1 3' Enhancer," The Journal of Biological Chemistry, vol. 285, pp. 392-400, 2010.

Shi, et al., "Generation of Hair Cells in Neonatal Mice by β-Catenin Overexpression in Lgr5-Positive Cochlear Progenitors," Proc Natl Acad Sci USA, vol. 110, No. 34, pp. 13851-13856, Aug. 20, 2013.

Shi, F., et al. "Wnt-Responsive Lgr5-Expressing Stem Cells Are Hair Cell Progenitors in the Cochlea", J. Neuroscience, 32 (28): 9639-9648 (2012).

Shih, et al., "Notch Signaling, Gamma-Secretase Inhibitors, and Cancer Therapy," Cancer Research, vol. 67, pp. 1879-1882, 2007.

Snippert, H. J., et al., "Intestinal crypt homeostasis results from neutral competition between symmetrically dividing Lgr5 stem cells," Cell, 143: 134-144 (2010).

Swan, et al., "inner Ear Drug Delivery for Auditory Applications," Adv. Drug. Deliv. Rev., vol. 60, No. 15, pp. 1583-1599, Dec. 14, 2008.

Tojo, et al., "The ALK-5 Inhibitor A-83-01 Inhibits Smad Signaling and Epithelial-to-Mesenchymal Transition by Transforming Growth Factor-β," Cancer Sci., vol. 96, No. 11, pp. 791-800, Nov. 2005.

Valdimarsdottir, et al., "Functions of the TGFβ Superfamily in Human Embryonic StempCells," APMIS, vol. 113, pp. 773-389, Nov.-Dec. 2005.

van der Flier, L.G., and Clevers, H., "Stem cells, self-renewal, and differentiation in the intestinal epithelium," Annual Review of Physiology, 71: 241-260 (2009).

(56) References Cited

OTHER PUBLICATIONS van Es, J.H., et al., "Intestinal stem cells lacking the Math1 tumour suppressor are refractory to Notch inhibitors", Nat. Commun., 1(18): 1-5 (2010).
van Es, J.H., et al., "Notch/gamma-secretase inhibition tuns proliferative cells in intestinal crypts and adenomas into goblet cells," Nature, 435: 959-963 (2005).
VanDussen, K.L., et al., "Notch signaling modulates proliferation and differentiation of intestinal crypt base columnar stem cells," Development, 139: 488-497 (2012).
Von Krics, et al., "Hot Spots in Beta-Catenin for Interactions with LEF-1, Conductin and APC," Nat. Struct. Biol., vol. 7, No. 9, pp. 800-807, Sep. 2000.
Voytik-Harbin, S.L, et al., "Small Intestinal Submucosa: A Tissue-Derived Extracellular Matrix That Promotes Tissue-Specific Growth and Differentiation of Cells in Vitro", Tissue Engineering, 4(2): 157-174 (1998).
Wang, et al., "Suppression of Androgen Receptor-Mediated Transactivation and Cell Growth by the Glycogen Synthase Kinase 3β in Prostate Cells," Journal of Biological Chemistry, vol. 279, No. 31, pp. 32444-32452, Jul. 30, 2004.
Warchol, et al., "Regenerative Proliferation in Organ Cultures of the Avian Cochlea: Identification of the Initial Progenitors and Determination of the Latency of the Proliferative Response," The Journal of Neuroscience : the Official Journal of the Society for Neuroscience, vol. 16, pp. 5466-5477, 1996.
White, et al., "Mammalian Cochlear Supporting Cells Can Divide and Trans-Differentiate Into Hair Cells," Nature, vol. 441, No. 7096, pp. 984-987, Jun. 22, 2006.
Wong, et al., "Mechanisms of sensorineural cell damage, death and survival in the cochlea," Frontiers in Aging Neuroscience, vol. 7, Article 58, pp. 1-15, Apr. 2015.
Yao, M., et al., "Prostate-regenerating capacity of cultured human adult prostate epithelial cells," Cells Tissues Organs, 191: 203-212 (2010).
Yilmaz, O.H., et al., "mTORC1 in the Paneth cell niche couples intestinal stem-cell function to calorie intake," Nature, 486: 490-495 (2012).
Yin, et al., "Niche-Independent High-Purity Cultures of Lgr5+ Intestinal Stem Cells and Their Progeny," Nat. Methods, vol. 11, No. 1, pp. 106-112, Jan. 2014.
Ying, Q.L., et al., "The ground state of embryonic stem cell self-renewal," Nature, 453: 519-523 (2008).
Yingling, et al., "Development of TGF-β Signalling Inhibitors for Cancer Therapy," Nature Reviews Drug Discovery, vol. 3, No. 12, pp. 1011-1022, Dec. 2004.
Yu, et al., "In vivo proliferation of postmitotic cochlear supporting cells by acute ablation of the retinoblastoma protein in neonatal mice," J Neurosci, vol. 30, pp. 5927-5936, Apr. 2010.
Yuge, I., et al., "Transplanted Human Amniotic Epithelial Cells Express Connexin 26 and Na-K-Adenosine Triphophatase in the Inner Ear," Transplantation, vol. 77, No. 9, pp. 1452-1454, 2004.
Yui, S., et al., "Functional engraftment of colon epithelium expanded in vitro from a single adult Lgr5+ stem cell," Nature Medicine, 18(4): 618-623 (2012).
Zahnert, T., "The Differential Diagnosis of Hearing Loss," Deutsches Arzteblatt International, vol. 108, pp. 433-443, quiz 44, 2011.
Zhang, F., et al., "Inhibitory Phosphorylation of Glycogen Synthase Kinase-3 (GSK-3) in Response to Lithium," J. Bio. Chem., 278(3): 33067-33077 (2003).
Almeida, et al., "In Situ Gelling Systems: A Strategy to Improve the Bioavailability of Ophthalmic Pharmaceutical Formulations," Drug Discov. Today, 19(4):400-12, (Apr. 2014), (Epub Oct. 11, 2013).
Arnold, et al., "Zinc for Attention-Deficit/Hyperactivity Disorder: Placebo-Controlled Double-Blind Pilot Trial Alone and Combined with Amphetamine," Journal of Child and Adolescent Psychopharmacology, vol. 21(1):1-19 (Jan. 2011).
Bermingham, et al., "Math 1: An Essential Gene for the Generation of Inner Ear Hair Cells," Science, 284:1837-1841 (Jun. 11, 1999).

Bohl, et al., "Development of a Specially Tailored Local Drug Delivery System for the Prevention of Fibrosis After Insertion of Cochlear Implants Into the Inner Ear," Journal of Materials Science Materials in Medicine, vol. 23:2151-2162 (2012).
Byfield, et al., "Lateral Signaling Enhances TGF-β Response Complexity," Trends Cell Biol., 14(3):107-111 (Mar. 2004).
Chen,G. et al., "Preliminary Study on Brain-Targeted Drug Delivery via Inner Ear," Yao xue xue bao = Acta pharmaceutica Sinica, 42:1102-1106 (2007).
Chen, et al., "Inner Ear Drug Delivery via a Reciprocating Perfusion System in the Guinea Pig," Journal of Controlled Release : Official Journal of the Controlled Release Society, 110:1-19 (2005).
Fujioka, et al., "Development of Auditory-Specific Brain Rhythm in Infants," European Journal of Neuroscience, 33:521-529 (Jan. 13, 2011).
Gale, J. and Jagger, D., "Cochlear Supporting Cells," Chapter 11 in Oxford Handbook of Auditory Science: The Ear, 31 pages (2010).
Gupta, et al., "Fast-Gelling Injectable Blend of Hyaluronan and Methylcellulose for Intrathecal, Localized Delivery to the Injured Spinal Cord," Biomaterials, 27:2370-2379 (2006).
Harding, G.W. et al, "The effect of an age-related hearing loss gene (Ahl) on noise-induced hearing loss and cochlear damage from low-frequency noise," Hearing Research, 204:90-100 (2005).
Herraiz, et al., "Intratympanic Drug Delivery for the Treatment of Inner Ear Diseases," Acta Otorrinolaringologica Espanola, 61(3):225-232 (2010).
Hoskison, et al., "Drug Delivery to the Ear," Therapeutic Delivery, 4(1):115-124 (Jan. 2013).
Huang, et al., "Systematic and Integrative Analysis of Large Gene Lists Using DAVID Bioinformatics Resources," Nature Protocols, 4(1):44-57 (2009) (pub. online, Dec. 18, 2008).
Izumikawa, et al., "Auditory Hair Cell Replacement and Hearing Improvement by Atoh1 Gene Therapy in Deaf Mammals," Nat Med., 11(3):271-276 (Mar. 2005).
Kim, et al., "Development of a Drug Delivery System for the Inner Ear Using Poly(amino acid)-Based Nanoparticles," Drug Delivery, 22(3):367-374 (2015).
Lajud, S.A., et al., "A Regulated Delivery System for Inner Ear Drug Application," Journal of Controlled Release : Official Journal of the Controlled Release Society, 166:268-276 (2013).
Lehner, et al., "A Totally Implantable Drug Delivery System for Local Therapy of the Middle and Inner Ear," Ear, Nose, & Throat Journal, 76(8):567-570 (1997).
Li, et al., "A Novel Aerosol-Mediated Drug Delivery System for Inner Ear Therapy: Intratympanic Aerosol Methylprednisolone Can Attenuate Acoustic Trauma," IEEE Transactions on Bio-Medical Engineering, 60(9):2450-2460 (2013).
Lumpkin, et al., "Math1-Driven GFP Expression in the Developing Nervous System of Transgenic Mice," Gene Expr Patters, 3(4):389-395 (Aug. 2003).
Mills, D. M., "Determining the Cause of Hearing Loss: Differential Diagnosis Using a Comparison of Audiometric and Otoacoustic Emission Responses," Ear and Hearing, 27(5):508-525 (2006).
Mimura, T. et al., "Topical Ocular Drug Delivery to Inner Ear Disease and Sinusitis," Southern Medical Journal, 99(11):1287-1289 (2006).
Mundada, A.S. et al., "In Situ Gelling Polymers in Ocular Drug Delivery Systems: A Review," Critical Reviews in Therapeutic Drug Carrier Systems, 26(1):85-118 (2009). (Impact Factor-3.99).
Nakagawa, et al., "Local Drug Delivery to the Inner Ear Using Biodegradable Materials," Therapeutic Delivery, 2(6):807-814 (Jun. 2011).
Oshima, et al., "Phylogenetic Relationships Among Mycoplasmas Based on the Whole Genomic Information," J. Mol. Evol., 65(3):249-258 (Sep. 2007), (Epub Aug. 9, 2007).
Paasche, et al., "Technical Report: Modification of a Cochlear Implant Electrode for Drug Delivery to the Inner Ear," Otology & Neurotology, 24:222-227 (2003).
Pararas, et al., "Microsystems Technologies for Drug Delivery to the Inner Ear," Advanced Drug Delivery Reviews, 64:1650-1660 (2012).

(56) References Cited

OTHER PUBLICATIONS

Pararas, et al., "Kinetics of Reciprocating Drug Delivery to the Inner Ear," Journal of Controlled Release : Official Journal of the Controlled Release Society, 152:270-277 (2011).
Paulson, et al., "A Novel Controlled Local Drug Delivery System for Inner Ear Disease," Otology/Basic and Clinical Research; The Laryngoscope, vol. 118:706-711 (2008).
Peer, et al., "Nanocarriers as an Emerging Platform for Cancer Therapy," Nature Nanotechnology, 2:751-760 (2007).
Plontke, et al. "Randomized Double Blind, Placebo Controlled Trial on the Safety and Efficacy of Continuous Intratympanic Dexamethasone Delivered via a Round Window Catheter for Severe to Profound Sudden Idiopathic Sensorineural Hearing Loss After Failure of Systemic Therapy," The Laryngoscope, 119:359-369 (2009).
Plontke, et al., "Technical Note on Microcatheter implantation for Local Inner Ear Drug Delivery: Surgical Technique and Safety Aspects," Otology & Neurotology, 27(7):912-917 (2006).
Plontke, S. K., "Evaluation of the Round Window Niche Before Local Drug Delivery to the Inner Ear Using a New Mini-Otoscope," Otology & Neurotology, 32(1):183-185 (2011).
Plontke, et al., "Pharmacokinctic Considerations in Intratympanic Drug Delivery to the Inner Ear," Acta Oto-Rhino-Laryngologica Belgica, 56(4):369-370 (2002).
Plontke, et al., "Transtympanic Endoscopy for Drug Delivery to the Inner Ear Using a New Microendoscope," Advances in Oto-Rhino-Laryngology, 59:149-155 (2002).
Pritz, et al., "Nanomedicine Strategies for Drug Delivery to the Ear," Nanomedicine, 8(7):1155-1172 (Jul. 2013).
Purow, B., "Notch Inhibition as a Promising New Approach to Cancer Therapy," Advances in Experimental Medicine and Biology, 727:305-319 (2012).
Raphael, Y., "Evidence for Supporting Cell Mitosis in Response to Acoustic Trauma in the Avian Inner Ear," Journal of Neurocytology, 21:663-671 (1992).
Richardson, et al., "Novel Drug Delivery Systems for Inner Ear Protection and Regeneration After Hearing Loss," Expert Opinion on Drug Delivery, 5(I0):1059-1076 (Sep. 2008).
Rivera, et al., "Drug Delivery to the Inner Ear: Strategies and their Therapeutic Implications for Sensorineural Hearing Loss," Current Drug Delivery, 9(3):231-242 (May 2012).
Roy, et al., "Strategies for Drug Delivery to the Human Inner Ear by Multifunctional Nanoparticles," Nanomedicine, 7(1):55-63 (2012).
Roy, et al., "Cell-Specific Targeting in the Mouse Inner Ear Using Nanoparticles Conjugated with a Neurotrophin-Derived Peptide Ligand: Potential Tool for Drug Delivery," International Journal of Pharmaceutics, 390:214-224 (2010).
Ryals, et al., "Return of Function After Hair Cell Regeneration," Hearing Research, 297:113-120 (2013).
Sakamoto, T. et al., "Inner Ear Drug Delivery System from the Clinical Point of View," Acta Oto-Laryngologica, 130:sup563:101-104 (2010).
Salt, et al., "Dependence of Hearing Changes on the Dose of Intratympanically Applied Gentamicin: A Meta-Analysis Using Mathematical Simulations of Clinical Drug Delivery Protocols," The Laryngoscope, 118(10):1793-1800 (Oct. 2008).
Salt, A., "Dexamethasone Concentration Gradients Along Scala Tympani After Application to the Round Window Membrane," Otology & Neurotology, 29(3):401-406 (2008).
Salt, A., "Guest Editorial: Drug Delivery for Treatment of Inner Ear Disease: Current State of Knowledge," Ear and Hearing, vol. 31, p. 155 (2010).
Sataloff, R. T. et al., "Differential Diagnosis of Occupational Hearing Loss," Occupational Health & Safety, 70(9):126-129 (Sep. 2001).
Shoichet, M.S. et al., "Intrathecal Drug Delivery Strategy is Safe and Efficacious for Localized Delivery to the Spinal Cord," Progress in Brain Research, 161:385-392 (2007).
Staecker, et al., "Drug Delivery to the Inner Ear Using Gene Therapy," Otolaryngologic Clinics of North America, vol. 37, pp. 1091-1108, 2004.
Staecker, ct al., "Developments in Delivery of Medications for Inner Ear Disease," Expert Opinion on Drug Delivery, 10(5):639-650 (2013).
Surovtseva, et al., "Prestin Binding Peptides as Ligands for Targeted Polymersome Mediated Drug Delivery to Outer Hair Cells in the Inner Ear," International Journal of Pharmaceutics, 424:121-127 (2012).
Van Tomme, S.R. et al., "In Situ Gelling Hydrogels for Pharmaceutical and Biomedical Applications," Int. J. Pharm., 355(1-2):1-18 (2008).
Wang, Y .et al., "Dynamics of Noise-induced Cellular injury and Repair in the Mouse Cochlea," J. of the Assoc. of Research in Otolaryngology, 3:248-268 (2002).
Wise, A.K. et al, "Drug Delivery to the Inner Ear," Journal of Neural Engineering, 9(6):065002, 10 pages (Nov. 2012).
Wu, et al., "Modulation of Notch Signaling by Mastermind-Like (MAML) Transcriptional Co-Activators and Their Involvement in Tumorigenesis," Seminars in Cancer Biology, 14:348-356 (2004).
Yang, J. et al, "Functional Features of Trans-Differentiated Hair Cells Mediated by Atohl Reveals a Primordial Mechanism," J. of Neuroscience, 32(11):3712-3725 (Mar. 2012).
Yang, J. et al, "Ectopic Hair Cell-Like Cell Induction by Mathl Mainly Involves Direct Transdifferentiation in Neonatal Mammalian Cochlea," Neuroscience Letters, 549:7-11 (2013).
Zheng, et al., "Overexpresson of Math 1 Induces Robust Production of Extra Hair Cells in Postnatal Rat Inner Ears," Nature Neuroscience, 3(6):580-586 (Jun. 2000).
Zheng, J., "Polymers in Pharmaceuticals," China Medical Science and Technology Press, p. 219 (2009); accompanied by Search Report, 2nd Notification of Office Action, and Text of the Second Office Action, dated Nov. 4, 2020, in CN Patent Application No. 201580059582.3, titled "Compositions, Systems, and Methods for Generating Inner Ear Hair Cells for Treatment of Hearing Loss."
De Los Angeles, et al., "A chemical logic for reprogramming to pluripotency," Cell Research, vol. 23, No. 12, Dec. 2013, pp. 1337-1338.
Lin et al., "Inhibition of Notch Activity Promotes Nonmitotic Regeneration of Flair Cells in the Adult Mouse Utricles," The Journal of Neurosciencce, vol. 31, No. 43, Oct. 26, 2011, pp. 15329-15339.
McLean et al., "Clonal Expansion of Lgr5-Positive Cells from Mammalian Cochlea and High-Purity Generation of Sensory Hair Cells," Cell Reports 18, 1917-1929, 2017.
Liu et al., "Current Strategies for Drug Delivery to the Inner Ear," Acta Pharmaceutica Sinica B 2013; 3(2):86-96 (accepted Feb. 3, 2013).
Lyu, Jing-yu et al., "Differentiation of Rabbit Bone Mesenchymal Stem Cells into Islet Cells by 5-Azacytidine in vitro" Acta Veterinaria et Zootechnica Sinica, 2014,45(9): 1538-1543.
Van Landeghem, L., "Activation of two distinct Sox9-EGFP-expressing intestinal stem cell populations during crypt Yegeneration after irradiation," Am J Physiol Gastrointest Liver Physiol 302: G1111-G1132, (2012).

Cells from 6 week old Adult Mice

Cells from 6 week old Adult Mice

SEQUENCE LISTING

```
<160> NUMBER OF SEQ ID NOS: 7

<210> SEQ ID NO 1
<211> LENGTH: 30
<212> TYPE: DNA
<213> ORGANISM: Artificial Sequence
<220> FEATURE:
<223> OTHER INFORMATION: LacZ F primer

<400> SEQUENCE: 1
ttcactggcc gtcgttttac aacgtcgtga                                    30

<210> SEQ ID NO 2
<211> LENGTH: 30
<212> TYPE: DNA
<213> ORGANISM: Artificial Sequence
<220> FEATURE:
<223> OTHER INFORMATION: LacZ R primer

<400> SEQUENCE: 2
atgtgagcga gtaacaaccc gtcggattct                                    30
```

```
<210> SEQ ID NO 3
<211> LENGTH: 20
<212> TYPE: DNA
<213> ORGANISM: Artificial Sequence
<220> FEATURE:
<223> OTHER INFORMATION: Cre F primer

<400> SEQUENCE: 3
tgggcggcat ggtgcaagtt                                          20

<210> SEQ ID NO 4
<211> LENGTH: 20
<212> TYPE: DNA
<213> ORGANISM: Artificial Sequence
<220> FEATURE:
<223> OTHER INFORMATION: Cre R primer

<400> SEQUENCE: 4
cggtgctaac cagcgttttc                                          20

<210> SEQ ID NO 5
<211> LENGTH: 21
<212> TYPE: DNA
<213> ORGANISM: Artificial Sequence
<220> FEATURE:
<223> OTHER INFORMATION: oIMR7318 wild-type F

<400> SEQUENCE: 5
ctctgctgcc tcctggcttc t                                        21

<210> SEQ ID NO 6
<211> LENGTH: 21
<212> TYPE: DNA
<213> ORGANISM: Artificial Sequence
<220> FEATURE:
<223> OTHER INFORMATION: oIMR7319 wild-type R

<400> SEQUENCE: 6
cgaggcggat cacaagcaat a                                        21

<210> SEQ ID NO 7
<211> LENGTH: 19
<212> TYPE: DNA
<213> ORGANISM: Artificial Sequence
<220> FEATURE:
<223> OTHER INFORMATION: oIMR7320 mutant R

<400> SEQUENCE: 7
tcaatgggcg ggggtcgtt                                           19
```

COMPOSITIONS, SYSTEMS, AND METHODS FOR GENERATING INNER EAR HAIR CELLS FOR TREATMENT OF HEARING LOSS

RELATED APPLICATIONS

This application is a divisional of U.S. application Ser. No. 14/845,263, filed on Sep. 3, 2015, which claims the benefit of U.S. Provisional Application No. 62/045,506, filed on Sep. 3, 2014, and U.S. Provisional Application No. 62/051,003, filed on Sep. 16, 2014. The entire teachings of the above applications are incorporated herein by reference.

GOVERNMENT SUPPORT

This invention was made with government support under Grant No. R01 DE013023 awarded by the National Institutes of Health. This invention was made with government support under Grant No. HL095722 awarded by the National Institute of Health. The Government has certain rights in the invention.

INCORPORATION BY REFERENCE OF MATERIAL IN ASCII TEXT FILE

This application incorporates by reference the Sequence Listing contained in the following ASCII text file:
 a) File name: 00502282017_SEQUENCELISTING.txt; created Jan. 23, 2020, 2 KB in size.

BACKGROUND OF THE INVENTION

Permanent damage to the hair cells of the inner ear results in sensorineural hearing loss, leading to communication difficulties in a large percentage of the population. Hair cells are the receptor cells that transduce the acoustic stimulus. Regeneration of damaged hair cells provide an avenue for the treatment of a condition that currently has no therapies other than prosthetic devices. Although hair cells do not regenerate in the mammalian cochlea, new hair cells in lower vertebrates are generated from epithelial cells, called supporting cells, that surround hair cells.

The prevalence of hearing loss after damage to the mammalian cochlea has been thought to be due to a lack of spontaneous regeneration of hair cells and/or neurons, the primary components to detect sound (Wong and Ryan, 2015). Humans are born with about 15,000 inner ear hair cells and hair cells do not regenerate after birth. Supporting cells, which surround hair cells in the normal cochlear epithelium, have potential to differentiate into new hair cells in the neonatal mouse following ototoxic damage (Bramhall et al. 2014). Using lineage tracing, the new hair cells, predominantly outer hair cells, have been shown to arise from Lgr5-expressing inner pillar and third Deiters cells, and new hair cell generation has been shown to incrementally be increased by pharmacological inhibition of Notch (Bramhall et al. 2014, Mizutari et al. 2014). It has been postulated that the neonatal mammalian cochlea has some capacity for hair cell regeneration following damage alone (Cox et al. 2014) and that Lgr5-positive (Lgr5+) cells act as hair cell progenitors in the cochlea (Chai et al. 2011, Shi et al. 2012).

Auditory dysfunction in humans is an ongoing problem in the medical fields of otology and audiology. Auditory dysfunctions typically arise from both acute and chronic exposures to loud sounds, ototoxic chemicals, and aging. Sounds exceeding 85 decibels can cause hearing loss and is generated by sound sources such as, gun shots, exploding bombs, jet engines, power tools, and musical concerts. Other common everyday activities and products also give rise to high intensity noise such as use of hair dryers, MP3 players, lawn mowers, and blenders. Military personnel are particularly at risk for noise induced hearing loss due to typical military noise exposures. Side effects of noise-induced hearing loss include tinnitus (ringing in the ears), diminished speech understanding, hyperacusis, recruitment and various types of auditory processing impairments. Exposures to commonly used medications may also induce auditory dysfunctions. For instance, patients treated with anticancer therapies, antibiotics and other medications often develop hearing loss as a side effect. Furthermore, exposure to industrial chemicals and gasses may induce auditory impairments. Auditory dysfunction is a common consequence of aging in Western societies. Hearing impairments can be attributed to a wide variety of causes, including infections (e.g., otitis media), genetic predisposition, mechanical injury, tumors, loud sounds or prolonged exposure to noise, aging, and chemical-induced ototoxicity (e.g., antibiotics or platin drugs) that damages neurons and/or hair cells of the peripheral auditory system. This can be caused by acute noise or can be progressive over time.

Currently, very few cases of hearing loss can actually be cured. Audiological devices such as hearing aids have limitations including the inability to improve speech intelligibility. Of those impacted by hearing impairments, less than 20 percent presently use hearing instruments. In cases of age-related, noise- or drug-induced auditory dysfunctions, often the only effective way to currently "treat" the disorder or reduce its severity is prevention: avoiding excessive noise and using ear protectors, practicing a healthy lifestyle, and avoiding exposure to ototoxic drugs and substances if possible.

Once the hearing loss has developed, people may use a hearing aid to correct the hearing loss. However, despite advances in the performance of these prostheses, they still have significant limitations. For example, hearing aids mainly amplify sound and cannot correct for suprathreshold or retrocochlear impairments such as impaired speech intelligibility, speech in noise deficits, tinnitus, hyperacusis, loudness recruitment and various other types of central auditory processing disorders. Hearing aids essentially amplify sounds, which stimulate unimpaired cells, but there is no therapy for aiding recovery of impaired cells or maximizing the function of existing unimpaired cells.

In cases of complete or profound deafness, a cochlear implant may be used. This device transmits electrical stimuli via electrodes surgically implanted into the cochlea. A cochlear implant can be of particular help for deaf children if it is implanted around the age of two or three, the time when language skills are developing fastest. However, cochlear implants involve invasive surgery and are expensive. Furthermore, cochlear implants require viable neurons to achieve benefit.

Approximately 17 percent of Americans have hearing loss and half of that number are under the age of 65. It is predicted that the number of Americans with hearing loss will exceed 70 million by the year 2030.

About 300 million people worldwide currently suffer from moderate to severe hearing loss, and this number is expected to increase to 700 million by the year 2015. Most of these people will suffer from noise induced hearing loss and one in four Americans will develop permanent hearing loss as a result of occupational exposure to noise hazards. According to the Center for Commercialization of Advanced Technology, the Department of Defense and the VA, the VA spends over $1 billion on hearing loss compensation. The Navy, Marine Corps, and Air Force (combined) file 22,000 new hearing loss claims, and hearing loss costs the economy more than $56 billion per year.

Thus, there remains a long felt need to protect auditory cells before injury and preserve/promote the function of existing cells after injury. As disclosed below, in certain embodiments, the present invention provides compositions, systems, and methods for preventing and treating auditory dysfunctions.

There are many patient populations that could be helped with new therapies that prevent or treat hearing loss, for example, patients with vertigo, tinnitus, or patients who require a cochlear implant, those who have hearing loss but are not eligible for a cochlear implants, and those with chronic mild/moderate or severe hearing loss.

Previous work has shown that manipulating direct inhibitors of cycle activation (e.g., p27kip1, Rb1, p19ink4d, p21cip1) causes many cells, including hair cells, to proliferate. Hair cells that re-enter cell cycle subsequently die and hearing ability deteriorates (Salvi R. J. Hair Cell Regeneration Repair and Protection, Sage et al 2005, 2006). Differentiation to hair cells was not seen after supporting cell proliferation resulting from manipulation of cell cycle genes, such as $p27^{Kip1}$ or Rb (Yu et al. 2010, Liu et al. 2012).

Stem cells exhibit an extraordinary ability to generate multiple cell types in the body. Besides embryonic stem cells, tissue specific stem cells serve a critical role during development as well as in homeostasis and injury repair in the adult. Stem cells renew themselves through proliferation as well as generate tissue specific cell types through differentiation. The characteristics of different stem cells varies from tissue to tissue, and are determined by their intrinsic genetic and epigenetic status. However, the balance between self-renewal and differentiation of different stem cells are all stringently controlled. Uncontrolled self-renewal may lead to overgrowth of stem cells and possibly tumor formation, while uncontrolled differentiation may exhaust the stem cell pool, leading to an impaired ability to sustain tissue homeostasis. Thus, stem cells continuously sense their environment and appropriately respond with proliferation, differentiation or apoptosis. It would be desirable to drive regeneration by controlling the timing and extent of stem cell proliferation and differentiation. Controlling the proliferation with small molecules that are cleared over time would allow for control of the timing and extent of stem cell proliferation and differentiation. Remarkably, tissue stem cells from different tissues share a limited number of signaling pathways for the regulation of their self-renewal and differentiation, albeit in a very context dependent manner. One of these pathways is the Notch pathway.

The Notch pathway represents an evolutionarily conserved signaling pathway that possesses a simple but unique mode of action. The core Notch pathway contains only a small number of components. The canonical Notch pathway is activated through the binding of Notch ligand on the surface of signal-sending cells to the Notch receptor on neighbor signal-receiving cells. This event initiates a cascade of proteolytic cleavages of the Notch receptor, including γ-secretase-mediated release of the Notch Intracellular Domain (NICD). NICD fragment then enters the nucleus to induce target gene transcription. Under most circumstances, the canonical Notch pathway requires physical contact between neighboring cells, thus it links the fate of one cell to that of an immediate neighbor, providing a sophisticated way to control the self-renewal and differentiation of stem cells. The Notch pathway has been shown to regulate many types of stem cells, including embryonic stem cells, neural stem cells, hematopoietic stem cells as well as Lgr5 epithelial stem cells (Koch et al, 2013; VanDussen et al, 2012).

Lgr5 is expressed across a diverse range of tissues and has been identified as a biomarker of adult stem cells in certain tissues such as the gut epithelia (Barker et al. 2007), kidney, hair follicle, and stomach (Barker et al, 2010; Haegebarth & Clevers, 2009). It was first published in 2011, that mammalian inner ear hair cells are derived from LGR5$^+$ cells (Chai et al, 2011, Shi et al. 2012). Lgr5 is a known component of the Wnt/beta-catenin pathway, which has been shown to play major roles in differentiation, proliferation, and inducing stem cell characteristics (Barker et al. 2007).

Prior work has focused on transdifferentiation of supporting cells into hair cells through activation or forced expression of genes that lead to hair cell formation, with a particular focus on mechanisms to enhance expression of Atoh1 (Bermingham et al., 1999; Zheng and Gao, 2000; Izumikawa et al., 2005; Mizutari et al., 2013). Interestingly, cells transduced with Atoh1 vectors have been shown to acquire vestibular phenotypes (Kawamoto et al., 2003; Huang et al., 2009; Yang et al., 2012, 2013), and lack complete development. As mentioned, upregulating Atoh1 via gene insertion has been shown to create non-cochlear cell types that behave in a manner that is not found within the native cochlea. In addition, these methods increase hair cell numbers but decrease supporting cell numbers. Since supporting cells are known to have specialized roles (Ramirez-Camancho 2006, Dale and Jagger 2010), loss of these cells could create problems in proper cochlear function.

SUMMARY OF THE INVENTION

Among the various aspects of the present disclosure, therefore, may be noted a method for activating the Wnt pathway in a cochlear supporting cell population to increase the capacity of the population for self-renewal, i.e., the capacity for repeated generation of daughter cells with equivalent proliferation and 'cell fate specification' potential, and differentiation, i.e., the capacity for generation of daughter cells specified for differentiation. Preferably, the Wnt pathway is activated upstream of the c-myc gene in members of the population and without any genetic modification of the population. Instead, the Wnt pathway is preferably activated by small molecules that transiently induce such activity. Additionally, the supporting cell population preferably includes supporting cells that are LGR5$^+$ and endogenous to the Organ of Corti.

A further aspect of the present disclosure is a method for inducing the self-renewal of stem/progenitor supporting cells comprised by a cochlear cell population. That is, the stem/progenitor supporting cells are induced to proliferate (i.e., divide and form daughter cells) while maintaining, in the daughter cells, the capacity to differentiate into hair cells. In contrast, if the stem/progenitor supporting cells were merely induced to proliferate (without maintaining multipotency), the daughter cells would lack the capacity to divide into hair cells. Further, merely enforcing differentiation of a pre-existing stem/progenitor cell population has the potential to exhaust the stem cell pool. Accordingly, the present disclosure provides a method in which pre-existing cochlear supporting cells are induced to proliferate prior to differentiation and the expanded population is then permitted (or even induced in some embodiments) to differentiate into hair cells. Preferably, proliferation is induced by activating the Wnt pathway upstream of the c-myc gene in members of the population and without any genetic modification of the population. Instead, proliferation is preferably activated by small molecules that transiently induce such activity. Additionally, in certain embodiments the supporting cell population preferably includes supporting cells that are LGR5$^+$ and endogenous to the Organ of Corti.

In certain embodiments, therefore, the present disclosure provides compositions that have the capacity to induce self-renewal of a population of supporting cells. These compositions have the capacity to activate pathways and mechanisms that are known to be involved in inducing stem cell properties, such as those used to create "induced pluripotent stem cells" (combined Wnt stimulation, HDAC inhibition, TGF-beta inhibition, RAR activation, DKK1 suppression). Preferably, the pathways are activated with small molecules. For example, a preferred composition when applied in vitro to a supporting cell population induces the population to proliferate to a high degree and in high purity in a Stem Cell Proliferation Assay, and also allows the population to differentiate into a high purity population of hair cells in a Stem Cell Differentiation Assay. In one such embodiment, the composition induces and maintains stem cell properties by proliferating to produce stem cell that can divide for many generations and maintain the ability to have a high proportion of the resulting cells differentiate into hair cells. Further, the proliferating stem cells express stem cell markers which may include one or more of Lgr5, Sox2, Opem1, Phex, lin28, Lgr6, cyclin D1, Msx1, Myb, Kit, Gdnf3, Zic3, Dppa3, Dppa4, Dppa5, Nanog, Esrrb, Rex1, Dnmt3a, Dnmt3b, Dnmt31, Utf1, Tcl1, Oct4, Klf4, Pax6, Six2, Zic1, Zic2, Otx2, Bmi1, CDX2, STAT3, Smad1, Smad2, smad2/3, smad4, smad5, and smad7.

In certain embodiments, the disclosure provides a method for expanding a population of cochlear cells in a cochlear tissue comprising a parent population of cells. In this embodiment, the method comprises contacting the cochlear tissue with a stem cell proliferator to form an expanded population of cells in the cochlear tissue, wherein the stem cell proliferator is capable of (i) forming a proliferation assay final cell population from a proliferation assay initial cell population over a proliferation assay time period in a stem cell proliferation assay and (ii) forming a differentiation assay final cell population from a differentiation assay initial cell population over a differentiation assay time period in a stem cell differentiation assay wherein:

(a) the proliferation assay initial cell population has (i) a proliferation assay initial number of total cells, (ii) a proliferation assay initial number of Lgr5$^+$ cells, (iii) a proliferation assay initial number of hair cells, (iv) a proliferation assay initial Lgr5$^+$ cell fraction that equals the ratio of the proliferation assay initial number of Lgr5$^+$ cells to the proliferation assay initial number of total cells, and (v) a proliferation assay initial hair cell fraction that equals the ratio of the proliferation assay initial number of hair cells to the proliferation assay initial number of total cells;

(b) the proliferation assay final cell population has (i) a proliferation assay final number of total cells, (ii) a proliferation assay final number of Lgr5$^+$ cells, (iii) a proliferation assay final number of hair cells, (iv) a proliferation assay final Lgr5$^+$ cell fraction that equals the ratio of the proliferation assay final number of Lgr5$^+$ cells to the proliferation assay final number of total cells and (v) a proliferation assay final hair cell fraction that equals the ratio of the proliferation assay final number of hair cells to the proliferation assay final number of total cells;

(c) the differentiation assay initial cell population has (i) a differentiation assay initial number of total cells, (ii) a differentiation assay initial number of Lgr5$^+$ cells, (iii) a differentiation assay initial number of hair cells, (iv) a differentiation assay initial Lgr5 cell fraction that equals the ratio of the differentiation assay initial number of Lgr5$^+$ cells to the differentiation assay initial number of total cells, and (v) a differentiation assay initial hair cell fraction that equals the ratio of the differentiation assay initial number of hair cells to the differentiation assay initial number of total cells;

(d) the differentiation assay final cell population has (i) a differentiation assay final number of total cells, (ii) a differentiation assay final number of Lgr5$^+$ cells, (iii) a differentiation assay final number of hair cells, (iv) a differentiation assay final Lgr5$^+$ cell fraction that equals the ratio of the differentiation assay final number of Lgr5$^+$ cells to the differentiation assay final number of total cells, and (v) a differentiation assay final hair cell fraction that equals the ratio of the differentiation assay final number of hair cells to the differentiation assay final number of total cells;

(e) the proliferation assay final number of Lgr5$^+$ cells exceeds the proliferation assay initial number of Lgr5$^+$ cells by a factor of at least 10; and (f) the differentiation assay final number of hair cells is a non-zero number.

In certain embodiments, the stem cell proliferator comprises Stemness Driver. In certain embodiments, the stem cell proliferator comprises a Differentiation Inhibitor. In certain embodiments, the stem cell proliferator comprises a Stemness Driver and a Differentiation Inhibitor.

In certain embodiments, the disclosure provides a method for increasing the cell density of supporting cells in a population of cochlear cells. The method comprises activating pathways and mechanisms that induce stem cell properties in the supporting cells, proliferating the activated supporting cells (while maintaining the multi-potent character of the supporting cells in the newly formed daughter cells) and thereafter allowing (or even inducing) the expanded population to differentiate into hair cells to form an expanded cochlear cell population wherein the cell density of hair cells in the expanded cochlear cell population exceeds the cell density of hair cells in the original (non-expanded) cochlear cell population. In some embodiments, the supporting cell population is an in vitro supporting cell population. In other embodiments, the supporting cell population is an in vivo supporting cell population. Additionally, the proliferation stage is preferably controlled to substantially maintain the native organization of the cochlear structure. Preferably, proliferation is induced by small molecules that transiently induce such activity rather than by induction of c-myc and without any genetic modification of the population. Additionally, in certain embodiments the supporting cell population preferably includes supporting cells that are LGR5' and endogenous to the Organ of Corti.

In certain embodiments, the disclosure provides a method for increasing the cell density of Lgr5$^+$ supporting cells in a population of cochlear cells. The method comprises activating pathways and mechanisms that induce or maintain stem cell properties in the Lgr5+ supporting cells, proliferating the activated Lgr5$^+$ supporting cells (while maintaining such stem cell properties) and thereafter allowing (or even inducing) the expanded population to differentiate into hair cells to form an expanded cochlear cell population wherein the cell density of hair cells in the expanded cochlear cell population exceeds the cell density of hair cells in the original (non-expanded) cochlear cell population. In some embodiments, the Lgr5$^+$ supporting cell population is an in vitro Lgr5$^+$ stem cell population. In other embodiments, the Lgr5+ supporting cell population is an in vivo supporting cell population. Additionally, in certain embodiments the proliferation stage is preferably controlled to substantially maintain the native organization of the cochlear structure.

In certain embodiments, a composition containing a Stemness Driver and a Differentiation Inhibitor is administered to a cochlear cell population to induce proliferation of stem cells and to inhibit differentiation of the stem cells until the desired expansion of the stem cell population is achieved. Thereafter, the expanded population is permitted (or optionally even induced) to differentiate into hair cells. Additionally, the proliferation stage is preferably controlled to substantially maintain the native organization of the cochlear structure. In some embodiments, the Stemness Driver and Differentiation inhibitor are small molecules. In some embodiments, the stem cell population is an in vivo stem cell population. In other embodiments, the stem cell population is an in vitro stem cell population. In some embodiments, the stem cell population is an in vivo Lgr5$^+$ stem cell population. In other embodiments, the stem cell population is an in vitro Lgr5$^+$ stem cell population.

In certain embodiments, the disclosure provides a method for increasing the cell density of hair cells in an initial population of cochlear cells, the initial population (which may be an in vivo or an in vitro population) comprises hair cells, Lgr$^-$ supporting cells, and Lgr5$^+$ supporting cells. The method comprises administering to the initial population a composition that contains a Stemness Driver and a Differentiation Inhibitor wherein the composition has the capacity to induce the expansion of the number of Lgr5$^+$ supporting cells in the population in a Stem Cell Proliferation Assay, and allows Lgr5$^+$ supporting cells within the population to differentiate into a population of hair cells in a Stem Cell Differentiation Assay.

In certain embodiments, the method produces stem cells in a Stem Cell Proliferation Assay that express stem cells markers Lgr5$^+$. In certain embodiments, if a mixed population of Lgr5$^+$ and non-Lgr5$^+$ stems are placed in a Stem Cell Proliferation Assay, the method increases the fraction of cells in the population that are Lgr5$^+$.

Expanding supporting cell populations to a degree that destroys the native organization of the cochlear structure could inhibit cochlear function. Driving proliferation of existing supporting cells with a small molecule signal may allow for a more controlled regeneration of hair cells than using gene delivery, which is incapable of targeting a specific cell type and permanently alters a cell's genetic information. An approximately normal cochlear structure is desired with rows of hair cells that have supporting cells between them, and hair cells do not contact other hair cells. Further, it would be desirable to avoid using genetic modification to drive proliferation to create large cell aggregations in the cochlea that disrupt the organ's anatomy. In certain embodiments, it may be preferable to use a composition that is non-oncogenic. In certain embodiments, it may be preferable to use a composition that proliferates stem cells independent of the operation of the c-myc pathway, for instance in a mechanism which is effective in a c-myc knock-out or where c-myc is inhibited or silenced.

In certain embodiments, the disclosure provides a composition comprising a Stemness Driver that may be used to drive the selective expansion of cochlea supporting cells. In some cases, a Stemness Driver may also induce differentiation of the supporting cells to hair cells if a Differentiation Inhibitor is not present at an Effective Differentiation Inhibition Concentration. Examples of Stemness Drivers that may drive both proliferation and differentiation include GSK3Beta inhibitors and Wnt agonists. In certain embodiments, the proliferation of the stem cells may be enhanced by adding a modulator of cell cycle regulators, such as the p27 or TgfBeta pathways. In certain of these embodiments, the composition comprises the Stemness Driver and Differentiation Inhibitor in a formulation that releases the Stemness Driver and Differentiation inhibitor at different rates in a Release Assay. Thus, for example, in one such embodiment the formulation may provide a constant, sustained, extended, delayed or pulsatile rate of release of the an active agent into the inner ear environment and thus avoid any variability in drug exposure.

In some embodiments, a Stemness Driver may be used to drive the proliferation of Lgr5$^+$ stem cells. In some cases, a Stemness Driver may also induce differentiation of LGR5+ cells to hair cells if a Differentiation Inhibitor is not present at an Effective Differentiation Inhibition Concentration. Examples of Stemness Drivers that may drive both proliferation and differentiation include GSK3Beta inhibitors and Wnt agonists. In certain of these embodiments, the composition comprises the Stemness Driver and a Differentiation Inhibitor in a formulation that releases the Stemness Driver and Differentiation Inhibitor at different rates in a Release Assay. Thus, for example, in one such embodiment the formulation may provide a constant, sustained, extended, delayed or pulsatile rate of release of the an active agent into the inner ear environment and thus avoid any variability in drug exposure.

In certain embodiments, the disclosure provides a method for increasing the cell density of hair cells in an initial population of cochlear cells comprising hair cells and supporting cells. The method comprises selectively expanding the number of supporting cells in the initial population to form an intermediate cochlear cell population wherein the ratio of the number of supporting cells to hair cells in the intermediate cochlear cell population exceeds the ratio of the number of supporting cells to hair cells in the initial cochlear cell population. The method further comprises generating hair cells in the intermediate cochlear cell population to form an expanded cochlear cell population wherein the ratio of the number of hair cells to supporting cells in the expanded cochlear cell population exceeds the ratio of the number of hair cells to supporting cells in the intermediate cochlear cell population.

In certain embodiments, the disclosure provides a method for increasing the number of Lgr5$^+$ supporting cells or increasing the Lgr5$^+$ activity in an initial population of cochlear cells, wherein the initial population comprises supporting cells and hair cells. For example, in one such method an intermediate population is formed in which the number of Lgr5$^+$ supporting cells is expanded relative to the initial population. Alternatively, in one such method an intermediate population is formed in which the Lgr5 activity of the supporting cells relative to the initial population is increased. Alternatively, a method where the number of Lgr5$^+$ cells is increased relative to the initial cell population by activating Lgr5$^+$ expression in cell types that normally lack or have very low levels of Lgr5. By way of further example, an intermediate population is formed in which the number of Lgr5$^+$ supporting cells is expanded and the Lgr5$^+$ activity is increased relative to the initial cochlear cell population. Thereafter, hair cells in the intermediate cochlear cell population may be generated to form an expanded cochlear cell population wherein the ratio of hair cells to supporting cells in the expanded cochlear cell population exceeds the ratio of the number of hair cells to supporting cells in the intermediate cochlear cell population.

In some embodiments, the method applied to an adult mammal produces a population of adult mammalian Lgr5+ cells that are in S-phase.

In each of the aforementioned embodiments of the present disclosure, the Differentiation Inhibitor may be a Notch agonist or HDAC inhibitor. In some such embodiments, there may be a first Proliferation Period with an Effective Stemness Driver Concentration and an Effective Differentiation Inhibition Concentration of a Differentiation Inhibitor, followed by a Differentiation Period with an Effective Stemness Driver Concentration and without an Effective Differentiation Inhibition Concentration of a Differentiation Inhibitor. In each of these embodiments, the Stemness Driver and Differentiation Inhibitor are provided to the cochlear cells in a formulation that releases the Stemness Driver and Differentiation inhibitor at different rates. For example, the formulation may provide a constant, sustained, extended, delayed or pulsatile rate of release of the Stemness Driver and the Differentiation Inhibitor into the inner ear environment. Significantly, however, the formulation releases the Stemness Driver and Differentiation Inhibitor in a manner to provide a first Proliferation Period with an Effective Stemness Driver Concentration and an Effective Differentiation Inhibition Concentration of the Differentiation Inhibitor, followed by a Differentiation Period with an Effective Stemness Driver Concentration and without an Effective Differentiation Inhibition Concentration of the Differentiation Inhibitor.

In certain embodiments, the method further comprises performing high throughput screening on inner ear progenitor/stem cells to identify Stemness Drivers and/or Differentiation Inhibitors, as used in a Stem Cell Proliferation Assay or Stem Cell Differentiation Assay.

In each of the aforementioned embodiments of the present disclosure, there may be a first Proliferation Period with an Effective Stemness Driver Concentration of a Wnt agonist or GSK3Beta inhibitor and an Effective Differentiation Inhibition Concentration of a Notch agonist or HDAC inhibitor, followed by a Differentiation Period with an Effective Stemness Driver Concentration of a Wnt agonist or GSK3Beta inhibitor and without an Effective Differentiation Inhibition Concentration of a Notch agonist or HDAC inhibitor. In each of these embodiments, therefore, the formulation may provide a constant, sustained, extended, delayed or pulsatile rate of release of the Wnt agonist or GSK3Beta inhibitor and the Notch agonist or HDAC inhibitor into the inner ear environment. Significantly, however, the formulation releases the Wnt agonist or GSK3Beta inhibitor and the Notch agonist or HDAC inhibitor in a manner to provide a first Proliferation Period with an Effective Stemness Driver Concentration of the Wnt agonist or GSK3Beta inhibitor and an Effective Differentiation Inhibition Concentration of the Notch agonist or HDAC inhibitor, followed by a Differentiation Period with an Effective Stemness Driver Concentration of the Wnt agonist or GSK3Beta inhibitor and without an Effective Differentiation Inhibition Concentration of the Notch agonist or HDAC inhibitor.

In some embodiments, the Differentiation inhibitor is also a Stemness Driver. In some embodiments, the Differentiation inhibitor is a Notch agonist and is also a Stemness Driver. In some embodiments, the Differentiation inhibitor is Valproic Acid, which may be a Stemness Driver. If a Differentiation Inhibitor is also a Stemness Driver, the concentration of the Differentiation Inhibitor should fall below the Effective Differentiation Inhibition Concentration during the Differentiation Period.

In each of the aforementioned embodiments, the Differentiation inhibitor and Stemness Driver may be contained within a sustained release polymer gel. In certain embodiments, the gel may be injected through a needle but becomes solid in the middle ear space. In certain embodiments, the gel is comprised of a thermoreversible polymer such as Poloxamer 407.

The Notch pathway is known to be a key regulator of the differentiation process from supporting cells to hair cells (Lanford et al. 1999). In some embodiments, a Stemness Driver and Differentiation Inhibitor are applied such that the Notch activity level in supporting cells remains at 10, 20, 30, 40, 50, 60, 70, 80, 90, or 100% of the Notch activity level in supporting cells in the native state.

In certain embodiments, the disclosure provides a method of and compositions for generating hair cells, the method comprising: administering or causing to be administered to a stem cell population (e.g., of an in vitro, ex vivo, or in vivo sample/subject) a composition comprising both of (i) and (ii): (i) a GSK3-beta inhibitor (or a derivative or pharmaceutically acceptable salt thereof) and/or Wnt agonist (or a derivative or pharmaceutically acceptable salt thereof), and (ii) a Notch agonist (or a derivative or pharmaceutically acceptable salt thereof) and/or HDAC inhibitor (or a derivative or pharmaceutically acceptable salt thereof), thereby proliferating stem cells in the stem cell population and resulting in an expanded population of stem cells; and exposing the expanded population of stem cells to a GSK3-beta inhibitor (or a derivative or pharmaceutically acceptable salt thereof) and/or a Wnt agonist (or a derivative or pharmaceutically acceptable salt thereof), and, optionally, a notch inhibitor (or a derivative or pharmaceutically acceptable salt thereof), thereby facilitating generation of inner ear hair cells from the expanded population of stem cells.

In certain embodiments, the disclosure provides compositions, systems, and methods for preventing and treating auditory dysfunction. For example, in certain embodiments, the disclosure provides methods for preventing or treating auditory impairments in a subject comprising administering to said subject an effective amount of a composition comprising (a) (i) an HDAC inhibitor and/or Notch activator and (ii) a GSK3-beta inhibitor, a derivative thereof, e.g., a derivative of an HDAC inhibitor, a derivative of a Notch activator, and/or a derivative of a GSK3-beta inhibitor, a pharmaceutically acceptable salt thereof, [e.g., a pharmaceutically acceptable salt of an HDAC inhibitor, a pharmaceutically acceptable salt of a Notch activator, and/or a pharmaceutically acceptable salt of a GSK3-beta inhibitor, or a combination thereof and (b) a pharmaceutically acceptable carrier or excipient, so as to treat auditory impairments in the subject. Thus, for example, the composition may comprise (a) an HDAC inhibitor (or a derivative or pharmaceutically acceptable salt thereof) and a GSK3-beta inhibitor (or a derivative or pharmaceutically acceptable salt thereof), and (b) a pharmaceutically acceptable carrier or excipient. By way of further example, the composition may comprise (a) a Notch activator (or a derivative or pharmaceutically acceptable salt thereof) and a GSK3-beta inhibitor (or a derivative or pharmaceutically acceptable salt thereof), and (b) a pharmaceutically acceptable carrier or excipient. By way of further example, the composition may comprise (a) an HDAC inhibitor (or a derivative or pharmaceutically acceptable salt thereof), a Notch activator (or a derivative or pharmaceutically acceptable salt thereof), and a GSK3-beta inhibitor (or a derivative or pharmaceutically acceptable salt thereof), and (b) a pharmaceutically acceptable carrier or excipient.

In certain embodiments, the present disclosure also relates to ex-vivo uses of cells described herein. For example, approaches described herein can be used for hi and for discovery purposes. For example, certain embodiments of the present disclosure are useful for identifying agents that proliferate hair cell progenitors and/or increase numbers of hair cells, and also agents that protect supporting cells and/or hair cells (e.g. to support their survival), and also for identifying agents that are toxic or not toxic to supporting cells or differentiated progeny including hair cells.

In certain embodiments, the disclosure provides methods for preventing or treating auditory impairments in a subject in need of treatment comprising administering to said subject an effective amount of a composition comprising, an HDAC inhibitor and/or Notch activator and a GSK3beta inhibitor or derivative thereof or pharmaceutically acceptable salt thereof and an acceptable carrier or excipient, so as to treat auditory impairments in the subject.

In certain embodiments, the disclosure provides for methods for inhibiting the loss or death of the cells of the auditory system in a subject comprising administering to said subject an effective amount of a composition described herein or derivative thereof or pharmaceutically acceptable salt thereof and an acceptable carrier or excipient, thereby inhibiting loss or death of the cells of the auditory system in the subject.

In certain embodiments, the disclosure provides methods for maintaining or promoting the growth of cells of the auditory system in a subject comprising administering to said subject a composition comprising as an agent described herein or derivative thereof or pharmaceutically acceptable salt thereof and an acceptable carrier or excipient in an effective amount so as to augment or initiate endogenous repair, thereby maintaining or promoting the growth of cells of the auditory system in the subject.

The methods and compositions of the present disclosure allow greater and thus more effective dosing with these ototoxicity-inducing pharmaceutical drugs, while concomitantly preventing or reducing ototoxic effects caused by these drugs. The methods of the present disclosure provide a safe, effective, and prolonged means for prophylactic or curative treatment of hearing impairments related to inner ear tissue damage, loss, or degeneration, particularly sound or aging-induced, and ototoxin-induced, and particularly involving inner ear hair cells. In certain embodiments, the present disclosure provides compositions and methods that address one or more of these or other goals.

This disclosure generally relates to compositions, systems, and methods for inducing, promoting, or enhancing the growth, proliferation, or regeneration of inner ear tissue, for example, inner ear supporting cells and/or inner ear hair cells.

Also described herein is a method for expanding a population of cochlear cells in a cochlear tissue comprising a parent population of cells, the parent population including supporting cells and a number of $Lgr5^+$ cells, the method comprising contacting the cochlear tissue with a stem cell proliferator to form an expanded population of cells in the cochlear tissue, wherein the stem cell proliferator is capable (i) in a stem cell proliferation assay of increasing the number of $Lgr5^+$ cells in a stem cell proliferation assay cell population by a factor of at least 10 and (ii) in a stem cell differentiation assay of forming hair cells from a cell population comprising $Lgr5^+$ cells.

Also described herein is a method for expanding a population of cochlear cells in a cochlear tissue comprising a parent population of cells, the parent population including supporting cells, the method comprising contacting the cochlear tissue with a stem cell proliferator to form an expanded population of cells in the cochlear tissue. The stem cell proliferator can be capable of (i) forming a proliferation assay final cell population from a proliferation assay initial cell population over a proliferation assay time period in a stem cell proliferation assay and (ii) forming a differentiation assay final cell population from a differentiation assay initial cell population over a differentiation assay time period in a stem cell differentiation assay wherein: (a) the proliferation assay initial cell population has (i) a proliferation assay initial number of total cells, (ii) a proliferation assay initial number of $Lgr5^+$ cells, (iii) a proliferation assay initial number of hair cells, (iv) a proliferation assay initial $Lgr5^+$ cell fraction that equals the ratio of the proliferation assay initial number of $Lgr5^+$ cells to the proliferation assay initial number of total cells, and (v) a proliferation assay initial hair cell fraction that equals the ratio of the proliferation assay initial number of hair cells to the proliferation assay initial number of total cells; (b) the proliferation assay final cell population has (i) a proliferation assay final number of total cells, (ii) a proliferation assay final number of $Lgr5^+$ cells, (iii) a proliferation assay final number of hair cells, (iv) a proliferation assay final $Lgr5^+$ cell fraction that equals the ratio of the proliferation assay final number of $Lgr5^+$ cells to the proliferation assay final number of total cells and (v) a proliferation assay final hair cell fraction that equals the ratio of the proliferation assay final number of hair cells to the proliferation assay final number of total cells; (c) the differentiation assay initial cell population has (i) a differentiation assay initial number of total cells, (ii) a differentiation assay initial number of $Lgr5^+$ cells, (iii) a differentiation assay initial number of hair cells, (iv) a differentiation assay initial $Lgr5^+$ cell fraction that equals the ratio of the differentiation assay initial number of $Lgr5^+$ cells to the differentiation assay initial number of total cells, and (v) a differentiation assay initial hair cell fraction that equals the ratio of the differentiation assay initial number of hair cells to the differentiation assay initial number of total cells; (d) the differentiation assay final cell population has (i) a differentiation assay final number of total cells, (ii) a differentiation assay final number of $Lgr5^+$ cells, (iii) a differentiation assay final number of hair cells, (iv) a differentiation assay final $Lgr5^+$ cell fraction that equals the ratio of the differentiation assay final number of $Lgr5^+$ cells to the differentiation assay final number of total cells, and (v) a differentiation assay final hair cell fraction that equals the ratio of the differentiation assay final number of hair cells to the differentiation assay final number of total cells; (e) the proliferation assay final number of $Lgr5^+$ cells exceeds the proliferation assay initial number of $Lgr5^+$ cells by a factor of at least 10; and (f) the differentiation assay final number of hair cells is a non-zero number.

The proliferation assay final number of $Lgr5^+$ cells can be greater than the proliferation assay initial number of $Lgr5^+$ cells by a factor of at least 50, or by a factor of at least 100. The expanded population of cells in the cochlear tissue can include a greater number of hair cells than does the parent population. The proliferation assay final $Lgr5^+$ cell fraction can be greater than the differentiation assay initial $Lgr5^+$ cell fraction by at least a factor of 2. The differentiation assay final hair cell fraction can be greater than the proliferation assay initial hair cell fraction by at least a factor of 2. The proliferation assay final hair cell fraction can be at least 25% less than the proliferation assay initial hair cell fraction. The proliferation assay final Lgr5$^+$ cell fraction can be at least 10% greater than proliferation assay initial Lgr5$^+$ cell fraction. One of more morphological characteristics of the cochlear tissue can be maintained. Native morphology can be maintained. The at least one stem cell proliferator can be dispersed in a biocompatible matrix, which can be a biocompatible gel or foam. The composition can be a controlled release formulation. The cochlear tissue can be an in vivo cochlear tissue or an ex vivo cochlear tissue. The method can produce a population of Lgr5$^+$ cells that are in s-phase. The at least one stem cell proliferator can include both a stemness driver and a differentiation inhibitor. Contacting can provide to the cochlear tissue: in an initial phase, at least an effective proliferation concentration of the stemness driver and at least an effective differentiation inhibition concentration of the differentiation inhibitor; and in a subsequent phase, at least an effective proliferation concentration of the stemness driver and less than an effective differentiation inhibition concentration of the differentiation inhibitor. The cochlear tissue can be in a subject, and contacting the cochlear tissue with the composition can be achieved by administering the composition trans-tympanically to the subject. Contacting the cochlear tissue with the composition can result in improved auditory functioning of the subject.

Also described herein is a composition that includes a biocompatible matrix and at least one stem cell proliferator, wherein the at least one stem cell proliferator is capable, in a stem cell proliferation assay, of expanding an initial test population of Lgr5$^+$ cells to create an expanded test population, and wherein the expanded test population has at least 10-fold more Lgr5$^+$ cells than does the initial test population.

Also described herein is a composition that includes a biocompatible matrix and at least one stem cell proliferator, wherein the at least one stem cell proliferator is capable, in a stem cell proliferation assay, of expanding an initial cell population containing Lgr5$^+$ cells to create a final cell population, and wherein the final cell population has at least 10-fold more Lgr5$^+$ cells than does the initial cell population. Additionally, (a) the initial cell population has (i) an initial number of total cells, (ii) an initial number of Lgr5$^+$ cells, (iii) an initial number of hair cells, (iv) an initial Lgr5$^+$ cell fraction that equals the ratio of the proliferation assay initial number of Lgr5$^+$ cells to the proliferation assay initial number of total cells, and (v) an initial hair cell fraction that equals the ratio of the initial number of hair cells to initial number of total cells; and (b) the final cell population has (i) a final number of total cells, (ii) a final number of Lgr5 cells, (iii) a final number of hair cells, (iv) a final Lgr5$^+$ cell fraction that equals the ratio of the final number of Lgr5$^+$ cells to the final number of total cells and (v) a final hair cell fraction that equals the ratio of the final number of hair cells to the final number of total cells.

The final number of Lgr5$^+$ cells can be greater than the initial number of Lgr5$^+$ cells by a factor of at least 50, or by a factor of at least 100.

The at least one stem cell proliferator can be dispersed in a biocompatible matrix, which can be a biocompatible gel or foam. The proliferation assay final Lgr5$^+$ cell fraction can be at least 10% greater than the proliferation assay initial Lgr5$^+$ cell fraction. The at least one stem cell proliferator can include at least one of a stemness driver and a differentiation inhibitor. The at least one stem cell proliferator can include both a stemness driver and a differentiation inhibitor. The stem cell proliferator can include a stemness driver in a concentration that is 100-fold greater than an effective proliferation concentration of the stemness driver and a differentiation inhibitor in a concentration that is at least 100-fold greater than an effective differentiation inhibition concentration of the differentiation inhibitor. The composition can be a controlled release formulation. The controlled release formulation when administered to a subject trans-tympanically imparts an immediate release, a delayed release, a sustained release, an extended release, a variable release, a pulsatile release, or a bi-modal release of the stem cell proliferator. The controlled release formulation when administered to a subject can provide: (a) in an initial phase, at least an effective proliferation concentration of the stemness driver and at least an effective differentiation inhibition concentration of the differentiation inhibitor; and (b) in a subsequent phase, at least an effective proliferation concentration of the stemness driver and less than an effective differentiation inhibition concentration of the differentiation inhibitor.

In the methods and compositions, the stemness driver can be a gsk3-beta inhibitor, a gsk3-beta inhibitor derivative, a wnt agonist, a wnt agonist derivative, or a pharmaceutically acceptable salt of any of the foregoing. In the method and composition, the differentiation inhibitor can be a notch agonist; a notch agonist derivative; an hdac inhibitor; an hdac inhibitor derivative, or a pharmaceutically acceptable salt of any of the foregoing. In methods and compositions, the stemness driver can be selected from the group consisting of CHIR99021, LY2090314, lithium, A1070722, BML-284 and SKL2001.

In the methods and compositions, the differentiation inhibitor can be a Notch agonist or an HDAC inhibitor selected from the group consisting of valproic acid, SAHA and Tubastatin A Also dscribed herein is a method of treating a subject who has, or is at risk of developing, hearing loss. The method can include trans-tympanically administering to a cochlear tissue of the subject a composition comprising at least one stem cell proliferator. The at least one stem cell proliferator can include at least one of a stemness driver and a differentiation inhibitor. The at least one stem cell proliferator can include both a stemness driver and a differentiation inhibitor.

The stemness driver can be CHIR99021. The differentiation inhibitor can be valproic acid. In some methods, the cochlear tissue can be further contacted with epidermal growth factor, basic fibroblast growth factor, insulin-like growth factor 1, pVc, and 616452.

Also described herein is a method of generating Myo7a+ cochlear cells. The method can include contacting Lgr5+ cochlear cells with a composition comprising a stemness driver and a differentiation inhibitor, thereby generating an expanded population of Lgr5+ cells; and contacting the expanded population of Lgr5+ cells with a notch inhibitor and a stemness driver, thereby generating Myo7a+ cochlear cells. The stemness driver can be CHIR99021. The Differentiation Inhibitor can valproic acid. The notch inhibitor can be DAPT.

In some aspects, the invention includes compounds comprising one or more of the compounds described herein, such as a stem cell proliferator. In some aspects, the invention encompasses a kit, e.g., a kit comprising a kinase inhibitor. In some aspects, the kit includes instructions.

Other objects and features will be in part apparent and in part pointed out hereinafter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1A: Brightfield and GFP fluorescence images of Lgr5-GFP inner ear progenitor cells cultured for 10 days in media containing EGF, bFGF and IGF-1. FIG. 1B: Lgr5-GFP cells were cultured in conditions with the addition of CHIR and VPA. Scale bars 100 µm.

FIG. 2A: FACS histogram images of Lgr5-GFP cells under multiple conditions. FIG. 2B: Quantification of cell proliferation and GFP expression of cells as shown in FIG. 2A. FIG. 2C: Corresponding quantification of cells.

FIG. 5A: Cell number. FIG. 5B: GFP+ percentage.

FIG. 8A shows GFP fluorescence and bright-field images of single inner ear epithelial cells for 10 days in the presence of EGF, bFGF, IGF1 (EFI); EFI and CHIR99021, VPA, pVc, 616452 (EFICVP6). FIG. 8B shows quantification of Lgr5-GFP expression, cell proliferation (number of live cells), and number of GFP+ cells in inner ear epithelial cells cultured for 10 days in multiple conditions. Cell colonies were dissociated into single cells using trypsin. Total number of cells were counted using a hemocytometer. The cells were then stained with propidium iodide (PI) and analyzed using a flow cytometer for Lgr5-GFP expression. Number of GFP+ cells were calculated by multiplying the total number of cells with percentage of GFP+ cells. EFICVP6 indicates culture conditions containing all the factors including EGF, bFGF, IGF1, CHIR, VPA, pVc, and 616452, which showed the best results in supporting cell proliferation and GFP expression. Each individual factor was then removed from the culture media and tested. Removing bFGF or CHIR from the media greatly impacted cell proliferation and removing CHIR also greatly impacted GFP expression. Removing EGF, 616452 showed greater impact on cell proliferation, while removing VPA or pVc showed greater impact on GFP maintenance. Removing IGF-1 showed marginal effect on cell proliferation or GFP maintenance. These results suggest bFGF and CHIR are important, and other factors are also important, in promoting cell proliferation and GFP expression. FIG. 8C shows GFP fluorescence and brightfield images of cultures as shown in (b). Scale bars: 200 m (a) and 400 µm (c).

FIG. 9A shows GFP expression of cultured inner ear epithelial cells in multiple conditions. W: Wnt3a. R: R-Spondin 1. FIG. 9B_shows histogram images of GFP expression of cells cultured in multiple conditions. FIG. 9C shows GFP fluorescence and brightfield images of Lgr5-GFP inner ear epithelial cells culture for 7 days in conditions as indicated. FIG. 9D shows GFP fluorescence and brightfield images of Atoh1-GFP inner ear epithelial cells 7 days in culture conditions as indicated. GFP+ cells were differentiated cells. Results show VPA inhibited the differentiation of inner ear progenitor cells towards Atoh1 positive hair cells. FIG. 9E shows a screen for supportive factors for inner ear progenitor cells. Shown are GFP expression of Lgr5-GFP inner ear progenitor cells cultured in multiple conditions. Small molecules were added based on control (EFICV) condition. Laminin 511 was added into Matrigel. Two batches of cells were used for screening as shown as Exp 1 and Exp 2. Results show pVc promoted GFP expression from Lgr5-GFP inner ear progenitor cells. FIG. 9F shows fluorescence and brightfield images of Lgr5-GFP cells cultured in conditions as indicated. Shown are cells at day 10 of passage 2. 616452 enables the passage of cultured inner ear progenitor cells. Scale bars: 400 µm.

FIG. 12A shows that the combination with Gsk3β inhibitor (e.g. CHIR) and Notch inhibitor (e.g. DAPT) induce the generation of Myo7a positive and Prestin positive outer hair cells (upper panel) and Myo7a positive and Prestin negative inner hair cells (lower panel). FIG. 12B shows that in the presence of Wnt inhibitor IWP-2, hair cell generation is rarely observed from cultured inner ear progenitor cells. Scale bars: 100 µm.

FIG. 13A: Isolated cochlear from 9-week old mice was cultured in the presence of EFICVP6 for 9 days. Showing out-growth of Lgr5-GFP cells. FIG. 13B: The same culture at day 13. Showing expansion of Lgr5-GFP cells. FIG. 13C: Passage 2 of the same culture at day 5 after passage (Day 19). All scale bars: 100 μm. Specifically, cochlear was isolated from 9-week old adult mice, directly mixed with Matrigel and plated at the center of well of a 24-well plate. Cell culture medium in the presence of EGF, bFGF, IGF-1, CHIR99021, VPA, L-Ascorbic acid 2-phosphate (pVc) and a TGF-β RI Kinase Inhibitor II (616452) was added following gelation of Matrigel. The tissue was cultured for 2 weeks until Lgr5-GFP cells expanded and form out-growth. After 2 weeks (Day 14) the tissue was then dissociated using trypsin, re-plated and further cultured. Results comparing Day 9 to Day 13 show that our culture system can be used to support the growth and expansion of adult Lgr5-GFP cells from inner ear epithelium. The results also show that using these culture conditions Lgr5$^+$ cells from adult cochlea can be passaged (FIG. 13C).

Corresponding reference characters indicate corresponding parts throughout the drawings.

Definitions

Figure 1A:
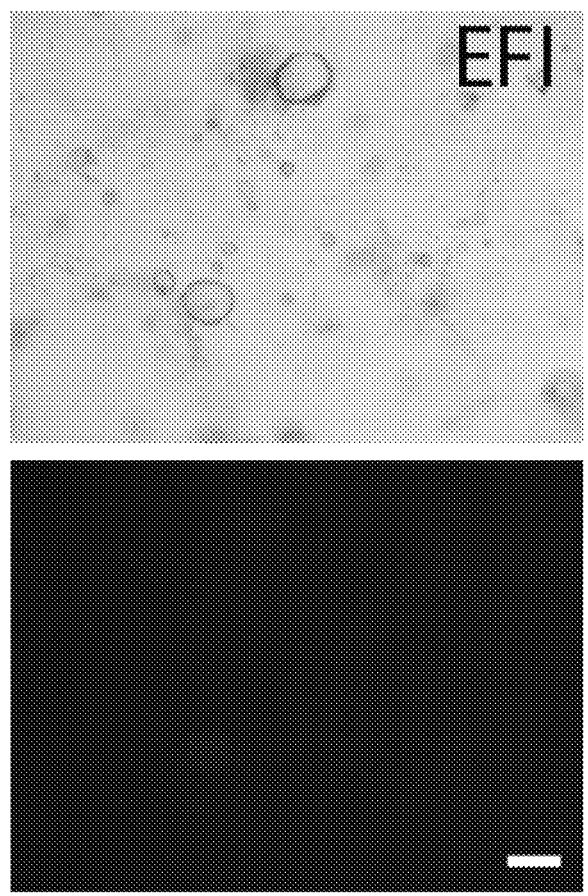
FIGS. 1A-B: Expansion of Lgr5-GFP inner ear supporting cells in multiple conditions.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11% 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration" refers to introducing a substance into a subject. In some embodiments, administration is auricular, intraauricular, intracochlear, Intravestibular, or transtympanically, e.g., by injection. In some embodiments, administration is directly to the inner ear, e.g. injection through the round window, otic capsule, or vestibular canals. In some embodiments, administration is directly into the inner ear via a cochlear implant delivery system. In some embodiments, the substance is injected transtympanically to the middle ear. In certain embodiments "causing to be administered" refers to administration of a second component after a first component has already been administered (e.g., at a different time and/or by a different actor).

An "antibody" refers to an immunoglobulin polypeptide, or fragment thereof, having immunogen binding ability.

As used herein, an "agonist" is an agent that causes an increase in the expression or activity of a target gene, protein, or a pathway, respectively. Therefore, an agonist can bind to and activate its cognate receptor in some fashion, which directly or indirectly brings about this physiological effect on the target gene or protein. An agonist can also increase the activity of a pathway through modulating the activity of pathway components, for example, through inhibiting the activity of negative regulators of a pathway. Therefore, a "Wnt agonist" can be defined as an agent that increases the activity of Wnt pathway, which can be measured by increased TCF/LEF-mediated transcription in a cell. Therefore, a "Wnt agonist" can be a true Wnt agonist that bind and activate a Frizzled receptor family member, including any and all of the Wnt family proteins, an inhibitor of intracellular beta-catenin degradation, and activators of TCF/LEF. A "Notch agonist" can be defined as an agent that increase the activity of Notch pathway, which can be determined by measuring the transcriptional activity of Notch.

An "antagonist" refers to an agent that binds to a receptor, and which in turn decreases or eliminates binding by other molecules.

"Anti-sense" refers to a nucleic acid sequence, regardless of length, that is complementary to the coding strand or mRNA of a nucleic acid sequence. Antisense RNA can be introduced to an individual cell, tissue or organanoid. An anti-sense nucleic acid can contain a modified backbone, for example, phosphorothioate, phosphorodithioate, or other modified backbones known in the art, or may contain non-natural internucleoside linkages.

As referred to herein, a "complementary nucleic acid sequence" is a nucleic acid sequence capable of hybridizing with another nucleic acid sequence comprised of complementary nucleotide base pairs. By "hybridize" is meant pair to form a double-stranded molecule between complementary nucleotide bases (e.g., adenine (A) forms a base pair with thymine (T), as does guanine (G) with cytosine (C) in DNA) under suitable conditions of stringency. (See, e.g., Wahl, G. M. and S. L. Berger (1987) Methods Enzymol. 152:399; Kimmel, A. R. (1987) Methods Enzymol. 152:507).

"Auricular administration" refers to a method of using a catheter or wick device to administer a composition across the tympanic membrane to the inner ear of the subject. To facilitate insertion of the wick or catheter, the tympanic membrane may be pierced using a suitably sized syringe or pipette. The devices could also be inserted using any other methods known to those of skill in the art, e.g., surgical implantation of the device. In particular embodiments, the wick or catheter device may be a stand-alone device, meaning that it is inserted into the ear of the subject and then the composition is controllably released to the inner ear. In other particular embodiments, the wick or catheter device may be attached or coupled to a pump or other device that allows for the administration of additional compositions. The pump may be automatically programmed to deliver dosage units or may be controlled by the subject or medical professional.

"Biocompatible Matrix" as used herein is a polymeric carrier that is acceptable for administration to humans for the release of therapeutic agents. A Biocompatible Matrix may be a biocompatible gel or foam.

"Cell Aggregate" as used herein shall mean a body cells in the Organ of Corti that have proliferated to form a cluster of a given cell type that is greater than 40 microns in diameter and/or produced a morphology in which greater than 3 cell layers reside perpendicular to the basilar membrane. A "Cell Aggregate" can also refer a process in which cell division creates a body of cells that cause one or more cell types to breach the reticular lamina, or the boundary between endolymph and perilymph "Cell Density" as used herein in connection with a specific cell type is the mean number of that cell type per area in a Representative Microscopy Sample. The cell types may include but are not limited to Lgr5$^+$ cells, hair cells, or supporting cells. The Cell Density may be assessed with a given cell type in a given organ or tissue, including but not limited to the cochlea or Organ of Corti. For instance, the Lgr5$^+$ Cell Density in the Organ of Corti is the Cell Density of Lgr5$^+$ cells as measured across the Organ of Corti. Typically, supporting cells and Lgr5$^+$ cells will be enumerated by taking cross sections of the Organ of Corti. Typically, hair cells will be enumerated by looking down at the surface of the Organ of Corti, though cross sections may be used in some instances, as described in a Representative Microscopy Sample. Typically, Cell Density of Lgr5$^+$ cells will be measured by analyzing whole mount preparations of the Organ of Corti and counting the number of Lgr5 cells across a given distance along the surface of the epithelia, as described in a Representative Microscopy Sample. Hair cells may be identified by their morphological features such as bundles or hair cell specific stains (e.g., Myosin VIIa, Prestin, vGlut3, Pou4f3, Espin, conjugated-Phalloidin, PMCA2, Ribeye, Atoh1, etc). Lgr5+ cells may be identified by specific stains or antibodies (e.g. Lgr5-GFP transgenic reporter, anti-Lgr5 antibody, etc.)

"CHIR99021" is a chemical composition having the chemical formula $C_{22}H_{18}Cl_2N_8$ and the following alternate names: CT 99021; 6-[[2-[[4-(2,4-dichlorophenyl)-5-(5-methyl-1H-imidazol-2-yl)-2-pyrimidinyl]amino]ethyl]amino]-3-pyridinecarbonitrile. Its chemical structure is as follows:

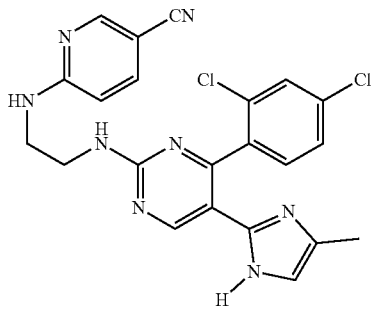 [SMILES: Cc1c[nH]c(-c2cnc(NCCNc3ccc(C#N)cn3)nc2-c2ccc(Cl)cc2Cl)n1]

"Cochlear Concentration" as used herein will be the concentration of a given agent as measured through sampling cochlear fluid. Unless otherwise noted, the sample should contain a substantial enough portion of the cochlear fluid so that it is approximately representative of the average concentration of the agent in the cochlea. For example, samples may be drawn from a vestibular canal, and a series of fluid samples drawn in series such that individual samples are comprised of cochlear fluid in specified portions of the cochlea "Complementary nucleic acid sequence" refers to a nucleic acid sequence capable of hybridizing with another nucleic acid sequence comprised of complementary nucleotide base pairs.

"Cross-Sectional Cell Density" as used herein in connection with a specific cell type is the mean number of that cell type per area of cross section through a tissue in a Representative Microscopy Sample. Cross sections of the Organ of Corti can also be used to determine the number of cells in a given plane. Typically, hair cells Cross-sectional Cell Density will be measured by analyzing whole mount preparations of the Organ of Corti and counting the number of hair cells across a given distance in cross sections taken along a portion of the epithelia, as described in a Representative Microscopy Sample. Typically, Cross-sectional Cell Density of Lgr5$^+$ cells will be measured by analyzing whole mount preparations of the Organ of Corti and counting the number of Lgr5$^+$ cells across a given distance in cross sections taken along a portion of the epithelia, as described in a Representative Microscopy Sample. Hair cells may be identified by their morphological features such as bundles or hair cell specific stains (suitable stains include e.g., Myosin VIIa, Prestin, vGlut3, Pou4f3, conjugated-Phalloidin, PMCA2, Atoh1, etc.). Lgr5$^+$ cells may be identified by specific stains or antibodies (suitable stains and antibodies include fluorescence in situ hybridization of Lgr5 mRNA, Lgr5-GFP transgenic reporter system, anti-Lgr5 antibodies, etc.).

"Decreasing" refers to decreasing by at least 5%, for example, 5, 6, 7, 8, 9, 10, 15, 20, 25, 30, 35, 40, 45, 50, 55, 60, 65, 70, 75, 80, 85, 90, 95, 99 or 100%, for example, as compared to the level of reference.

"Decreases" also means decreases by at least 1-fold, for example, 1, 2, 3, 4, 5, 6, 7, 8, 9, 10, 15, 20, 30, 40, 50, 60, 70, 80, 90, 100, 200, 500, 1000-fold or more, for example, as compared to the level of a reference.

"Differentiation Inhibitor" as used herein is an agent which may inhibit differentiation of an inner ear stem cell into an inner ear hair cell. Some differentiation inhibitors maintain expression of post-natal Stem Cell Markers. Some Differentiation Inhibitors include, without limitation, Notch agonists and HDAC inhibitors.

"Differentiation Period" as used herein is the duration of time in which there is an Effective Stemness Driver Concentration without an Effective Differentiation Inhibition Concentration.

"Effective Concentration" may be the Effective Stemness Driver Concentration for a Stemness Driver or the Effective Diffusion Inhibition Concentration for a Diffusion Inhibitor.

"Effective Differentiation Inhibition Concentration" is the minimum concentration of a Differentiation Inhibitor that does not allow more than a 50% increase in the fraction of the total population of cells that are hair cells at the end of the Stem Cell Proliferation Assay compared to the start of the Stem Cell Proliferation Assay In measuring the Effective Differentiation Inhibition Concentration, a Hair Cell stain for cells may be used with flow cytometry to quantify hair cells for a mouse strain that is not an Atoh1-GFP mouse. Alternatively, and Atoh1-GFP mouse strain may be used.

"Effective Release Rate" (mass/time) as used herein is the Effective Concentration (mass/volume)*30 uL/1 hour.

"Effective Stemness Driver Concentration" is the minimum concentration of a Stemness Driver that induces at least 1.5-fold increase in number of LGR5+ cells in a Stem Cell Proliferation Assay compared to the number of Lgr5+ cells in a Stem Cell Proliferation Assay performed without the Stemness Driver and with all other components present at the same concentrations.

"Eliminate" means to decrease to a level that is undetectable.

"Engraft" or "engraftment" refers to the process of stem or progenitor cell incorporation into a tissue of interest in vivo through contact with existing cells of the tissue. "Epithelial progenitor cell" refers to a multipotent cell which has the potential to become restricted to cell lineages resulting in epithelial cells.

"Epithelial stem cell" refers to a multipotent cell which has the potential to become committed to multiple cell lineages, including cell lineages resulting in epithelial cells.

"Fragment" refers to a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"GSK3beta," "GSK3β," and "GSK3B" as used interchangeably herein are acronyms for glycogen synthase kinase 3 beta, "GSK3beta inhibitor" is a composition that inhibits the activity of GSK3beta.

"HDAC" as used herein is an acronym for histone deacetylase.

"HDAC inhibitor" is a composition that inhibits the activity of HDAC.

"Hybridize" refers to pairing to form a double-stranded molecule between complementary nucleotide bases (e.g., adenine (A) forms a base pair with thymine (T), as does guanine (G) with cytosine (C) in DNA) under suitable conditions of stringency. (See, e.g., Wahl, G. M. and S. L. Berger (1987) Methods Enzymol. 152:399; Kimmel, A. R. (1987) Methods Enzymol. 152:507).

An "inhibitor" refers to an agent that causes a decrease in the expression or activity of a target gene or protein, respectively. An "antagonist" can be an inhibitor, but is more specifically an agent that binds to a receptor, and which in turn decreases or eliminates binding by other molecules.

As used herein, an "inhibitory nucleic acid" is a double-stranded RNA, RNA interference, miRNA, siRNA, shRNA, or antisense RNA, or a portion thereof, or a mimetic thereof, that when administered to a mammalian cell results in a decrease in the expression of a target gene. Typically, a nucleic acid inhibitor comprises at least a portion of a target nucleic acid molecule, or an ortholog thereof, or comprises at least a portion of the complementary strand of a target nucleic acid molecule. Typically, expression of a target gene is reduced by 10%, 25%, 50%, 75%, or even 90-100%.

"In Vitro Lgr5 activity" refers to the level of expression or activity of Lgr5 in an in vitro population of cells. It may be measured, for example, in cells derived from a Lgr5-GFP expressing mouse such as a B6.129P2-Lgr5tm1(cre/ERT2) Cle/J mouse (also known as Lgr5-EGFP-IRES-creERT2 or Lgr5-GFP mouse, Jackson Lab Stock No: 008875) by dissociating cells to single cells, staining with propidium iodide (PI), and analyzing the cells using a flow cytometer for Lgr5-GFP expression. Inner ear epithelial cells from wild-type (non-Lgr5-GFP) mice that passing the same culturing and analyzing procedures can be used as a negative control.

Typically, two population of cells are shown in the bivariate plot with GFP/FITC as one variable, which include both GFP positive and GFP negative populations. Lgr5-positive cells are identified by gating GFP positive cell population. The percentage of Lgr5-positive cells are measured by gating GFP positive cell population against both GFP negative population and the negative control. The number of Lgr5-positive cells is calculated by multiplying the total number of cells by the percentage of Lgr5-positive cells. For cells derived from non-Lgr5-GFP mice, Lgr5 activity can be measured using an anti-Lgr5 antibody or quantitative-PCR on the Lgr5 gene.

"In Vivo Lgr5 activity" as used herein is the level of expression or activity of Lgr5 in a subject. It may be measured, for example, by removing an animal's inner ear and measuring Lgr5 protein or Lgr5 mRNA. Lgr5 protein production can be measured using an anti-Lgr5 antibody to measure fluorescence intensity as determined by imaging cochlear samples, where fluorescence intensity is used as a measure of Lgr5 presence. Western blots can be used with an anti-Lgr5 antibody, where cells can be harvested from the treated organ to determine increases in Lgr5 protein. Quantitative-PCR or RNA in situ hybridization can be used to measure relative changes in Lgr5 mRNA production, where cells can be harvested from the inner ear to determine changes in Lgr5 mRNA. Alternatively, Lgr5 expression can be measured using an Lgr5 promoter driven GFP reporter transgenic system, where the presence or intensity GFP fluoresce can be directly detected using flow cytometry, imaging, or indirectly using an anti-GFP antibody.

"Increases" also means increases by at least 1-fold, for example, 1, 2, 3, 4, 5, 6, 7, 8, 9, 10, 15, 20, 30, 40, 50, 60, 70, 80, 90, 100, 200, 500, 1000-fold or more, for example, as compared to the level of a as compared to the level of a reference standard.

"Increasing" refers to increasing by at least 5%, for example, 5, 6, 7, 8, 9, 10, 15, 20, 25, 30, 35, 40, 45, 50, 55, 60, 65, 70, 75, 80, 85, 90, 95, 99, 100% or more, for example, as compared to the level of a reference.

"Intraauricular administration" refers to administration of a composition to the middle or innerear of a subject by directly injecting the composition.

"Intracochlear" administration refers to direct injection of a composition across the tympanic membrane and across the round window membrane into the cochlea.

"Intravestibular" administration refers to direct injection of a composition across the tympanic membrane and across the round window membrane into the vestibular organs.

"Isolated" refers to a material that is free to varying degrees from components which normally accompany it as found in its native state. "Isolate" denotes a degree of separation from original source or surroundings.

"Lgr5" is an acronym for the Leucine-rich repeat-containing G-protein coupled receptor 5, also known as G-protein coupled receptor 49 (GPR49) or G-protein coupled receptor 67 (GPR67). It is a protein that in humans is encoded by the Lgr5 gene.

"Lgr5 activity" is defined as the level of activity of Lgr5 in a population of cells. In an in vitro cell population, Lgr5 activity may be measured in an in vitro Lgr5 Activity assay. In an in vivo cell population, Lgr5 activity may be measured in an in vivo Lgr5 Activity assay.

"Lgr5+ cell" or "Lgr5-positive cell" as used herein is a cell that expresses Lgr5. "Lgr5− cell" as used herein is a cell that is not Lgr5+.

"Lineage Tracing" as used herein is using a mouse line that enables fate tracing of any cell that expresses a target gene at the time of reporter induction. This can include hair cell or supporting cells genes (Sox2, Lgr5, MyosinVIIa, Pou4f3, etc). For example, lineage tracing may use an Lgr5-EGFP-IRES-creERT2 mouse crossed with a reporter mouse, which upon induction, allows one to trace the fate of cells that expressed Lgr5 at the time of induction. By further example, Lgr5 cells can be isolated into single cells and cultured in a Stem Cell Proliferation Assay to generate colonies, then subsequently differentiated in a Differentiation Assay and analyzed for cell fate by staining for hair cell and/or supporting cell proteins and determining the reporter colocalization with either hair cell or supporting cell staining to determine the Lgr5 cells' fate. In addition, lineage tracing can be performed in cochlear explants to track supporting cell or hair cell fate within the intact organ after treatment. For example, Lgr5 cell fate can be determined by isolating the cochlea from a Lgr5-EGFP-IRES-creERT2 mouse crossed with a reporter mouse, and inducing the reporter in Lgr5 cells before or during treatment. The organ can then be analyzed for cell fate by staining for hair cell and/or supporting cell proteins and determining the reporter colocalization with either hair cell or supporting cell staining to determine the Lgr5 cells' fate. In addition, lineage tracing can be performed in vivo track supporting cell or hair cell fate within the intact organ after treatment. For example, Lgr5 cell fate can be determined inducing a reporter in an Lgr5-EGFP-IRES-creERT2 mouse crossed with a reporter mouse, treating the animal, then isolating the cochlea. The organ can then be analyzed for cell fate by staining for hair cell and/or supporting cell proteins and determinning the reporter colocalization with either hair cell or supporting cell staining to determine the Lgr5 cells' fate. Lineage tracing may be performed using alternative reporters of interest as is standard in the art.

"Mammal" refers to any mammal including but not limited to human, mouse, rat, sheep, monkey, goat, rabbit, hamster, horse, cow or pig.

"Mean Release Time" as used herein is the time in which one-half of an agent is released into phosphate buffered saline from a carrier in a Release Assay.

"Native Morphology" as used herein is means that tissue organization largely reflects the organization in a healthy tissue. For example, "Native Morphology" for a cochlea means that hair cells are surrounded by supporting cells in a rosette pattern formed by lateral inhibition of Notch, hair cells do not contact each other, 2-3 cell layers form the organ of Corti epithelia, and cells do not breach the reticular lamina (ie. do not breach the border between endolymph and perilymph).

"Non-human mammal", as used herein, refers to any mammal that is not a human.

"Notch activity assay" as used herein refers to an assay to determine the Notch activity in a population using standard techniques, such as determining the expression of Hes5/Hes1 using, for example, qPCR.

As used in relevant context herein, the term "number" of cells can be 0, 1, or more cells.

"Organ of Corti" as used herein refers to the sensory cells (inner and outer hair cells) of the hearing organ located in the cochlea.

"Organoid" or "epithelial organoid" refers to a cell cluster or aggregate that resembles an organ, or part of an organ, and possesses cell types relevant to that particular organ.

"Population" of cells refers to any number of cells greater than 1, but is preferably at least $1 \times 10^3$ cells, at least $1 \times 10^4$ cells, at least at least $1 \times 10^5$ cells, at least $1 \times 10^6$ cells, at least $1 \times 10^7$ cells, at least $1 \times 10^8$ cells, at least $1 \times 10^9$ cells, or at least $1 \times 10^{10}$ cells.

"Progenitor cell" as used herein refers to a cell that, like a stem cell, has the tendency to differentiate into a specific type of cell, but is already more specific than a stem cell and is pushed to differentiate into its "target" cell.

"Proliferation Period" as used herein is the duration of time in which there is an Effective Stemness Driver Concentration and a Differentiation Inhibition Concentration of a Differentiation Inhibitor.

"Reference" means a standard or control condition (e.g., untreated with a test agent or combination of test agents).

"Release Assay" as used herein is a test in which the rate of release of an agent from a Biocompatible Matrix through dialysis membrane to a saline environment. An exemplary Release Assay may be performed by placing 30 microliters of a composition in 1 ml Phosphate Buffered Saline inside saline dialysis bag with a suitable cutoff, and placing the dialysis bag within 10 mL of Phosphate Buffered Saline at 37 C. The dialysis membrane size may be chosen based on agent size in order to allow the agent being assessed to exit the membrane. For small molecule release, a 3.5-5 kDa cutoff may be used. The agent may be a Stemness Driver, Differentiation Inhibitor, or other agent. The Release Rate for a composition may change over time and may be measured in 1 hour increments.

"Representative Microscopy Sample" as used herein describes a sufficient number of fields of view within a cell culture system, a portion of extracted tissue, or an entire extracted organ that the average feature size or number being measured can reasonably be said to represent the average feature size or number if all relevant fields were measured. For example, in order to assess the hair cell counts at a frequency range on the Organ of Corti, ImageJ software (NIH) can used to measure the total length of cochlear whole mounts and the length of individual counted segments. The total number of inner hair cells, outer hair cells, and supporting cells can be counted in the entire or fraction of any of the four cochlear segments of 1200-1400 m (apical, mid-apical, mid-basal, and basal) at least 3 fields of view at 100 μm field size would be reasonably considered a Representative Microscopy Sample. A Representative Microscopy sample can include measurements within a field of view, which can be measured as cells per a given distance. A Representative Microscopy sample can be used to assess morphology, such as cell-cell contacts, cochlear architecture, and cellular components (e.g., bundles, synapses).

"Rosette Patterning" is a characteristic cell arrangement in the cochlea in which <5% hair cells are adjacent to other hair cells.

The term "sample" refers to a volume or mass obtained, provided, and/or subjected to analysis. In some embodiments, a sample is or comprises a tissue sample, cell sample, a fluid sample, and the like. In some embodiments, a sample is taken from (or is) a subject (e.g., a human or animal subject). In some embodiments, a tissue sample is or comprises brain, hair (including roots), buccal swabs, blood, saliva, semen, muscle, or from any internal organs, or cancer, precancerous, or tumor cells associated with any one of these. A fluid may be, but is not limited to, urine, blood, ascites, pleural fluid, spinal fluid, and the like. A body tissue can include, but is not limited to, brain, skin, muscle, endometrial, uterine, and cervical tissue or cancer, precancerous, or tumor cells associated with any one of these. In an embodiment, a body tissue is brain tissue or a brain tumor or cancer. Those of ordinary skill in the art will appreciate that, in some embodiments, a "sample" is a "primary sample" in that it is obtained from a source (e.g., a subject); in some embodiments, a "sample" is the result of processing of a primary sample, for example to remove certain potentially contaminating components and/or to isolate or purify certain components of interest.

"Self-renewal" refers to the process by which a stem cell divides to generate one (asymmetric division) or two (symmetric division) daughter cells with development potentials that are indistinguishable from those of the mother cell. Self-renewal involves both proliferation and the maintenance of an undifferentiated state.

"siRNA" refers to a double stranded RNA. Optimally, an siRNA is 18, 19, 20, 21, 22, 23 or 24 nucleotides in length and has a 2 base overhang at its 3' end. These dsRNAs can be introduced to an individual cell or culture system. Such siRNAs are used to downregulate mRNA levels or promoter activity.

"Stem cell" refers to a multipotent cell having the capacity to self-renew and to differentiate into multiple cell lineages.

"Stem Cell Differentiation Assay" as used herein is an assay to determine the differentiation capacity of stem cells. In an exemplary Stem Cell Differentiation Assay, the number of cells for an initial cell population is harvested from a Atoh1-GFP mouse between the age of 3 to 7 days, by isolating the Organ of Corti sensory epithelium, dissociating the epithelium into single cells, and passing the cells through a 40 um cell strainer. Approximately 5000 cells are entrapped in 40 µl of culture substrate (for example: Matrigel (Corning, Growth Factor Reduced)) and placed at the center of wells in a 24-well plate with 500 µl of an appropriate culture media, growth factors and agent being tested. Appropriate culture media and growth factors include Advanced DMEM/F12 with media Supplements (1×N2, 1×B27, 2 mM Glutamax, 10 mM HEPES, 1 mM N-acetylcysteine, and 100 U/ml Penicillin/100 µg/ml Streptomycin) and growth factors (50 ng/ml EGF, 50 ng/ml bFGF, and 50 ng/ml IGF-1) as well as the agent(s) being assessed are added into each well. Cells are cultured for 10 days in a standard cell culture incubator at 37° C. and 5% $CO_2$, with media change every 2 days. These cells are then cultured by removing the Stem Cell Proliferation Assay agents and replacing with Basal culture media and molecules to drive differentiation. An appropriate Basal culture media is Advanced DMEM/F12 supplemented with 1×N2, 1×B27.2 mM Glutamax, 10 mM HEPES, 1 mM N-acetylcysteine, and 100 U/ml Penicillin/100 µg/ml Streptomycin and appropriate molecules to drive differentiation are 3 µM CHIR99021 and 5 µM DAPT for 10 days, with media change every 2 days. The number of hair cells in a population may be measured by using flow cytometry for GFP. Hair cell differentiation level can further be assessed using qPCR to measure hair cell marker (e.g., Myo7a) expression level normalized using suitable and unregulated references or housekeeping genes (e.g., Hprt). Hair cell differentiation level can also be assessed by immunostaining for hair cell markers (eg. Myosin7a, vGlut3, Espin, PMCAs, Ribeye, conjugated-phalloidin, Atoh1, Pou4f3, etc). Hair cell differentiaton level can also be assessed by Western Blot for Myosin7a, vGlut3, Espin, PMCAs, Prestin, Ribeye, Atoh1, Pou4f3.

"Stem Cell Assay" as used herein is an assay in which a cell or a cell population are tested for a series of criteria to determine whether the cell or cell population are stem cells or enriched in stem cells or stem cell markers. In a stem cell assay, the cell/cell population are tested for stem cell characteristics such as expression of Stem Cell Markers, and further optionally are tested for stem cell function, including the capacity of self-renewal and differentiation.

"Stem Cell Proliferator" as used herein is a composition that induces an increase in a population of cells which have the capacity for self-renewal and differentiation.

"Stem Cell Proliferation Assay" as used herein is an assay to determine the capacity for agent(s) to induce the creation of stem cells from a starting cell population. In an exemplary Stem Cell Proliferation Assay, the number of cells for an initial cell population is harvested from a Lgr5-GFP mouse such as a B6.129P2-Lgr5tm1(cre/ERT2)Cle/J mouse (also known as Lgr5-EGFP-IRES-creERT2 or Lgr5-GFP mouse, Jackson Lab Stock No: 008875) between the age of 3 to 7 days, by isolating the Organ of Corti sensory epithelium and dissociating the epithelium into single cells. Approximately 5000 cells are entrapped in 40 µl of culture substrate (for example: Matrigel (Corning, Growth Factor Reduced)) and placed at the center of wells in a 24-well plate with 500 µl of an appropriate culture media, growth factors and agent being tested. Appropriate culture media and growth factors include Advanced DMEM/F12 with media Supplements (1×N2, 1×B27, 2 mM Glutamax, 10 mM HEPES, 1 mM N-acetylcysteine, and 100 U/ml Penicillin/100 µg/ml Streptomycin) and growth factors (50 ng/ml EGF, 50 ng/ml bFGF, and 50 ng/ml IGF-1) as well as the agent(s) being assessed are added into each well. Cells are cultured for 10 days in a standard cell culture incubator at 37° C. and 5% $CO_2$, with media change every 2 days. The number of $Lgr5^+$ cells is quantified by counting the number of cells identified as Lgr5+ in an In Vitro Lgr5 activity assay. The fraction of cells that are $Lgr5^+$ is quantified by dividing the number of cells identified as $Lgr5^+$ in a cell population by the total number of cells present in the cell population. The average $Lgr5^+$ activity of a population is quantified by measuring the average mRNA expression level of Lgr5 of the population normalized using suitable and unregulated references or housekeeping genes (e.g., Hprt). The number of hair cells in a population may be measured by staining with hair cell marker (e.g., MyosinVIIa), or using an endogenous reporter of hair cell genes (eg. Pou4f3-GFP, Atoh1-nGFP) and analyzing using flow cytometry. The fraction of cells that are hair cells is quantified by dividing the number of cells identified as hair cells in a cell population by the total number of cells present in the cell population. Lgr5 activity can be measured by qPCR.

"Stem Cell Markers" as used herein can be defined as gene products (e.g. protein, RNA, etc) that specifically expressed in stem cells. One type of stem cell marker is gene products that are directly and specifically support the maintenance of stem cell identity. Examples include Lgr5 and Sox2. Additional stem cell markers can be identified using assays that were described in the literatures. To determine whether a gene is required for maintenance of stem cell identity, gain-of-function and loss-of-function studies can be used. In gain-of-function studies, over expression of specific gene product (the stem cell marker) would help maintain the stem cell identity. While in loss-of-function studies, removal of the stem cell marker would cause loss of the stem cell identity or induced the differentiation of stem cells. Another type of stem cell marker is gene that only expressed in stem cells but does not necessary to have specific function to maintain the identity of stem cells. This type of markers can be identified by comparing the gene expression signature of sorted stem cells and non-stem cells by assays such as micro-array and qPCR. This type of stem cell marker can be found in the literature. (e.g. Liu Q. et al., *Int J Biochem Cell*

Biol. 2015 March; 60:99-111. http://www.ncbi.nlm.nih.gov/pubmed/25582750). Potential stem cell markers include Ccdc121, Gdf10, Opcm1, Phex, etc. The expression of stem cell markers such as Lgr5+ or Sox2 in a given cell or cell population can be measure using assays such as qPCR, immunohistochemistry, western blot, and RNA hybridization. The expression of stem cell markers can also be measured using transgenic cells express reporters which can indicate the expression of the given stem cell markers, e.g. Lgr5-GFP or Sox2-GFP. Flow cytometry analysis can then be used to measure the activity of reporter expression. Fluorescence microscopy can also be used to directly visualize the expression of reporters. The expression of stem cell markers may further be determined using microarray analysis for global gene expression profile analysis. The gene expression profile of a given cell population or purified cell population can be compared with the gene expression profile of the stem cell to determine similarity between the 2 cell populations. Stem cell function can be measured by colony forming assay or sphere forming assay, self-renewal assay and differentiation assay. In colony (or sphere) forming assay, when cultured in appropriate culture media, the stem cell should be able to form colonies, on cell culture surface (e.g. cell culture dish) or embedded in cell culture substrate (e.g. Matrigel) or be able to form spheres when cultured in suspension. In colony/sphere forming assay, single stem cells are seeded at low cell density in appropriate culture media and allowed to proliferate for a given period of time (7-10 days). Colony formed are then counted and scored for stem cell marker expression as an indicator of stemness of the original cell. Optionally, the colonies that formed are then picked and passaged to test its self-renewal and differentiation potential. In self-renewal assay, when cultured in appropriate culture media, the cells should maintain stem cell marker (e.g. Lgr5) expression over at least one (e.g. 1, 2, 3, 4, 5, 10, 20, etc) cell divisions. In a Stem Cell Differentiation Assay, when cultured in appropriate differentiation media, the cells should be able to generate hair cell which can be identified by hair cell marker expression measured by qPCR, immunostaining, western blot, RNA hybridization or flow cytometry.

"Stemness Driver" as used herein is a composition that induces proliferation of LGR5+ cells, upregulates Lgr5 in cells, or maintains Lgr5 expression in cells, while maintaining the potential for self-renewal and the potential to differentiate into hair cells. Generally, stemness drivers upregulate at least one biomarker of post-natal stem cells. Stemness Drivers include but are not limited to Wnt agonists and GSK3Beta inhibitors.

"Subject" includes humans and mammals (e.g., mice, rats, pigs, cats, dogs, and horses). In many embodiments, subjects are be mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

"Supporting Cell" as used herein in connection with a cochlear epithelium comprises epithelial cells within the organ of Corti that are not hair cells. This includes inner pillar cells, outer pillar cells, inner phalangeal cells, Deiter cells, Hensen cells, Boettcher cells, and/or Claudius cells.

"Synergy" or "synergistic effect" is an effect which is greater than the sum of each of the effects taken separately; a greater than additive effect.

"TgfBeta inhibitor" as used herein is a composition that reduces activity of TgfBeta "Tissue" is an ensemble of similar cells from the same origin that together carry out a specific function including, for example, tissue of cochlear, such as the Organ of Corti.

"Transtympanic" administration refers to direct injection of a composition across the tympanic membrane into the middle ear.

"Treating" as used herein in connection with a cell population means delivering a substance to the population to effect an outcome. In the case of in vitro populations, the substance may be directly (or even indirectly) delivered to the population. In the case of in vivo populations, the substance may be delivered by administration to the host subject.

"Valproic acid" (VPA) has chemical formula $C_8H_{16}O_2$ and the following alternate name: 2-propylpentanoic acid. Its chemical structure is as follows:

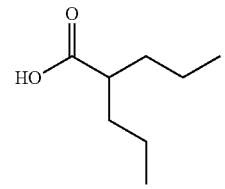

"Wnt activation" as used herein in connection with a composition is an activation of the Wnt signaling pathway.

The use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, /toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. For example, inorganic salts include, but are not limited to, ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Example organic bases used in certain embodiments include isopropylamine, diethylamine, ethanolamine, trimethylamine, dicyclohexylamine, choline and caffeine.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions described herein can be formulated in any manner suitable for a desired delivery route, e.g., transtympanic injection, transtympanic wicks and catheters, and injectable depots. Typically, formulations include all physiologically acceptable compositions incuding derivatives or prodrugs, solvates, stereoisomers, racemates, or tautomers thereof with any physiologically acceptable carriers, diluents, and/or excipients.

DETAILED DESCRIPTION OF THE INVENTION

A description of example embodiments of the invention follows.

The present disclosure relates to compositions, methods, and systems to prevent, reduce or treat the incidence and/or severity of inner ear disorders and hearing impairments involving inner ear tissue, particularly inner ear hair cells, their progenitors, and optionally, the stria vascularis, and associated auditory nerves. Of particular interest are those conditions that lead to permanent hearing loss where reduced number of hair cells may be responsible and/or decreased hair cell function. Also of interest are those arising as an unwanted side-effect of ototoxic therapeutic drugs including cisplatin and its analogs, aminoglycoside antibiotics, salicylate and its analogs, or loop diuretics. In certain embodiments, the present disclosure relates to inducing, promoting, or enhancing the growth, proliferation or regeneration of inner ear tissue, particularly inner ear supporting cells and hair cells.

Among other things, the compounds presented here are useful for the preparation of pharmaceutical formulations for the prophylaxis and/or treatment of acute and chronic ear disease and hearing loss, dizziness and balance problems especially of sudden hearing loss, acoustic trauma, hearing loss due to chronic noise exposure, presbycusis, trauma during implantation of the inner ear prosthesis (insertion trauma), dizziness due to diseases of the inner ear area, dizziness related and/or as a symptom of Meniere's disease, vertigo related and/or as a symptom of Meniere's disease, tinnitus, and hearing loss due to antibiotics and cytostatics and other drugs.

Advantageously, compositions disclosed herein have the capacity to activate pathways and mechanisms that are known to be involved in inducing stem cell properties, such as those used to create "induced pluripotent stem cells" (e.g., combined Wnt stimulation, HDAC inhibition, TGF-beta inhibition, RAR activation, and/or DKK1 suppression). When cochlea supporting cell populations are treated with such a composition, whether the population is in vivo or in vitro, the treated supporting cells exhibit stem-like behavior in that the treated supporting cells have the capacity to proliferate and differentiate and, more specifically, differentiate into cochlear hair cells. Preferably, the composition induces and maintains the supporting cells to produce daughter stem cells that can divide for many generations and maintain the ability to have a high proportion of the resulting cells differentiate into hair cells. In certain embodiments, the proliferating stem cells express stem cell markers which may include Lgr5, Sox2, Opem1, Phex, lin28, Lgr6, cyclin D1, Msx1, Myb, Kit, Gdnf3, Zic3, Dppa3, Dppa4, Dppa5, Nanog, Esrrb, Rex1, Dnmt3a, Dnmt3b, Dnmt3l, Utf1, Tcl1, Oct4, Klf4, Pax6, Six2, Zic1, Zic2, Otx2, Bmi1, CDX2, STAT3, Smad1, Smad2, smad2/3, smad4, smad5, and/or smad7.

In some embodiments, a composition of the present disclosure may be used to maintain, or even transiently increase stemness (i.e., self-renewal) of a pre-existing supporting cell population prior to significant hair cell formation. In some embodiments, the pre-existing supporting cell population comprises inner pillar cells, outer pillar cells, inner phalangeal cells, Deiter cells, Hensen cells, Boettcher cells, and/or Claudius cells. Morphological analyses with immunostaining (including cell counts) and lineage tracing across a Representative Microscopy Samples may be used to confirm expansion of one or more of these cell-types. In some embodiments, the pre-existing supporting cells comprise Lgr5$^+$ cells. Morphological analyses with immunostaining (including cell counts) and qPCR and RNA hybridization may be used to confirm Lgr5 upregulation amongst the cell population.

Advantageously, the methods and compositions of the present disclosure achieve these goals without the use of genetic manipulation. Germ-line manipulation used in many academic studies is not a therapeutically desirable approach to treating hearing loss. In general, the therapy preferably involves the administration of a small molecule, peptide, antibody, or other non-nucleic acid molecule or nucleic acid delivery vector unaccompanied by gene therapy. In certain embodiments, the therapy involves the administration of a small organic molecule. Preferably, hearing protection or restoration is achieved through the use of a (non-genetic) therapeutic that is injected in the middle ear and diffuses into the cochlea.

The cochlea relies heavily on all present cell types, and the organization of these cells is important to their function. As supporting cells play an important role in neurotransmitter cycling and cochlear mechanics. Thus, maintaining a rosette patterning within the organ of Corti may be important for function. Cochlear mechanics of the basilar membrane activate hair cell transduction. Ectopic hair cells have been created via Atoh1 viral transduction, but it is unlikely that these cells can contribute to a hearing response due to their mislocation in relation to the sensory and mismatch with tectorial membrane. Furthermore, these cells appear to be more similar to vestibular or non-mammalian hair cells. Thus, more signaling than just Atoh1 or Notch inhibition is necessary for cochlear hair cell development. Due to the high sensitivity of cochlear mechanics, it is also desirable to avoid masses of cells. In all, maintaining proper distribution and relation of hair cells and supporting cells along the basilar membrane, even after proliferation, is likely a desired feature for hearing as supporting cell function and proper mechanics is necessary for normal hearing.

In a native cochlea, patterning of hair cells and supporting cells occurs through Notch lateral inhibition, wherein a cell that becomes a hair cells signals to nearby supporting cells to suppress Atoh1 (a gene necessary for hair cells fate), thereby creating epithelial rosettes. In one embodiment of the present disclosure, the cell density of hair cells in a cochlear cell population is expanded in a manner that maintains, or even establishes, the rosette pattern characteristic of cochlear epithelia.

In accordance with one aspect of the present disclosure, the cell density of hair cells may be increased in a population of cochlear cells comprising both hair cells and supporting cells. The cochlear cell population may be an in vivo population (i.e., comprised by the cochlear epithelium of a subject) or the cochlear cell population may be an in vitro (ex vivo) population. If the population is an in vitro population, the increase in cell density may be determined by reference to a Representative Microscopy Sample of the population taken prior and subsequent to any treatment. If the population is an in vivo population, the increase in cell density may be determined indirectly by determining an effect upon the hearing of the subject with an increase in hair cell density correlating to an improvement in hearing.

In one embodiment, supporting cells placed in a Stem Cell Proliferation Assay in the absence of neuronal cells form ribbon synapses.

In a native cochlea, patterning of hair cells and supporting cells occurs in a manner parallel to the basilar membrane. In one embodiment of the present disclosure, the proliferation of supporting cells in a cochlear cell population is expanded in a manner that the basilar membrane characteristic of cochlear epithelia.

In one such embodiment when a composition is applied to cochlear tissue, the number of contiguous hair cells in an expanded cochlear cell population is less than 5% of the hair cells in the population. By way of further example, in one such embodiment the number of contiguous hair cells in an expanded cochlear cell population is less than 4% of the hair cells in the population. By way of further example, in one such embodiment the number of contiguous hair cells in an expanded cochlear cell population is less than 3% of the hair cells in the population. By way of further example, in one such embodiment the number of contiguous hair cells in an expanded cochlear cell population is less than 2% of the hair cells in the population. By way of further example, in one such embodiment the number of contiguous hair cells in an expanded cochlear cell population is less than 1% of the hair cells in the population. In some embodiments, the composition expands inner ear supporting cells to generate additional hair cells in which the epithelial tissue resembles Native Morphology which does not have adjacent hair cells for more than 5% of hair cells viewed by microscopy In some embodiments, the composition expands inner ear supporting cells in animals more than 2 weeks old to generate additional hair cells in which the epithelial tissue resembles Native Morphology which does not have adjacent hair cells for more than 5% of hair cells in a Representative Microscopy Sample.

In some embodiments, the composition results in >5% of hair cells contacting both supporting cells and neurons in a Representative Microscopy Sample.

In some embodiments, the composition results in hair cells adjacent to other hair cells less than 5% of the time in a Representative Microscopy Sample.

In one embodiment, the number of supporting cells in an initial cochlear cell population is selectively expanded by treating the initial cochlear cell population with a composition of the present disclosure (e.g., a composition containing an Effective Concentration of a Stemness Driver and an Effective Concentration of a Differentiation Inhibitor) to form an intermediate cochlear cell population and wherein the ratio of supporting cells to hair cells in the intermediate cochlear cell population exceeds the ratio of supporting cells to hair cells in the initial cochlear cell population. The expanded cochlear cell population may be, for example, an in vivo population, an in vitro population or even an in vitro explant. In one such embodiment, the ratio of supporting cells to hair cells in the intermediate cochlear cell population exceeds the ratio of supporting cells to hair cells in the initial cochlear cell population. For example, in one such embodiment the ratio of supporting cells to hair cells in the intermediate cochlear cell population exceeds the ratio of supporting cells to hair cells in the initial cochlear cell population by a factor of 1.1. By way of further example, in one such embodiment the ratio of supporting cells to hair cells in the intermediate cochlear cell population exceeds the ratio of supporting cells to hair cells in the initial cochlear cell population by a factor of 1.5. By way of further example, in one such embodiment the ratio of supporting cells to hair cells in the intermediate cochlear cell population exceeds the ratio of supporting cells to hair cells in the initial cochlear cell population by a factor of 2. By way of further example, in one such embodiment the ratio of supporting cells to hair cells in the intermediate cochlear cell population exceeds the ratio of supporting cells to hair cells in the initial cochlear cell population by a factor of 3. In each of the foregoing embodiments, the capacity of a composition of the present disclosure to expand a cochlear cell population as described in this paragraph may be determined by means of a Stem Cell Proliferation Assay.

In one embodiment, the number of stem cells in a cochlear cell population is expanded to form an intermediate cochlear cell population by treating a cochlear cell population with a composition of the present disclosure (e.g., a composition containing an Effective Concentration of a Stemness Driver and an Effective Concentration of a Differentiation Inhibitor) wherein the cell density of stem cells in the intermediate cochlear cell population exceeds the cell density of stem cells in the initial cochlear cell population. The treated cochlear cell population may be, for example, an in vivo population, an in vitro population or even an in vitro explant. In one such embodiment, the cell density of stem cells in the treated cochlear cell population exceeds the cell density of stem cells in the initial cochlear cell population by a factor of at least 1.1. For example, in one such embodiment the cell density of stem cells in the treated cochlear cell population exceeds the cell density of stem cells in the initial cochlear cell population by a factor of at least 1.25. For example, in one such embodiment the cell density of stem cells in the treated cochlear cell population exceeds the cell density of stem cells in the initial cochlear cell population by a factor of at least 1.5. By way of further example, in one such embodiment the cell density of stem cells in the treated cochlear cell population exceeds the cell density of stem cells in the initial cochlear cell population by a factor of at least 2. By way of further example, in one such embodiment the cell density of stem cells in the treated cochlear cell population exceeds the cell density of stem cells in the initial cochlear cell population by a factor of at least 3. In vitro cochlear cell populations may expand significantly more than in vivo populations; for example, in certain embodiments the cell density of stem cells in an expanded in vitro population of stem cells may be at least 4, 5, 6, 7, 8, 9, 10, 15, 20, 25, 30, 35, 40, 45, 50, 75, 100, 200, 300, 400, 500, 600, 700, 800, 900, 1000, 2,000 or even 3,000 times greater than the cell density of the stem cells in the initial cochlear cell population. In each of the foregoing embodiments, the capacity of a composition of the present disclosure to expand a cochlear cell population as described in this paragraph may be determined by means of a Stem Cell Proliferation Assay.

In accordance with one aspect of the present disclosure, a cochlea supporting cell population is treated with a composition of the present disclosure (e.g., a composition containing an Effective Concentration of a Stemness Driver and an Effective Concentration of a Differentiation Inhibitor) to increase the Lgr5 activity of the population. For example, in one embodiment the composition has the capacity to increase and maintain the Lgr5 activity of an in vitro population of cochlea supporting cells by factor of at least 1.2. By way of further example, in one such embodiment the composition has the capacity to increase the Lgr5 activity of an in vitro population of cochlea supporting cells by factor of 1.5. By way of further example, in one such embodiment the composition has the capacity to increase the Lgr5 activity of an in vitro population of cochlea supporting cells by factor of 2, 3, 5 10, 100, 500, 1,000, 2,000 or even 3,000. Increases in Lgr5 activity may also be observed for in vivo populations but the observed increase may be somewhat more modest. For example, in one embodiment the composition has the capacity to increase the Lgr5 activity of an in vivo population of cochlea supporting cells by at least 5%. By way of further example, in one such embodiment the composition has the capacity to increase the Lgr5 activity of an in vivo population of cochlea supporting cells by at least 10%. By way of further example, in one such embodiment the composition has the capacity to increase the Lgr5 activity of an in vivo population of cochlea supporting cells by at least 20%. By way of further example, in one such embodiment the composition has the capacity to increase the Lgr5 activity of an in vivo population of cochlea supporting cells by at least 30%. In each of the foregoing embodiments, the capacity of the composition for such an increase in Lgr5 activity may be demonstrated, for example, in an In Vitro $Lgr5^+$ Activity Assay and in an in vivo population may be demonstrated, for example, in an In Vivo $Lgr5^+$ Activity Assay, as measured by isolating the organ and performing morphological analyses using immunostaining, endogenous fluorescent protein expression of Lgr5 (eg. Lgr5, Sox2), and qPCR for Lgr5.

In addition to increasing the Lgr5 activity of the population, the number of $Lgr5^+$ supporting cells in a cochlea cell population may be increased by treating a cochlea cell population containing $Lgr5^+$ supporting cells (whether in vivo or in vitro) with a composition of the present disclosure (e.g., a composition containing an Effective Concentration of a Stemness Driver and an Effective Concentration of a Differentiation Inhibitor). In general, the cell density of the stem/progenitor supporting cells may expand relative to the initial cell population via one or more of several mechanisms. For example, in one such embodiment, newly generated $Lgr5^+$ supporting cells may be generated that have increased stem cell propensity (i.e., greater capacity to differentiate into hair cell). By way of further example, in one such embodiment no daughter $Lgr5^+$ cells are generated by cell division, but pre-existing $Lgr5^+$ supporting cells are induced to differentiate into hair cells. By way of further example, in one such embodiment no daughter cells are generated by cell division, but $Lgr5^-$ supporting cells are activated to a greater level of Lgr5 activity and the activated supporting cells are then able to differentiate into hair cells. Regardless of the mechanism, in one embodiment a composition of the present disclosure has the capacity to increase the cell density of Lgr5$^+$ supporting cells in an in vitro isolated cell population of cochlea supporting cells by factor of at least 5. By way of further example, in one such embodiment the composition has the capacity to increase the cell density of Lgr5$^+$ supporting cells in an in vitro population of cochlea supporting cells by factor of at least 10. By way of further example, in one such embodiment the composition has the capacity to increase the cell density of Lgr5$^+$ supporting cells in an in vitro population of cochlea supporting cells by factor of at least 100, at least 500, at least 1,000 or even at least 2,000. Increases in the cell density of Lgr5$^+$ supporting cells may also be observed for in vivo populations but the observed increase may be somewhat more modest. For example, in one embodiment the composition has the capacity to increase the cell density of Lgr5$^+$ supporting cells in an in vivo population of cochlea supporting cells by at least 5%. By way of further example, in one such embodiment the composition has the capacity to increase the cell density of Lgr5$^+$ supporting cells in an in vivo population of cochlea supporting cells by at least 10%. By way of further example, in one such embodiment the composition has the capacity to increase the cell density of Lgr5$^+$ supporting cells in an in vivo population of cochlea-supporting cells by at least 20%. By way of further example, in one such embodiment the composition has the capacity to increase the cell density of Lgr5$^+$ supporting cells in an in vivo population of cochlea supporting cells by at least 30%. The capacity of the composition for such an increase in Lgr5$^+$ supporting cells in an in vitro population may be demonstrated, for example, in a Stem Cell Proliferation Assay or in an appropriate in vivo assay. In one embodiment, a composition of the present disclosure has the capacity to increase the number of Lgr5$^+$ cells in the cochlea by inducing expression of Lgr5 in cells with absent or low detection levels of the protein, while maintaining Native Morphology. In one embodiment, a composition of the present disclosure has the capacity to increase the number of Lgr5$^+$ cells in the cochlea by inducing expression of Lgr5 in cells with absent or low detection levels of the protein, while maintaining Native Morphology and without producing Cell Aggregates.

In addition to increasing the cell density of Lgr5$^+$ supporting cells, in one embodiment a composition of the present disclosure has the capacity to increase the ratio of Lgr5$^+$ cells to hair cells in a cochlear cell population. In one embodiment, the number of Lgr5$^+$ supporting cells in an initial cochlear cell population is selectively expanded by treating the initial cochlear cell population with a composition of the present disclosure (e.g., a composition containing an Effective Concentration of a Stemness Driver and an Effective Concentration of a Differentiation Inhibitor) to form an expanded cell population and wherein the number of Lgr5$^+$ supporting cells in the expanded cochlear cell population at least equals the number of hair cells. The expanded cochlear cell population may be, for example, an in vivo population, an in vitro population or even an in vitro explant. In one such embodiment, the ratio of Lgr5$^+$ supporting cells to hair cells in the expanded cochlear cell population is at least 1:1. For example, in one such embodiment the ratio of Lgr5$^+$ supporting cells to hair cells in the expanded cochlear cell population is at least 1.5:1. Byway of further example, in one such embodiment the ratio of Lgr5$^+$ supporting cells to hair cells in the expanded cochlear cell population is at least 2:1. By way of further example, in one such embodiment the ratio of Lgr5$^+$ supporting cells to hair cells in the expanded cochlear cell population is at least 3:1. By way of further example, in one such embodiment the ratio of Lgr5$^+$ supporting cells to hair cells in the expanded cochlear cell population is at least 4:1. By way of further example, in one such embodiment the ratio of Lgr5$^+$ supporting cells to hair cells in the expanded cochlear cell population is at least 5:1. In each of the foregoing embodiments, the capacity of a composition of the present disclosure to expand a cochlear cell population as described in this paragraph may be determined by means of a Stem Cell Proliferation Assay.

In certain embodiments, the composition increases the fraction of the Lgr5$^+$ cells to total cells on the sensory epithelium by at least 10%, 20%, 50%, 100%, 250% 500%, 1,000% or 5000%.

In certain embodiments, the composition increases the Lgr5$^+$ cells until they become at least 10, 20, 30, 50, 70, or 85% of the cells on the sensory epithelium, e.g. the Organ of Corti.

In general, excessive proliferation of supporting cells in the cochlea is preferably avoided. In one embodiment, a composition of the present disclosure has the capacity to expand a cochlear cell population without creating a protrusion of new cells beyond the native surface of the cochlea, e.g a Cell Aggregate. In some embodiments, 30 days after placing a composition on the round window membrane, the cochlear tissue has Native Morphology. In some embodiments, 30 days after placing a composition on the round window membrane, the cochlear tissue has Native Morphology and lacks Cell Aggregates. In some embodiments, 30 days after placing a composition on the round window membrane, the cochlear tissue has Native Morphology and at least 10, 20, 30, 50, 75, 90, 95, 98, or even at least 99% of the Lgr5$^+$ cells in the Organ of Corti are not part of Cell Aggregates.

In addition to expanding supporting cell populations, generally, and Lgr5$^+$ supporting cells, specifically, as described above, compositions of the present disclosure (e.g., a composition containing an Effective Concentration of a Stemness Driver and an Effective Concentration of a Differentiation Inhibitor) have the capacity to maintain, in the daughter cells, the capacity to differentiate into hair cells. In in vivo populations, the maintenance of this capacity may be indirectly observed by an improvement in a subject's hearing. In in vitro populations, the maintenance of this capacity may be directly observed by an increase in the number of hair cells relative to a starting population or indirectly by measuring LGR5 activity, SOX2 activity or one or more of the other stem cell markers identified elsewhere herein.

In one embodiment, the capacity of a composition to increase the stemness of a population of cochlear supporting cells, in general, or a population of Lgr5$^+$ supporting cells, in particular, may be correlated with an increase of Lgr5 activity of an in vitro population of isolated Lgr5$^+$ cells as determined by an Lgr5 Activity Assay. As previously noted, in one such embodiment, the composition has the capacity to increase the Lgr5 activity of stem cells in the intermediate cell population by a factor of 5 on average relative to the Lgr5 activity of the cells in the initial cell population. By way of further example, in one such embodiment the composition has the capacity to increase the Lgr5 activity of the stem cells genes in the intermediate cell population by a factor of 10 relative to the Lgr5 activity of the cells in the initial cell population. By way of further example, in one such embodiment the composition has the capacity to increase the Lgr5 activity of the stem cells in the intermediate cell population by a factor of 100 relative to the Lgr5 activity of the cells in the initial cell population. By way of further example, in one such embodiment the composition has the capacity to increase the Lgr5 activity of the stem cells in the intermediate cell population by a factor of 1000 relative to the Lgr5 activity of the cells in the initial cell population. In each of the foregoing embodiments, the increase in the activity of stem cells in the cell population may be determined in vitro by immunostaining or endogenous fluorescent protein expression for target genes and analysis of their relative intensities via imaging analysis or flowcytometry, or using qPCR for target stem cell genes. The identity of the resulting stem cell population may optionally be further determined by stem cell assays including stem cell marker expression assay, colony forming assay, self-renewal assay and differentiation assay as defined in Stem cell assay.

In some embodiments, the method applied to an adult mammal produces a population of adult mammalian Lgr5+ cells that are in S-phase.

In one embodiment, after applying a composition to the round window of a mouse, the in vivo Lgr5+ Activity of a cell population in the Organ of Corti increases 1.3×, 1.5×, up to 20× over baseline for a population that has not been exposed to the composition. In some embodiments, applying a composition to the round window of a mouse increases the average In vivo Lgr5+ Activity for cells in the Organ of Corti is increased 1.3×, 1.5×, up to 20× over baseline for a population that has not been exposed to the composition.

In certain embodiments, the composition increases the Lgr5+ cells until they become at least 10%, 7.5%, 10%, up to 100% of the supporting cell population by number.

In some cases, a Stemness Driver may also induce differentiation of the supporting cells to hair cells if a Differentiation Inhibitor is not present at an Effective Differentiation Inhibition Concentration. Examples of Stemness Drivers that may drive both proliferation and differentiation include GSK3Beta inhibitors and Wnt agonists. In certain embodiments, the proliferation of the stem cells may be enhanced by adding a modulator of pathways that regulate cell cycle or plasticity, such as the p27 or TgfBeta pathways.

In some embodiments, a Stemness Driver may be used to drive the proliferation of Lgr5+ stem cells. In some cases, a Stemness Driver may also induce differentiation of Lgr5+ cells to hair cells if a Differentiation Inhibitor is not present at an Effective Differentiation Inhibition Concentration. Examples of Stemness Drivers that may drive both proliferation and differentiation include GSK3Beta inhibitors and Wnt agonists. In some embodiments, the Differentiation inhibitor is also a Stemness Driver. In some embodiments, the Differentiation inhibitor is a Notch agonist and is also a Stemness Driver. In some embodiments, the Differentiation inhibitor is Valproic Acid, which may be a Stemness Driver. If a Differentiation Inhibitor is also a Stemness Driver, the concentration of the Differentiation Inhibitor should fall below the Effective Differentiation Inhibition Concentration during the Differentiation Period.

In certain embodiments, a combination of (i) a GSK3-beta inhibitor and/or Wnt agonist, and (ii) a notch agonist and/or HDAC inhibitor is used, which has the capacity to increase stem cell population by at least 3 times larger than the stem cell population prior to the administering step when applied to Lgr5+ cells obtained from inner ear of mice.

In certain embodiments, a composition has the capacity to increase the percentage of Lgr5+ cell in a cochlea by 5%, 10%, 25%, 50%, or 80%. In certain embodiments, a combination of (i) a GSK3-beta inhibitor and/or Wnt agonist, and (ii) a notch agonist and/or HDAC inhibitor is used, which has the capacity to increase the percentage of Lgr5+ cell in a cochlea by 5%, 10%, 25%, 50%, or 80%.

Stemness Drivers

Exemplary GSK3-beta inhibitors within the present disclosure appear in Table 1.

TABLE 1

| GSK3β Inhibitors | |
|---|---|
| Column A<br>Class | Column B<br>Agent |
| Aloisines | Aloisine A |
| Aloisines | Aloisine B |
| Aminopyridine | CT20026 |
| Aminopyrimidine | CHIR99021 (CT99021) |
| Aminopyrimidine | CHIR98014 (CT98014) |
| Aminopyrimidine | CHIR98023 (CT98023) |
| Aminopyrimidine | TWS119 |
| Anilinoarylmaleimide | I5 |
| Arylindolemaleimide | SB-216763 |
| Arylindolemaleimide | SB-415286 (SB-41528) |
| Azaindolylmaleimide | Compound 29 |
| Azaindolylmaleimide | Compound 46 |
| Benzazepinone | Kenpaullone |
| Benzazepinone | Alsterpaullone |
| Benzazepinone | Azakenpaullone |
| Bis-Indole | Indirubin-30-oxime |
| Bis-Indole | 6-Bromoindirubin-30-oxime (BIO) |
| Bis-Indole | 6-Bromoindirubin-30-acetoxime |
| Bisindolylmaleimide | Staurosporine |
| Bisindolylmaleimide | Compound 5a |
| Bisindolylmaleimide | GF109203x (bisindolylmaleimide I) |
| Bisindolylmaleimide | Ro318220 (bisindolylmaleimide IX) |
| Bisindolylmaleimide | Bisindolylmaleimide × hydrochloride |
| Bisindolylmaleimide | Enzastaurin |
| Chloromethyl thienyl ketone | Compound 17 |
| Flavone | Flavopiridol |
| Furanosesquiterpenes | Palinurine |
| Furanosesquiterpenes | Tricantine |

TABLE 1-continued

GSK3β Inhibitors

| Column A<br>Class | Column B<br>Agent |
|---|---|
| Halomethylketones | HMK-32 |
| Indirubins | Indirubin-3'-monoxime |
| Indirubins | 6-BIO |
| Indirubins | 5-Iodo-indirubin-3'-monoxime |
| Indirubins | Indirubin-5-sulfonic acid sodium salt |
| Inorganic atom | Lithium |
| Inorganic atom | Beryllium |
| Inorganic atom | Zinc |
| Inorganic atom | Tungstate |
| Manzamines | Manzamine A |
| Oxindole | SU9516 |
| Organometallic | HB12 |
| Organometallic | DW12 |
| Organometallic | NP309 |
| Organometallic | (RRu)-HB1229 |
| Organometallic | (RRu)-NP549 |
| Organometallic | GSK3 inhibitor XV |
| Paullones | Kenpaullone |
| Paullones | Alsterpaullone |
| Paullones | Cazpaullone |
| Paullones | 9-Cyanopaullone |
| Peptide | FRATtide |
| Peptide | L803 |
| Peptides | L803-mts |
| Phenylaminopyrimidine | CGP60474 |
| Pyrazolopyridine | Pyrazolopyridine 9 |
| Pyrazolopyridine | Pyrazolopyridine 18 |
| Pyrazolopyridine | Pyrazolopyridine 34 |
| Pyrazolopyrimidine | Compound 1A |
| Pyrazoloquinoxaline | Compound 1 |
| Pyridyloxadiazole | Compound 12 |
| Pyrroloazepine | Hymenialdisine |
| Pyrrolopyrazine | Aloisine A |
| Pyrrolopyrazine | Aloisine B |
| Pyrrolopyrimidine | TWS119 |
| Thiadiazolidindiones | TDZD-8 |
| Thiadiazolidindiones | NP00111 |
| Thiadiazolidindiones | NP031115 |
| Thiadiazolidindiones | NP031112 (Tideglusib) |
| Thiazoles | AR-A014418 |
| Thiazoles | AZD-1080 |
| Triazole | Compound 8b |
| Miscellaneous | Hymenialdisine |
| Miscellaneous | Dibromocantharelline |
| Miscellaneous | KT 5720 |
| Miscellaneous | CID 755673 |
| Miscellaneous | GSK-3β Inhibitor VII |
| Miscellaneous | Hymenidin |
| Miscellaneous | 3F8 |
| Miscellaneous | TCS 2002 |
| Miscellaneous | TCS 21311 |
| Miscellaneous | A 1070722 |
| Miscellaneous | TC-G 24 |
| Miscellaneous | Bikinin |
| Miscellaneous | LY2090314 |
| Miscellaneous | 10Z-Hymenialdisine |
| Miscellaneous | NSC 693868 |
| Miscellaneous | IM-12 |
| Miscellaneous | Indirubin |
| Miscellaneous | AZD2858 (AR28) |
| Miscellaneous | GSK-3β Inhibitor I |
| Miscellaneous | GSK-3 Inhibitor II |
| Miscellaneous | GSK-3β Inhibitor VIII |
| Miscellaneous | GSK-3 Inhibitor XXII |
| Miscellaneous | Indirubin-3'-monoxime-5-sulphonic Acid |
| Miscellaneous | GSK-3 Inhibitor XIII |
| Miscellaneous | GSK3β Inhibitor XIX |
| Miscellaneous | GSK-3β Inhibitor XXVII |
| Miscellaneous | GSK-3beta Inhibitor XXVI |
| Miscellaneous | GSK-3β Inhibitor XII |
| Miscellaneous | GSK-3β Inhibitor XXIV |
| Miscellaneous | GSK-3 Inhibitor XV |
| Miscellaneous | GSK-3β Inhibitor VI |
| Miscellaneous | GSK-3β Inhibitor XVIII |
| Miscellaneous | GSK-3 Inhibitor XXIX |

TABLE 1-continued

GSK3β Inhibitors

| Column A<br>Class | Column B<br>Agent |
|---|---|
| Miscellaneous | GSK-3 Inhibitor IV |
| Miscellaneous | GSK-3β Inhibitor VII |
| Miscellaneous | GSK-3 Inhibitor IX |
| Miscellaneous | GSK-3 Inhibitor X |
| Miscellaneous | GSK-3β Inhibitor XXV |
| Miscellaneous | GSK-3 Inhibitor XVI |
| Miscellaneous | GSK-3β Inhibitor XI |
| Miscellaneous | GSK-3 inhibitor 1 |
| Miscellaneous | A-1070722 |
| Miscellaneous | 3-Amino-1H-pyrazolo[3,4-b]quinoxaline |
| Miscellaneous | GSK3 Inhibitor, 2 |
| Miscellaneous | GSK-3beta Inhibitor III |
| Miscellaneous | AR-AO 14418-d3 |
| Miscellaneous | ML320 |
| Miscellaneous | BIP-135 |
| Miscellaneous | CP21R7 |
| Publication | NP-103 |
| Publication | CG-301338 |
| Publication | SAR 502250 |
| Publication | XD-4241 |
| Publication | CEP-16805 |
| Lithium Chloride and other inorganic atoms. | Lithium, Beryllium, Zinc, Tungstate |
| Maleimide Derivatives such as SB-216763 | e.g. Compound 1-30, SB-216763, etc |
| Staurosporine and Organometallic inhibitors | e.g. Compound 31-37, etc |
| Indole Derivatives such as Indirubin-3'-monoxime and BIO | e.g. Compound 38-50, BIO, etc |
| Paullone Derivatives such as Kenpallone and Alsterpaullone | e.g. Compound 51-64, Kenpaullone, etc |
| Pyrazolamide derivatives | e.g. Compound 65-78, etc |
| Pyrimidine and Furopyrimidine derivatives such as CHIR99021 and CHIR98014 | e.g. Compound 79-102, CHIR99021, CHIR98014, etc |
| Oxadiazole derivatives | e.g. Compound 103-127, etc |
| Thiazole derivatives such as AR-A014418 | e.g. Compound 128-130, AR-A01448, etc |
| Miscellaneous Heterocyclic derivative | Compound 131-154 |
| Publication | AR79 |
| Publication | AZ13282107 |
| Publication | AR28 (AZD2858) |
| Patent | GI179186X |
| Patent | CT118637 |
| Patent | CP-70949 |
| Patent | GW784752X |
| Patent | GW784775X |
| Publication | CT73911 |
| Publication | CT20026 |
| Publication | LY2064827 |
| Publication | 705701 |
| Publication | 708244 |
| Publication | 709125 |
| Patent | WO 2008077138 A1 |
| Patent | WO 2003037891 A1 |
| Patent | U.S. Pat. No. 8,207,216 B2 |
| Patent | U.S. Pat. No. 8,071,591 B2 |
| Patent | CN 1319968 C |
| Patent | U.S. Pat. No. 7,514,445 B2 |
| Patent | CN 101341138 B |
| Patent | EP 1961748 A2 |
| Patent | WO 2010104205 A1 |
| Patent | U.S. 20100292205 A1 |
| Patent | WO 2014003098 A1 |
| Patent | WO 2011089416 A1 |
| Patent | EP 1739087 A1 |
| Patent | WO 2001085685 A1 |
| Patent | U.S. 20070088080 A1 |
| Patent | WO 2006018633 A1 |
| Patent | WO 2009017453 A1 |
| Patent | WO 2014050779 A1 |
| Patent | WO2006100490A1/EP 1863904 A1 |
| Patent | WO 2014013255 A1 |
| Patent | WO 2009017455 A1 |
| Patent | EP 2765188 A1 |
| Patent | WO 2014083132 A1 |
| Patent | U.S. Pat. No. 8,771,754 B2 |
| Patent | WO 2013124413 A1 |
| Patent | WO 2014059383 A1 |
| Patent | WO 2010075551 A1 |

TABLE 1-continued

GSK3β Inhibitors

| Column A<br>Class | Column B<br>Agent |
|---|---|
| Patent | U.S. Pat. No. 8,686,042 B2 |
| Patent | WO 2007102770 A1 |
| Aminopyrimidine | CHIR99021 (CT99021) |
| Miscellaneous | LY2090314 |
| Aminopyrimidine | TWS119 |
| Arylindolemaleimide | SB-216763 |
| Benzazepinone | Azakenpaullone |
| Paullones | Cazpaullone |
| Pyrazolopyridine | Pyrazolopyridine 9 |
| Miscellaneous | TCS 2002 |
| Miscellaneous | A 1070722 |
| Aminopyrimidine | CHIR98014 (CT98014) |
| Benzazepinone | Kenpaullone |
| Inorganic atom | Lithium |
| Miscellaneous | ML320 |
| Miscellaneous | CP21R7 |

Classes of GSK3-beta inhibitors for use in various embodiments of the compositions and methods disclosed herein include but are not limited to those listed in Column A of Table 1. Specific GSK3-beta inhibitors for use in various embodiments of the compositions and methods disclosed herein include but are not limited to those listed in Column B of Table 1. Classes of Wnt agonists for use in various embodiments of the compositions and methods disclosed herein include but are not limited to those listed in Column A of Table 2. Specific Wnt agonists for use in various embodiments of the compositions and methods disclosed herein include but are not limited to those listed in Column B of Table 2. Classes of notch agonists for use in various embodiments of the compositions and methods disclosed herein include but are not limited to those listed in Column A of Table 3. Specific notch agonists for use in various embodiments of the compositions and methods disclosed herein include but are not limited to those listed in Column B of Table 3. Classes of HDAC inhibitors for use in various embodiments of the compositions and methods disclosed herein include but are not limited to those listed in Column A of Table 4. Specific HDAC inhibitors for use in various embodiments of the compositions and methods disclosed herein include but are not limited to those listed in Column B of Table 4. All agents listed in Table 1 column B, Table 2 column B, Table 3 column B, Table 4 column B are understood to include derivatives or pharmaceutically acceptable salts thereof. All classes listed in Table 1 column A, Table 2 column A, Table 3 column A, Table 4 column A are understood to include both agents comprising that class and derivatives or pharmaceutically acceptable salts thereof. Members of each of these classes also include but are not limited to those described in pages 51-55 of Appendix A and pages 90-102 or Appendix A.

GSK3-beta inhibitors also include but are not limited to those agents that reduce GSK3-beta activity by more than 5, 10, 20, 30, or 50% when an otic cell line or primary cells obtained from otic tissue is exposed to the inhibitor at pharmaceutically acceptable concentrations and activity is assessed via Western blotting or other standard methods in the literature. A pharmaceutically acceptable concentration, as used herein, is a concentration of an active agent in a formulation that is non-toxic and can be delivered to the tissue of interest. In certain embodiments, the composition comprises a GSK3-beta inhibitor reducing GSK3-beta activity by more than 5, 10, 20, 30, or 50% using conditions described in this paragraph in combination with a notch agonist and/or HDAC inhibitor. "Highly potent GSK3-beta inhibitors are those that reduce GSK3-beta activity by more than 50% when an otic cell line or primary cells obtained from otic tissue is exposed to the inhibitor at pharmaceutically acceptable concentrations and activity is assessed via Western blotting or other standard methods in the literature.

Wnt Agonists

Exemplary Wnt agonists within the present disclosure appear in Table 2.

TABLE 2

Wnt Agonist

| Column A | Column B |
|---|---|
| Wnt Ligand | Wnt1/Int-1 |
| | Wnt-2/Irp (Int-I-related protein) |
| | Wnt-2b/13 |
| | Wnt-3/Int-4 |
| | Wnt-3a |
| | Wnt-4 |
| | Wnt-5a |
| | Wnt-5b |
| | Wnt-6 |
| | Wnt-7a |
| | Wnt-7b |
| | Wnt-8a/8d |
| | Wnt-8b |
| | Wnt-9a/14 |
| | Wnt-9b/14b/15 |
| | Wnt-10a |
| | Wnt-10b/12 |
| | Wnt-11 |
| | Wnt-16 |
| Wnt Related Protein | R-Spondin 1/2/3/4 |
| | Norrin |
| GSK3b inhibitor | |
| Other Wnt modulator | (hetero)arylpyrimidines |
| | Wnt Agonist |
| | IQ 1 |
| | DCA |
| | QS 11 |
| | WASP-1, ZINC00087877 |
| | WAY 316606, HCl |
| | WAY-262611, HCl |
| | HLY78 |
| | SKL2001 |
| | Cpd1 |
| | Cpd2 |

TABLE 2-continued

| Wnt Agonist | |
|---|---|
| Column A<br>Wnt Ligand | Column B<br>Wnt1/Int-1 |
| | cmpd 109 |
| | ISX 9 |
| | Cmpd 71 |
| | Cmpd 2 |
| | Selumetinib (AZD6244) |
| | Radicicol |
| | (hetero)arylpyrimidines |
| | Wnt Agonist |
| | WAY 316606, HCl |
| | WAY-262611, HCl |
| | SKL2001 |
| | ISX 9 |

Wnt-agonists also include but are not limited to those agents that increase Wnt activity by more than 5, 10, 20, 30, or 50% when an otic cell line or primary cells obtained from otic tissue is exposed to the agonist at pharmaceutically acceptable concentrations and activity is assessed via Western blotting or other standard methods in the literature. In certain embodiments, the composition comprises a Wnt agonist increasing Wnt activity by more than 5, 10, 20, 30, or 50% using conditions described in this paragraph in combination with a notch agonist and/or HDAC inhibitor. "Highly potent Wnt agonist are those that increase Wnt activity by more than 50% when an otic cell line or primary cells obtained from otic tissue is exposed to the agonist at pharmaceutically acceptable concentrations and activity is assessed via Western blotting or other standard methods in the literature.

Differentiation Inhibitors

Notch Agonists

Exemplary Notch agonists within the present disclosure appear in Table 3.

TABLE 3

| Notch Agonist | |
|---|---|
| Column A | Column B |
| Natural receptor Ligands | Jagged 1 |
| | Jagged 2 |
| | Delta-like 1 |
| | Delta-like 2 |
| | Delta-like 3 |
| | Delta-like 4 |
| | DSL peptide |
| | Delta 1 |
| | Delta D |
| Receptor antibodies | Notch 1 antibody |
| HDAC inhibitors | VPA |
| | TSA |
| | Tubastatin A |
| | Compound 7 |

Notch-agonistsalsoincludebutarenotlimitedtothoseagentsthatincreaseNotch activity by more than 5, 10, 20, 30, or 5000 when an otic cell line or primary cells obtained from otic tissue is exposed to the agonist at pharmaceutically acceptable concentrations and activity is assessed via Western blotting or other standard methods in the literature. In certain embodiments, the composition comprises a Notch agonist increasing Notch activity by more than 5, 10, 20, 30, or 50% using conditions described in this paragraph in combination with a GSK3-beta inhibitor or Wnt agonist. "Highly potent Notch agonist are those that increase Notch activity by more than 50% when an otic cell line or primary cells obtained from otic tissue is exposed to the agonist at pharmaceutically acceptable concentrations and activity is assessed via Western blotting or other standard methods in the literature.

HDAC Inhibitors

Exemplary HDAC Inhibitors within the present disclosure appear in Table 4.

TABLE 4

| HDAC Inhibitors | |
|---|---|
| Column A<br>Class | Column B<br>Agent |
| Hydroxamates | Trichostatin A (TSA) |
| Hydroxamates | SAHA (Zolinza, vorinostat) |
| Hydroxamates | 4-iodo-SAHA |
| Hydroxamates | SBHA |
| Hydroxamates | CBHA |
| Hydroxamates | LAQ-824 |
| Hydroxamates | PDX-101 (belinostat) |
| Hydroxamates | LBH-589 (panobinostat) |
| Hydroxamates | ITF2357 (Givinostat) |
| Hydroxamates | PCI-34051 |
| Hydroxamates | PCI-24781 (Abexinostat) |
| Hydroxamates | Tubastatin A |
| Hydroxamates | CUDC-101 |
| Hydroxamates | Compound 7 |
| Hydroxamates | Oxamflatin |
| Hydroxamates | ITF2357 |
| Hydroxamates | Bufexamac |
| Hydroxamates | APHA Compound 8 |
| Hydroxamates | JNJ-26481585 (Quisinostat) |
| Hydroxamates | Suberoylanilide-d5 Hydroxamic Acid |
| Hydroxamates | HDAC Inhibitor XXIV |
| Hydroxamates | Tubacin |
| Hydroxamates | Butyrylhydroxamic acid |
| Hydroxamates | 1-Naphthohydroxamic Acid |
| Hydroxamates | MC 1568 |
| Hydroxamates | SB939 (Pracinostat) |
| Hydroxamates | 4SC-201 (Resminostat) |
| Hydroxamates | Tefinostat (CHR-2845) |
| Hydroxamates | CHR-3996 |
| Hydroxamates | CG200745 |
| Cyclic peptide | Depsipeptide (Romidepsin, FK-228, FR 901228) |
| Cyclic peptide | Trapoxin A |
| Cyclic peptide | HC Toxin |
| Aliphatic Acid | Valproic Acid |
| Aliphatic Acid | VAHA |
| Aliphatic Acid | Phenyl butyrate |
| Aliphatic Acid | Butyrate |
| Aliphatic Acid | AN-9 |
| Benzamides | MS-275 (Entinostat) |
| Benzamides | MGCD0103 (Mocetinostat) |
| Benzamides | CI994 (Tacedinaline; PD-123654; GOE-5549; Acetyldinaline) |
| Benzamides | BML-210 |
| Hydroxamates | M 344 |
| Benzamides | Chidamide |
| Hydroxamates | 4-(dimethylamino)-N-[6-(hydroxyamino)-6-oxohexyl]-benzamide |
| Miscellaneous | Luteolin |
| Prodrug of thiol | PTACH |
| Miscellaneous | L-Carnitine |
| Miscellaneous | Biphenyl-4-sulfonyl chloride |
| Miscellaneous | SIRT1/2 Inhibitor VII |
| Hydroxamates | (S)-HDAC-42 |
| Hydroxamates | Indole-3-acetamide |
| Miscellaneous | NSC 3852 |
| Miscellaneous | PPM-18 |
| Miscellaneous | Ratjadone A, Synthetic |
| Benzamides | N-(2-Aminophenyl)-N'-phenylheptanediamide |

TABLE 4-continued

HDAC Inhibitors

| Column A Class | Column B Agent |
|---|---|
| Miscellaneous | Dihydrochlamydocin |
| Miscellaneous | 7-Aminoindole |
| Miscellaneous | Apicidin |
| Miscellaneous | Parthenolide |
| Hydroxamates | HNHA |
| Miscellaneous | Splitomicin |
| Benzamides | RGFP109 |
| Benzamides | RGFP136 |
| Benzamides | RGFP966 |
| Benzamides | 4SC-202 |
| Hydroxamates | ACY1215 |
| Miscellaneous | ME-344 |
| Miscellaneous | Sulforaphane |
| CF3Methyl Ketones | 6H |
| CF3Methyl Ketones | 27 |
| Aryl Ketones | 25 |
| Non classical | 5 |
| | Nexturastat A |
| | Droxinostat |
| | AR-42 |
| | Romidepsin (FK228, Depsipeptide) |
| | Scriptaid |
| | Sodium Phenylbutyrate |
| | TMP269 |
| | Thailandepsin A |
| | BRD9757 |
| | LMK235 |
| | HPOB |
| | CAY10603 |
| | Tasquinimod |
| | HDAC6 Inhibitor III |
| | HDAC Inhibitor XXIV |
| | HDAC Inhibitor IV |
| | HDAC Inhibitor XIX |
| | HDAC Inhibitor XXII |
| | HDAC Inhibitor VII |
| | HDAC Inhibitor II |
| | HDAC Inhibitor VI |
| | (−)-Depudecin |
| | KD 5170 |
| | TC-H 106 |
| | TCS HDAC6 20b |
| | Pyroxamide |
| | Chidamide |
| | HDAC-IN-1 |
| | HC Toxin |
| Hydroxamates | SAHA (Zolinza, vorinostat) |
| Hydroxamates | LBH-589 (panobinostat) |
| Hydroxamates | JNJ-26481585 (Quisinostat) |
| Cyclic peptide | Depsipeptide (Romidepsin, FK-228, FR 901228) |
| Benzamides | MGCD0103 (mocetinostat) |
| Prodrug of thiol | PTACH |
| Miscellaneous | Ratjadone A, Synthetic |
| Miscellaneous | Apicidin |
| CF3Methyl Ketones | 27 |
| Non classical | 5 |
| | Nexturastat A |
| | Droxinostat |
| | Scriptaid |
| | BRD9757 |
| | HPOB |
| | CAY10603 |
| | HDAC6 Inhibitor III |
| Hydroxamates | ACY1215 |
| Hydroxamates | Tubastatin A |
| Hydroxamates | Tubacin |
| Hydroxamates | Trichostatin A (TSA) |

HDAC inhibitors also include but are not limited to those agents that reduce HDAC activity by more than 5, 10, 20, 30, or 50% when an otic cell line or primary cells obtained from otic tissue is exposed to the inhibitor and activity is assessed via Western blotting or other standard methods in the literature. In certain embodiments, the composition comprises a HDAC inhibitor decreasing HDAC activity by more than 5, 10, 20, 30, or 50% using conditions described in this paragraph in combination with a GSK3-beta inhibitor or Wnt agonist. "Highly potent HDAC agonist are those that decreases HDAC activity by more than 50% when an otic cell line or primary cells obtained from otic tissue is exposed to the inhibitor at pharmaceutically acceptable concentrations and activity is assessed via Western blotting or other standard methods in the literature.

Representative methods to assess HDAC inhibitors may be found in:

Mak B C, Takemaru K, Kenerson H L, Moon R T, Yeung R S (2003). "The tuberin-hamartin complex negatively regulates beta-catenin signaling activity". J. Biol. Chem. 278(8): 5947-51. doi:10.1074/jbc.C200473200. PMID 12511557.

Nakamura T, Hamada F, Ishidate T, Anai K, Kawahara K, Toyoshima K, Akiyama T (1998). "Axin, an inhibitor of the Wnt signalling pathway, interacts with beta-catenin, GSK-3beta and APC and reduces the beta-catenin level". Genes Cells 3 (6): 395-403.doi:10.1046/j.1365-2443.1998.00198.x. PMID 9734785.

von Kries J P, Winbeck G, Asbrand C, Schwarz-Romond T, Sochnikova N, Dell'Oro A, Behrens J, Birchmeier W (2000). "Hot spots in beta-catenin for interactions with LEF-1, conductin and APC". Nat. Struct. Biol. 7 (9): 800-7. doi:10.1038/79039.PMID 10966653.

Schwarz-Romond T, Asbrand C, Bakkers J, Kühl M, Schaeffer H J, Huelsken J, Behrens J, Hammerschmidt M, Birchmeier W (2002). "The ankyrin repeat protein Diversin recruits Casein kinase Iepsilon to the beta-catenin degradation complex and acts in both canonical Wnt and Wnt/JNK signaling". Genes Dev. 16 (16): 2073-84. doi:10.1101/gad.230402.PMC 186448. PMID 12183362.

Wang L, Lin H K, Hu Y C, Xie S, Yang L, Chang C (2004). "Suppression of androgen receptor-mediated transactivation and cell growth by the glycogen synthase kinase 3 beta in prostate cells". J. Biol. Chem. 279 (31): 32444-52. doi:10.1074/jbc.M313963200.PMID 15178691.

Davies G, Jiang W G, Mason M D (2001). "The interaction between beta-catenin, GSK3beta and APC after motogen induced cell-cell dissociation, and their involvement in signal transduction pathways in prostate cancer". Int. J. Oncol. 18 (4): 843-7.doi:10.3892/ijo.18.4.843. PMID 11251183.

Kishida S, Yamamoto H, Hino S, Ikeda S, Kishida M, Kikuchi A (1999). "DIX domains of Dvl and axin are necessary for protein interactions and their ability to regulate beta-catenin stability". Mol. Cell. Biol. 19 (6): 4414-22. PMC 104400. PMID 10330181.

Hong Y R, Chen C H, Cheng D S, Howng S L, Chow C C (1998). "Human dynamin-like protein interacts with the glycogen synthase kinase 3beta". Biochem. Biophys. Res. Commun. 249 (3): 697-703. doi:10.1006/bbrc.1998.9253. PMID 9731200.

Wu, Xiaoyang; Shen Q T; Oristian D S; Lu C P; Zheng Q; Wang H W; Fuchs E (2011). "Skin Stem Cells Orchestrate Directional Migration by Regulating Microtubule-ACF7 Connections through GSK3b". Cell 144. doi:10.1016/j.cell.2010.12.033.

Li Y, Bharti A, Chen D, Gong J, Kufe D (1998). "Interaction of glycogen synthase kinase 3beta with the DF3/MUC1 carcinoma-associated antigen and beta-catenin". Mol. Cell. Biol. 18 (12): 7216-24. PMC 109303. PMID 9819408.

Li Y, Kuwahara H, Ren J, Wen G, Kufe D (2001). "The c-Src tyrosine kinase regulates signaling of the human DF3/MIUC1 carcinoma-associated antigen with GSK3 beta and beta-catenin". J. Biol. Chem. 276 (9): 6061-4. doi:10.1074/jbc.C000754200.PMID 11152665.

Guo X, Ramirez A, Waddell D S, Li Z, Liu X, Wang X F (2008). "Axin and GSK3-control Smad3 protein stability and modulate TGF-signaling". Genes Dev. 22 (1): 106-20.doi:10.1101/gad.1590908. PMC 2151009. PMID 18172167.

Foltz D R, Santiago M C, Berechid B E, Nye J S (2002). "Glycogen synthase kinase-3beta modulates notch signaling and stability". Curr. Biol. 12 (12): 1006-11. doi:10.1016/50960-9822(02)00888-6. PMID 12123574.

Espinosa L, Ingles-Esteve J, Aguilera C, Bigas A (2003). "Phosphorylation by glycogen synthase kinase-3 beta down-regulates Notch activity, a link for Notch and Wnt pathways". J. Biol. Chem. 278 (34): 32227-35. doi:10.1074/jbc.M304001200. PMID 12794074.

Watcharasit P, Bijur G N, Zmijewski J W, Song L, Zmijewska A, Chen X, Johnson G V, Jope R S (2002). "Direct, activating interaction between glycogen synthase kinase-3beta and p53 after DNA damage". Proc. Natl. Acad. Sci. U.S.A. 99 (12): 7951-5.doi:10.1073/pnas.122062299. PMC 123001. PMID 12048243.

Dai F, Yu L, He H, Chen Y, Yu J, Yang Y, Xu Y, Ling W, Zhao S (2002). "Human serum and glucocorticoid-inducible kinase-like kinase (SGKL) phosphorylates glycogen syntheses kinase 3 beta (GSK-3beta) at serine-9 through direct interaction". Biochem. Biophys. Res. Commun. 293 (4): 1191-6. doi:10.1016/0006-291X(02)00349-2. PMID 12054501.

In some embodiments, the Differentiation Inhibitor is chosen to have solubility properties relative to the Stemness Driver that favors faster release of the Differentiation Inhibitor relative to the Stemness Driver in an aqueous environment. In some embodiments, the Differentiation Inhibitor has a solubility in phosphate buffered saline that is 5, 10, 50, 100, 500, 1000, or 5000-fold higher than that of the Stemness Driver.

TGF-β Inhibitors

In certain embodiments, the one or more additional agents comprises a TGFβ type I receptor inhibitor. Exemplary TGF-β Inhibitors appear in Table 5. TGF-beta type I receptor inhibitors include but are not limited to 2-(3-(6-Methylpyridin-2-yl)-1H-pyrazol-4-yl)-1,5 napththyridine, [3-(Pyridin-2-yl)-4-(4-quinoyl)]-1H-pyrazole, and 3-(6-Methylpyridin-2-yl)-4-(4-quinolyl)-1-phenylthiocarbamoyl-1H-pyrazole, which can be purchased from Calbiochem (San Diego). Other small molecule inhibitors include, but are not limited to, SB-431542 (see e.g., Halder et al., 2005; Neoplasia 7(5):509-521), SM16 (see e.g., Fu, K et al., 2008; Arteriosclerosis, Thrombosis and Vascular Biology 28(4):665), and SB-505124 (see e.g., Dacosta Byfield, S., et al., 2004; Molecular Pharmacology 65:744-52), among others.

TABLE 5

TGF-β Inhibitors

| Class | Agent | Alternative Name |
| --- | --- | --- |
| Tgf-beta-R1 inhibitor | LY-364947 | 616451, TGF-β RI Kinase Inhibitor I, CAS 396129-53-6, [3-(Pyridin-2-yl)-4-(4-quinonyl)]-1H-pyrazole, ALK5 Inhibitor I, LY-364947, HTS-466284 |
| Tgf-beta-R1 inhibitor | Repsox | 616452, TGF-β RI Kinase Inhibitor II, CAS 446859-33-2, 2-(3-(6-Methylpyridin-2-yl)-1H-pyrazol-4-yl)-1,5-naphthyridine |
| Tgf-beta-R1 inhibitor | SB-505124 | 616453, TGF-β RI Kinase Inhibitor III, CAS 356559-13-22-(5-Benzo[1,3]dioxol-4-yl-2-tert-butyl-1H-imidazol-4-yl)-6-methylpyridine, HCl, ALK5 Inhibitor III, SB-505124, HCl |
| Tgf-beta-R1 inhibitor | A-83-01 | 616454, TGF-β RI Kinase Inhibitor IV - CAS 909910-43-6, 3-(6-Methylpyridin-2-yl)-4-(4-quinolyl)-1-phenylthiocarbamoyl-1H-pyrazole, A-83-01, ALK5 Inhibitor IV |
| Tgf-beta-R1 inhibitor | SD-208 | 616456, TGF-β RI Kinase Inhibitor V, CAS 627536-09-8, 2-(5-Chloro-2-fluorophenyl)pteridin-4-yl)pyridin-4-yl amine, SD-208, ALK5 Inhibitor V |
| Tgf-beta-R1 inhibitor | SB-431542 | 616461, TGF-β RI Kinase Inhibitor VI, SB431542 - CAS 301836-41-9, 4-[4-(3,4-Methylenedioxyphenyl)-5-(2-pyridyl)-1H-imidazol-2-yl]benzamide, Dihydrate, 4-[4-(1,3-Benzodioxol-5-yl)-5-(2-pyridyl)-1H-imidazol-2-yl]benzamide, Dihydrate |
| Tgf-beta-R1 inhibitor | TGF-β RI Kinase Inhibitor VII | 616458, TGF-β RI Kinase Inhibitor VII - CAS 666729-57-3, 1-(2-((6,7-Dimethoxy-4-quinolyl)oxy)-(4,5-dimethylphenyl)-1-ethanone, ALK5 Inhibitor VII |
| Tgf-beta-R1 inhibitor | SB-525334 | 616459, TGF-β RI Kinase Inhibitor VIII - CAS 356559-20-1, SB-525334, 6-(2-tert-Butyl-5-(6-methyl-pyridin-2-yl)-1H-imidazol-4-yl)-quinoxaline, ALK5 Inhibitor VIII |
| Tgf-beta-R1 inhibitor | TGF-β RI Kinase Inhibitor IX | 616463, TGF-β RI Kinase Inhibitor IX, 4-((4-((2,6-Dimethylpyridin-3-yl)oxy)pyridin-2-yl)amino)benzenesulfonamide, ALK5 Inhibitor IX |
| Tgf-beta-R1 inhibitor | GW788388 | 4-(4-(3-(pyridin-2-yl)-1H-pyrazol-4-yl)pyridin-2-yl)-N-(tetrahydro-2H-pyran-4-yl)benzamide |

TABLE 5-continued

TGF-β Inhibitors

| Class | Agent | Alternative Name |
|---|---|---|
| Tgf-beta-R1 inhibitor | LY2109761 | 7-(2-morpholinoethoxy)-4-(2-(pyridin-2-yl)-5,6-dihydro-4H-pyrrolo[1,2-b]pyrazol-3-yl)quinoline |
| Tgf-beta-R1 inhibitor | Galunisertib (LY2157299) | 4-(2-(6-methylpyridin-2-yl)-5,6-dihydro-4H-pyrrolo[1,2-b]pyrazol-3-yl)quinoline-6-carboxamide |
| Tgf-beta-R1 inhibitor | EW-7197 | N-(2-fluorophenyl)-5-(6-methyl-2-pyridinyl)-4-[1,2,4]triazolo[1,5-a]pyridin-6-yl-1H-imidazole-2-methanamine |
| Tgfb production inhibitor | Pirfenidone | 2(1H)-Pyridinone, 5-methyl-1-phenyl- |
| Tgf-beta-R1 inhibitor | K02288 | 3-[(6-Amino-5-(3,4,5-trimethoxyphenyl)-3-pyridinyl]phenol |
| Tgf-beta-R1 inhibitor | D 4476 | 4-[4-(2,3-Dihydro-1,4-benzodioxin-6-yl)-5-(2-pyridinyl)-1H-imidazol-2-yl]benzamide |
| Tgf-beta-R1 inhibitor | R 268712 | 4-[2-Fluoro-5-[3-(6-methyl-2-pyridinyl)-1H-pyrazol-4-yl]phenyl]-1H-pyrazole-1-ethanol |
| Other | ITD 1 | 4-[1,1'-Biphenyl]-4-yl-1,4,5,6,7,8-hexahydro-2,7,7-trimethyl-5-oxo-3-quinolinecarboxylic acid ethyl ester |
| Smad3 inhibitor | SIS3 | 1,2,3,4-Tetrahydro-6,7-dimethoxy-2-[(2E)-3-(1-phenyl-1H-pyrrolo[2,3-b]pyridin-3-yl)-1-oxo-2-propenyl]-isoquinoline hydrochloride |
| Tgf-beta-R1 inhibitor | A77-01 | 4-[5-(6-methylpyridin-2-yl)-1H-pyrazol-4-yl]quinoline |
| Other | Asiaticoside | |
| Tgf-beta-R1 inhibitor | SM16 | 4-(5-(benzo[d][1,3]dioxol-5-yl)-4-(6-methylpyridin-2-yl)-1H-imidazol-2-yl)bicyclo[2.2.2]octane-1-carboxamide |
| Tgf-beta antibody | ID11 | |
| Tgf-beta antibody | 2G7 | |
| Tgf-beta antibody | GC-1008 | Fresolimumab |
| Tgf-beta antibody | CAT-152 | Lerdelimimab |
| Tgf-beta antibody | CAT-192 | Metelimumab |
| TGf-beta Receptor antibody | PF-03446962 | |
| Tgf-beta antibody | SR-2F | |
| Tgf-beta antibody | 2G7 | |
| Tgf-beta antibody | LY2382770 | |
| Tgf-beta antibody | IMC-TR1 | |
| Tgf-beta antibody | STX-100 | |
| TGF-beta antagonist Recombinant protein | TGF-PRII: Fc betaglycan/TGF-PRIII | |
| Oligonucleotide inhibitor | AP12009 | Trabedersen, antisense molecule |
| Oligonucleotide inhibitor | AP11014 | |
| Oligonucleotide inhibitor | AP15012 | |
| | LY-550410 | |
| | LY-580276 | |
| | LY-364947 | |
| | LY-2109761 | |
| | LY-2157299 | Galunisertib |
| | LY-573636 | Is this TGF b inhibitor/YES |
| | SB- 505124 | |
| | SB-431542 | |
| | SB-525234 | |
| | SD-208 | |
| | SD-093 | |
| | Ki-26894 | |
| | NPC-30345 | |
| | SX-007 | |
| | IN-1130 | |
| | pyrrole-imidazole polyamide | Gene siliencing |
| | EW-7203 | |
| | EW-7195 | Structure |
| | EW-7197 | |
| | GW6604 | |
| | U.S. Pat. No. 7,087,626 | Pyrrole derivatives as pharmaceutical agents |

TABLE 5-continued

TGF-β Inhibitors

| Class | Agent | Alternative Name |
|---|---|---|
|  | U.S. Pat. No. 6,476,031 | Quinazoline derivatives as medicaments |
|  | U.S. Pat. No. 7,723,486, and EP 0945464 | Antibodies to TGF-β |
| Peptide | Trx-xFoxHIb | Smad-interacting peptide aptamers |
| Peptide | Trx-Lefl |  |
| Peptide | Distertide (pI44) |  |
| Peptide | pI7 |  |
| Peptide | LSKL |  |
| dihydropyrrlipyrazole-based scaffold | See U.S. Patent U.S. Pat. No. 8,298,825 B1 |  |
| imidazole-based scaffold | See U.S. Patent U.S. Pat. No. 8,298,825 B1 |  |
| pyrazolopyridine-based scaffold | See U.S. Patent U.S. Pat. No. 8,298,825 B1 |  |
| pyrazole-based scaffold |  | See U.S. Patent U.S. Pat. No. 8,298,825 B1 |
| imidazopyridine-based scaffold | See U.S. Patent U.S. Pat. No. 8,298,825 B1 |  |
| triazole-based scaffold |  | See U.S. Patent U.S. Pat. No. 8,298,825 B1 |
| pyridopyrimidine-based scaffold | See U.S. Patent U.S. Pat. No. 8,298,825 B1 |  |
| pyrrolopyrazole-based scaffold | See U.S. Patent U.S. Pat. No. 8,298,825 B1 |  |
| isothiazole-based scaffold | See U.S. Patent U.S. Pat. No. 8,298,825 B1 |  |
| oxazole-based scaffold |  | See U.S. Patent U.S. Pat. No. 8,298,825 B1 |
| Tgf-beta-R1 inhibitor | Repsox | 616452, TGF-β RI Kinase Inhibitor II, CAS 446859-33-2, 2-(3-(6-Methylpyridin-2-yl)-1H-pyrazol-4-yl)-1,5-naphthyridine |
| Tgf-beta-R1 inhibitor | Galunisertib (LY2157299) | 4-(2-(6-methylpyridin-2-yl)-5,6-dihydro-4H-pyrrolo[1,2-b]pyrazol-3-yl)quinoline-6-carboxamide |
| Tgf-beta-R1 inhibitor | EW-7197 | N-(2-fluorophenyl)-5-(6-methyl-2-pyridinyl)-4-[1,2,4]triazolo[1,5-a]pyridin-6-yl-1H-imidazole-2-methanamine |
| Tgfb production inhibitor | Pirfenidone | 2(1H)-Pyridinone, 5-methyl-1-phenyl- |
|  | LY-2157299 | Galunisertib |
| Tgf-beta-R1 inhibitor | SB-505124 | 616453, TGF-β RI Kinase Inhibitor III, CAS 356559-13-22-(5-Benzo[1,3]dioxol-4-yl-2-tert-butyl-1H-imidazol-4-yl)-6-methylpyridine, HCl, ALK5 Inhibitor III, SB-505124, HCl |
| Tgf-beta-R1 inhibitor | SB-525334 | 616459, TGF-β RI Kinase Inhibitor VIII - CAS 356559-20-1, SB-525334, 6-(2-tert-Butyl-5-(6-methyl-pyridin-2-yl)-1H-imidazol-4-yl)-quinoxaline, ALK5 Inhibitor VIII |
| Tgf-beta-R1 inhibitor | TGF-β RI Kinase Inhibitor IX | 616463, TGF-β RI Kinase Inhibitor IX, 4-((4-((2,6-Dimethylpyridin-3-yl)oxy)pyridin-2-yl)amino)benzenesulfonamide, ALK5 Inhibitor IX |
| Tgf-beta-R1 inhibitor | R 268712 | 4-[2-Fluoro-5-[3-(6-methyl-2-pyridinyl)-1H-pyrazol-4-yl]phenyl]-1H-pyrazole-1-ethanol |
|  | SB- 505124 | Pyridine, 2-[4-(1,3-benzodioxol-5-yl)-2-(1,1-dimethylethyl)-1H-imidazol-5-yl]-6-methyl-, hydrochloride (1:1) |
|  | SD-208 |  |
|  | IN-1130 |  |
|  | EW-7197 |  |
| Tgf-beta-R1 inhibitor | A-83-01 | 616454, TGF-β RI Kinase Inhibitor IV - CAS 909910-43-6, 3-(6-Methylpyridin-2-yl)-4-(4-quinolyl)-1-phenylthiocarbamoyl-1H-pyrazole, A-83-01, ALK5 Inhibitor IV |
| Tgf-beta-R1 inhibitor | SB-431542 | 616461, TGF-β RI Kinase Inhibitor VI, SB431542 - CAS 301836-41-9, 4-[4-(3,4-Methylenedioxyphenyl)-5-(2-pyridyl)-1H-imidazol-2-yl]benzamide, Dihydrate, 4-[4-(1,3-Benzodioxol-5-yl)-5-(2-pyridyl)-1H-imidazol-2-yl]benzamide, Dihydrate |
| Tgf-beta-R1 inhibitor | R 268712 | 4-[2-Fluoro-5-[3-(6-methyl-2-pyridinyl)-1H-pyrazol-4-yl]phenyl]-1H-pyrazole-1-ethanol |

Additional Therapeutic Agents

In certain embodiments, the administering step comprises administering or causing to be administered to the stem cell population one or more additional agents (e.g., in addition to (i) and (ii)). In certain embodiments, the one or more additional agents comprises an ROS inhibitor or scavenger. ROS scavengers include but are not limited to enzymes catalase, glutathione peroxidase and ascorbate peroxidase. Additionally, vitamins A, E, and C are known to have scavenger activity. Minerals such as selenium and manganese can also be efficacious compounds for scavenging ROS.

ROS inhibitors include but are not limited to alpha lipoic acid, a superoxide dismutase mimetic, or a catalase mimetic. The superoxide dismutase mimetic or the catalase mimetic can be MnTBAP (Mn(III)tetrakis(4-benzoic acid)porphyrin chloride)(produced by Calbiochem), ZnTBAP (Zn(III)tetrakis(4-benzoic acid)porphyrin chloride), SC-55858 (manganese (11) dichloro (2R,3R,8R,9R-bis-cyclohexano-1,4,7,10, 13-pentaazacyclopentadecane)] Euk-134 (3,3'-methoxysalenMn(III)) (produced by Eukarion), M40403 (dichloro [(4aR,13 aR,17aR,21 aR)-1,2,3,4,4a,5,6,12,13,13 a,14,15,16,17,17a,18,19,20,21-eicosahydro-11,7-nitrilo-7H-dibenzo[1,4,7,10]tetraazacycloheptadecine-kappaNS, kappaN13,kappaN18,kappaN21,kappaN22] manganese) (produced by Metaphore), AEOL 10112, AEOL 10113, and AEOL 10150 (manganese(III) mesotetrakis (di-N-ethylimidazole) porphyrin)(all AEOL compounds being produced by Incara Pharmaceuticals). Alternatively, the ROS inhibitor can be an iron chelator. Of the iron chelators, deferoxamine or DFO may be the most important, because it is FDA-approved for treatment of iron excess in thallasemia. In addition, the ROS inhibitor can be a composition comprised of a mixture of iron chelators.

ROS inhibitors may be radiation protectors, and include such compounds as, for example, uric acid, buthionine sulfoximine, diethyl maleate, vitamin E, vitamin C, cysteine such as N-acetyl cysteine, or glutathione, metronidazole, and a retinoid such as, e.g., vitamin A. Additional ROS scavengers may be found at In certain embodiments, the one or more additional agents comprises vitamin C or a derivative thereof. In certain embodiments, the one or more additional agents comprises a TGFβ type I receptor inhibitor. TGF-beta type I receptor inhibitors include but are not limited to 2-(3-(6-Methylpyridin-2-yl)-1H-pyrazol-4-yl)-1,5 napththyridine, [3-(Pyridin-2-yl)-4-(4-quinoyl)]-1H-pyrazole, and 3-(6-Methylpyridin-2-yl)-4-(4-quinolyl)-1-phenylthiocarbamoyl-1H-pyrazole, which can be purchased from Calbiochem (San Diego, Calif.). Other small molecule inhibitors include, but are not limited to, SB-431542 (see e.g., Halder et al., 2005; Neoplasia 7(5):509-521), SM16 (see e.g., Fu, K et al., 2008; Arteriosclerosis, Thrombosis and Vascular Biology 28(4): 665), and SB-505124 (see e.g., Dacosta Byfield, S., et al., 2004; Molecular Pharmacology 65:744-52), among others.

In one embodiment, the ALK5 inhibitor 2-(3-(6-Methylpyridin-2-yl)-1H-pyrazol-4-yl)-1,5 napththyridine is used with the methods described herein. This inhibitor is also referred to herein as ALK5 inhibitor II and is available commercially from Calbiochem (Cat. No. 616452; San Diego, Calif.). In one embodiment, the inhibitor is SB 431542, an ALK-4, -5, -7inhibitor, commercially available from Sigma (product no. 54317; Saint Louis, Mo.). SB 431542 is also referred to by the following chemical names: 4-[4-(1,3-Benzodioxol-5-yl)-5-(2-pyridinyl)-1H-imidazol-2-yl]-benzamide, 4-[4-(3,4-methylenedioxyphenyl)-5-(2-pyridyl)-1H-imidazol-2-yl]-benzamide, or 4-(5-benzol[1,3] dioxol-5-yl-4-pyridin-2-yl-1H-imidazol-2-yl)-benzamide hydrate.

Small molecules inhibitors of TGF-β signaling can be classified based on the basic scaffold of the molecule. For example, TGF-β signaling inhibitors can be based on the dihydropyrrlipyrazole-based scaffold, imidazole-based scaffold, pyrazolopyridine-based scaffold, pyrazole-based scaffold, imidazopyridine-based scaffold, triazole-based scaffold, pyridopyrimidine-based scaffold, pyrrolopyrazole-based scaffold, isothiazole-based scaffold and oxazole-based scaffold.

Inhibitors of TGF-β signaling are described, for example, in Callahan, J. F. et al., J. Med. Chem. 45, 999-1001 (2002); Sawyer, J. S. et al., J. Med. Chem. 46, 3953-3956 (20031; Gellibert, F. et al., J. Med. Chem. 47, 4494-4506 (2004); Tojo, M. et al., Cancer Sci. 96: 791-800 (2005); Valdimarsdottir, G. et al., APMIS 113, 773-389 (2005); Petersen et al. Kidney International 73, 705-715 (2008); Yingling, J. M. et al., Nature Rev. Drug Disc. 3, 1011-1022 (2004); Byfield, S. D. et al., Mol. Pharmacol., 65, 744-752 (2004); Dumont, N, et al., Cancer Cell 3, 531-536 (2003); WO Publication No. 2002/094833; WO Publication No. 2004/026865; WO Publication No. 2004/067530; WO Publication No. 209/032667; WO Publication No. 2004/013135; WO Publication No. 2003/097639; WO Publication No. 2007/048857; WO Publication No. 2007/018818; WO Publication No. 2006/018967; WO Publication No. 2005/039570; WO Publication No. 2000/031135; WO Publication No. 1999/058128; U.S. Pat. Nos. 6,509,318; 6,090,383; 6,419,928; 9,927,738; 7,223,766; 6,476,031; 6,419,928; 7,030,125; 6,943,191; U.S. Publication No. 2005/0245520; U.S. Publication No. 2004/0147574; U.S. Publication No. 2007/0066632; U.S. Publication No. 2003/0028905; U.S. Publication No. 2005/0032835; U.S. Publication No. 2008/0108656; U.S. Publication No. 2004/015781; U.S. Publication No. 2004/0204431; U.S. Publication No. 2006/0003929; U.S. Publication No. 2007/0155722; U.S. Publication No. 2004/0138188 and U.S. Publication No. 2009/0036382, the contents of each which are herein incorporated by reference in their entirety.

Oligonucleotide based modulators of TGF-β signaling, such as siRNAs and antisense oligonucleotides, are described in U.S. Pat. Nos. 5,731,424; 6,124,449; U.S. Publication Nos. 2008/0015161; 2006/0229266; 2004/0006030; 2005/0227936 and 2005/0287128, each of which are herein incorporated by reference in their entirety. Other antisense nucleic acids and siRNAs can be obtained by methods known to one of ordinary skill in the art.

Exemplary inhibitors of TGF-β signaling include, but are not limited to, AP-12009 (TGF-β Receptor type II antisense oligonucleotide), Lerdelimumab (CAT 152, antibody against TGF-β Receptor type II) GC-1008 (antibody to all isoforms of human TGF-β), ID11 (antibody to all isoforms of murine TGF-0), soluble TGF-β, soluble TGF-β Receptor type II, dihydropyrroloimidazole analogs (e.g., SKF-104365), tri-arylimidazole analogs (e.g., SB-202620 (4-(4-(4-fluorophenyl)-5-(pyridin-4-yl)-1H-imidazol-2-yl)benzoic acid) and SB-203580 (4-(4-Fluorophenyl)-2-(4-methylsulfinyl phenyl)-5-(4-pyridyl)-1H-imidazole)), RL-0061425, 1,5-naphthyridine aminothiazole and pyrazole derivatives (e.g., 4-(6-methyl-pyridin-2-yl)-5-(1,5-naphthyridin-2-yl)-1,3-thiazole-2-amine and 2-[3-(6-methyl-pyridin-2-yl)-1H-pyrazole-4-yl]-1,5-naphthyridine), SB-431542 (4-(5-Benzol [1,3]dioxol-5-yl-4-pyridin-2-yl-1H-imidazol-2-yl)-benzamide), GW788388 (4-(4-(3-(pyridin-2-yl)-1H-pyrazol-4-yl)pyridin-2-yl)-N-(tetrahydro-2H-pyran-4-yl)

benzamide), A-83-01 (3-(6-Methyl-2-pyridinyl)-N-phenyl-4-(4-quinolinyl)-1H-pyrazole-1-carbothioamide), Decorin, Lefty 1, Lefty 2, Follistatin, Noggin, Chordin, Cerberus, Gremlin, Inhibin, BIO (6-bromo-indirubin-3'-oxime), Smad proteins (e.g., Smad6, Smad7), and Cystatin C.

Inhibitors of TGF-β signaling also include molecules which inhibit TGF-β Receptor type I. Inhibitors of TGF-β Receptortype I are described in Byfield, S. D., and Roberts, A. B., Trends Cell Biol. 14, 107-111 (2004); Sawyer J. S. et al., Bioorg. Med. Chem. Lett. 14, 3581-3584 (2004); Sawyer, J. S. et al., J. Med. Chem. 46, 3953-3956 (2003); Byfield, S. D. et al., Mol. Pharmacol. 65, 744-752 (2004); Gellibert, F. et al., J. Med. Chem. 47, 4494-4506 (2004); Yingling, J. M. et al., Nature Rev. Drug Disc. 3, 1011-1022 (2004); Dumont, N, et al., Cancer Cell 3, 531-536 (2003); Tojo, M. et al., Cancer Sci. 96: 791-800 (2005); WO Publication No. 2004/026871; WO Publication No. 2004/021989; WO Publication No. 2004/026307; WO Publication No. 2000/012497; U.S. Pat. Nos. 5,731,424; 5,731,144; 7,151,169; U.S. Publication No. 2004/00038856 and U.S. Publication No. 2005/0245508, contents of all of which are herein incorporated in their entireties.

Combinations of Agents

In certain embodiments, the composition comprises an agent within the classes of Table 1, Column A (or a derivative or pharmaceutically acceptable salt thereof) and an agent within the classes of Table 3, Column A (or a derivative or pharmaceutically acceptable salt thereof). In certain embodiments, the composition comprises an agent within the classes of Table 1, Column A (or a derivative or pharmaceutically acceptable salt thereof) and an agent within the classes of Table 4, Column A (or a derivative or pharmaceutically acceptable salt thereof). In certain embodiments, the composition comprises an agent within the classes of Table 2, Column A (or a derivative or pharmaceutically acceptable salt thereof) and an agent within the classes of Table 3, Column A (or a derivative or pharmaceutically acceptable salt thereof). In certain embodiments, the composition comprises an agent within the classes of Table 2, Column A (or a derivative or pharmaceutically acceptable salt thereof) and an agent within the classes of Table 4, Column A (or a derivative or pharmaceutically acceptable salt thereof).

In certain embodiments, the composition comprises an agent within the agents of Table 1, Column B (or a derivative or pharmaceutically acceptable salt thereof) and an agent within the agents of Table 3, Column B (or a derivative or pharmaceutically acceptable salt thereof). In certain embodiments, the composition comprises an agent within the agents of Table 1, Column B (or a derivative or pharmaceutically acceptable salt thereof) and an agent within the agents of Table 4, Column B (or a derivative or pharmaceutically acceptable salt thereof). In certain embodiments, the composition comprises an agent within the agents of Table 2, Column B (or a derivative or pharmaceutically acceptable salt thereof) and an agent within the agents of Table 3, Column B (or a derivative or pharmaceutically acceptable salt thereof). In certain embodiments, the composition comprises an agent within the agents of Table 2, Column B (or a derivative or pharmaceutically acceptable salt thereof) and an agent within the agents of Table 4, Column B (or a derivative or pharmaceutically acceptable salt thereof).

In certain embodiments, the composition comprises a combination of agents including (i) a GSK3-beta inhibitor and/or Wnt agonist (or a derivative or pharmaceutically acceptable salt thereof), and (ii) a notch agonist and/or HDAC inhibitor, where these agents are drawn from Table 1-4, respectively (or a derivative or pharmaceutically acceptable salt thereof).

In certain embodiments, the composition comprises (i) a GSK3-beta inhibitors drawn from aminopyrimidines, inorganic atoms, or thiadiazolidindiones (or a derivative or pharmaceutically acceptable salt thereof) and (ii) a notch agonist and/or HDAC inhibitor drawn from Table 3-4 (or a derivative or pharmaceutically acceptable salt thereof). In certain embodiments, the composition comprises (i) a Wnt agonist drawn from GSK3-beta inhibitors, Wnt ligand, or Wnt related protein (or a derivative or pharmaceutically acceptable salt thereof) and (ii) a notch agonist and/or HDAC inhibitor drawn from Table 3-4 (or a derivative or pharmaceutically acceptable salt thereof). In certain embodiments, the composition comprises (i) a Notch agonist drawn from HDAC inhibitors, or Natural receptor ligand (or a derivative or pharmaceutically acceptable salt thereof) and (ii) a GSK3-beta inhibitor and/or Wnt agonist drawn from Table 1-2 (or a derivative or pharmaceutically acceptable salt thereof). In certain embodiments, the composition comprises an HDAC inhibitor drawn from Hydroxamates, Aliphatic Acid, or Benzamides (or a derivative or pharmaceutically acceptable salt thereof) and (ii) a GSK3-beta inhibitor and/or Wnt agonist drawn from Table 1-2 (or a derivative or pharmaceutically acceptable salt thereof). In certain embodiments, the composition comprises a combination of agents including (i) a GSK3-beta inhibitor and/or Wnt agonist (or a derivative or pharmaceutically acceptable salt thereof) and (ii) a notch agonist and/or HDAC inhibitor (or a derivative or pharmaceutically acceptable salt thereof), where these agents are drawn from Table 1-4, respectively.

In certain embodiments, the composition comprises (i) a GSK3-beta inhibitors drawn from CHIR99021, Lithium, or NP031112(Tideglusib) (or a derivative or pharmaceutically acceptable salt thereof) and (ii) a notch agonist and/or HDAC inhibitor drawn from Table 3-4 (or a derivative or pharmaceutically acceptable salt thereof). In certain embodiments, the composition comprises (i) a Wnt agonist drawn from CHIR99021, Wnt3a, or R-spondin1 (or a derivative or pharmaceutically acceptable salt thereof) and (ii) a notch agonist and/or HDAC inhibitor drawn from Table 3-4 (or a derivative or pharmaceutically acceptable salt thereof). In certain embodiments, the composition comprises (i) a Notch agonist drawn from Valproic Acid, SAHA (vorinostat), Jagged 1, Delta-like1, or Delta-like 4 (or a derivative or pharmaceutically acceptable salt thereof) and (ii) a GSK3-beta inhibitor and/or Wnt agonist drawn from Table 1-2 (or a derivative or pharmaceutically acceptable salt thereof). In certain embodiments, the composition comprises an HDAC inhibitor drawn from Valproic Acid, SAHA (vorinostat), or Tubastatin A (or a derivative or pharmaceutically acceptable salt thereof) and (ii) a GSK3-beta inhibitor and/or Wnt agonist drawn from Table 1-2 (or a derivative or pharmaceutically acceptable salt thereof). In certain embodiments, the composition comprises a combination of agents including (i) a GSK3-beta inhibitor and/or Wnt agonist (or a derivative or pharmaceutically acceptable salt thereof) and (ii) a notch agonist and/or HDAC inhibitor, where these agents are drawn from Table 1-4 (or a derivative or pharmaceutically acceptable salt thereof), respectively.

In certain embodiments, the composition comprises (i) a GSK3-beta inhibitors drawn from aminopyrimidines, inorganic atoms, or thiadiazolidindiones (or a derivative or pharmaceutically acceptable salt thereof) and (ii) a highly potent notch agonist and/or highly potent HDAC inhibitor drawn from Table 3-4 (or a derivative or pharmaceutically acceptable salt thereof). In certain embodiments, the composition comprises (i) a Wnt agonist drawn from GSK3-beta inhibitors, Wnt ligand, or Wnt related protein (or a derivative or pharmaceutically acceptable salt thereof) and (ii) a highly potent notch agonist and/or highly potent HDAC inhibitor drawn from Table 3-4 (or a derivative or pharmaceutically acceptable salt thereof). In certain embodiments, the composition comprises (i) a Notch agonist drawn from HDAC inhibitors, or Natural receptor ligand (or a derivative or pharmaceutically acceptable salt thereof) and (ii) a highly potent GSK3-beta inhibitor and/or highly potent Wnt agonist drawn from Table 1-2 (or a derivative or pharmaceutically acceptable salt thereof). In certain embodiments, the composition comprises an HDAC inhibitor drawn from Hydroxamates, Aliphatic Acid, or Benzamides (or a derivative or pharmaceutically acceptable salt thereof) and (ii) a highly potent GSK3-beta inhibitor and/or highly potent Wnt agonist drawn from Table 1-2 (or a derivative or pharmaceutically acceptable salt thereof).

In certain embodiments, the composition comprises (i) a GSK3-beta inhibitors drawn from CHIR99021, Lithium, or NP031112(Tideglusib) (or a derivative or pharmaceutically acceptable salt thereof) and (ii) a highly potent notch agonist and/or highly potent HDAC inhibitor drawn from Table 3-4 (or a derivative or pharmaceutically acceptable salt thereof). In certain embodiments, the composition comprises (i) a Wnt agonist drawn from CHIR99021, Wnt3a, or R-spondin1 (or a derivative or pharmaceutically acceptable salt thereof) and (ii) a highly potent notch agonist and/or highly potent HDAC inhibitor drawn from Table 3-4 (or a derivative or pharmaceutically acceptable salt thereof). In certain embodiments, the composition comprises (i) a Notch agonist drawn from Valproic Acid, SAHA (vorinostat), Jagged 1, Delta-like1, or Delta-like 4 (or a derivative or pharmaceutically acceptable salt thereof) and (ii) a highly potent GSK3-beta inhibitor and/or highly potent Wnt agonist drawn from Table 1-2 (or a derivative or pharmaceutically acceptable salt thereof). In certain embodiments, the composition comprises an HDAC inhibitor drawn from Valproic Acid, SAHA (vorinostat), or Tubastatin A (or a derivative or pharmaceutically acceptable salt thereof) and (ii) a highly potent GSK3-beta inhibitor and/or highly potent Wnt agonist drawn from Table 1-2 (or a derivative or pharmaceutically acceptable salt thereof).

In certain embodiments, the composition comprises a combination of agents including (i) a GSK3-beta inhibitor and/or Wnt agonist (or a derivative or pharmaceutically acceptable salt thereof), and a second agent which is unique from the first agent and is (ii) a notch agonist and/or HDAC inhibitor (or a derivative or pharmaceutically acceptable salt thereof).

In certain embodiments, the composition comprises a combination of agents including (i) a highly potent GSK3-beta inhibitor and/or highly potent Wnt agonist (or a derivative or pharmaceutically acceptable salt thereof) and (ii) a highly potent notch agonist and/or highly potent HDAC inhibitor (or a derivative or pharmaceutically acceptable salt thereof). In certain embodiments the composition comprises a combination of agents including (i) a highly potent GSK3-beta inhibitor and/or highly potent Wnt agonist (or a derivative or pharmaceutically acceptable salt thereof) and (ii) a notch agonist and/or HDAC inhibitor (or a derivative or pharmaceutically acceptable salt thereof). In certain embodiments, the composition comprises a combination of agents including (i) a GSK3-beta inhibitor and/or Wnt agonist (or a derivative or pharmaceutically acceptable salt thereof), and (ii) a highly potent notch agonist and/or highly potent HDAC inhibitor (or a derivative or pharmaceutically acceptable salt thereof).

In certain embodiments, the composition comprises a Stemness Driver at 5, 10, 20, 50, 100, 200, 500, 1000, or 5000 times the Effective Stemness Driver Concentration. In some embodiments, the composition further comprises the Differentiation Inhibitor at 5, 10, 20, 50, 100, 200, 500, 1000, or 5000 times the Effective Differentiation Inhibition Concentration. Optionally, any of the previous composition may include one or more agents that target the ROS or TgfBeta. Optionally, any of the previous composition may include one or more neurotrophins.

Delivery Profile of Combined Agents

In some embodiments, a Stemness Driver may be used to drive the proliferation of Lgr5' stem cells. In some cases, a Stemness Driver may also induce differentiation of LGR5+ cells to hair cells if a Differentiation Inhibitor is not present at an Effective Differentiation Inhibition Concentration. Examples of Stemness Drivers that may drive both proliferation and differentiation include GSK3Beta inhibitors and Wnt agonists. In some embodiments, the Differentiation Inhibitor may be a Notch agonist or HDAC inhibitor. In some embodiments, there may be a first Proliferation Period with an Effective Stemness Driver Concentration and an Effective Differentiation Inhibition Concentration of a Differentiation Inhibitor, followed by a Differentiation Period with an Effective Stemness Driver Concentration and without an Effective Differentiation Inhibition Concentration of a Differentiation Inhibitor. In some embodiments, there may be a first Proliferation Period with an Effective Stemness Driver Concentration of a Wnt agonist or GSK3Beta inhibitor and an Effective Differentiation Inhibition Concentration of a Notch agonist or HDAC inhibitor, followed by a Differentiation Period with an Effective Sternness Driver Concentration of a Wnt agonist or GSK3Beta inhibitor and without an Effective Differentiation Inhibition Concentration of a Notch agonist or HDAC inhibitor. In some embodiments, there may be a first Proliferation Period with an Effective Stemness Driver Concentration of a GSK3Beta inhibitor and an Effective Differentiation Inhibition Concentration of an HDAC inhibitor, followed by a Differentiation Period with an Effective Stemness Driver Concentration of a GSK3Beta inhibitor and without an Effective Differentiation Inhibition Concentration of an HDAC inhibitor.

In some embodiments, the desired Proliferation period is 1, 2, 4, 8, 16, 24, 48, 72, 96, or 192 hours. In some embodiments, a composition maintains an Effective Release Rate of Stemness Driver throughout the desired Proliferation Period. In some embodiments, a composition maintains an Effective Release Rate of Stemness Driver for at least 1 hour. In some embodiments, it is desired to have a Stemness Driver release rate of 10, 20, 50, 100, 500, or 1000-fold the Effective Release Rate of Stemness Driver for the desired proliferation period.

In some embodiments, the desired Proliferation period is 1, 2, 4, 8, 16, 24, 48, 72, 96, or 192 hours. In some embodiments, a composition placed on the round window membrane of a mouse retains an Effective Stemness Driver Concentration in the cochlea throughout the desired Proliferation Period. In some embodiments, a composition placed on the round window membrane of a mouse retains an Effective Stemness Driver Concentration in the cochlea for at least 1 hour. In some embodiments, a composition placed on the round window membrane of a mouse retains an Effective Stemness Driver Concentration for at least 2, 4, 8, 16, 24, 48, 72, 96, or 192 hours.

In some embodiments, the desired Proliferation period is 1, 2, 4, 8, 16, 24, 48, 72, 96, or 192 hours. In some embodiments, a composition maintains an Effective Release Rate of Differentiation Inhibitor throughout the desired Proliferation Period. In some embodiments, a composition maintains an Effective Release Rate of Differentiation Inhibitor for at least 1 hour. In some embodiments, a composition placed on the round window membrane of a mouse retains an Effective Release Rate of Differentiation Inhibitor for at least 2, 4, 8, 16, 24, 48, 72, 96, or 192 hours.

In some embodiments, the desired Proliferation period is 1, 2, 4, 8, 16, 24, 48, 72, 96, or 192 hours. In some embodiments, a composition placed on the round window membrane of a mouse retains an Effective Differentiation Inhibition Concentration of a Differentiation Inhibitor in the cochlea throughout the desired Proliferation Period. In some embodiments, a composition placed on the round window membrane of a mouse retains an Effective Differentiation Inhibition Concentration in the cochlea for at least 1 hour. In some embodiments, a composition placed on the round window membrane of a mouse retains an Effective Differentiation Inhibition Concentration for at least 2, 4, 8, 16, 24, 48, 72, 96, or 192 hours.

In some embodiments, the desired Proliferation period is 1, 2, 4, 8, 16, 24, 48, 72, 96, or 192 hours. In some embodiments, a composition may release both a Stemness Driver and a Differentiation Inhibitor simultaneously. It may be advantageous to have the Differentiation Inhibitor mitigate the degree to which the Stemness Driver reduces Notch activity in the Lgr5+ cells targets for proliferation by the therapy. In some embodiments, the composition has a Release Rate of Stemness Driver and Differentiation Inhibitor throughout the Proliferation Period that if the mass of agent release in 1 hour is placed in 30 ul, and added to a Notch Activity Assay in cell culture, the Notch Activity would be at >20, 30, 40, 50, 60, 70, 80, or 90 of the Notch Activity of native state without the agents being applied.

In some embodiments, the desired Proliferation period is 1, 2, 4, 8, 16, 24, 48, 72, 96, or 192 hours. In some embodiments, a composition may release both a Stemness Driver and a Differentiation Inhibitor simultaneously. In some embodiments, a desired composition place on the round window membrane of a mouse releases an amount of a Stemness Driver and a Differentiation Inhibitor simultaneously to maintain Notch Activity at >20, 30, 40, 50, 60, 70, 80, or 90 of the Notch Activity of native state without the agents being applied.

In some embodiments, the desired Proliferation period is 1, 2, 4, 8, 16, 24, 48, 72, 96, or 192 hours. In some embodiments, a composition may release both a Stemness Driver and a Differentiation Inhibitor simultaneously. It may be advantageous to have the Differentiation Inhibitor mitigate the degree to which the Stemness Driver reduces Notch activity in the Lgr5+ cells targets for proliferation by the therapy. In some embodiments, the composition has a Release Rate of Stemness Driver and Differentiation Inhibitor throughout the Proliferation Period that if the mass of agent release in 1 hour is placed in 30 ul, and added to a Notch Activity Assay in cell culture, the Notch Activity is >2, 3, 4, 5, 10, 20, 50, 100, 500, 100× of the Notch Activity as that which would have achieved if the composition had contained the same amount of Stemness Driver without any Differentiation Inhibitor.

In some embodiments, the desired Proliferation period is 1, 2, 4, 8, 16, 24, 48, 72, 96, or 192 hours. In some embodiments, a composition may release both a Stemness Driver and a Differentiation Inhibitor simultaneously. It may be advantageous to have the Differentiation Inhibitor mitigate the degree to which the Stemness Driver reduces Notch activity in the Lgr5$^+$ cells targets for proliferation by the therapy. In some embodiments, when a composition comprising Stemness Driver and a Differentiation Inhibitor are placed on the round window membrane of a mouse, the Notch activity of Lgr5$^+$ cells in the cochlea are >2, 3, 4, 5, 10, 20, 50, 100, 500, 100× of the Notch activity as that which would have achieved if the composition had contained the same amount of Stemness Driver without any Differentiation Inhibitor.

In some embodiments, the desired Differentiation period is 1, 2, 4, 8, 16, 24, 48, 72, 96 days. In some embodiments, a composition does not achieve an Effective Release Rate of Differentiation Inhibitor at any time in the desired Differentiation Period. In some embodiments, a composition does not achieve an Effective Release Rate of Differentiation Inhibitor for more than 1 day. In some embodiments, a composition does not achieve an Effective Release Rate of Differentiation Inhibitor for at least 2, 4, 8, 16, 24, 48, 72, or 96 days.

In some embodiments, the desired Differentiation period is 1, 2, 4, 8, 16, 24, 48, 72, 96 days. In some embodiments, a composition placed on the round window membrane of a mouse does not retain an Effective Differentiation Inhibition Concentration of a Differentiation Inhibitor at any time in the desired Differentiation Period. In some embodiments, a composition placed on the round window membrane of a mouse does not retain an Effective Differentiation Inhibition Concentration for more than 1 day. In some embodiments, a composition does not retain an Effective Differentiation Inhibition Concentration for at least 2, 4, 8, 16, 24, 48, 72, or 96 days.

In some embodiments, it is desirable to release the Stemness Driver over a longer period of time than the Differentiation inhibitor. In some embodiments, the Mean Release Time of Stemness Driver is 2, 4, 8, 16, or 32 times great than the Mean Release Time of the Differentiation Inhibitor.

In certain embodiments, the stem cell population comprises supporting cells. In certain embodiments, the supporting cells are Lgr5$^+$ cells. In certain embodiments, the stem cell population comprises post-natal cells. In certain embodiments, the hair cells are inner ear hair cells. In certain embodiments, the hair cells are outer ear hair cells.

In certain embodiments, stem cells include progenitor cells.

In certain embodiments, the administering step comprises administering or causing to be administered to the stem cell population a notch agonist that is also an HDAC inhibitor. In certain embodiments, the administering step comprises administering or causing to be administered to the stem cell population a notch agonist that comprises a synthetic molecule. In certain embodiments, the administering step comprises administering or causing to be administered to the stem cell population valproic acid (VPA) (e.g., in a pharmaceutically acceptable form (e.g., salt)) (e.g., where VPA is a notch agonist that is also an HDAC inhibitor).

In certain embodiments, the administering step comprises administering or causing to be administered to the stem cell population a Wnt agonist that is also a GSK3-beta inhibitor. In certain embodiments, the administering step comprises administering or causing to be administered to the stem cell population a Wnt agonist that comprises a synthetic molecule. In certain embodiments, the administering step comprises administering or causing to be administered to the stem cell population CHIR99021 (e.g., in a pharmaceutically acceptable form (e.g., salt)) (e.g., where CHIR99021 is a GSK3-beta inhibitor.

In certain embodiments, the administering step comprises administering or causing to be administered to the stem cell population a notch inhibitor. In certain embodiments, the notch inhibitor comprises DAPT, LY411575, MDL-28170, Compound E, R04929097; DAPT (N-[(3,5-Difluorophenyl) acetyl]-L-alanyl-2-phenyl]glycine-1, 1-dimethylethyl ester); L-685458 ((5S)-(t-Butoxycarbonylamino)-6-phenyl-(4R) hydroxy-(2R)benzylhexanoyl)-L-leu-L-phe-amide); BMS-708163 (Avagacestat); BMS-299897 (2-[(1R)-1-[[(4-Chlorophenyl)sulfonyl](2,5-difluorophenyl)amino]ethyl-5-fluorobenzenebutanoic acid); M-0752; YO-01027; MDL28170 (Sigma); LY41 1575 (N-2((2S)-2-(3,5-difluoro-phenyl)-2-hydroxyethanoyl)-N 1-((7S)-5-methyl-6-oxo-6,7-dihydro-5H-dibenzo[b,d]azepin-7-yl)-1-alaninamide); ELN-46719 (2-hydroxy-valeric acid amide analog of LY41 1575; PF-03084014 ((S)-2-((S)-5,7-difluoro-1,2,3,4-tetra-hydronaphthalen-3-ylamino)-N-(1-(2-methyl-1-(neopenty-lamino)propan-2-yl)-1H-imidazol-4-yl)pentanamide); Compound E ((2S)-2-{[(3,5-Diflurophenyl)acetyl]amino}-N-[(3S)-1-methyl-2-oxo-5-phenyl-2,3-dihydro-1H-1,4-benzodiazepin-3-yl]propanamide; and Semagacestat (LY450139; (2S)-2-hydroxy-3-methyl-N-((1 S)-1-methyl-2-{[(1 S)-3-methyl-2-oxo-2,3,4,5-tetrahydro-1H-3-benzazepin-1-yl]amino}-2-oxoethyl)butanamide), or pharmaceutically acceptable salts thereof. (e.g., in a pharmaceutically acceptable form (e.g., salt)), In certain embodiments, the administering step comprises administering or causing to be administered to the stem cell population: (i) CHIR99021 (e.g., in a pharmaceutically acceptable form (e.g., salt)) and (ii) VPA (e.g., in a pharmaceutically acceptable form (e.g., salt)) (e.g., where (i) comprises CHIR99021 and (ii) comprises VPA). In certain embodiments, the administering step further comprises administering or causing to be administered to the stem cell population DAPT (e.g., where DAPT is a notch inhibitor).

In certain embodiments, the administering step is carried out by performing one or more injections into the ear (e.g., transtympanically). In certain embodiments, the one or more injections are into the middle ear. In certain embodiments, the one or more injections are into the inner ear. In certain embodiments, performing the one or more injections comprises anesthetizing the tympanic membrane and/or surrounding tissue, placing a needle through the tympanic membrane into the middle ear, and injecting one or both of (i) and (ii).

In certain embodiments, the administering step comprises administering the notch agonist and/or HDAC inhibitor in a pulsatile manner and administering the GSK3-beta inhibitor and/or Wnt agonist in a sustained manner. In certain embodiments, the formulation administered is sterile. In certain embodiments, the formulation administered is pyrogen-free. In certain embodiments, a pharmaceutically acceptable formulation is administered as described in Appendix pages 21-36. In certain embodiments, the formulation is a combination of (i) a GSK3-beta inhibitor and/or Wnt agonist, and (ii) a notch agonist and/or HDAC inhibitor administered in a pharmaceutically acceptable formulation as described in Appendix pages 21-36.

In certain embodiments, the stem cell population is of an in vivo subject, and the method is a treatment for hearing loss and/or vestibular dysfunction (e.g., wherein the generation of inner ear hair cells from the expanded population of stem cells results in partial or full recovery of hearing loss and/or improved vestibular function). In certain embodiments, the stem cell population is of an in vivo subject, and the method further comprises delivering a drug to the subject (e.g., for treatment of a disease and/or disorder unrelated to hearing loss and/or vestibular dysfunction) at a higher concentration than a known safe maximum dosage of the drug for the subject (e.g., the known safe maximum dosage if delivered in the absence of the generation of inner ear hair cells resulting from the method) (e.g., due to a reduction or elimination of a dose-limiting ototoxicity of the drug).

In certain embodiments, the method further comprises performing high throughput screening using the generated inner ear hair cells. In certain embodiments, the method comprises using the generated inner ear hair cells to screen molecules for toxicity against inner ear hair cells. In certain embodiments, the method comprises using the generated inner ear hair cells to screen molecules for ability to improve survival of inner ear hair cells (e.g., inner ear hair cells exposed to said molecules).

In another aspect, the disclosure is directed to a method of producing an expanded population of stem cells, the method comprising: administering or causing to be administered to a stem cell population (e.g., of an in vitro, ex vivo, or in vivo sample/subject) both of (i) and (ii): (i) a GSK3-beta inhibitor and/or Wnt agonist, and (ii) a notch agonist and/or HDAC inhibitor, thereby proliferating stem cells in the stem cell population and resulting in an expanded population of stem cells. In certain embodiments, the stem cell population comprises Lgr5+ cells. In certain embodiments, the stem cell population comprises post-natal stem cells. In certain embodiments, the stem cell population comprises epithelial stem cells. In certain embodiments, stem cells include progenitor cells.

In certain embodiments, the administering step comprises administering or causing to be administered to the stem cell population a notch agonist that is also an HDAC inhibitor. In certain embodiments, the administering step comprises administering or causing to be administered to the stem cell population a notch agonist that comprises a synthetic molecule. In certain embodiments, the administering step comprises administering or causing to be administered to the stem cell population VPA (e.g., in a pharmaceutically acceptable form (e.g., salt)) (e.g., where VPA is a notch agonist that is also an HDAC inhibitor).

In certain embodiments, the administering step comprises administering or causing to be administered to the stem cell population a Wnt agonist that is also a GSK3-beta inhibitor. In certain embodiments, the administering step comprises administering or causing to be administered to the stem cell population a Wnt agonist comprising a synthetic molecule. In certain embodiments, the administering step comprises administering or causing to be administered to the stem cell population CHIR99021 (e.g., in a pharmaceutically acceptable form (e.g., salt)) (e.g., where CHIR99021 is a GSK3 beta inhibitor).

In certain embodiments, the administering step is carried out by performing one or more injections into the ear (e.g., transtympanically into the middle ear and/or inner ear).

In certain embodiments, the administering step comprises administering the notch agonist and/or HDAC inhibitor in a pulsatile manner and administering the GSK3-beta inhibitor and/or Wnt agonist in a sustained manner.

In certain embodiments, the stem cells are inner ear stem cells and/or supporting cells.

In certain embodiments, the method further comprises performing high throughput screening using the generated expanded population of stem cells. In certain embodiments, the method further comprises using the generated stem cells to screen molecules for toxicity against stem cells and/or their progeny. In certain embodiments, the method comprises using the generated stem cells to screen molecules for ability to improve survival of stem cells and/or their progeny.

In another aspect, the disclosure is directed to a method of treating a subject who has, or is at risk of developing, hearing loss and/or vestibular dysfunction, the method comprising: identifying a subject who has experienced, or is at risk for developing, hearing loss and/or vestibular dysfunction, administering or causing to be administered to the subject both of (i) and (ii): (i) a GSK3-beta inhibitor and/or Wnt agonist, and (ii) a notch agonist and/or HDAC inhibitor, thereby treating or preventing the hearing loss and/or vestibular dysfunction in the subject.

In certain embodiments, the stem cell population comprises Lgr5+ cells. In certain embodiments, the stem cell population comprises post-natal cells. In certain embodiments, the stem cell population comprises epithelial stem cells. In certain embodiments, stem cells include progenitor cells.

In certain embodiments, the administering step comprises administering or causing to be administered to the subject a notch agonist that is also an HDAC inhibitor. In certain embodiments, the administering step comprises administering or causing to be administered to the subject a notch agonist comprising a synthetic molecule. In certain embodiments, the administering step comprises administering or causing to be administered to the subject VPA (e.g., in a pharmaceutically acceptable form (e.g., salt)) (e.g., where VPA is a notch agonist that is also an HDAC inhibitor).

In certain embodiments, the administering step comprises administering or causing to be administered to the subject a Wnt agonist that is also a GSK3-beta inhibitor. In certain embodiments, the administering step comprises administering or causing to be administered to the subject a Wnt agonist comprising a synthetic molecule. In certain embodiments, the administering step comprises administering or causing to be administered to the subject CHIR99021 (e.g., in a pharmaceutically acceptable form (e.g., salt)) (e.g., where CHIR99021 is a GSK3-beta inhibitor).

In certain embodiments, the step of administering is carried out by performing one or more injections into the ear (e.g., transtympanically into the middle ear and/or inner ear).

In certain embodiments, the method comprises administering the notch agonist and/or the HDAC inhibitor in a pulsatile manner and administering the GSK3-beta inhibitor and/or Wnt agonist in a sustained manner.

In another aspect, the disclosure is directed to a kit comprising: (a) a set of one or more compositions, the set comprising (i) and (ii): (i) a GSK3-beta inhibitor and/or Wnt agonist, and (ii) a notch agonist and/or HDAC inhibitor, each of the one or more compositions provided in a pharmaceutically acceptable carrier and (b) instructions for using the set of one or more compositions to treat an inner ear disorder.

In certain embodiments, the set of one or more compositions also comprises a TGFβ inhibitor. In certain embodiments, the set of one or more compositions also comprises an ROS scavenger. In certain embodiments, the ROS scavenger is vitamin C or a derivative thereof. In certain embodiments, the set of one or more compositions is/are in a form that can be injected (e.g. via syringe). In certain embodiments, the set of one or more compositions is/are in a form that can be injected into the middle ear.

In another aspect, the disclosure is directed to a pharmaceutical composition comprising a GSK3-beta inhibitor and a notch agonist in lyophilized form.

In another aspect, the disclosure is directed to a pharmaceutical composition comprising a GSK3-beta inhibitor and a notch agonist in hydrated form.

In certain embodiments, the GSK3-beta inhibitor is CHIR99021 (e.g., in a pharmaceutically acceptable form (e.g., salt)). In certain embodiments, the notch agonist is VPA (e.g., in a pharmaceutically acceptable form (e.g., salt)).

In another aspect, the disclosure is directed to a method of generating inner ear hair cells, the method comprising: proliferating stem cells in an initial stem cell population (e.g., of an in vitro, ex vivo, or in vivo sample/subject), resulting in an expanded population of stem cells (e.g., such that the expanded population is a factor of at least 1.25, 1.5, 1.75, 2, 3, 5, 10, or 20 greater than the initial stem cell population); and exposing the expanded population of stem cells to a GSK3-beta inhibitor and/or a Wnt agonist, and, optionally, a notch inhibitor, thereby facilitating generation of inner ear hair cells from the expanded population of stem cells.

In another aspect, the disclosure is directed to a method of generating inner ear hair cells, the method comprising administering CHIR99021 (e.g., in a pharmaceutically acceptable form (e.g., salt)) to a cell population in an inner ear of a subject, thereby facilitating generation of inner ear hair cells.

In another aspect, the disclosure is directed to a method of generating inner ear hair cells, the method comprising: proliferating post-natal LGR5+ cells in an initial population (e.g., of an in vitro, ex vivo, or in vivo sample/subject), resulting in an expanded population of LGR5+ cells (e.g., such that the expanded population is a factor of at least 1.25, 1.5, 1.75, 2, 3, 5, 10, or 20 greater than the initial stem cell population), said expanded population of LGR5+ cells resulting in generation of inner ear hair cells. In certain embodiments, stem cells include progenitor cells.

In another aspect, the disclosure is directed to a method of treating a disease or disorder, the method comprising: proliferating post-natal Lgr5+ epithelial cells in an initial population of a subject (in vivo), resulting in an expanded population of Lgr5+ epithelial cells (e.g., such that the expanded population is a factor of at least 1.25, 1.5, 1.75, 2, 3, 5, 10, or 20 greater than the initial post-natal Lgr5+ epithelial cell population).

In some embodiments, Lgr5+ cells are differentiated into hair cells. In certain embodiments, differentiation is induced by use of a notch inhibitor. Notch pathway regulators include but are not limited to those listed, referenced 69, or disclosed in U.S. Pat. No. 8,377,886, which is incorporated by reference herein in its entirety.

R04929097; DAPT (N-[(3,5-Difluorophenyl)acetyl]-L-alanyl-2-phenyl]glycine-1,1-dimethylethyl ester); L-685458 ((5S)-(t-Butoxycarbonylamino)-6-phenyl-(4R)hydroxy-(2R)benzylhexanoyl)-L-leu-L-phe-amide); BMS-708163 (Avagacestat); BMS-299897 (2-[(1R)-1-[[(4-Chlorophenyl)sulfonyl](2,5-difluorophenyl)amino]ethyl-5-fluorobenzenebutanoic acid); M-0752; YO-01027; MDL28170 (Sigma); LY41 1575 (N-2((2S)-2-(3,5-difluorophenyl)-2-hydroxyethanoyl)-N 1-((7S)-5-methyl-6-oxo-6,7-dihydro-5H-dibenzo[b,d]azepin-7-yI)-1-alaninamide); ELN-46719 (2-hydroxy-valeric acid amide analog of LY41 1575; PF-03084014 ((S)-2-((S)-5,7-difluoro-1,2,3,4-tetrahydronaphthalen-3-ylamino)-N-(1-(2-methyl-1-(neopentylamino)propan-2-yl)-1H-imidazol-4-yl)pentanamide);

Compound E ((2S)-2-{[(3,5-Diflurophenyl)acetyl]amino}-N-[(3S)-1-methyl-2-oxo-5-phenyl-2,3-dihydro-1H-1,4-benzodiazepin-3-yl]propanamide; and Semagacestat (LY450139; (2S)-2-hydroxy-3-methyl-N-((1 S)-1-methyl-2-{[(1 S)-3-methyl-2-oxo-2,3,4,5-tetrahydro-1H-3-benzazepin-1-yl]amino}-2-oxoethyl)butanamide), or pharmaceutically acceptable salts thereof.

Administration

The membrane of the round window is the biological barrier to the inner ear space and represents the major obstacle for the local treatment of hearing impairment. The administered drug must overcome this membrane to reach the inner ear space. The drug can operatively (e.g., injection through the tympanic membrane) be placed locally to the round window membrane and can then penetrate through the round window membrane. Substances that penetrate the round window typically distribute in the perilymph and thus reach the hair cells and supporting cells.

In certain embodiments, pharmaceutical formulations are adapted to administer the drug locally to the round window membrane. The pharmaceutical formulations may also contain a membrane penetration enhancer, which supports the passage of the agents mentioned herein through the round window membrane. Accordingly, liquid, gel or foam formulations may be used. It is also possible to apply the active ingredient orally or to employ a combination of delivery approaches.

Intratympanic (IT) delivery of drugs to the ear is increasingly used for both clinical and research purposes. Some groups have applied drugs in a sustained manner using microcatheters and microwicks, while the majority have applied them as single or as repeated IT injections (up to 8 injections over periods of up to 2 weeks) 8.

Intratympanically applied drugs are thought to enter the fluids of the inner ear primarily by crossing the round window (RW) membrane. Calculations show that a major factor controlling both the amount of drug entering the ear and the distribution of drug along the length of the ear is the duration the drug remains in the middle ear space. Single, 'one-shot' applications or applications of aqueous solutions for few hours' duration result in steep drug gradients for the applied substance along the length of the cochlea and rapidly declining concentration in the basal turn of the cochlea as the drug subsequently becomes distributed throughout the ear.

Other injection approaches include by osmotic pump, or, by combination with implanted biomaterial, and more preferably, by injection or infusion. Biomaterials that can aid in controlling release kinetics and distribution of drug include hydrogel materials, degradable materials. One class of materials that is most preferably used includes in situ gelling materials. All potential materials and methodologies mentioned in these reference are included herein by reference.[11, 13-58] Other materials include collagen or other natural materials including fibrin, gelatin, and decelluarized tissues. Gelfoam may also be suitable.

Delivery may also be enhanced via alternate means including but not limited to agents added to the delivered composition such as penetration enhancers, or could be through devices via ultrasound, electroporation, or high speed jet.

Methods described herein can also be used for inner ear cell types that may be produced using a variety of methods know to those skilled in the art including those cell types described in PCT Application No. WO2012103012 A1.

With regard to human and veterinary treatment, the amount of a particular agent(s) that is administered may be dependent on a variety of factors, including the disorder being treated and the severity of the disorder; activity of the specific agent(s) employed; the age, body weight, general health, sex and diet of the patient; the time of administration, route of administration, and rate of excretion of the specific agent(s) employed; the duration of the treatment; drugs used in combination or coincidental with the specific agent(s) employed; the judgment of the prescribing physician or veterinarian; and like factors known in the medical and veterinary arts.

The agents described herein may be administered in a therapeutically effective amount to a subject in need of treatment. Administration of compositions described herein can be via any of suitable route of administration, particularly by intratympanically. Other routes include ingestion, or alternatively parenterally, for example intravenously, intra-arterially, intraperitoneally, intrathecally, intraventricularly, intraurethrally, intrasternally, intracranially, intramuscularly, intranasally, subcutaneously, sublingually, transdermally, or by inhalation or insufflations, or topical by ear instillation for absorption through the skin of the ear canal and membranes of the eardrum. Such administration may be as a single or multiple oral dose, defined number of ear drops, or a bolus injection, multiple injections, or as a short- or long-duration infusion. Implantable devices (e.g., implantable infusion pumps) may also be employed for the periodic parenteral delivery over time of equivalent or varying dosages of the particular formulation. For such parenteral administration, the compounds are preferably formulated as a sterile solution in water or another suitable solvent or mixture of solvents. The solution may contain other substances such as salts, sugars (particularly glucose or mannitol), to make the solution isotonic with blood, buffering agents such as acetic, citric, and/or phosphoric acids and their sodium salts, and preservatives. The preparation of suitable, and preferably sterile, parenteral formulations is described in detail in the section entitled "Compositions", above.

Compositions described herein can be administered by a number of methods sufficient to deliver the composition to the inner ear. Delivering a composition to the inner ear includes administering the composition to the middle ear, such that the composition may diffuse across the round window to the inner ear and administering a composition to the inner ear by direct injection through the round window membrane. Such methods include, but are not limited to auricular administration, by transtympanic wicks or catheters, or parenteral administration, for example, by intraauricular, transtympanic, or intracochlear injection.

In particular embodiments, the compositions and formulations of the disclosure are locally administered, meaning that they are not administered systemically.

In one embodiment, a syringe and needle apparatus is used to administer compositions to a subject using auricular administration. A suitably sized needle is used to pierce the tympanic membrane and a wick or catheter comprising the composition is inserted through the pierced tympanic membrane and into the middle ear of the subject. The device may be inserted such that it is in contact with the round window or immediately adjacent to the round window. Exemplary devices used for auricular administration include, but are not limited to, transtympanic wicks, transtympanic catheters, round window microcatheters (small catheters that deliver medicine to the round window), and Silverstein Microwicks™ (small tube with a "wick" through the tube to the round window, allowing regulation by subject or medical professional).

In another embodiment, a syringe and needle apparatus is used to administer compositions to a subject using transtympanic injection, injection behind the tympanic membrane into the middle and/or inner ear. The formulation may be administered directly onto the round window membrane via transtympanic injection or may be administered directly to the cochlea via intracochlear injection or directly to the vestibular organs via intravestibular injection.

In some embodiments, the delivery device is an apparatus designed for administration of compositions to the middle and/or inner ear. By way of example only: GYRUS Medical Gmbh offers micro-otoscopes for visualization of and drug delivery to the round window niche; Arenberg has described a medical treatment device to deliver fluids to inner ear-structures in U.S. Pat. Nos. 5,421,818; 5,474,529; and 5,476,446, each of which is incorporated by reference herein for such disclosure. U.S. patent application Ser. No. 08/874,208, which is incorporated herein by reference for such disclosure, describes a surgical method for implanting a fluid transfer conduit to deliver compositions to the inner ear. U.S. Patent Application Publication 2007/0167918, which is incorporated herein by reference for such disclosure, further describes a combined otic aspirator and medication dispenser for transtympanic fluid sampling and medicament application.

In some embodiments, a composition disclosed herein is administered to an subject in need thereof once. In some embodiments, a composition disclosed herein is administered to an subject in need thereof more than once. In some embodiments, a first administration of a composition disclosed herein is followed by a second, third, fourth, or fifth administration of a composition disclosed herein.

The number of times a composition is administered to an subject in need thereof depends on the discretion of a medical professional, the disorder, the severity of the disorder, and the subject's response to the formulation. In some embodiments, a composition disclosed herein is administered once to an subject in need thereof with a mild acute condition. In some embodiments, a composition disclosed herein is administered more than once to an subject in need thereof with a moderate or severe acute condition. In the case wherein the subject's condition does not improve, upon the doctor's discretion the composition may be administered chronically, that is, for an extended period of time, including throughout the duration of the subject's life in order to ameliorate or otherwise control or limit the symptoms of the subject's disease or condition.

In the case wherein the subject's status does improve, upon the doctor's discretion the composition may administered continuously; alternatively, the dose of drug being administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once the subject's hearing and/or balance has improved, a maintenance dose can be administered, if necessary. Subsequently, the dosage or the frequency of administration, or both, is optionally reduced, as a function of the symptoms, to a level at which the improved disease, disorder or condition is retained. In certain embodiments, subjects require intermittent treatment on a long-term basis upon any recurrence of symptoms.

Formulations

The biologically active compositions described herein (sometimes referred to herein as "biologically active agents" or more simply, as "agents") may be formulated in any manner suitable for a desired delivery route to an in vitro population or to an in vivo population of cells, e.g., transtympanic injection, transtympanic wicks and catheters, and injectable depots. Typically, such formulations include all physiologically acceptable forms of the biologically active compositions, including free acid forms, free base forms, acid addition salts, base addition salts, other derivative thereof (such as a prodrug or solvate thereof), racemic, optically active, or tautomer thereof with any physiologically acceptable carriers, diluents, and/or excipients.

Solid formulations of the compositions described herein, such as dragees, capsules, pills and granules, may optionally be scored or prepared with coatings and shells, such as enteric coatings and other coatings. Solid dosage forms may also be formulated so as to provide slow or controlled release of the ion channel modulating compound. Thus, solid formulations could include any material that could provide a desired release profile of the ion channel modulating compound, including but not limited to hydroxypropylmethyl cellulose in varying proportions, or other polymer matrices, liposomes and/or microspheres.

Pharmaceutically acceptable carriers can include but are not limited to: water, ethanol, oils, including those of petroleum, animal, vegetable or synthetic origin, such as peanut oil, soybean oil, mineral oil, sesame oil, and the like, an excipient such as methylcellulose, carageenan, and the like.

Liquid dosage formulations may include pharmaceutically acceptable emulsions, microemulsions, solutions, suspensions, syrups and elixirs. In addition, the liquid dosage formulations may contain inert diluents commonly used in the art, including but not limited to water or other solvents; solubilizing agents and emulsifiers, such as ethyl alcohol, isopropyl alcohol, ethyl carbonate, ethyl acetate, benzyl alcohol, benzyl benzoate, propylene glycol, 1,3-butylene glycol; oils (in particular, cottonseed, groundnut, corn, germ, olive, castor and sesame oils); glycerol; tetrahydrofuryl alcohol; polyethylene glycols; and fatty acid esters of sorbitan, and mixtures thereof.

Suspensions formulations include, without limitation, ethoxylated isostearyl alcohols; polyoxyethylene sorbitol and sorbitan esters; microcrystalline cellulose; aluminum metahydroxide; bentonite; agar-agar; tragacanth; and mixtures thereof.

Proper fluidity of liquid, suspension and other formulations of the ion channel modulating compounds can be maintained by the use of coating materials such as lecithin; by the maintenance of the required particle size in the case of dispersions; or by the use of surfactants.

Formulations may also include anti-contamination agents for the prevention of microorganism contamination. Anti-contamination agents may include but are not limited to antibacterial and antifungal agents, for example, paraben, chlorobutanol, phenol sorbic acid, antibiotics, and the like.

Formulations may also be sterilized by, for example, by filtration through a bacteria-retaining filter, or by incorporating sterilizing agents in the form of sterile solid formulations which can be dissolved in sterile water, or some other sterile medium immediately before use or formulation.

Formulations may also be endotoxin free. As used herein, the term "endotoxin free" refers to compositions or formulations that contain at most trace amounts (i.e., amounts having no adverse physiological effects to a subject) of endotoxin, and preferably undetectable amounts of endotoxin. By "substantially free of endotoxin" is meant that there is less endotoxin per dose of cells than is allowed by the FDA for a biologic, which is a total endotoxin of 5 EU/kg body weight per day, which for an average 70 kg person is 350 EU per total dose of cells. In one embodiment, the term "endotoxin free" refers to a composition or formulation that is at least 95%, at least 96%, at least 97%, at least 98%, at least 99%, or 100% endotoxin free. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipooligosaccharides (LOS) found in the outer membrane of various Gram-negative bacteria, and which represent a central pathogenic feature in the ability of these bacteria to cause disease. Small amounts of endotoxin in humans can produce fever, a lowering of the blood pressure, and activation of inflammation and coagulation, among other adverse physiological effects. Therefore, it is often desirable to remove most or all traces of endotoxin from drug product containers, because even small amounts may cause adverse effects in humans.

Pharmaceutical compositions described herein are formulated so as to allow the active ingredients contained therein to be bioavailable upon administration of the composition to a subject. For example, pharmaceutical compositions described herein can be prepared by combining a Notch Activator and/or HDAC inhibitor and a GSK3b inhibitor and/or WNT activator and/or small molecules with an appropriate pharmaceutically acceptable carrier, diluent or excipient, and may be formulated into preparations in solid, semi-solid, liquid, gels, and microspheres, including those formulations adapted for auricular administration, by transtympanic wicks or catheters, or parenteral administration, for example, by intraauricular, transtympanic, or intracochlear injection. However, in certain embodiments the subject compounds may be simply dissolved or suspended in sterile water.

Coated, gel, or encapsulating formulations of a Notch Activator and/or HDAC inhibitor and a GSK3b inhibitor and/or WNT activator or derivatives and/or small molecules may also be formulated to deliver pulsatile, sustained, or extended release. For example, one method of pulsatile release could be achieved by layering multiple coatings of agents or derivatives and/or small molecules, or by incorporating the agents derivatives and/or small molecules within different regions of the formulation having different release times.

Injectable depot formulations can be made by forming microencapsulated matrices of the composition in biodegradable polymers. Examples of biodegradable polymers include, but are not limited to polylactide-polyglycolide, poly(orthoesters) and poly(anhydrides). The ratio of composition to polymer and the nature of the particular polymer employed can affect the rate of release of Notch Activators and/or HDAC inhibitor and a GSK3b inhibitor and/or WNT activators, or derivatives and/or small molecules from the composition. Depot injectable formulations can also be prepared by entrapping the drug in liposomes or microemulsions.

Pharmaceutical compositions may further comprise one or more components that enhance the bioavailability of the active ingredients of the composition, e.g., penetration enhancers, stabilizing agents, and one or more components that provide slow or controlled release of the Notch Activator and/or HDAC inhibitor and a GSK3b inhibitor and/or WNT activator derivatives and/or small molecules in the composition, e.g., biocompatible polymers and/or gels.

In particular embodiments, compositions comprising penetration enhancers will facilitate the delivery of the composition across biological barriers that separate the middle and inner ear, e.g., the round window, thereby efficiently delivery a therapeutically effective amount of the composition to the inner ear. Efficient delivery to the cochlea, Organ of Corti, and/or vestibular organs is desired because these tissues host the support cells that promote sensory hair cell regeneration when treated or contacted with compositions described herein.

A "penetration enhancer" or "permeability enhancer" includes a polyol such as polyethylene glycol (PEG), glycerol (glycerin), maltitol, sorbitol etc.; diethylene glycol monoethyl ether, azone, benzalkonium chloride (ADBAC), cetylperidium chloride, cetylmethylammonium bromide, dextran sulfate, lauric acid, menthol, methoxy salicylate, oleic acid, phosphatidylcholine, polyoxyethylene, polysorbate 80, sodium glycholate, sodium lauryl sulfate, sodium salicylate, sodium taurocholate, sodium taurodeoxycholate, sulfoxides, sodium deoxycholate, sodium glycodeoxycholate, sodium taurocholate and surfactants such as sodium lauryl sulfate, laureth-9, cetylpyridinium chloride and polyoxyethylene monoalkyl ethers, benzoic acids, such as sodium salicylate and methoxy salicylate, fatty acids, such as lauiic acid, oleic acid, undpcanoic acid and methyl oleate, fatty alcohols, such as octanol and nonanol, laurocapram, cyclodextrins, thymol, limonene, urea, chitosan and other natural and synthetic polymers.

Other penetration enhancers include but are not limited to those described in US patent application publication number: US20110166060.

Suitable polyols for inclusion in the solutions described herein include glycerol and sugar alcohols such as sorbitol, mannitol or xylitol, polyethylene glycol and derivatives thereof. In some embodiments the composition further includes a preservative. Accepted preservatives such as benzalkonium chloride and disodium edetate (EDTA) are included in the compositions described herein in concentrations sufficient for effective antimicrobial action, about 0.0001 to 0.1%, based on the weight of the composition.

In particular embodiments, compositions of the present disclosure also include stabilizers to increase the therapeutic lifetime of the compositions in vivo. Exemplary stabilizers include fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In further embodiments, the chosen stabilizer changes the hydrophobicity of the formulation (e.g., oleic acid, waxes), or improves the mixing of various components in the formulation (e.g., ethanol), affects the moisture level in the formula (e.g., PVP or polyvinyl pyrrolidone), affects the mobility of the phase (substances with melting points higher than room temperature such as long chain fatty acids, alcohols, esters, ethers, amides etc. or mixtures thereof;

waxes), and/or improves the compatibility of the formula with encapsulating materials (e.g., oleic acid or wax). In other embodiments, stabilizers are present in sufficient amounts to inhibit the degradation of the Notch Activator and/or HDAC inhibitor and a GSK3b inhibitor and/or WNT activator derivatives and small molecules in the composition. Examples of such stabilizing agents, include, but are not limited to: (a) about 0.5%> to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosan polysulfate and other heparinoids, (m) divalent cations such as magnesium and zinc; or (n) combinations thereof.

In particular embodiments, compositions of the disclosure are formulated as controlled release formulations. In general, controlled release drug formulations impart control over the release of drug with respect to site of release and time of release in vivo. Controlled release includes to immediate release, delayed release, sustained release, extended release, variable release, pulsatile release and bi-modal release.

Advantages offered by controlled release include: less frequent dosing; more efficient drug utilization; localized drug delivery by placement of a delivery device or formulation at a treatment site in vivo; and the opportunity to administer and release two or more different drugs, each having a unique release profile, or to release the same drug at different rates or for different durations, by means of a single dosage unit.

Controlled release formulations may be made by formulating the compositions with biocompatible polymers, viscosity agents, gels, paints, foams, xerogels, microparticles, hydrogels, nanocapsules, and thermoreversible gels, or combinations thereof. In certain embodiments, the polymer or gels are biodegradable. Release properties are often controlled by the particular combination of polymers or gels used to formulate the composition. These methods are well known in the art.

Exemplary polymers suitable for formulating the biologically active compositions of the present disclosure include, but are not limited to polyamides, polycarbonates, polyalkylenes (polyethylene glycol (PEG)), polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly (ortho)esters, poly(butic acid), poly(valeric acid), poly (lactide-co-caprolactone), polysaccharides, proteins, polyhyaluronic acids, polycyanoacrylates, and blends, mixtures, or copolymers thereof.

In one embodiment, a biologically active composition of the present disclosure is formulated in a ABA-type or BAB-type triblock copolymer or a mixture thereof, wherein the A-blocks are relatively hydrophobic and comprise biodegradable polyesters or poly(orthoester), and the B-blocks are relatively hydrophilic and comprise polyethylene glycol (PEG). The biodegradable, hydrophobic A polymer block comprises a polyester or poly(ortho ester), in which the polyester is synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxyhexanoic acid, γ-butyrolactone, γ-hydroxybutyric acid, δ-valerolactone, δ-hydroxyvaleric acid, hydroxybutyric acids, malic acid, and copolymers thereof.

Exemplary viscosity agents suitable for use in formulating compositions described herein include, but are not limited to, hydroxypropyl methylcellulose, hydroxyethyl cellulose, polyvinylpyrrolidone, carboxymethyl cellulose, polyvinyl alcohol, sodium chondroitin sulfate, sodium hyaluronate, acacia (gum arabic), agar, agarose, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose (HPMC), sodium carboxymethylcellulose (CMC), silicon dioxide, or polyvinylpyrrolidone (PVP: povidone).

Suitable gelling agents for use in preparation of the gel formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum and any combinations or mixtures thereof.

A variety of suitable biocompatible polymers can be used for the delivery of compounds to the ear. Preferably, the polymers can form a gel. Examples of suitable gel forming biocompatible polymers include hyaluronic acid, hyaluronates, lecithin gels, (poly)alanine derivatives, pluronics, poly(ethyleneglycol), poloxamers, chitosans, xyloglucans, collagens, fibrins, polyesters, poly(lactides), poly(glycolide) or their co-polymers PLGA, sucrose acetate isobutyrate, and glycerol monooleate.

Hyaluronic acid is a naturally-occurring, biocompatible polysaccharide that binds water and forms a degradable gel with high viscosity. Polyethylene glycol (PEG) is a biocompatible polymer, hydrophilic polymer.

Thermosetting polymers that are fluids at low temperature, but are more viscous at higher temperatures, are also suitable. Common reversible thermosetting systems are poloxamers. When dissolved, the solutions can remain liquid at low temperatures, but can form more viscous, solid-like implants when the temperature increases.

Chitosan is a biocompatible and has antibacterial properties, and a chitosan-glycerolphosphate solution is able to form a reversible thermosetting gel.

The gel may be also formed from an enzymatically degradable polypeptide polymer. The polypeptide bonds in the polypeptide polymer are more stable against hydrolysis than the ester bonds in PEG/PLGA polymer systems, and the polypeptide can also include a biodegradable polymer having a biodegradable polypeptide block linked to a second polymer block to form a graft or linear polymer. An example for a polypeptide polymer is poly(alanine) and derivatives thereof. The polypeptide carrier may also be a protein matrix known as fibrin. Fibrinogen is a naturally occurring protein which, when combined with the enzyme thrombin, another naturally occurring protein, forms a bio-matrix known as fibrin.

Other biocompatible polymers include starches, celluloses, gelatin-pluronics, tetronics, the latter two being poly(ethylene oxide)/poly(propylene oxide) materials. Other materials that may be used include the chondroitin sulfates and the general class of mucopolysaccharides (e.g., glycosaminoglycans) and other biocompatible polymers having characteristics similar to hyaluronic acid.

In some instances, the biocompatible polymer may be cross linked. Various cross linking agents for biodegradable materials are known in the art. Preferably, cross linking is accomplished so that the final cross linked material for the delivery unit are substantially non-toxic (e.g., by use of thermal cross linking, gamma irradiation, ultraviolet irradiation, chemical cross linking, etc.). In general, the degree of cross linking relates inversely to the degree of swelling or absorption of water by the shaped polymer structure. The degree of swelling or water absorption regulates the rate of drug transport by the polymer structure.

In some embodiments, the drug is administered across the eardrum, e.g., by piercing, injection, etc. In some embodiments, the drug is administered across the eardrum without piercing it, e.g., absorption across eardrum.

In some embodiments, it is desirable that the formulation be sufficiently viscous that it remain in an area of administration for a suitable period of time, e.g., 1 min, 5 min, 10 min, 30 min., 1 hour, 5 hours, 12, hours, 1 day, 2 days, 7 days. The desired area may be external to the eardrum, but in contact therewith, e.g., where it can be desired that a layer of solution remain in contact with the eardrum (e.g., not flow out of ear) when the recipient subject is upright; even if some of a viscous formulation exits the ear canal, a viscous film of layer can, in some embodiments, be let in contact with the eardrum. Similarly, in embodiments be administered across the eardrum, e.g., by It should be appreciated that formulations can be altered in some embodiments by adjusting the liquid-gel transition such that it is rapid and reproducible, while loaded with drug.

For one carrier, poloxamer 407, gelation can decrease with increasing the concentration of poloxamer 407, at least in the absence of drug. Addition of some drugs, e.g., hydrophilic drugs, including VPA and pVc, at concentrations greater than 88 mg/ml and 14 mg/ml, respectively, inhibited gelation of poloxamer-407 solution. Therefore, gels were prepared using 18% (w/w) poloxamer solutions with concentrations of VPA and pVc to be equal to or less than 88 mg/ml and 14 mg/ml, respectively. Hydrophobic drugs, including CHIR, Repsox and TTNPB, appropriate volumes from their stock solutions in DMSO were added into the poloxamer-407 solutions containing the hydrophilic drugs, and mixed by pipetting at 4° C. Concentrations of drugs in stock solutions were maintained at 55.6-69.5 mg/ml, 23-28.75 mg/ml and 35 mg/ml for CHIR, Repsox and TTNPB, respectively to ensure total DMSO concentration in final formulation to be less than 5-6%. Higher concentration of DMSO significantly lowered the gelation temperature of the formulations. The final formulation was a viscous liquid at storage temperature (4° C.), and formed a semisolid gel above its liquid-gel transition temperature (37° C.).

In some cases, compositions have a viscosity of less than 100,000 centipoise (cps) at 25° C. Compositions also have a minimum yield stress that is sufficient for maintaining the formulation against the tympanic membrane. Yield stress is the amount of force that causes a solid material to exhibit liquid-like behavior in that it continues to deform with no further increase in stress. Minimum yield stress is dependent on the thickness of the applied gel, but is independent of the geometry of the gel and the temperature of the environment. Minimum yield stress of a composition refers to an applied gel having a thickness of 4 mm and a density of 1 g/L. Yield stress ($\sigma_0$) is represented as $\sigma_0 = \rho g h$, where $\rho$ is density, g is the acceleration due to gravity, and h is the layer thickness. Typically, minimum yield stress is about 39 pascals (Pa).

Viscogenic agents are typically polymers or other chemical moieties that increase the viscosity of a fluid. Suitable viscogenic agents, when included in a composition, allow the composition to transform from a liquid-like state (e.g., flowable) at 25° C. to a solid-like state (e.g., a gel) after contact with the tympanic membrane, and can be non-biodegradable, (e.g., not broken down by chemicals or enzymes naturally present in a mammal, or biodegradable). Compositions include an amount of viscogenic agent effective to yield a viscosity of the composition of less than 100,000 cps at 25° C. (e.g., less than 90,000, 60,000, 30,000, 20,000, or 10,000 cps) and, generally, a minimum yield stress of 39 Pa after application to the tympanic membrane. Typically, a composition includes 0.05 to 50% of a viscogenic agent (e.g., 0.15 to 25, 5 to 45, 10 to 40, 12 to 37, 15 to 35, 17 to 33, or 20 to 30% of a viscogenic agent).

Exemplary viscogenic agents include gellan (GELRITE or KELCOGEL), CARBOPOL 940 with hydroxypropylmethylcellulose (HPMC), N-isopropyl acrylamide (NiPAAm) with sodium acrylate and n-N-alkylacrylamide, polyacrylic acid with polyethylene glycol (PEG) or polymethacryhc acid with PEG, cellulose acetate hydrogen phthalate latex (CAP), sodium alginate, and nonionic surfactants such as poloxamers (PLURIONIC) and polyoxamine (TETRONIC) reversible temperature-dependent gelling systems. Gellan is a natural polymer, anionic deacetylated exocellular polysaccharide, secreted by *Pseudomonas elodea*. The tetrasaccharide repeating unit consists of one α-L-rhamnose, one β-D-glucuronic acid, and two β-D-glucose moieties. The in situ gelling mechanism of gellan is cation-induced (e.g., presence of calcium ions) and temperature-dependent (e.g., physiologic temperature). Gelation is thermally reversible. CARBOPOL 940 with HPMC gels in situ in a pH-dependent manner. CARBOPOL is the gelling agent and the HPMC is used to enhance the viscosity of the gel. NiPAAm with sodium acrylate and n-N-alkylacrylamide is a terpolymer hydrogel that can undergo a temperature based reversible sol-gel transformation. Sodium acrylate and n-N-alkylacrylamide are used to modify the properties of the hydrogel, and in particular, the transition temperature.

Polyacrylic acid with PEG or polymethacryhe acid with PEG is thought to gel based on hydrogen bonding. Polyacrylic acid can be dissolved in hydroalcoholic solution and after being injected, the alcohol diffuses out causing the polymers to precipitate and gelling of the solution. CAP is a nanoparticulate system that gels in a pH-dependent manner. The active compound (pharmacologic agent) is adsorbed partially onto the surface of the polymer particles. Sodium alginate gels in the presence of calcium or other polyvalent ion.

Poloxamers are triblock copolymers formed of (i.e., hydrophilic poly(oxyethylene) blocks and hydrophobic poly(oxypropylene) blocks) configured as a triblock of poly(oxyethylene)-poly(oxypropylene)-poly(oxyethylene).

Poloxamers are one class of block copolymer surfactants having a propylene oxide block hydrophobe and an ethylene oxide hydrophile. Poloxamers are commercially available (e.g., Pluronic® polyols are available from BASF Corporation). Alternatively, polaxamers can be synthesized by known techniques.

Formulations described herein are suitable for inhalation or intravenous, intraperitoneal, intramuscular, subcutaneous, mucocutaneous, oral, rectal, transdermal, topical, buccal, intradermal, intragastric, intradermal, intranasal, intrabuccal, percutaneous or sublingual administration. In certain embodiments administration is via injection into the middle ear as well as topical administration to the drum. Formulations may also be administered directly to the inner ear. Formulations can be administered via multiple vehicles including biomaterials, solutions, devices (including but not limited to hearing aids, cochlear implants, headphones, and earbuds).

The pharmaceutical compositions can be prepared and administered in the form of transdermal delivery system (patch film), drops, pills, tablets, film-coated tablets, multi-layer tablets, gels, ointments, syrups, granules, suppositories, emulsions, dispersions, microcapsules, nanoparticles, microparticles, capsules, powders or injectable solutions. Pharmaceutical formulations preferably in form of liposomes, emulsions and gels and combinations thereof.

Embodiments described herein also include pharmaceutical compositions, which were prepared using at least one compound described herein, or salts thereof.

The pharmaceutical compositions may also contain a pharmacologically acceptable carrier, excipient and/or solvent.

Such formulations are suitable for inhalation or intravenous, intraperitoneal, intramuscular, subcutaneous, mucocutaneous, oral, rectal, transdermal, topical, buccal, intradermal, intragastric, intradermal, intranasal, intrabuccal, percutaneous or sublingual administration. In certain embodiments, administration is via injection into the middle ear as well as topical administration to the drum.

The pharmaceutical compositions can be prepared and administered in the form of transdermal delivery system (patch film), drops, pills, tablets, film-coated tablets, multi-layer tablets, gels, ointments, syrups, granules, suppositories, emulsions, dispersions, microcapsules, capsules, powders or injectable solutions. Pharmaceutical formulations may be in form of liposomes, emulsions and gels.

For preparing suppositories, low melting waxes, fatty acid esters and glycerides can be used. Pharmaceutical compositions for any route of administration of beta-carbolines contain a sufficient therapeutic effect for the amount of ß-carboline and, if necessary, inorganic or organic, solid or liquid pharmaceutically acceptable carriers. Pharmaceutical compositions which are suitable for enteral or parenteral administration include tablets or gelatine capsules or aqueous solutions or suspensions as described above.

The pharmaceutical compositions may be sterilized and/or contain adjuvants, such as preservatives, stabilizers, wetting agents and/or emulsifiers, salts for regulating the osmotic pressure and/or buffers. The inventive pharmaceutical composition may, if desired, contain other active ingredients. These pharmaceutical compositions may be prepared by any method that is known from the prior art are prepared, for example, by conventional methods such as mixing, granulating, packaging, and lyophilization solution and can range from about 0.01 to 100 percent, preferably between 0, 1, and 50 percent in Lyophilizates contain up to 100 percent of ß-carboline.

Certain compositions of the invention for topical administration may be other pharmaceutically acceptable substances and/or substances. In certain embodiments of the present invention, a topical excipient is selected that does not increase the delivery of beta-carbolines and optionally further active ingredient or ingredients into the blood circulatory system or the central nervous system if it is verbreicht at the ear, in the ear or in the ear canal. For example, it is may be desired that the topical excipient does not have a substantial exclusion property which enhances percutaneous transmission through the mucosa into the systemic circulatory system. Such carriers include hydro-carboxylic acids, such as anhydrous absorbent hydrophilic petrolatum (Vaseline) and anhydrous lanolin (for example, Aquaphor), and means on the basis of water-oil emulsions such as lanolin and cold cream. Certain embodiments include carriers which are non-exclusive substantially and typically include those support materials which are water soluble, as well as materials based on oil-in-water emulsions (creams or hydrophilic ointments) and substance water-soluble base, such as for polyethylene glycol-based excipients and aqueous solutions gelled with various agents were as methyl cellulose, hydroxyethyl cellulose and hydroxpropylmethylcellulose.

All delivery methods and materials mentioned in U.S. Pat. Nos. 5,837,681 and 6,593,290 are incorporated herein by reference.

If desired, the composition to be administered may also contain minor amounts of nontoxic auxiliary carrier or excipient substances such as wetting agents, emulsifying agents, or solubilizing agents, antioxidants, antimicrobials, pH buffering agents and the like, for example, sodium acetate, sodium citrate, cyclodextrin derivatives, sorbitan monolaurate, triethanolamine acetate, triethanolamine oleate, etc. Actual methods of preparing such dosage forms are known, or will be apparent, to those skilled in this art; for example, see Remington: The Science and Practice of Pharmacy, Mack Publishing Company, Easton, Pa., 20th Edition, 2000. The composition or formulation to be administered will, in any event, contain a quantity of the active compound in an amount effective to alleviate the symptoms of the subject being treated. As those in the art will appreciate, the agents described herein may also be formulated for targeted delivery to a subset of tissues or cells in a subject. In general, targeted delivery is accomplished by formulating a compound of the agents with a targeting moiety. Such moieties include lipids, liposomes, and ligands for molecules that bind, or are bound by, other molecules in vivo.

Any derived form of the agents (example synthetic or natural), or a conjugate thereof, can be prepared as an acid salt or as a base salt, as well as in free acid or free base forms. Such compositions if used to prevent or treat auditory dysfunctions are covered under in certain embodiments described herein.

In some embodiments, the compositions herein also target supporting cells that do not express Lgr5. In certain embodiments, the agents described herein in addition to promoting the proliferation of supporting cells, also impact the differentiation of the supporting cells to cell types that can help enhancing hearing. In some embodiments the agents described herein also impact the survival of the supporting cells.

The amount of the agent required for use in treatment may vary not only with the particular agent and salt selected, but also with the route of administration, the nature of the condition being treated, and the age and condition of the patient, among other factors, and ultimately is determined at the discretion of the attending physician or clinician. The desired dose may conveniently be presented in a single dose or as divided doses administered at appropriate intervals, for example, as two, three, four or more sub-doses per day. The sub-dose itself may be further divided, for example, into a number of discrete, loosely spaced administrations, such as multiple ingestions of pill doses, or liquid doses.

Further still, the agents, and their respective acid or base salts, can be formulated into liquid, preferably aqueous, formulations for storage and administration, as well as dried formulations that may, for example, be used as powders for administration or be reconstituted into liquid form just prior to administration to a subject. Liquid pharmaceutically administrable compositions can, for example, be prepared by dissolving, dispersing, etc. the particular agent and optional pharmaceutical adjuvants in an aqueous carrier. Aqueous carriers include water (particularly water for injection into humans), alcoholic/aqueous solutions, and emulsions and suspensions. Pharmaceutically acceptable aqueous carriers include sterile buffered isotonic saline solutions. Vehicles may include sodium chloride solution, Ringer's dextrose, dextrose, and sodium chloride, lactated Ringer's, or fixed oils. Intravenous vehicles include fluid and nutrient replenishers, electrolyte replenishers (such as those based on Ringer's dextrose), and the like. Preservatives and other additives may also be present, such as, for example, antimicrobials, antioxidants, chelating agents, and inert gases and the like. Non-aqueous solvents may also be used including propylene glycol, ethanol, polyethylene glycol, vegetable oils such as olive oil, and injectable organic esters such as ethyl oleate. The neutraceutical, pharmaceutical and veterinary compositions of the agents, whether dry or liquid, are preferably can also be formulated for oral administration.

As used herein, paints (also known as film formers) are solutions comprised of a solvent, a monomer or polymer, an active agent, and optionally one or more pharmaceutically-acceptable excipients. After application to a tissue, the solvent evaporates leaving behind a thin coating comprised of the monomers or polymers, and the active agent. By way of non-limiting example, paints include collodions (e.g., Flexible Collodion, USP), and solutions comprising saccharide siloxane copolymers and a cross-linking agent. The paints contemplated for use herein, are flexible such that they do not interfere with the propagation of pressure waves through the ear. Further, the paints may be applied as a liquid (i.e., solution, suspension, or emulsion), a semisolid (i.e., a gel, foam, paste, or jelly) or an aerosol.

Examples of suitable foamable carriers for use in the compositions disclosed herein include, but are not limited to, alginate and derivatives thereof, carboxymethylcellulose and derivatives thereof, collagen, polysaccharides, including, for example, dextran, dextran derivatives, pectin, starch, modified starches such as starches having additional carboxyl and/or carboxamide groups and/or having hydrophilic side-chains, cellulose and derivatives thereof, agar and derivatives thereof, such as agar stabilized with polyacrylamide, polyethylene oxides, glycol methacrylates, gelatin, gums such as xanthum, guar, karaya, gellan, arabic, tragacanth and locust bean gum, or combinations thereof. The formulation optionally further comprises a foaming agent, which promotes the formation of the foam, including a surfactant or external propellant. Examples of suitable foaming agents include cetrimide, lecithin, soaps, silicones and the like. Commercially available surfactants such as Tween™ are also suitable.

In particular embodiments, gel formulations that are useful in practicing methods described herein include, but are not limited to, glycerin-based gels, glycerin-derived compounds, conjugated, or crosslinked gels, matrices, hydrogels, and polymers, as well as gelatins and their derivatives, alginates, and alginate-based gels, and various native and synthetic hydrogel and hydrogel-derived compounds.

In some embodiments, the compositions described herein have a concentration of each pharmaceutically active ingredient (i.e., Notch Activator and/or DAC inhibitor and a GSK3b inhibitor and/or WNT activator or derivatives, small molecules, pharmaceutically acceptable salts, prodrugs, solvates, stereoisomers, racemates, or tautomers thereof) of between about 0.01% to about 90%>, between about 0.01) to about 50%), between about 0.1% to about 70%>, between about 0.1% to about 50%0, between about 0.1% to about 40%>, between about 0.1% to about 30%, between about 0.1%) to about 20%, between about 0.1% to about 10%, or between about 0.1% to about 5%), of the each active ingredient, by weight of the composition.

In some embodiments, the compositions described herein have a concentration of each active pharmaceutical agent between about 1% to about 50%, between about 5% to about 50%, between about 10% to about 40%, or between about 10% to about 30%, of the active ingredient, or pharmaceutically acceptable salt, prodrug, solvate, stereoisomer, racemate, or tautomer thereof, by weight of the composition.

In some embodiments, the formulations described herein have a concentration of active pharmaceutical ingredient of between about 0.1 to about 70 mg/mL, between about 0.5 mg/mL to about 70 mg/mL, between about 0.5 mg/mL to about 50 mg/mL, between about 0.5 mg/mL to about 20 mg/mL, between about 1 mg to about 70 mg/mL, between about 1 mg to about 50 mg/mL, between about 1 mg/mL and about 20 mg/mL, between about 1 mg/mL to about 10 mg/mL, or between about 1 mg/mL to about 5 mg/mL, of the active agent, or pharmaceutically acceptable salt, prodrug, solvate, stereoisomer, racemate, or tautomer thereof, by volume of the formulation.

In one embodiment, the formulations disclosed herein additionally provide an immediate release of one or more pharmaceutically active ingredients (i.e., a Notch Activator and/or HDAC inhibitor and a GSK3b inhibitor and/or WNT activator or other small molecules, pharmaceutically acceptable salts, prodrugs, solvates, stereoisomers, racemates, or tautomers thereof) from the composition, or within 1 minute, or within 5 minutes, or within 10 minutes, or within 15 minutes, or within 30 minutes, or within 60 minutes or within 90 minutes. In other embodiments, a therapeutically effective amount of at least one pharmaceutically active ingredient (i.e., a Notch Activator and/or HDAC inhibitor and a GSK3b inhibitor and/or WNT activator or derivatives, small molecules, pharmaceutically acceptable salts, prodrugs, solvates, stereoisomers, racemates, or tautomers thereof) is released from the composition immediately, or within 1 minute, or within 5 minutes, or within 10 minutes, or within 15 minutes, or within 30 minutes, or within 60 minutes or within 90 minutes.

In other embodiments, the composition is formulated as an extended release formulation. In certain embodiments, diffusion of at least one pharmaceutically active ingredient (including a Notch Activator and/or HDAC inhibitor and a GSK3b inhibitor and/or WNT activator), small molecules, pharmaceutically acceptable salts, prodrugs, solvates, stereoisomers, racemates, or tautomers thereof) from the formulation occurs for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year. In other embodiments, a therapeutically effective amount of at least one pharmaceutically active ingredient (including a Notch Activator and/or HDAC inhibitor and a GSK3b inhibitor and/or WNT activator) is released from the formulation for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year.

In further embodiments, the formulation provides both an immediate release and an extended release formulation. In particular embodiments, the formulation contains a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations. In a further embodiment the formulation provides an immediate release of a first pharmaceutically active ingredient (i.e., small molecules, pharmaceutically acceptable salts, prodrugs, solvates, stereoisomers, racemates, or tautomers thereof) and an extended release of a second pharmaceutically active ingredient or other therapeutic agent. In some embodiments, the formulation provides a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations of a first pharmaceutically active ingredient and second pharmaceutically active ingredient.

The combination of immediate release, delayed release and/or extended release compositions or formulations may be combined with other pharmaceutical agents, as well as the excipients, diluents, stabilizers, carrier agents and other components disclosed herein. As such, depending upon the components of the composition, the thickness or viscosity desired, or the mode of delivery chosen, alternative aspects of the embodiments disclosed herein are combined with the immediate release, delayed release and/or extended release embodiments accordingly F. Administration In certain embodiments, pharmaceutical formulations are adapted to administer the drug locally to the round window membrane. The pharmaceutical formulations may also contain a membrane penetration enhancer, which supports the passage of the agents mentioned herein through the round window membrane. Accordingly, in such embodiments liquid or gel formulations may be used. It is also possible to apply the active ingredient orally or to employ a combination of delivery approaches.

The long-acting formulation that prolongs drug release and/or improved stability may be in the form of agents mentioned herein complexed, or covalently conjugated (by reversible or irreversible bonding) to a macromolecule such as a water-soluble polymer selected from PEG and polypropylene glycol homopolymers and polyoxyethylene polyols, i.e., those that are soluble in water at room temperature. Alternatively, the agent mentioned herein may be complexed or bound to a polymer to increase its drug release and/or half-life. Examples of polyethylene polyols and polyoxyethylene polyols useful for this purpose include polyoxyethylene glycerol, polyethylene glycol, polyoxyethylene sorbitol, polyoxyethylene glucose, or the like. The glycerol backbone of polyoxyethylene glycerol is the same backbone occurring in, for example, animals and humans in mono-, di-, and triglycerides. Agents mentioned herein can be encapsulated in materials and/or conjugated to materials. For delivery of more than one agent, one or more delivery vehicle may be used. The delivery kinetics for multiple agents can be the same or different. For example in one case it may be beneficial to include a short pulse of one drug and have another be released for a longer duration.

Liquid formulations include solutions, suspensions, emulsions and sprays. For example, injection solutions, water-based or water-propylene glycol for parenteral injection.

Pharmaceutical compositions suitable for topical administration in the middle ear include aqueous solutions or suspensions which can be prepared prior to administration in the middle ear, such as in the case of lyophilized formulations that contain a composition of the present disclosure, alone or together with a carrier. The pharmaceutical compositions further include gels, which is biodegradable or non-biodegradable, aqueous or non-aqueous or microspheres are based. Examples of such gels and other suitable materials include poloxamers, Hyaluronate, xyloglucans, chitosan, polyesters, polylactide, polyglycolide and their copolymers PLGA polymer, poly anhydrides, poly caprolactone sucrose and glycerol monooleate.

The pharmaceutical compositions may be sterilized and/or contain adjuvants, such as preservatives, stabilizers, wetting agents and/or emulsifiers, salts for regulating the osmotic pressure and/or buffers. The pharmaceutical composition may, if desired, contain other active ingredients in addition to those previously described herein.

These pharmaceutical compositions may be prepared by any method that is known from the prior art are prepared, for example, by conventional methods such as mixing, granulating, packaging, and lyophilization solution.

The pharmaceutical composition may also include agents to help with controlled delivery and/or excipients described in US patent application no. US20110166060.

In certain embodiments, the inventive pharmaceutical composition is formulated for topical administration. Suitable carriers for an otogenic administration are organic or inorganic substances, which are pharmaceutically acceptable and which do not react with the described agents, and/or other active compounds, for example saline, alcohols, vegetable oils, benzyl alcohols, Alkylglycole, polyethylene glycols, Glycerintriacetate, gelatin, carbohydrates such as lactose or starch, magnesium oxide (magnesia, chalk), stearate (waxes), talc and petrolatum (Vaseline). The compositions described above can be sterilized and/or contain auxiliaries such as lubricants, preservatives such as thimerosal, for example, 50 percent by weight), stabilizers and/or wetting agents, emulsifiers, salts for influencing the osmotic pressure, buffer substances, colorants and/or flavorings. These compositions may contain one or more other active ingredients if necessary. Otogenic inventive compositions may comprise different materials and/or substances, including other biologically active substances such as antibiotics, anti-inflammatory agents such as steroids, cortisone, analgesics, antipyrine, benzocaine, procaine, etc.

Intratympanic (IT) delivery of drugs to the ear is increasingly used for both clinical and research purposes. Some groups have applied drugs in a sustained manner using microcatheters and microwicks, while the majority have applied them as single or as repeated IT injections (up to 8 injections over periods of up to 2 weeks).

Intratympanically applied drugs are thought to enter the fluids of the inner ear primarily by crossing the round window (RW) membrane. Calculations show that a major factor controlling both the amount of drug entering the ear and the distribution of drug along the length of the ear is the duration the drug remains in the middle ear space. Single, 'one-shot' applications or applications of aqueous solutions for few hours' duration result in steep drug gradients for the applied substance along the length of the cochlea and rapidly declining concentration in the basal turn of the cochlea as the drug subsequently becomes distributed throughout the ear.

Methods for delivering (including relevant materials and permutations thereof) and methods studying distribution and kinetics of drug delivered to the inner ear are known in the art. For example, in one embodiment a 20% (w/w) stock solution of poloxamer 407 gel (Spectrum Chemical MFG Corp., Gardena, Calif., USA) is prepared by slowly adding it to cold 10 m M phosphate-buffered saline at pH 7.4. Other poloxamers or other materials may be used. Additional buffer solution is added to obtain a 17% w/w concentration of poloxamer 407 gel. This solution is liquid when refrigerated or at room temperature but solidifies at body temperature. The gel can be tinted blue with a die such as Evans blue dye (50 ppm) and sterilized by filtration. Using aseptic techniques, sterilized micronized dex (pure dex in a crystalline, powder form; Pfizer Inc., Kalamazoo, Mich., USA) is suspended with an appropriate amount of sterile poloxamer 407 solution to obtain a 4.5% solution. Samples of the formulation are stored under refrigeration and re-suspended immediately before administration.

Poloxamer-407 hydrogels were prepared using the "cold-method". Briefly, a weighed amount of poloxamer-407 was added to 40 ml cold ultra pure water or cold PBS (pH 7.4), and stirred overnight at 4° C. on a magnetic stir plate to effect complete solubilization. Multiple concentrations of poloxamer-407 solution ranging from 18% (w/w) to 25% (w/w) were prepared. Hydrophilic drugs, including valproic acid (VPA) and phosphorylated ascorbic acid (PAC) were added to the 5 ml poloxamer-407 solution and dissolved at 4° C. on a magnetic stir plate. Weight ratio of poloxamer-407 to the drug was varied to understand the effects of drugs on the gelation properties of poloxamer-407, and to determine the optimal formulation that gels at 37° C. with maximum possible loading of the hydrophilic drugs. The gelation temperatures of the formulations were determined by the "visual tube inversion method". Briefly, glass vials containing poloxamer 407 solutions, with or without the hydrophilic drugs were placed in a water bath. The temperature was slowly increased and the temperature at which the solution stopped flowing on tilting the glass vial was noted as the gelation temperature.

To encapsulate hydrophobic drugs, including CHIR 99021 (CHIR), Repsox and TTNPB, appropriate volumes from their stock solutions in DMSO were added into the poloxamer-407 solutions containing the hydrophilic drugs, and mixed by pipetting at 4° C. Maximum DMSO concentration to be added with the hydrophobic drugs was limited to 5-6% (v/v) with respect to the total volume of the gel. Higher concentration of DMSO reduced the gelation temperature of the gel. Gelation temperature of the formulation was determined by the "visual tube inversion method", as described before.

The biologically active agents of the present disclosure may be prepared as an acid salt or as a base salt, as well as in free acid or free base forms. The amount of the agent required for use in treatment may vary not only with the particular agent and salt selected, but also with the route of administration, the nature of the condition being treated, and the age and condition of the patient, among other factors, and ultimately is determined at the discretion of the attending physician or clinician. The desired dose may conveniently be presented in a single dose or as divided doses administered at appropriate intervals.

Further still, the active agents, and their respective acid or base salts, can be formulated into liquid, preferably aqueous, formulations for storage and administration, as well as dried formulations that may, for example, be used as powders for administration or be reconstituted into liquid form just prior to administration to a subject. Liquid pharmaceutically administrable compositions can, for example, be prepared by dissolving, dispersing, etc. the particular agent and optional pharmaceutical adjuvants in an aqueous carrier. Aqueous carriers include water (particularly water for injection into humans), alcoholic/aqueous solutions, and emulsions and suspensions. Pharmaceutically acceptable aqueous carriers include sterile buffered isotonic saline solutions. Vehicles may include sodium chloride solution, Ringer's dextrose, dextrose, and sodium chloride, lactated Ringer's, or fixed oils. Intravenous vehicles include fluid and nutrient replenishers, electrolyte replenishers (such as those based on Ringer's dextrose), and the like. Preservatives and other additives may also be present, such as, for example, antimicrobials, antioxidants, chelating agents, and inert gases and the like. Non-aqueous solvents may also be used including propylene glycol, ethanol, polyethylene glycol, vegetable oils such as olive oil, and injectable organic esters such as ethyl oleate.

Measuring Hearing

Hearing can be measured using behavioral and or electrical audiometry.

Tests to diagnose hearing loss in humans may include but are not limited to:

General screening tests. A doctor may ask to cover one ear at a time to see how well one hears words spoken at various volumes and how they respond to other sounds.

Tuning fork tests. Tuning forks are two-pronged, metal instruments that produce sounds when struck. Simple tests with tuning forks can help your doctor detect hearing loss. A tuning fork evaluation may also reveal whether hearing loss is caused by damage to the vibrating parts of your middle ear (including your eardrum), damage to sensors or nerves of your inner ear, or damage to both.

Audiometer tests. During these more-thorough tests conducted by an audiologist, one wears earphones and hear sounds directed to one ear at a time. The audiologist presents a range of sounds of various tones and asks you to indicate each time you hear the sound. Each tone is repeated at faint levels to find out when you can barely hear. The audiologist will also present various words to determine one's hearing ability.

Other tests may include:

Auditory Brainstem Response (ABR) Test or Brainstem Auditory Evoked Response (BAER) Test that checks the brain's response to sound. Because this test does not rely on a person's response behavior, the person being tested can be sound asleep during the test.

Otoacoustic Emissions (OAE) is a test that checks the inner ear response to sound. Because this test does not rely on a person's response behavior, the person being tested can be sound asleep during the test.

Behavioral Audiometry Evaluation tests how a person responds to sound overall. Behavioral Audiometry Evaluation tests the function of all parts of the ear. The person being tested must be awake and actively respond to sounds heard during the test.

In the case of children, With the parents' permission, the audiologist will share the results with the child's primary care doctor and other experts, such as:

An ear, nose and throat doctor, also called an otolaryngologist, An eye doctor, also called an ophthalmologist, A professional trained in genetics, also called a clinical geneticist or a genetics counselor.

Exemplary Embodiments

The present disclosure further includes the following exemplary embodiments.

In some embodiments "stem cells" includes progenitor cells.

In some embodiments, an FGF1 agonist is used. In some embodiments this may replace or be added to the Notch activator and/or HDAC inhibitor. In some embodiments molecules are selected that activate the FGF1 gene promoter. (e.g FGF-1B)

In certain embodiments, cell populations described herein can be delivered into the inner ear to populate the inner ear and/or enhance hearing. Cell populations have been previously shown to survive following transplantation into the inner ear as described in this patent CN103361300 A and paper.

"In addition, transplanted into the inner ear of guinea pigs, human amniotic epithelial cells have been shown to survive for up to three weeks, and the expression of important proteins to maintain homeostasis (Yuge, 1. et al (2004): 77 (9) 1452-1471)."

In certain embodiments, Lgr5+ cells from the inner ear are differentiated using a combination of at least one WNT activator and at least one NOTCH inhibitor.

In certain embodiments, polyoxyethylene-polyoxypropylene triblock copolymer or derivatives thereof can be used to deliver molecules or factors described herein to the middle ear and/or for controlled release.

In certain embodiments, methods comprise determining a baseline level of hearing at one or more frequencies before administering the composition, and a subsequent level of hearing at the same one or more frequencies after administering the composition, and administering one or more additional doses of the composition until a desired level of hearing at the one or more frequencies is recovered.

In certain embodiments, the subsequent level of hearing is determined one week, two weeks, three weeks, one month, two months, three months, four months, six months, and/or twelve months after administering the composition.

Methods are presented herein wherein the mammal is a child, adolescent or adult, e.g., above the age of 1, 2, 3, 4, 5, 6, 7, 8, 9, 10, 11, 12 or 13 years.

Methods are presented herein wherein the mammal is an adult of at least 40 years of age, e.g., at least 45, 50, 55, 60, 65, 70 years of age.

Methods are presented herein wherein the composition is delivered to a mammal.

Methods are presented herein wherein the mammal is a human.

Use of a cell population is described herein, for use in an ototoxicity assay, for example, use of Lgr5+ cells in 96 or 384 well plates (or other plate format) to screen agents to boost generation of supporting cells, or proteins expressed by supporting cells (or to screen for agents to suppress protein expression), and/or their differentiation . . . or to identify agents to generate hair cells for ototoxicity or agents to boost survival of hair cells that is useful to sustain hearing following damage to hair cells or to sustain hair cells following regeneration. or to screen specific agents to kill specific cells populations (Lgr5+ cells or their progeny including hair cells) if needed. Also use of Lgr5+ cells produced herein to serve as cell population for reprogramming or programming protocols.

In certain embodiments, a gamma-secretase inhibitor in addition to a GSK3b inhibitor is used to promote differentiation of supporting cells into hair cells.

Methods are presented herein that expand Lgr5+ supporting cells with at least one wnt activator and at least one notch activator (and/or HDAC inhibitor) followed by differentiation to hair cells with at least one WNT activator (preferable embodiment use CHIR) and one notch inhibitor.

A method of treating a subject who has or is at risk of developing hearing loss or vestibular dysfunction, the method comprising: Identifying a subject who has experienced, or is at risk for developing, hearing loss or vestibular dysfunction; Administering to the ear of the subject a composition comprising one or more compounds that increase wnt expression or activity and inhibits HDAC (and/or activates NOTCH) in a cell in the subject's ear; thereby treating the hearing loss or vestibular dysfunction in the subject.

A method of treating a subject who has or is at risk of developing hearing loss or vestibular dysfunction, the method comprising identifying a subject who has experienced, or is at risk for developing, hearing loss or vestibular dysfunction, administering to the ear of the subject a composition comprising CHIR99021

A method of treating a subject who has or is at risk of developing hearing loss or vestibular dysfunction, the method comprising selecting a subject in need of treatment, obtaining a population of cells capable of differentiating into hair cells, contacting the population of cells in vitro with an effective amount of a composition comprising one or more compounds that increase wnt expression or activity and inhibits HDAC (and/or activates NOTCH) for a time sufficient to induce at least some of the cells to express one or more of WNT, or reduce or limit expression of HDAC and/or express NOTCH or homologues thereof, and administering the population of cells, or a subset thereof, to the subject's ear.

In one embodiment, cell populations describe herein can be used to screen for γ-secretase inhibitors that induce hair cell differentiation from inner ear stem cells In one embodiment, a tube in tympanic membrane is placed for continuous and or repeat dosing into the middle ear.

In a particular embodiment, the composition comprises a biodegradable polymer.

In another embodiment, the composition comprises one or more small molecules that decrease the gene expression of Atoh1.

In one embodiment, the composition comprises one or more small molecules that decrease the protein expression of Atoh1.

In another embodiment, the composition comprises one or more small molecules that increase the gene expression of Atoh1.

In one embodiment, the composition comprises one or more small molecules that increase the protein expression of Atoh1.

In a certain embodiment, the composition comprises one or more small molecules that increase the activity of Atoh1 protein.

In a further embodiment, the one or more small molecules that increase gene expression of Atoh 1, increase protein expression of Atoh1, or increase the activity of Atoh1 protein is selected from the group consisting of: CHIR99021, 1-Azakenpaullone, and (2'Z,3'E)-6-Bromoindirubin-3'-oxime (BIO).

In a particular embodiment, the composition comprises a biodegradable polymer.

In an additional embodiment, the composition is administered to the middle ear of the subject.

In another embodiment, the composition is administered onto or adjacent to the round window membrane.

In one embodiment, the composition is administered to the inner ear of the subject.

In one particular embodiment, the composition is administered to the cochlea of the subject. In one certain embodiment, the composition is administered to the Organ of Corti of the subject.

In one additional embodiment, the composition is administered by transtympanic administration.

In one further embodiment, the composition is administered by transtympanic wick.

In another embodiment, the composition is administered by transtympanic catheter.

In yet another embodiment, the composition is administered by intracochlear injection.

In various embodiments, the disclosure contemplates, in part, a method for promoting cochlear hair cell regeneration comprising administering, to a middle or inner of a subject, a composition comprising a notch activator (and or HDAC inhibitor) and wnt activator in an amount effective and for a time sufficient to promote cochlear hair cell proliferation, thereby promoting cochlear hair cell regeneration.

In one embodiment, the subject has a partial or complete loss of hearing or balance.

In a particular embodiment, the subject has sensorineural hearing loss due to acute or chronic exposure to ototoxic compounds, acute or chronic exposure to noise, age related hearing loss, a genetic related hearing loss, or has auditory neuropathy.

In a certain embodiment, the subject is at risk of developing sensorineural hearing loss or auditory neuropathy.

Methods and agents described in following references are included here in their entirety.

Mammalian cochlear supporting cells can divide and transdifferentiate into hair cells. White P M, Doetzlhofer A, Lee Y S, Groves A K, Segil N. Nature. 2006 Jun. 22; 441(7096):984-7.

Lgr5-positive supporting cells generate new hair cells in the postnatal cochlea. Bramhall N F, Shi F, Arnold K, Hochedlinger K, Edge A S. Stem Cell Reports. 2014 Feb. 20; 2(3):311-22. doi: 10.1016/j.stemcr.2014.01.008. eCollection 2014 Mar. 11.

Notch inhibition induces cochlear hair cell regeneration and recovery of hearing after acoustic trauma. Mizutari K, Fujioka M, Hosoya M, Bramhall N, Okano H J, Okano H, Edge A S. Neuron. 2013 Jan. 9; 77(1):58-69. doi: 10.1016/j.neuron.2012.10.032. Erratum in: Neuron. 2013 Apr. 24; 78(2):403.

Generation of hair cells in neonatal mice by β-catenin overexpression in Lgr5-positive cochlear progenitors. Shi F, Hu L, Edge A S. Proc Natl Acad Sci USA. 2013 Aug. 20; 110(34):13851-6. doi: 10.1073/pnas.1219952110. Epub 2013 Aug. 5.

Notch signaling alters sensory or neuronal cell fate specification of inner earstem cells. Jeon S J, Fujioka M, Kim S C, Edge A S. J Neurosci. 2011 Jun. 8; 31(23):8351-8. doi: 10.1523/JNEUROSCI.6366-10.2011.

Wnt-responsive Lgr5-expressing stem cells are hair cell progenitors in the cochlea. Shi F, Kempfle J S, Edge A S. J Neurosci. 2012 Jul. 11; 32(28):9639-48. doi: 10.1523/JNEUROSCI.1064-12.2012. PMID:

Spontaneous hair cell regeneration in the neonatal mouse cochlea in vivo. Cox B C, Chai R, Lenoir A, Liu Z, Zhang L, Nguyen D H, Chalasani K, Steigelman K A, Fang J, Rubel E W, Cheng A G, Zuo J. Development. 2014 February; 141(4):816-29. doi: 10.1242/dev.103036.

Those skilled in the art will realize that there are many permutations to how agents described herein or their derivatives may be used and delivered. Combinations with other agents can also be employed. Relevant patent references describing other agents that may be used in combination with agents described herein but not limited to (and describing methodologies that can be used): US20130324594 A1, WO2011079841 A1, U.S. Pat. No. 7,498,031 B2, U.S. Pat. No. 6,177,434 B1, CA2268331 C, WO2008010852 A2, U.S. Pat. No. 7,387,614 B2, WO1996040094 A1, WO2008076556 A2.

Additional Background Information

Auditory Hair Cells in Birds

Currently, hearing loss in mammals is permanent. While frogs, fish, and birds6 with hearing loss regain their hearing naturally, mammals lost that ability as much as 300 million years ago, and so far scientists have been unsuccessful in solving that problem. The ultimate goal of hair cell regeneration is to restore functional hearing. Because birds begin perceiving and producing song early in life, they provide a propitious model for studying not only whether regeneration of lost hair cells can return auditory sensitivity but also whether this regenerated periphery can restore complex auditory perception and production. They are a rare example of where hair cell regeneration occurs naturally after hair cell loss and where the ability to correctly perceive and produce complex acoustic signals is critical to procreation and survival. Thus the biology exists for regeneration of the inner ear cells to enhance or restore hearing.

Importantly, acoustic overstimulation can lead to sensory cell (hair cell) loss in the auditory epithelium. Damaged hair cells in the organ of Corti (the mammalian auditory end-organ) degenerate and are replaced by non-sensory cells (supporting cells) which construct an irreversible scar. In birds, however, auditory hair cells which are damaged by acoustic trauma or ototoxic drugs may be replaced by new hair cells. Supporting cells in damaged regions of the avian auditory epithelium incorporate the DNA-specific marker bromodeoxyuridine as early as one day after noise exposure7. Following acoustic insult to the avian inner ear, supporting cells which reside within the sensory epithelium divide near the luminal surface and repopulate the epithelium. These results suggest that supporting cells participate in scar formation during hair cell degeneration, and produce new cells for regeneration.

Hearing Loss and Destruction of Hair Cells

Hair cells of the inner ear are critical to hearing and vestibular function. In mammals, the loss of sensory hair cells is permanent, as there is no significant capacity for regeneration of these cells. Drugs such as aminoglycoside antibiotics and many anti-neoplastic drugs are often used despite unfortunate side effects. One such side effect is hearing loss due to death of the sensory hair cells of the inner ear. Aminoglycosides are clinically used drugs that cause dose-dependent sensorineural hearing loss (Smith et al., New Engl J Med. (1977) 296:349-53) and are known to kill hair cells in the mammalian inner ear (Theopold, Acta Otolaryngol (1977) 84:57-64). In the U.S. over 2,000,000 people receive treatment with aminoglycosides per year. The clinical efficacy of these drugs in treating resistant bacterial infections and their low cost globally account for their continued use and need. Cisplatin, a chemotherapeutic agent, is also used for its benefit to life despite its toxic effects on the hair cells of the inner ear. High frequency hearing loss (>8 kHZ) has been reported to be as high as 90% in children undergoing cisplatin therapy (Allen, et al., Otolaryngol Head Neck Surg (1998) 118:584-588). The incidence of vestibulotoxic effects of such drugs on patient populations has been less well studied. Estimates range between 3% and 6% with continued reports in the literature of patients with aminoglycoside induced vestibulotoxicity (Dhanireddy et al., Arch Otolarngol Head Neck Surg (2005) 131:46-48). Other clinically important and commonly used drugs also have documented ototoxic effects, including loop diuretics (Greenberg, Am J Med Sci. (2000) 319:10-24) and antimalarial quinines (Claessen, et al., Trop Med Int Health, (1998) 3:482-9) salicylates (Matz, Ann Otol Rhinol Laryngol Suppl (1990) 148:39-41).

Research in the past few decades has uncovered some of the key intracellular events that can cause hair cell death. Several candidate protectants have been evaluated such as antioxidants, caspase inhibitors, and jun kinase inhibitors (Kopke R D, et al. Am J Otol 1997, 18:559-571; Liu W, et al. Neuroreport 1998, 9:2609-2614; Yamasoba T. et al. Brain Res 1999, 815:317-325: Matsui J I, et al. J Neurosci 2002, 22:1218-1227; Sugahara K, et al. Hear Res 2006, 221:128-135.) A few of these candidate otoprotectants have progressed to human trials (Sha S H, et al. N Engl J Med 2006, 354:1856-1857; Campbell K C, et al. Hear Res 2007, 226:92-103). Further, different cell death pathways may be triggered in response to different forms of damage, and many protective molecules offer incomplete hair cell protection, hinting that polypharmacy approaches may offer the greatest benefit. Several examples of agents being explored to protect hair cells are included in US Patent Application Publication No. US20110135756 A1.

Hearing loss or impairment is a common occurrence for mammals Impairment anywhere along the auditory pathway from the external auditory canal to the central nervous system may result in hearing loss. Auditory apparatus can be divided into the external and middle ear, inner ear and auditory nerve and central auditory pathways. While having some variations from species to species, the general characterization is common for all mammals. Auditory stimuli are mechanically transmitted through the external auditory canal, tympanic membrane, and ossicular chain to the inner ear. The middle ear and mastoid process are normally filled with air. Disorders of the external and middle ear usually produce a conductive hearing loss by interfering with this mechanical transmission. Common causes of a conductive hearing loss include obstruction of the external auditory canal, as can be caused by aural atresia or cerumen, thickening or perforation of the tympanic membrane, as can be caused by trauma or infection, fixation or resorption of the components of the ossicular chain, and obstruction of the Eustachian tube, resulting in a fluid-filled middle-ear space. Auditory information is transduced from a mechanical signal to a neurally conducted electrical impulse by the action of neuro-epithehal cells (hair cells) and SGN in the inner ear.

All central fibers of SGN form synapses in the cochlear nucleus of the pontine brain stem. The auditory projections from the cochlear nucleus are bilateral, with major nuclei located in the inferior col culus, medial geniculate body of the thalamus, and auditory cortex of the temporal lobe. The number of neurons involved in hearing increases dramatically from the cochlea to the auditory brain stem and the auditory cortex. All auditory information is transduced by a limited number of hair cells, which are the sensory receptors of the inner ear, of which the so-called inner hair cells, numbering a comparative few, are critically important, since they form synapses with approximately 90 percent of the primary auditory neurons. By comparison, at the level of the cochlear nucleus, the number of neural elements involved is measured in the hundreds of thousands. Thus, damage to a relatively few cells in the auditory periphery can lead to substantial hearing loss. Hence, many causes of sensorineural loss can be ascribed to lesions in the inner ear. This hearing loss can be progressive. In addition, the hearing becomes significantly less acute because of changes in the anatomy of the ear as the animal ages.

During embryogenesis, the vestibular ganglion, spiral ganglion, and the otic vesicle are derived from the same neurogenic ectoderm, the otic placode. The vestibular and auditory systems thus share many characteristics including peripheral neuronal innervations of hair cells and central projections to the brainstem nuclei. Both of these systems are sensitive to ototoxins that include therapeutic drugs, antineoplastic agents, contaminants in foods or medicines, and environmental and industrial pollutants. Ototoxic drugs include the widely used chemotherapeutic agent cisplatin and its analogs (Fleischman et al, 1975; Stadnicki et al., 1975; Nakai et al., 1982; Berggren et al., 1990; Dublin, 1976; Hood and Berlin, 1986), commonly used aminoglycoside antibiotics, e.g. gentamicin, for the treatment of infections caused by Gram-negative bacteria, (Sera et al., 1987; Hinojosa and Lerner, 1987; Bareggi et al., 1990), quinine and its analogs, salicylate and its analogs, and loop-diuretics.

The toxic effects of these drugs on auditory cells and spiral ganglion neurons are often the limiting factor for their therapeutic usefulness. For example, antibacterial aminoglycosides such as gentamicins, streptomycins, kanamycins, tobramycins, and the like are known to have serious toxicity, particularly ototoxicity and nephrotoxicity, which reduce the usefulness of such antimicrobial agents (see Goodman and Gilman's The Pharmacological Basis of Therapeutics, 6th ed., A. Goodman Gilman et al., eds; Macmillan Publishing Co., Inc., New York, pp. 1169-71 (1980) or most recent edition). Aminoglycoside antibiotics are generally utilized as broad spectrum antimicrobials effective against, for example, gram-positive, gram-negative and acid-fast bacteria. Susceptible microorganisms include *Escherichia* spp., *Hemophilus* spp., *Listeria* spp., *Pseudomonas* spp., *Nocardia* spp., *Yersinia* spp., *Klebsiella* spp., *Enterobacter* spp., *Salmonella* spp., *Staphylococcus* spp., *Streptococcus* spp., *Mycobacteria* spp., *Shigella* spp., and *Serratia* spp. Nonetheless, the aminoglycosides are used primarily to treat infections caused by gram-negative bacteria and, for instance, in combination with penicillins for the synergistic effects. As implied by the generic name for the family, all the aminoglycoside antibiotics contain aminosugars in glycosidic linkage. Otitis media is a term used to describe infections of the middle ear, which infections are very common, particularly in children. Typically antibiotics are systemically administered for infections of the middle ear, e.g., in a responsive or prophylactic manner. Systemic administration of antibiotics to combat middle ear infection generally results in a prolonged lag time to achieve therapeutic levels in the middle ear, and requires high initial doses in order to achieve such levels. These drawbacks complicate the ability to obtain therapeutic levels and may preclude the use of some antibiotics altogether. Systemic administration is most often effective when the infection has reached advanced stages, but at this point permanent damage may already have been done to the middle and inner ear structure. Clearly, ototoxicity is a dose-limiting side-effect of antibiotic administration. For example, nearly 75% of patients given 2 grams of streptomycin daily for 60 to 120 days displayed some vestibular impairment, whereas at 1 gram per day, the incidence decreased to 25% (U.S. Pat. No. 5,059,591). Auditory impairment was observed from 4 to 15% of patients receiving 1 gram per day for greater than 1 week develop measurable hearing loss, which slowly becomes worse and can lead to complete permanent deafness if treatment continues. Ototoxicity is also a serious dose-limiting side-effect for cisplatin, a platinum coordination complex, that has proven effective on a variety of human cancers including testicular, ovarian, bladder, and head and neck cancer. Cisplatin damages auditory and vestibular systems (Fleischman et al, 1975, Stadnicki et al, 1975, Nakai et al, 1982, Carenza et al, 1986, Sera et al, 1987, Bareggi et al, 1990) Sa cylates, such as aspirin, are the most commonly used therapeutic drugs for their anti-inflammatory, analgesic, anti-pyretic and anti-thrombotic effects. Unfortunately, they have ototoxic side effects They often lead to tinnitus ("ringing in the ears") and temporary hearing loss (Myers and Bernstein, 1965). However, if the drug is used at high doses for a prolonged time, the hearing impairment can become persistent and irreversible, as reported clinically (Jarvis, 1966)

Pertinent Biology

Fish and birds generate inner ear hair cells where supporting cells in the cochlea serve as precursor cells. It is believed that hair cell regeneration occurs by two methods: direct transdifferentiation, where supporting cells directly become hair cells; and mitotic regeneration, in which supporting hair cells divide and one or both of the resulting cells develops into a hair cell.

It has been established that hair cell regeneration in the auditory and vestibular systems does occur in chickens and other non-mammals, though not in humans. This spontaneous regeneration leads to restoration of hearing and balance.

Additional Embodiments and Related Aspects

1. A method of facilitating the generation of inner ear hair cells, the method comprising:
   administering or causing to be administered to a stem cell population a first composition comprising (i) and (ii):
   (i) a GSK3-beta inhibitor or derivative or a pharmaceutically acceptable salt thereof and/or Wnt agonist or derivative or a pharmaceutically acceptable salt thereof, and
   (ii) a notch agonist or derivative or a pharmaceutically acceptable salt thereof and/or HDAC inhibitor or derivative or a pharmaceutically acceptable salt thereof, to expand the stem cell population; and
   exposing the expanded stem cell population to a second composition comprising GSK3-beta inhibitor and/or a Wnt agonist, and, optionally, a notch inhibitor, thereby facilitating generation of inner ear hair cells from the expanded population of stem cells.

1A. The method of embodiment 1 wherein the stem cell population is an in vitro stem cell population.

1B. The method of embodiment 1 wherein the stem cell population is an ex vivo stem cell population.

1C. The method of embodiment 1 wherein the stem cell population is an in vivo stem cell population.

1D. The method of embodiment 1 wherein the stem cell population is an in vivo stem cell population comprised by a subject and the first composition is administered to the stem cell population by administration of the first composition to the subject.

1E. The method of any of the preceding embodiments wherein the first composition comprises a Wnt agonist.

1F. The method of any of the preceding embodiments wherein the first composition comprises a GSK3-beta inhibitor.

1G. The method of any of the preceding embodiments wherein the first composition comprises a notch agonist.

1H. The method of any of the preceding embodiments wherein the first composition comprises a HDAC inhibitor.

1I. The method of any of the preceding embodiments wherein the second composition comprises a Wnt agonist.

1J. The method of any of the preceding embodiments wherein the second composition comprises a GSK3-beta inhibitor.

1K. The method of any of the preceding embodiments wherein the second composition comprises a notch agonist.

1L. The method of any of the preceding embodiments wherein the second composition comprises a HDAC inhibitor.

1M. The method of any of the preceding embodiments wherein the first and second compositions are the same composition.

1N. The method of embodiment 1 or any of embodiments 1A-1L wherein the first and second compositions are different compositions.

2. The method of any of the preceding embodiments, wherein the stem cell population comprises supporting cells.

3. The method of embodiment 2, wherein the supporting cells are Lgr5+ cells.

4. The method of any of the preceding embodiments, wherein the stem cell population comprises post-natal cells.

5. The method of any of the preceding embodiments, wherein the hair cells are inner ear hair cells.

6. The method of any of the preceding embodiments, wherein the hair cells are outer ear hair cells.

7. The method of any of the preceding embodiments, wherein the administering step comprises administering or causing to be administered to the stem cell population a notch agonist that is also an HDAC inhibitor.

8. The method of any of the preceding embodiments, wherein the administering step comprises administering or causing to be administered to the stem cell population a notch agonist that comprises a synthetic molecule.

9. The method of any of the preceding embodiments, wherein the administering step comprises administering or causing to be administered to the stem cell population VPA (e.g., in a pharmaceutically acceptable form (e.g., salt)) (e.g., where VPA is a notch agonist that is also an HDAC inhibitor).

10. The method of any of the preceding embodiments, wherein the administering step comprises administering or causing to be administered to the stem cell population a Wnt agonist that is also a GSK3-beta inhibitor.

11. The method of any of the preceding embodiments, wherein the administering step comprises administering or causing to be administered to the stem cell population a Wnt agonist that comprises a synthetic molecule.

12. The method of any of the preceding embodiments, wherein the administering step comprises administering or causing to be administered to the stem cell population CHIR99021 (e.g., in a pharmaceutically acceptable form (e.g., salt)) (e.g., where CHIR99021 is a GSK3-beta inhibitor.

13. The method of any of the preceding embodiments, wherein the administering step comprises administering or causing to be administered to the stem cell population a notch inhibitor.

14. The method of embodiment 13, wherein the notch inhibitor comprises DAPT (e.g., in a pharmaceutically acceptable form (e.g., salt)).

15. The method of any of the preceding embodiments, wherein the administering step comprises administering or causing to be administered to the stem cell population: (i) CHIR99021 (e.g., in a pharmaceutically acceptable form (e.g., salt)) and (ii) VPA (e.g., in a pharmaceutically acceptable form (e.g., salt)) (e.g., where (i) comprises CHIR99021 and (ii) comprises VPA).

16. The method of embodiment 15, wherein the administering step further comprises administering or causing to be administered to the stem cell population DAPT (e.g., where DAPT is a notch inhibitor).

17. The method of any of the preceding embodiments, wherein the administering step is carried out by performing one or more injections into the ear (e.g., transtympanically).

18. The method of embodiment 17, wherein the one or more injections are into the middle ear.

19. The method of embodiment 17, wherein the one or more injections are into the inner ear.

20. The method of embodiment 17, wherein performing the one or more injections comprises anesthetizing the tympanic membrane and/or surrounding tissue, placing a needle through the tympanic membrane into the middle ear, and injecting one or both of (i) and (ii).

21. The method of any of the preceding embodiments, wherein the administering step comprises administering or causing to be administered to the stem cell population one or more additional agents (e.g., in addition to (i) and (ii)).

22. The method of embodiment 21, wherein the one or more additional agents comprises an ROS inhibitor.

23. The method of embodiment 21 or 22, wherein the one or more additional agents comprises vitamin C or a derivative thereof.

24. The method of any of embodiments 21 to 23, wherein the one or more additional agents comprises a TGFβ type I receptor inhibitor.

25. The method of any of the preceding embodiments, wherein the expanded population of stem cells is at least 3 times larger than the stem cell population prior to the administering step.

26. The method of any of the preceding embodiments, wherein the administering step comprises administering the notch agonist and/or HDAC inhibitor in a pulsatile manner and administering the GSK3-beta inhibitor and/or Wnt agonist in a sustained manner.

27. The method of any of the preceding embodiments, wherein the stem cell population is of an in vivo subject, and the method is a treatment for hearing loss and/or vestibular dysfunction (e.g., wherein the generation of inner ear hair cells from the expanded population of stem cells results in partial or full recovery of hearing loss and/or improved vestibular function).

28. The method of any of the preceding embodiments, wherein the stem cell population is of an in vivo subject, and wherein the method further comprises delivering a drug to the subject (e.g., for treatment of a disease and/or disorder unrelated to hearing loss and/or vestibular dysfunction) at a higher concentration than a known safe maximum dosage of the drug for the subject (e.g., the known safe maximum dosage if delivered in the absence of the generation of inner ear hair cells resulting from the method) (e.g., due to a reduction or elimination of a dose-limiting ototoxicity of the drug).

29. The method of any of the preceding embodiments, further comprising performing high throughput screening using the generated inner ear hair cells.

30. The method of embodiment 29, comprising using the generated inner ear hair cells to screen molecules for toxicity against inner ear hair cells.

31. The method of embodiment 29, comprising using the generated inner ear hair cells to screen molecules for ability to improve survival of inner ear hair cells (e.g., inner ear hair cells exposed to said molecules).

32. A method of producing an expanded population of stem cells, the method comprising:
  administering or causing to be administered to a stem cell population (e.g., of an in vitro, ex vivo, or in vivo sample/subject) both of (i) and (ii):
  (i) a GSK3-beta inhibitor and/or Wnt agonist, and
  (ii) a notch agonist and/or HDAC inhibitor,
  thereby proliferating stem cells in the stem cell population and resulting in an expanded population of stem cells.

33. The method of embodiment 32, wherein the stem cell population comprises Lgr5+ cells.

34. The method of embodiment 33, wherein the stem cell population comprises post-natal stem cells.

35. The method of any of embodiments 32 to 34, wherein the stem cell population comprises epithelial stem cells.

36. The method of any of embodiments 32 to 35, wherein the administering step comprises administering or causing to be administered to the stem cell population a notch agonist that is also an HDAC inhibitor.

37. The method of any of embodiments 32 to 36, wherein the administering step comprises administering or causing to be administered to the stem cell population a notch agonist that comprises a synthetic molecule.

38. The method of any of embodiments 32 to 37, wherein the administering step comprises administering or causing to be administered to the stem cell population VPA (e.g., in a pharmaceutically acceptable form (e.g., salt)) (e.g., where VPA is a notch agonist that is also an HDAC inhibitor).

39. The method of any of embodiments 32 to 38, wherein the administering step comprises administering or causing to be administered to the stem cell population a Wnt agonist that is also a GSK3-beta inhibitor.

40. The method of any of embodiments 32 to 39, wherein the administering step comprises administering or causing to be administered to the stem cell population a Wnt agonist comprising a synthetic molecule.

41. The method of any of embodiments 32 to 40, wherein the administering step comprises administering or causing to be administered to the stem cell population CHIR99021 (e.g., in a pharmaceutically acceptable form (e.g., salt)) (e.g., where CHIR99021 is a GSK3 beta inhibitor).

42. The method of any of embodiments 32 to 41, wherein the administering step is carried out by performing one or more injections into the ear (e.g., transtympanically into the middle ear and/or inner ear).

43. The method of any of embodiments 32 to 42, wherein the administering step comprises administering the notch agonist and/or HDAC inhibitor in a pulsatile manner and administering the GSK3-beta inhibitor and/or Wnt agonist in a sustained manner.

44. The method of any of embodiments 32 to 43, wherein the stem cells are inner ear stem cells.

45. The method of any of embodiments 32 to 44, further comprising performing high throughput screening using the generated expanded population of stem cells.

46. The method of embodiment 45, comprising using the generated stem cells to screen molecules for toxicity against stem cells and/or their progeny.

47. The method of embodiment 45, comprising using the generated stem cells to screen molecules for ability to improve survival of stem cells and/or their progeny.

48. A method of treating a subject who has, or is at risk of developing, hearing loss and/or vestibular dysfunction, the method comprising:
    identifying a subject who has experienced, or is at risk for developing, hearing loss and/or vestibular dysfunction,
    administering or causing to be administered to the subject both of (i) and (ii):
        (i) a GSK3-beta inhibitor and/or Wnt agonist, and
        (ii) a notch agonist and/or HDAC inhibitor,
    thereby treating or preventing the hearing loss and/or vestibular dysfunction in the subject.

49. The method of embodiment 48, wherein the stem cell population comprises Lgr5+ cells.

50. The method of embodiment 48 or 49, wherein the stem cell population comprises post-natal cells.

51. The method of any of embodiments 48 to 50, wherein the stem cell population comprises epithelial stem cells.

52. The method of any of embodiments 48 to 51, wherein the administering step comprises administering or causing to be administered to the subject a notch agonist that is also an HDAC inhibitor.

53. The method of any of embodiments 48 to 52, wherein the administering step comprises administering or causing to be administered to the subject a notch agonist comprising a synthetic molecule.

54. The method of any of embodiments 48 to 53, wherein the administering step comprises administering or causing to be administered to the subject VPA (e.g., in a pharmaceutically acceptable form (e.g., salt)) (e.g., where VPA is a notch agonist that is also an HDAC inhibitor).

55. The method of any of embodiments 48 to 54, wherein the administering step comprises administering or causing to be administered to the subject a Wnt agonist that is also a GSK3-beta inhibitor.

56. The method of any of embodiments 48 to 55, wherein the administering step comprises administering or causing to be administered to the subject a Wnt agonist comprising a synthetic molecule.

57. The method of any of embodiments 48 to 56, wherein the administering step comprises administering or causing to be administered to the subject CHIR99021 (e.g., in a pharmaceutically acceptable form (e.g., salt)) (e.g., where CHIR99021 is a GSK3-beta inhibitor).

58. The method of any of embodiments 48 to 57, wherein the step of administering is carried out by performing one or more injections into the ear (e.g., transtympanically into the middle ear and/or inner ear).

59. The method of any of embodiments 48 to 58, comprising administering the notch agonist and/or the HDAC inhibitor in a pulsatile manner and administering the GSK3-beta inhibitor and/or Wnt agonist in a sustained manner.

60. A composition comprising the first or second composition of any of the preceding embodiments.

61. A composition comprising (a) (i) a GSK3-beta inhibitor or derivative or a pharmaceutically acceptable salt thereof and/or Wnt agonist or derivative or a pharmaceutically acceptable salt thereof, and (ii) a notch agonist or derivative or a pharmaceutically acceptable salt thereof and/or HDAC inhibitor or derivative or a pharmaceutically acceptable salt thereof, and (b) a pharmaceutically acceptable carrier or excipient.

62. A composition comprising (a) (i) a GSK3-beta inhibitor or derivative or a pharmaceutically acceptable salt thereof, and (ii) a notch agonist or derivative or a pharmaceutically acceptable salt thereof and (b) a pharmaceutically acceptable carrier or excipient.

63. A composition comprising (a) (i) a Wnt agonist or derivative or a pharmaceutically acceptable salt thereof, and (ii) a notch agonist or derivative or a pharmaceutically acceptable salt thereof; and (b) a pharmaceutically acceptable carrier or excipient.

64. A composition comprising (a) (i) a GSK3-beta inhibitor or derivative or a pharmaceutically acceptable salt thereof and (ii) a HDAC inhibitor or derivative or a pharmaceutically acceptable salt thereof, and (b) a pharmaceutically acceptable carrier or excipient.

65. A composition comprising (a) (i) a Wnt agonist or derivative or a pharmaceutically acceptable salt thereof, and (ii) a HDAC inhibitor or derivative or a pharmaceutically acceptable salt thereof, and (b) a pharmaceutically acceptable carrier or excipient.

65A. The composition of any of embodiments 61 to 65 wherein the composition comprises a GSK3-beta inhibitor.

65B. The composition of any of embodiments 61 to 65 wherein the composition comprises a Wnt agonist.

65C. The composition of any of embodiments 61 to 65 wherein the composition comprises a notch agonist.

65D. The composition of any of embodiments 61 to 65 wherein the composition comprises a HDAC inhibitor, 66. A pharmaceutical composition comprising a GSK3-beta inhibitor and a notch agonist in lyophilized form.

67. A pharmaceutical composition comprising a GSK3-beta inhibitor and a notch agonist in hydrated form.

68. The pharmaceutical composition of embodiment 66 or 67, wherein the GSK3-beta inhibitor is CHIR99021 (e.g., in a pharmaceutically acceptable form (e.g., salt)).

69. The pharmaceutical composition of any of embodiments 66 to 68, wherein the notch agonist is VPA (e.g., in a pharmaceutically acceptable form (e.g., salt)).

70. A method of generating inner ear hair cells, the method comprising:
    proliferating stem cells in an initial stem cell population (e.g., of an in vitro, ex vivo, or in vivo sample/subject), resulting in an expanded population of stem cells (e.g., such that the expanded population is at least 2 times, 3 times, 5 times, 10 times, or 20 times greater than the initial stem cell population); and
    exposing the expanded population of stem cells to a GSK3-beta inhibitor and/or a Wnt agonist, and, optionally, a notch inhibitor, thereby facilitating generation of inner ear hair cells from the expanded population of stem cells.

71. A method of generating inner ear hair cells, the method comprising administering CHIR99021 (e.g., in a pharmaceutically acceptable form (e.g., salt)) to a cell population in an inner ear of a subject, thereby facilitating generation of inner ear hair cells.

72. A method of generating inner ear hair cells, the method comprising proliferating post-natal LGR5+ cells in an initial population (e.g., of an in vitro, ex vivo, or in vivo sample/subject), resulting in an expanded population of LGR5+ cells (e.g., such that the expanded population is at least 2 times, 3 times, 5 times, 10 times, or 20 times greater than the initial stem cell population), said expanded population of LGR5+ cells resulting in generation of inner ear hair cells.

73. A method of treating a disease or disorder, the method comprising proliferating post-natal Lgr5+ epithelial cells in an initial population of a subject (in vivo), resulting in an expanded population of Lgr5+ epithelial cells (e.g., such that the expanded population is at least 2 times, 3 times, 5 times, 10 times, or 20 times greater than the initial post-natal Lgr5+ epithelial cell population).

74. A method of proliferating stem cells, the method comprising:
administering or causing to be administered to a stem cell population (e.g., of an in vitro, ex vivo, or in vivo sample/subject) both of (i) and (ii):
(i) a GSK3-beta inhibitor and/or Wnt agonist, and
(ii) a notch agonist and/or HDAC inhibitor,
thereby proliferating stem cells in the stem cell population and resulting in an expanded population of stem cells; and
generating inner ear hair cells from the expanded population of stem cells.

75. A kit comprising:
(a) a set of one or more compositions, the set comprising (i) and (ii):
(i) a GSK3-beta inhibitor and/or Wnt agonist, and
(ii) a notch agonist and/or HDAC inhibitor,
each of the one or more compositions provided in a pharmaceutically acceptable carrier and
(b) instructions for using the set of one or more compositions to treat an inner ear disorder.

76. The kit of embodiment 75, wherein the set of one or more compositions also comprises a TGFβ inhibitor.

77. The kit of embodiment 75 or 76, wherein the set of one or more compositions also comprises an ROS inhibitor.

78. The kit of embodiment 77, wherein the ROS inhibitor is vitamin C or a derivative thereof.

79. The kit of any of embodiments 75 to 77, wherein the set of one or more compositions is/are in a form that can be injected (e.g. via syringe).

80. The kit of embodiment 79, wherein the set of one or more compositions is/are in a form that can be injected into the middle ear.

81. A method for enhancing the stem cell potential of a population of cochlear supporting cells.

82. The method of embodiment 81 wherein the method comprises activating the Wnt pathway in the cochlear supporting cell population.

83. The method of any preceding embodiment wherein the method comprises activating the Wnt pathway in the cochlear supporting cell population upstream of c-myc.

84. The method of any preceding enumerated embodiment wherein the cochlear supporting cells are endogenous to the Organ of Corti.

85. The method of any preceding embodiment wherein the cochlear supporting cell population comprises a population of Lgr5$^+$ supporting cells.

86. The method of any preceding embodiment wherein the cochlear supporting cell population comprises Lgr5$^+$ supporting cells and the method further comprises inducing the Lgr5$^+$ supporting cells divide, giving rise to a multipotent Lgr5$^+$ daughter cells.

87. The method of any preceding embodiment in which the parent and/or daughter Lgr5$^+$ cells subsequently differentiate into hair cell(s).

88. The method of any preceding embodiment in which Lgr5 expression in a given supporting cell is maintained within 25% of its baseline level.

89. A method of any preceding embodiment in which Lgr5 is upregulated in a supporting cell by a factor of at least 1.25, 1.5, 2, 5, 10, 100, or 1,000 of its baseline expression level.

90. A method of any preceding embodiment in which Lgr5 is upregulated in a supporting cell population, on average, by a factor of at least 1.25, 1.5, 2, 5, 10, 100, or 1,000 of the baseline expression level, for the population, and the supporting cell subsequently proliferates.

91. A method of any preceding embodiment in which Lgr5 is upregulated in a supporting cell population, on average, by a factor of at least 1.25, 1.5, 2, 5, 10, 100, or 1,000 of the baseline expression level, for the population, and members of the supporting cell population divide and differentiate into a hair cell 92. A method for inducing the self-renewal of stem/progenitor supporting cells comprised by a cochlear cell population, the method comprising inducing the stem/progenitor cells to proliferate while maintaining, in the daughter cells, the capacity to differentiate into hair cells.

93. The method of embodiment 92 wherein the daughter cells are permitted to differentiate into hair cells.

94. The method of embodiment 92 wherein the daughter cells are induced to differentiate into hair cells.

95. The method of embodiment 92 wherein the daughter cells are induced to differentiate into hair cells by activating the Wnt pathway upstream of the c-myc gene and without any genetic modification of the population.

96. The method of embodiment 92 wherein the daughter cells are induced to differentiate into hair cells by activating the Wnt pathway upstream of the c-myc gene with small organic molecules that transiently induce such activity.

97. The of any of embodiments 92-96 wherein the supporting cell population includes LGR5$^+$ supporting cells that are endogenous to the Organ of Corti.

98. A composition having the capacity to induce self-renewal of a population of supporting cells by activation or inhibition of a pathway involved in inducing stem cell properties.

99. The composition of embodiment 98 wherein the pathway is selected from the group consisting of Wnt, HDAC, TGF-beta, RAR, DKK1, and combinations thereof.

100. The composition of embodiment 98 or 99 wherein the composition comprises a small organic molecule that activates or inhibits the pathway.

101. The composition of embodiment 98, 99 or 100 wherein the composition comprises a Biocompatible Matrix.

102. The composition of any of embodiments 98-101 wherein when applied in vitro to a supporting cell population, the composition induces the population to proliferate to a high degree and in high purity in a Stem Cell Proliferation Assay, and also allows the population to differentiate into a high purity population of hair cells in a Stem Cell Differentiation Assay.

103. The composition of any of embodiments 98-102 wherein the composition induces and maintains stem cell properties by proliferating the supporting cell population to produce stem cells that can divide for many generations and maintain the ability to have a high proportion of the resulting cells differentiate into hair cells.

104. The composition of any of embodiments 98-102 wherein the proliferating cells express stem cell markers including one or more of Lgr5, Sox2, Opem1, Phex, lin28, Lgr6, cyclin D1, Msx1, Myb, Kit, Gdnf3, Zic3, Dppa3, Dppa4, Dppa5, Nanog, Esrrb, Rex1, Dnmt3a, Dnmt3b, Dnmt31, Utf1, Tcl1, Oct4, Klf4, Pax6, Six2, Zic1, Zic2, Otx2, Bmi1, CDX2, STAT3, Smad1, Smad2, smad2/3, smad4, smad5, and smad7.

105. A method for increasing the cell density of supporting cells in a population of cochlear cells comprising activating pathways and mechanisms that induce stem cell properties in the supporting cells, proliferating the activated supporting cells while maintaining the multi-potent character of the supporting cells in the newly formed daughter cells and thereafter allowing or inducing the expanded population to differentiate into hair cells to form an expanded cochlear cell population wherein the cell density of hair cells in the expanded cochlear cell population exceeds the cell density of hair cells in the original (non-expanded) cochlear cell population.

106. The method of embodiment 105 wherein the expanded population is allowed differentiate into hair cells.

107. The method of embodiment 105 wherein the expanded population is induced to differentiate into hair cells.

108. The method of any of embodiments 105-107 wherein the supporting cell population is comprised by a cochlear tissue.

109. The method of any of embodiments 105-108 wherein the supporting cell population is an in vitro supporting cell population.

110. The method of any of embodiments 105-108 wherein the supporting cell population is an in vivo supporting cell population.

111. The method of any of embodiments 105-110 wherein the proliferation stage is preferably controlled to substantially maintain the native organization of the cochlear structure.

112. The method of any of embodiments 105-111 wherein the proliferation is transiently induced by induction of a pathway upstream of c-myc and without any genetic modification of the population.

113. The method of any of embodiments 105-112 wherein the proliferation is transiently induced by induction of a pathway upstream of c-myc with a small organic molecule and without any genetic modification of the population.

114. The method of any of embodiments 105-113 wherein the supporting cell population includes supporting cells that are Lgr5$^+$ and endogenous to the Organ of Corti.

115. A method for increasing the cell density of Lgr5$^+$ supporting cells in a population of cochlear cells, the method comprising activating pathways and mechanisms that induce or maintain stem cell properties in the Lgr5$^+$ supporting cells, proliferating the activated Lgr5$^+$ supporting cells while maintaining such stem cell properties and thereafter allowing or inducing the expanded population to differentiate into hair cells to form an expanded cochlear cell population wherein the cell density of hair cells in the expanded cochlear cell population exceeds the cell density of hair cells in the original (non-expanded) cochlear cell population.

116. The method of embodiment 115 wherein the expanded population is induced to differentiate into hair cells.

117. The method of embodiment 115 wherein the expanded population is induced to differentiate into hair cells.

118. The method of any of embodiments 115-117 wherein the supporting cell population is comprised by a cochlear tissue.

119. The method of any of embodiments 115-118 wherein the supporting cell population is an in vitro supporting cell population.

120. The method of any of embodiments 115-118 wherein the supporting cell population is an in vivo supporting cell population.

121. The method of any of embodiments 115-120 wherein the proliferation stage is preferably controlled to substantially maintain the native organization of the cochlear structure.

122. The method of any of embodiments 115-121 wherein the proliferation is transiently induced by induction of a pathway upstream of c-myc and without any genetic modification of the population.

123. The method of any of embodiments 115-122 wherein the proliferation is transiently induced by induction of a pathway upstream of c-myc with a small organic molecule and without any genetic modification of the population.

124. The method of any of embodiments 115-123 wherein the supporting cell population includes Lgr5$^+$ cells endogenous to the Organ of Corti.

125. A method for increasing the cell density of hair cells in an initial population of cochlear cells, the initial population comprises hair cells, Lgr$^-$ supporting cells, and Lgr5$^+$ supporting cells, the method comprising administering to the initial population a Stem Cell Proliferator composition that contains a Stemness Driver and a Differentiation Inhibitor wherein the composition has the capacity to induce the expansion of the number of Lgr5$^+$ supporting cells in the population in a Stem Cell Proliferation Assay, and allows Lgr5$^+$ supporting cells within the population to differentiate into a population of hair cells in a Stem Cell Differentiation Assay.

126. The method of embodiment 125 wherein the expanded population is induced to differentiate into hair cells.

127. The method of embodiment 125 wherein the expanded population is induced to differentiate into hair cells.

128. The method of any of embodiments 125-127 wherein the supporting cell population is comprised by a cochlear tissue.

129. The method of any of embodiments 125-128 wherein the supporting cell population is an in vitro supporting cell population.

130. The method of any of embodiments 125-128 wherein the supporting cell population is an in vivo supporting cell population.

131. The method of any of embodiments 125-130 wherein the proliferation stage is preferably controlled to substantially maintain the native organization of the cochlear structure.

132. The method of any of embodiments 125-131 wherein the proliferation is transiently induced by induction of a pathway upstream of c-myc and without any genetic modification of the population.

133. The method of any of embodiments 125-132 wherein the proliferation is transiently induced by induction of a pathway upstream of c-myc with a small organic molecule and without any genetic modification of the population.

134. The method of any of embodiments 125-133 wherein the supporting cell population includes Lgr5$^+$ cells endogenous to the Organ of Corti.

135. The method of any of embodiments 125-134 wherein the method produces stem cells in a Stem Cell Proliferation Assay that express one or more stem cells markers selected from the group consisting of Sox2, Opem1, Phex, lin28, Lgr6, cyclin D1, Msx1, Myb, Kit, Gdnf3, Zic3, Dppa3, Dppa4, Dppa5, Nanog, Esrrb, Rex1, Dnmt3a, Dnmt3b, Dnmt31, Utf1, Tcl1, Oct4, Klf4, Pax6, Six2, Zic1, Zic2, Otx2, Bmi1, CDX2, STAT3, Smad1, Smad2, smad2/3, smad4, smad5, and smad7.

136. The method of any of embodiments 125-135 wherein the fraction of cells in the population that are $Lgr5^+$ is increased.

137. A method for increasing the cell density of hair cells in an initial population of cochlear cells comprising hair cells and supporting cells, the method comprising selectively expanding the number of supporting cells in the initial population to form an intermediate cochlear cell population wherein the ratio of the number of supporting cells to hair cells in the intermediate cochlear cell population exceeds the ratio of the number of supporting cells to hair cells in the initial cochlear cell population, and selectively expanding the number of hair cells in the intermediate cochlear cell population to form an expanded cochlear cell population wherein the ratio of the number of hair cells to supporting cells in the expanded cochlear cell population exceeds the ratio of the number of hair cells to supporting cells in the intermediate cochlear cell population.

138. The method of embodiment 137 wherein the intermediate population is induced to differentiate into hair cells.

139. The method of embodiment 137 wherein the intermediate population is induced to differentiate into hair cells.

140. The method of any of embodiments 137-139 wherein the initial cochlear cell population is comprised by a cochlear tissue.

141. The method of any of embodiments 137-139 wherein the initial cochlear cell population is an in vitro population.

142. The method of any of embodiments 137-139 wherein the initial cochlear cell population is an in vivo population.

143. The method of any of embodiments 137-142 wherein the selective expansion of the supporting cells is controlled to substantially maintain the native organization of the cochlear structure.

144. The method of any of embodiments 137-143 wherein the selective expansion of the supporting cells is transiently induced by induction of a pathway upstream of c-myc and without any genetic modification of the population.

145. The method of any of embodiments 137-144 wherein the selective expansion of the supporting cells is induced by induction of a pathway upstream of c-myc with a small organic molecule and without any genetic modification of the population.

146. The method of any of embodiments 137-145 wherein the supporting cell population includes $Lgr5^+$ cells endogenous to the Organ of Corti.

147. The method of any of embodiments 137-146 wherein the method produces stem cells in a Stem Cell Proliferation Assay that express one or more stem cells markers selected from the group consisting of Lgr5, Sox2, Opem1, Phex, lin28, Lgr6, cyclin D1, Msx1, Myb, Kit, Gdnf3, Zic3, Dppa3, Dppa4, Dppa5, Nanog, Esrrb, Rex1, Dnmt3a, Dnmt3b, Dnmt31, Utf1, Tcl1, Oct4, Klf4, Pax6, Six2, Zic1, Zic2, Otx2, Bmi1, CDX2, STAT3, Smad1, Smad2, smad2/3, smad4, smad5, and smad7.

148. The method of any of embodiments 137-147 wherein the fraction of cells in the intermediate population that are $Lgr5^+$ is greater than the fraction of cells in the initial population that are $Lgr5^+$.

149. A method for increasing the number of $Lgr5^+$ supporting cells or increasing the Lgr5 activity in an initial population of cochlear cells, wherein the initial population comprises supporting cells and hair cells.

150. The method of embodiment 149 wherein an intermediate population is formed in which the number of $Lgr5^+$ supporting cells is expanded relative to the initial population.

151. The method of embodiment 149 or 150 wherein an intermediate population is formed in which the $Lgr5^+$ activity of the supporting cells relative to the initial population is increased.

152. The method of any of embodiments 149-151 wherein the number of $Lgr5^+$ cells is increased relative to the initial cell population by activating $Lgr5^+$ expression in cell types that normally lack or have very low levels of Lgr5.

153. The method of any of embodiments 149-151 wherein an intermediate population is formed in which the number of $Lgr5^+$ supporting cells is expanded and the Lgr5 activity is increased relative to the initial cochlear cell population.

154. The method of any of embodiments 149-151 wherein an intermediate population is formed in which the number of $Lgr5^+$ supporting cells is expanded and the Lgr5 activity is increased relative to the initial cochlear cell population and the number of hair cells in the intermediate cochlear cell population is thereafter selectively expanded to form an expanded cochlear cell population wherein the ratio of hair cells to supporting cells in the expanded cochlear cell population exceeds the ratio of the number of hair cells to supporting cells in the intermediate cochlear cell population.

155. The method of any of embodiments 81-97 and 105-154 wherein the method produces a population of $Lgr5^+$ cells that are in S-phase.

156. The method of any of embodiments 81-97 and 105-154 wherein the method is used with adult mammal cochlear cells and the method produces a population of adult mammalian $Lgr5^+$ cells that are in S-phase.

157. The method of any of embodiments 81-97 and 105-156 wherein the method comprises contacting the cochlear cell population with a Stem Cell Proliferator.

158. The method of any of embodiments 81-97 and 105-156 wherein the method comprises contacting the cochlear cell population with a Stem Cell Proliferator containing a Stemness Driver.

159. The method of any of embodiments 81-97 and 105-156 wherein the method comprises contacting the cochlear cell population with a Differentiation Inhibitor.

160. The method of any of embodiments 81-97 and 105-156 wherein the method comprises contacting the cochlear cell population with a Stem Cell Proliferator containing a Stemness Driver and a Differentiation Inhibitor.

161. The method of any of embodiments 81-97 and 105-160 wherein a Stemness Driver is used to drive the proliferation of $Lgr5^+$ stem cells.

162. The method of any of embodiments 81-97 and 105-161 wherein a Stemness Driver is used to induce differentiation of LGR5+ cells to hair cells when a Differentiation Inhibitor is not present at an Effective Differentiation Inhibition Concentration.

163. The method of any of embodiments 81-97 and 105-162 wherein the Stemness Driver that drives both proliferation and differentiation comprises GSK3Beta inhibitors and Wnt agonists.

164. The method of any of embodiments 81-97 and 105-163 wherein the composition comprises a Stemness Driver and a Differentiation Inhibitor in a formulation that releases the Stemness Driver and Differentiation inhibitor at different rates in a Release Assay.

165. The method of any of embodiments 81-97 and 105-163 wherein the composition comprises a Stemness Driver and a Differentiation Inhibitor in a formulation that releases the Stemness Driver and Differentiation inhibitor at a constant, sustained, extended, delayed or pulsatile rate of release of the active agent into the inner ear environment.

166. The method or composition of any of the previous embodiments in which the Differentiation Inhibitor may be a Notch agonist or HDAC inhibitor.

167. The method or composition of any of the previous embodiments in which there is a first Proliferation Period with an Effective Stemness Driver Concentration and an Effective Differentiation Inhibition Concentration of a Differentiation Inhibitor, followed by a Differentiation Period with an Effective Stemness Driver Concentration and without an Effective Differentiation Inhibition Concentration of a Differentiation Inhibitor.

168. The method or composition of any of the previous embodiments in which the Stemness Driver and Differentiation Inhibitor are provided to the cochlear cells in a formulation that releases the Stemness Driver and Differentiation inhibitor at different rates.

169. The method or composition of any of the previous embodiments in which the formulation provides a constant, sustained, extended, delayed or pulsatile rate of release of the Stemness Driver and the Differentiation Inhibitor into the inner ear environment.

170. The method or composition of any of the previous embodiments in which the formulation releases the Stemness Driver and Differentiation Inhibitor in a manner to provide a first Proliferation Period with an Effective Stemness Driver Concentration and an Effective Differentiation Inhibition Concentration of the Differentiation Inhibitor, followed by a Differentiation Period with an Effective Stemness Driver Concentration and without an Effective Differentiation Inhibition Concentration of the Differentiation Inhibitor.

171. The method or composition of any of the previous embodiments in which there is a first Proliferation Period with an Effective Stemness Driver Concentration of a Wnt agonist or GSK3Beta inhibitor and an Effective Differentiation Inhibition Concentration of a Notch agonist or HDAC inhibitor, followed by a Differentiation Period with an Effective Stemness Driver Concentration of a Wnt agonist or GSK3Beta inhibitor and without an Effective Differentiation Inhibition Concentration of a Notch agonist or HDAC inhibitor.

172. The method or composition of embodiment 171 wherein the formulation provides a constant, sustained, extended, delayed or pulsatile rate of release of the Wnt agonist or GSK3Beta inhibitor and the Notch agonist or HDAC inhibitor into the inner ear environment.

173. The method or composition of embodiment 171 or 172 wherein the formulation releases the Wnt agonist or GSK3Beta inhibitor and the Notch agonist or HDAC inhibitor in a manner to provide a first Proliferation Period with an Effective Stemness Driver Concentration of the Wnt agonist or GSK3Beta inhibitor and an Effective Differentiation Inhibition Concentration of the Notch agonist or HDAC inhibitor, followed by a Differentiation Period with an Effective Stemness Driver Concentration of the Wnt agonist or GSK3Beta inhibitor and without an Effective Differentiation Inhibition Concentration of the Notch agonist or HDAC inhibitor.

174. The method or composition of any of the previous embodiments wherein the Differentiation inhibitor is also a Stemness Driver.

175. The method or composition of any of the previous embodiments wherein the Differentiation inhibitor is a Notch agonist and is also a Stemness Driver.

176. The method or composition of any of the previous embodiments wherein the Differentiation inhibitor is Valproic Acid.

177. The method or composition of any of the previous embodiments wherein if the Differentiation Inhibitor is also a Stemness Driver, the concentration of the Differentiation Inhibitor falls below the Effective Differentiation Inhibition Concentration during the Differentiation Period.

178. The method or composition of any of the previous embodiments wherein the Differentiation inhibitor and Stemness Driver are be contained within a sustained release polymer gel.

179. The method or composition of any of the previous embodiments wherein the gel is (or is adapted to be) injected through a needle and become solid in the middle ear space.

180. The method or composition of embodiment 179 wherein the gel comprises a thermoreversible polymer.

181. The method or composition of embodiment 179 wherein the gel comprises Poloxamer 407.

182. The method or composition of any previous embodiment wherein the Notch activity level in supporting cells remains at least 10, 20, 30, 40, 50, 60, 70, 80, 90, or 100% of the Notch activity level in supporting cells in the native state.

183. A method of and compositions for generating hair cells, the method comprising: administering or causing to be administered to a stem cell population (e.g., of an in vitro, ex vivo, or in vivo sample/subject) a composition comprising both of (i) and (ii): (i) a GSK3-beta inhibitor (or a derivative or pharmaceutically acceptable salt thereof) and/or Wnt agonist (or a derivative or pharmaceutically acceptable salt thereof), and (ii) a Notch agonist (or a derivative or pharmaceutically acceptable salt thereof) and/or HDAC inhibitor (or a derivative or pharmaceutically acceptable salt thereof), thereby proliferating stem cells in the stem cell population and resulting in an expanded population of stem cells; and exposing the expanded population of stem cells to a GSK3-beta inhibitor (or a derivative or pharmaceutically acceptable salt thereof) and/or a Wnt agonist (or a derivative or pharmaceutically acceptable salt thereof), and, optionally, a notch inhibitor (or a derivative or pharmaceutically acceptable salt thereof), thereby facilitating generation of inner ear hair cells from the expanded population of stem cells.

184. A method for preventing or treating auditory impairments in a subject comprising administering to said subject an effective amount of a composition comprising (a) (i) an HDAC inhibitor and/or Notch activator and (ii) a GSK3-beta inhibitor, a derivative thereof [e.g., a derivative of an HDAC inhibitor, a derivative of a Notch activator, and/or a derivative of a GSK3-beta inhibitor], a pharmaceutically acceptable salt thereof [e.g., a pharmaceutically acceptable salt of an HDAC inhibitor, a pharmaceutically acceptable salt of a Notch activator, and/or a pharmaceutically acceptable salt of a GSK3-beta inhibitor], or a combination thereof and (b) a pharmaceutically acceptable carrier or excipient, so as to treat auditory impairments in the subject. Thus, for example, the composition may comprise (a) an HDAC inhibitor (or a derivative or pharmaceutically acceptable salt thereof) and a GSK3-beta inhibitor (or a derivative or pharmaceutically acceptable salt thereof), and (b) a pharmaceutically acceptable carrier or excipient. By way of further example, the composition may comprise (a) a Notch activator (or a derivative or pharmaceutically acceptable salt thereof) and a GSK3-beta inhibitor (or a derivative or pharmaceutically acceptable salt thereof), and (b) a pharmaceutically acceptable carrier or excipient. By way of further example, the composition may comprise (a) an HDAC inhibitor (or a derivative or pharmaceutically acceptable salt thereof), a Notch activator (or a derivative or pharmaceutically acceptable salt thereof), and a GSK3-beta inhibitor (or a derivative or pharmaceutically acceptable salt thereof), and (b) a pharmaceutically acceptable carrier or excipient.

185. A method for identifying agents that proliferate hair cell progenitors and/or increase numbers of hair cells, and also agents that protect supporting cells and/or hair cells (e.g. to support their survival), and also for identifying agents that are toxic or not toxic to supporting cells or differentiated progeny including hair cells.

186. A method for preventing or treating auditory impairments in a subject in need of treatment comprising administering to said subject an effective amount of a composition comprising, an HDAC inhibitor and/or Notch activator and a GSK3beta inhibitor or derivative thereof or pharmaceutically acceptable salt thereof and an acceptable carrier or excipient, so as to treat auditory impairments in the subject.

187. A method for inhibiting the loss or death of the cells of the auditory system in a subject comprising administering to said subject an effective amount of a composition described herein or derivative thereof or pharmaceutically acceptable salt thereof and an acceptable carrier or excipient, thereby inhibiting loss or death of the cells of the auditory system in the subject.

188. A method for maintaining or promoting the growth of cells of the auditory system in a subject comprising administering to said subject a composition comprising as an agent described herein or derivative thereof or pharmaceutically acceptable salt thereof and an acceptable carrier or excipient in an effective amount so as to augment or initiate endogenous repair, thereby maintaining or promoting the growth of cells of the auditory system in the subject.

189. The method of any of the previous embodiments wherein the average in vitro Lgr5 Activity in the cell population upon completion of the Stem Cell Proliferation Assay is no less than 25, 50, 75, or 90% of the average in vitro Lgr5 Activity in the cell population at the start of the Stem Cell Proliferation Assay.

190. The method of any of the previous embodiments wherein the average in vitro notch activity in the cell population upon completion of the Stem Cell Proliferation Assay is no less than 25, 50, 75, or 90% of the average in vitro notch activity in the cell population used at the start of the Stem Cell Proliferation Assay.

191. A method for expanding a population of cochlear stem cells in a cochlear tissue comprising a parent population of cells, the parent population including supporting cells, the method comprising contacting the cochlear tissue with a Stem Cell Proliferator to form an expanded population of cells in the cochlear tissue, the Stem Cell Proliferator is capable (i) in a Stem Cell Proliferation Assay of increasing the number of Lgr5$^+$ cells in a Stem Cell Proliferation Assay cell population by a factor of at least 10 and (ii) in a Stem Cell Differentiation Assay of forming hair cells from a cell population comprising Lgr5$^+$ cells.

192. The method of embodiment 191, wherein the at least one Stem Cell Proliferator is capable, in a Stem Cell Proliferation Assay, of increasing the number of Lgr5$^+$ cells in the Stem Cell Proliferation Assay cell population by a factor of at least 50.

193. The method of embodiment 191, wherein the Stem Cell Proliferator at least one Stem Cell Proliferator is capable, in the Stem Cell Proliferation Assay, of increasing the number of Lgr5$^+$ cells in a Stem Cell Proliferation Assay cell population by a factor of at least 100.

194. The method as in any of embodiments 191-193 wherein the expanded population of cells comprises a greater number of hair cells than the parent population.

195. The method as in any of embodiments 191-194 wherein the fraction of total cells in the Stem Cell Proliferation Assay cell population that are Lgr5$^+$ cells increases from the start to the end of the Stem Cell Proliferation assay by at least 2-fold.

196. The method as in any of embodiments 191-195 wherein the fraction of total cells in the Stem Cell Differentiation Assay cell population that are hair cells increases from the start to the end of the Stem Cell Differentiation assay by at least 2-fold.

197. The method as in any of embodiments 191-196 wherein the fraction of total cells in the Stem Cell Proliferation Assay cell population that are hair cells decreases from the start to the end of the Stem Cell Proliferation assay by at least 25%.

198. The method as in any of embodiments 191-197 wherein the average Lgr5$^+$ activity per cell in the Stem Cell Proliferation Assay cell population increases in the Stem Cell Proliferation Assay by at least 10%.

199. The method as in any of embodiments 191-198 wherein the average in vitro Lgr5 Activity in the cell population upon completion of the Stem Cell Proliferation Assay is no less than 25, 50, 75, or 90% of the average in vitro Lgr5 Activity in the cell population at the start of the Stem Cell Proliferation Assay.

200. The method as in any of embodiments 191-199 wherein the average in vitro notch activity in the cell population upon completion of the Stem Cell Proliferation Assay is no less than 25, 50, 75, or 90% of the average in vitro notch activity in the cell population used at the start of the Stem Cell Proliferation Assay.

201. The method as in any of embodiments 191-200 wherein the cochlear tissue maintains Native Morphology.

202. The method as in any of embodiments 191-201 wherein the at least one Stem Cell Proliferator is dispersed in a Biocompatible Matrix.

203. The method of embodiment 202 wherein the Biocompatible Matrix is a Biocompatible Gel or Foam.

204. The method as in any of embodiments 191-203 wherein the composition is a controlled release formulation.

205. The method as in any of embodiments 191-204 wherein the cochlear tissue is an in vivo cochlear tissue.

206. The method as in any of embodiments 191-204 wherein the cochlear tissue is an ex vivo cochlear tissue.

207. The method as in any of embodiments 191-205 wherein the method produces a population of Lgr5$^+$ cells that are in S-phase.

208. The method as in any of embodiments 191-207 wherein the at least one Stem Cell Proliferator comprises both a Stemness Driver and a Differentiation Inhibitor.

209. The method as in any of embodiments 191-208 wherein the contacting provides to the cochlear tissue:

in an Initial Phase, at least an Stemness Driver Concentration and at least an Effective Differentiation Inhibition Concentration of the Differentiation Inhibitor; and in a Subsequent Phase, at least an Stemness Driver Concentration and less than an Effective Differentiation Inhibition Concentration of the Differentiation Inhibitor.

210. The method as in any of embodiments 191-209, wherein the cochlear tissue is in a subject, and wherein the contacting the cochlear tissue with the composition is achieved by administering the composition trans-tympanically to the subject.

211. The method of embodiment 210 wherein the contacting the cochlear tissue with the composition results in improved Auditory Functioning of the subject.

212. A composition comprising a Biocompatible Matrix and at least one Stem Cell Proliferator, wherein the at least one Stem Cell Proliferator is capable, in a Stem Cell Proliferation Assay, of expanding an initial test population of LGR5$^+$ cells to create an expanded test population, and wherein the expanded test population has at least 10-fold more LGR5$^+$ cells than does the initial test population.

213. The composition of embodiment 212 wherein the at least one Stem Cell Proliferator is capable, in the Stem Cell Proliferation Assay, of increasing the number of Lgr5$^+$ cells in a Stem Cell Proliferation Assay cell population by a factor of at least 50.

214. The composition of embodiment 212, wherein the at least one Stem Cell Proliferator is capable, in the Stem Cell Proliferation Assay, of increasing the number of Lgr5+ cells in a Stem Cell Proliferation Assay cell population by a factor of at least 100.

215. The composition of any of embodiments 212-214, wherein the at least one Stem Cell Proliferator is dispersed in a Biocompatible Matrix.

216. The composition of embodiment 215, wherein the Biocompatible Matrix is a Biocompatible Gel or Foam.

217. The composition of embodiment 215 wherein the at least one Stem Cell Proliferator is capable, in the Stem Cell Proliferation Assay, of increasing the average Lgr5+ activity per cell in the Stem Cell Proliferation Assay cell population by at least 10%.

218. The composition of any of embodiments 212-217 wherein the at least one Stem Cell Proliferator comprises at least one of a Stemness Driver and a Differentiation Inhibitor.

219. The composition of any of embodiments 212-218, wherein the at least one Stem Cell Proliferator comprises both a Stemness Driver and a Differentiation Inhibitor.

220. The composition of any of embodiments 212-219, wherein the Stem Cell Proliferator comprises a Stemness Driver in a concentration that is 100-fold greater than an Effective Stemness Driver Concentration and a Differentiation Inhibitor in a concentration that is at least 100-fold greater than an Effective Differentiation Inhibition Concentration of the Differentiation Inhibitor.

221. The composition of any of embodiments 212-220, wherein the composition is a controlled release formulation.

222. The composition of embodiment 221 wherein the controlled release formulation when administered to a subject trans-tympanically imparts an immediate release, a delayed release, a sustained release, an extended release, a variable release, a pulsatile release, or a bi-modal release of the stem cell proliferator.

223. The composition of embodiment 221 or 222 wherein the controlled release formulation when administered to a subject provides: (a) in an InitialPhase, at least an Effective Stemness Driver Concentration and at least an Effective Differentiation Inhibition Concentration of the Differentiation Inhibitor; and (b) in a Subsequent Phase, at least an Effective Stemness Driver Concentration and less than an Effective Differentiation Inhibition Concentration of the Differentiation Inhibitor.

224. The method as in any of embodiments 191-211 or the composition as in any of embodiments 212-223 wherein the Stemness Driver is: a GSK3-beta inhibitor, a GSK3-beta inhibitor derivative, a Wnt agonist, a Wnt agonist derivative, or a pharmaceutically acceptable salt of any of the foregoing.

225. The method as in any of embodiments 191-211 or the composition as in any of embodiments 212-223 wherein the Differentiation Inhibitor is: a notch agonist, a notch agonist derivative; an HDAC inhibitor; an HDAC inhibitor derivative, or a pharmaceutically acceptable salt of any of the foregoing.

226. The method as in any of embodiments 191-211 or the composition as in any of embodiments 212-223, wherein the Stemness Driver is selected from the group consisting of CHIR99021, LY2090314, lithium, A1070722, BML-284 and SKL2001

227. The method as in any of embodiments 191-211 or the composition as in any of embodiments 212-223, wherein the Differentiation Inhibitor is a Notch agonist or an HDAC inhibitor selected from the group consisting of valproic acid, SAHA and Tubastatin A.

228. A method of treating a subject who has, or is at risk of developing, hearing loss, the method comprising trans-tympanically administering to a cochlear tissue of the subject a composition comprising at least one Stem Cell Proliferator.

229. The method of embodiment 228, wherein the at least one Stem Cell Proliferator comprises at least one of a Stemness Driver and a Differentiation Inhibitor.

230. The method of embodiment 228 or 229, wherein the at least one Stem Cell Proliferator comprises both a Stemness Driver and a Differentiation Inhibitor. CLAIMS 231. A method for expanding a population of cochlear cells in a cochlear tissue comprising a parent population of cells, the method comprising contacting the cochlear tissue with a stem cell proliferator to form an expanded population of cells in the cochlear tissue, wherein the stem cell proliferator is capable of (i) forming a proliferation assay final cell population from a proliferation assay initial cell population over a proliferation assay time period in a stem cell proliferation assay and (ii) forming a differentiation assay final cell population from a differentiation assay initial cell population over a differentiation assay time period in a stem cell differentiation assay wherein:

(a) the proliferation assay initial cell population has (i) a proliferation assay initial number of total cells, (ii) a proliferation assay initial number of Lgr5$^+$ cells, (iii) a proliferation assay initial number of hair cells, (iv) a proliferation assay initial Lgr5$^+$ cell fraction that equals the ratio of the proliferation assay initial number of Lgr5$^+$ cells to the proliferation assay initial number of total cells, and (v) a proliferation assay initial hair cell fraction that equals the ratio of the proliferation assay initial number of hair cells to the proliferation assay initial number of total cells;

(b) the proliferation assay final cell population has (i) a proliferation assay final number of total cells, (ii) a proliferation assay final number of Lgr5$^+$ cells, (iii) a proliferation assay final number of hair cells, (iv) a proliferation assay final Lgr5$^+$ cell fraction that equals the ratio of the proliferation assay final number of Lgr5$^+$ cells to the proliferation assay final number of total cells and (v) a proliferation assay final hair cell fraction that equals the ratio of the proliferation assay final number of hair cells to the proliferation assay final number of total cells;

(c) the differentiation assay initial cell population has (i) a differentiation assay initial number of total cells, (ii) a differentiation assay initial number of Lgr5$^+$ cells, (iii) a differentiation assay initial number of hair cells, (iv) a differentiation assay initial Lgr5$^+$ cell fraction that equals the ratio of the differentiation assay initial number of Lgr5$^+$ cells to the differentiation assay initial number of total cells, and (v) a differentiation assay initial hair cell fraction that equals the ratio of the differentiation assay initial number of hair cells to the differentiation assay initial number of total cells;

(d) the differentiation assay final cell population has (i) a differentiation assay final number of total cells, (ii) a differentiation assay final number of Lgr5$^+$ cells, (iii) a differentiation assay final number of hair cells, (iv) a differentiation assay final Lgr5$^+$ cell fraction that equals the ratio of the differentiation assay final number of Lgr5$^+$ cells to the differentiation assay final number of total cells, and (v) a differentiation assay final hair cell fraction that equals the ratio of the differentiation assay final number of hair cells to the differentiation assay final number of total cells;

(e) the proliferation assay final number of Lgr5$^+$ cells exceeds the proliferation assay initial number of Lgr5$^+$ cells by a factor of at least 10; and (f) the differentiation assay final number of hair cells is a non-zero number.

232. The method of embodiment 231, wherein the proliferation assay final number of Lgr5$^+$ cells is greater than the proliferation assay initial number of Lgr5$^+$ cells by a factor of at least 50.

233. The method of embodiment 231, wherein the proliferation assay final number of Lgr5$^+$ cells is greater than the proliferation assay initial number of Lgr5$^+$ cells by a factor of at least 100.

234. The method as in any of embodiments 231-233, wherein the expanded population of cells in the cochlear tissue comprises a greater number of hair cells than does the parent population.

235. The method as in any of embodiments 231-234, wherein the proliferation assay final Lgr5$^+$ cell fraction is greater than the proliferation assay initial Lgr5$^+$ cell fraction by at least a factor of 2.

236. The method as in any of embodiments 231-235, wherein the differentiation assay final hair cell fraction is greater than the differentiation assay initial hair cell fraction by at least a factor of 2.

237. The method as in any of embodiments 231-236, wherein the proliferation assay final hair cell fraction is at least 25% less than the proliferation assay initial hair cell fraction 238. The method as in any of embodiments 231-237, wherein the proliferation assay final Lgr5$^+$ cell fraction is at least 10% greater than proliferation assay initial Lgr5$^+$ cell fraction.

239. The method as in any of embodiments 231-238, wherein the cochlear tissue maintains Native Morphology.

240. The method as in any of embodiments 231-238, wherein the at least one stem cell proliferator is dispersed in a biocompatible matrix.

241. The method as in any of embodiments 231-240, wherein the proliferation assay final number of Lgr5$^+$ cells is greater than the proliferation assay initial number of Lgr5$^+$ cells by a factor of at least 100.

242. The method as in any of embodiments 231-240, wherein the proliferation assay final number of Lgr5$^+$ cells is greater than the proliferation assay initial number of Lgr5$^+$ cells by a factor of at least 500.

243. The method as in any of embodiments 231-242, wherein the proliferation assay final Lgr5$^+$ cell fraction is greater than the proliferation assay initial Lgr5$^+$ cell fraction by at least a factor of 2.

244. The method as in any of embodiments 231-242, wherein the proliferation assay final Lgr5$^+$ cell fraction is greater than the proliferation assay initial Lgr5$^+$ cell fraction by at least a factor of 4.

245. The method as in any of embodiments 231-242, wherein the proliferation assay final Lgr5$^+$ cell fraction is greater than the proliferation assay initial Lgr5$^+$ cell fraction by at least a factor of 8.

246. The method as in any of embodiments 231-242, wherein the proliferation assay final Lgr5$^+$ cell fraction is greater than the proliferation assay initial Lgr5$^+$ cell fraction by at least a factor of 16.

247. The method as in any of embodiments 231-242, wherein the proliferation assay final Lgr5$^+$ cell fraction is greater than the proliferation assay initial Lgr5+ cell fraction by at least a factor of 32.

248. The method as in any of embodiments 231-247, wherein the proliferation assay final hair cell fraction is at least 25% less than the proliferation assay initial hair cell fraction.

249. The method as in any of embodiments 231-247, wherein the proliferation assay final hair cell fraction is at least 50% less than the proliferation assay initial hair cell fraction.

250. The method as in any of embodiments 231-247, wherein the proliferation assay final hair cell fraction is at least 75% less than the proliferation assay initial hair cell fraction.

251. The method as in any of embodiments 231-250, wherein the proliferation assay final Lgr5$^+$ cell fraction is at least 10% greater than proliferation assay initial Lgr5$^+$ cell fraction.

252. The method as in any of embodiments 231-250, wherein the proliferation assay final Lgr5$^+$ cell fraction is at least 10% greater than proliferation assay initial Lgr5$^+$ cell fraction.

253. The method as in any of embodiments 231-250, wherein the proliferation assay final Lgr5$^+$ cell fraction is at least 20% greater than proliferation assay initial Lgr5$^+$ cell fraction.

254. The method as in any of embodiments 231-250, wherein the proliferation assay final Lgr5$^+$ cell fraction is at least 30% greater than proliferation assay initial Lgr5$^+$ cell fraction.

255. The method as in any of embodiments 231-250, wherein the proliferation assay final Lgr5$^+$ cell fraction is at least 50% greater than proliferation assay initial Lgr5$^+$ cell fraction.

Further Embodiments Include

A method for expanding a population of LGR5+ cells in a cochlear tissue having an LGR5+ cell population, comprising:

contacting the cochlear tissue with a composition comprising at least one Stem Cell Proliferator.

The method of Claim 1, wherein the at least one Stem Cell Proliferator is capable, in a Stem Cell Proliferation Assay, of expanding an initial test population of LGR5+ cells to create an expanded test population, wherein the expanded test population has at least 10-fold more LGR5+ cells than does the initial test population.

The method of Claim 2, wherein the expanded test population has at least 2-fold more Differentiation-Capable LGR5+ cells than does the initial test population.

The method of Claim 2, wherein the expanded test population has at least 10-fold more Differentiation-Capable LGR5+ cells than does the initial test population.

The method as in any of Claims 1-4, wherein one of more Morphological Characteristics of the cochlear tissue are maintained.

The method as in any of Claims 1-5, wherein the at least one Stem Cell Proliferator is dispersed in a Biocompatible Matrix.

The method of Claim 6, wherein the Biocompatible Matrix is a Biocompatible Gel or Foam.

The method as in any of Claims 1-7, wherein the composition is a controlled release formulation.

The method as in any of Claims 1-8, wherein the cochlear tissue is an in vivo cochlear tissue.

The method as in any of Claims 1-8, wherein the cochlear tissue is an ex vivo cochlear tissue.

The method as in any of Claims 1-10, wherein the at least one Stem Cell Proliferator comprises at least one of a Stemness Driver and a Differentiation Inhibitor.

The method of Claim 11, wherein the at least one Stem Cell Proliferator comprises both a Stemness Driver and a Differentiation Inhibitor.

The method of Claim 12, wherein the contacting provides:

in an Initial Phase, at least an Effective Proliferation Concentration of the Stemness Driver and at least an Effective Differentiation Inhibition Concentration of the Differentiation Inhibitor; and in a Subsequent Phase, at least an Effective Proliferation Concentration of the Stemness Driver and less than an Effective Differentiation Inhibition Concentration of the Differentiation Inhibitor.

The method as in any of Claims 1-9 or 11-13, wherein the cochlear tissue is in a subject, and wherein the contacting the cochlear tissue with the composition is achieved by administering the composition trans-tympanically to the subject.

The method of Claim 14, wherein the contacting the cochlear tissue with the composition results in improved Auditory Functioning of the subject.

A composition comprising:

at least one Stem Cell Proliferator, wherein the at least one Stem Cell Proliferator is capable, in a Stem Cell Proliferation Assay, of expanding an initial test population of LGR5+ cells to create an expanded test population, and wherein the expanded test population has at least 10-fold more LGR5+ cells than does the initial test population.

The composition of Claim 16, wherein the expanded test population has at least 2-fold more Differentiation-Capable LGR5+ cells than does the initial test population. [Please confirm that this is an appropriate factor.]

The composition of Claim 16, wherein the expanded test population has at least 10-fold more Differentiation-Capable LGR5+ cells than does the initial test population.

The composition of Claim 16 or 18, wherein the at least one Stem Cell Proliferator is dispersed in a Biocompatible Matrix.

The composition of Claim 19, wherein the Biocompatible Matrix is a Biocompatible Gel or Foam.

A composition comprising:

at least one Stem Cell Proliferator dispersed in a Biocompatible Matrix Suitable For Cochlear Administration.

The composition as in any of Claims 16-21, wherein the at least one Stem Cell Proliferator comprises at least one of a Stemness Driver and a Differentiation Inhibitor.

The composition as in any of Claims 16-22, wherein the at least one Stem Cell Proliferator comprises both a Stemness Driver and a Differentiation Inhibitor.

The composition as in any of Claims 16-23, wherein the composition is a controlled release formulation.

The composition of Claim 24, wherein the controlled release formulation when administered to a subject trans-tympanically imparts an immediate release, a delayed release, a sustained release, an extended release, a variable release, a pulsatile release, or a bi-modal release of the stem cell proliferator.

The composition of Claim 24 or 25, wherein the controlled release formulation when administered to a subject provides: (a) in an Initial Phase, at least an Effective Proliferation Concentration of the Stemness Driver and at least an Effective Differentiation Inhibition Concentration of the Differentiation Inhibitor; and (b) in a Subsequent Phase, at least an Effective Proliferation Concentration of the Stemness Driver and less than an Effective Differentiation Inhibition Concentration of the Differentiation Inhibitor.

The method as in any of Claims 11-15 or the composition as in any of Claims 16-26, wherein the Stemness Driver is: a GSK3-beta inhibitor, a GSK3-beta inhibitor derivative, a Wnt agonist, a Wnt agonist derivative, or a pharmaceutically acceptable salt of any of the foregoing.

The method as in any of Claims 11-15 or 27, or the composition as in any of Claims 16-26 or 27, wherein the Differentiation Inhibitor is: a notch agonist, a notch agonist derivative; an HDAC inhibitor; an HDAC inhibitor derivative, or a pharmaceutically acceptable salt of any of the foregoing.

The method of Claim 27 or 28 or the composition of Claim 27 or 28, wherein the Stemness Driver is selected from the group consisting of: CHIR99021, LY2090314, lithium, A1070722, BML-284 and SKL2001.

The method as in any of Claims 27-29 or the composition as in any of Claims 27-29, wherein the Differentiation Inhibitor is a Notch agonist or an HDAC inhibitor selected from the group consisting of valproic acid, SAHA and Tubastatin A.

A method of treating a subject who has, or is at risk of developing, hearing loss, the method comprising:

trans-tympanically administering to a cochlear tissue of the subject a composition comprising at least one Stem Cell Proliferator.

The method of Claim 31, wherein the at least one Stem Cell Proliferator comprises at least one of a Stemness Driver and a Differentiation Inhibitor.

The method of Claim 31 or 32, wherein the at least one Stem Cell Proliferator comprises both a Stemness Driver and a Differentiation Inhibitor.

A proliferating Lgr5 post-natal mammalian inner ear cell population that expresses at least one of the following compared to the non-proliferating native state: reduced histone deacetylase, higher Notch, optionally wherein: where the cell in a supporting cell; where the supporting cell is Lgr5+; where notch agonist is an HDAC inhibitor; where a Wnt agonist is also included; where Wnt agonist is a GSK3-beta inhibitor; and/or where the GSK3-beta inhibitor is CHIR99021

A method of administering to the ear of the subject a composition comprising VPA.

A method of administering to the ear of the subject a composition comprising CHIR99021, A method of administering to the ear of the subject a composition comprising VPA and CHIR99021

A method to increase the ratio of hair cells to Lgr5+ support cells by providing an agonist of the Wnt pathway and an agonist of notch pathway or an antagonist of histone deacetylase, optionally where: WNT activation is achieved by providing one or more antagonists of GSK3b; and/or the antagonist of histone deacetylase or Notch activation is achieved by providing VPA A Method to expand Lgr5 cells by at least 3× and/or upregulate Lgr5 expression by at least 3× by providing one or more Wnt agonists and one or more antagonists of histone deacetylase or notch agonists.

A Method for expanding inner ear precursor cells by contacting the cells with one or more agonists of Notch or antagonists of histone deacetylase and an agonist of Wnt such that the cell proliferates, optionally where: in vitro the cell is exposed to additional growth factors; and/or additional factors include the one or more agonist of Notch or antagonists of histone deacetylase and an agonist of Wnt are administered in vivo to achieve a transient proliferation response.

An in vitro differentiated population of hair cells obtained from culture-expanded Lgr5 cells with one or more Notch agonists and/or antagonists of histone deacetylase and/or one or more wnt agonists.

A Method for differentiation of Lgr5 precursor cells comprising contacting the cell with an amount of Notch inhibitor and CHIR99021, optionally where differentiation is into hair cells A Method for differentiation of Lgr5 precursor cells into hair cells comprising contacting the Lgr5 expressing cells with CHIR99021 and a Notch antagonist.

Any composition herein with the addition of antagonist of ROS to enhance Lgr5 expression and/or cell number expansion.

Any composition herein where Notch agonist is an HDAC inhibitor.

Any composition herein where HDAC inhibitor is VPA

Any composition herein where Wnt agonist is CHIR99021.

Delivery of CHIR to ear to expand and/or increase expression of Lgr5+ supporting cells Delivery of CHIR to the ear to increase the number of hair cells Delivery of HDAC inhibitor (e.g VPA) to ear to expand and/or increase expression of Lgr5+ supporting cells Delivery of both an HDAC inhibitor (e.g. VPA) and CHIR99021 to ear to increase expression of Lgr5+ supporting cells Any composition herein that is delivered to the middle and/or inner ear.

Any composition herein where Notch agonist or antagonists of histone deacetylase are delivered in a pulsatile manner and Wnt agonist is delivered in a sustained manner.

A method of treating or preventing hearing loss through administration of CHIR99021 in a pharmaceutically relevant vehicle, optionally where the vehicle used herein is saline.

Any composition herein that is administered to the middle ear and/or inner ear

A method where tympanic membrane and/or surrounding tissue is anesthetized, a needle is placed into the middle ear, and agents described herein are injected.

A method to enhance transport of agents described herein in ear via permeation enhancers, ultrasound, electroporation, and other methods described to those described in the art.

Any methods described herein be used in combination with agents that can increase survival of supporting cells and or hairs cells.

Any suitable agent described herein delivered to a patient to enable delivery of higher concentrations of drugs that are associated with dose-limiting ototoxicity.

A method where cells produced in vitro from agents or methods described herein are used for research purposes and/or high throughput screening.

Methods or compositions where screening is used to identify agents to boost proliferation of Lgr5+ supporting cells, and or to test toxicity of drugs against supporting cells and/or their progeny, and or to test ability of agents to improve survival of hair cells.

Any compositions herein that also includes at least one protective drug (that can enhance survival or prevent death of cells in the inner ear including but not limited to hair cells)

A kit comprising: a container comprising, in a pharmaceutically acceptable carrier an inner-ear-supporting-cell-proliferation-inducing amount of Notch activators and/or HDAC inhibitors in combination with GSK3β inhibitors; and instructions for using the contents of container to treat an inner ear disorder.

A method of treating or preventing hearing loss through administration of a GSK3b inhibitor in a pharmaceutically relevant vehicle.

A method of producing Atoh-1+ in inner ear cells by treatment with CHIR99021, optionally where inner ear cells are Lgr5+ and differentiate in presence of CHIR99021 to produce Atoh-1+ cells and/or where Atoh-1+ cells are hair cells.

A method of identifying a candidate agent that promotes proliferation of epithelial stem cells that can differentiate to expresses atoh-1.

A method of identifying a candidate agent that promotes differentiation of epithelial stem cells that can express expresses atoh-1.

A method of identifying a candidate agent that promotes survival of epithelial stem cells or atoh-1 expressing cells.

Additional Remarks Regarding Methodologies

Common methods for experimentation.

Those skilled in the art will recognize that there are many methodologies for applying, testing, and treating with the agents described herein. Some non-limiting examples are described below.

Animals

For the experiments using inner ear spheres, C57BL/6 (The Jackson Laboratory) or Atoh1-nGFP reporter mice (Lumpkin et al., 2003) (a gift from Jane Johnson, University of Texas) of both sexes were used. To create organ of Corti explants with ablated hair cells, we crossed Mos-iCsp3 mice (line 17) (Fujioka et al., 2011) with Pou4f3-Cre mice (Sage et al., 2005) (a gift from Douglas Vetter, Tufts University). For all in vivo experiments, we used a Cre reporter line, mT/mG (The Jackson Laboratory), crossed to a Sox2-CreER mouse (Arnold et al., 2011) (a gift from Konrad Hochedlinger, Mass. General Hospital) at 4 weeks of age. After genotyping, double-transgenic animals were used for lineage tracing. We used young adult wild-type littermates of the mT/mG; Sox2-CreER mice to prevent strain effects in the response to noise, which are known to vary depending on background (Harding et al., 2005; Wang et al., 2002). Mice were genotyped by PCR. All protocols were approved by the Institutional Animal Care and Use Committee of Massachusetts Eye and Ear Infirmary or the by the ethics committee of Keio University Union on Laboratory Animal Medicine, in compliance with the Public Health Service policy on humane care and use of laboratory animals.

Isolation of Inner Ear Spheres

The utricles and cochleae of 1- to 3-day-old postnatal mice of both sexes were dissected and, after careful removal of the nerve trunk and mesenchymal tissues, were trypsinized and dissociated. Dissociated cells were centrifuged, and the pellet was resuspended and filtered through a 70 m cell strainer (BD Biosciences Discovery Labware) in DMEM/F12 medium with N2/B27 supplement, EGF (20 ng/ml), IGF1 (50 ng/ml), bFGF (10 ng/ml), and heparan sulfate (50 ng/ml) (Sigma). The single cells were cultured in nonadherent Petri dishes (Greiner Bio-One) to initiate clonal growth of spheres (Martinez-Monedero et al., 2008). Spheres that formed after 2-3 days in culture were passaged every 4-6 days. The spheres were centrifuged, and the pellet was mechanically dissociated with a pipette tip and resuspended in medium. Passage 3-4 spheres were used for experiments described here. These cells are negative for hair cell markers (Oshima et al., 2007) before the initiation of differentiation. For differentiation, floating spheres were transferred to fibronectin-coated 4-well plates (Greiner Bio-One) as described before (Martinez-Monedero et al., 2008; Oshima et al., 2007). Attached spheres were differentiated for 5-7 days in DMEM/F12 medium with N2/B27 supplement but without growth factors. γ-secretase inhibitors, DAPT, L-685458, MDL28170 (Sigma), and LY411575 (Santa Cruz) were added at several concentrations on the day after cell attachment.

Neonatal Cochlear Explants

Cochleae of 3-day-old postnatal C57BL/6 or Mos-iCsp3; Pou4f3-Cre double-transgenic mice of both sexes were dissected in Hanks solution (Invitrogen). To obtain a flat cochlear surface preparation, we removed thespiral ganglion, Reissner's membrane, and the most basal cochlear segment. Explants were plated onto 4-well plates (Greiner Bio-One) coated with poly-L-ornithine (0.01%, Sigma) and laminin (50 μg/ml, Becton Dickinson). Cochlear explants were cultured in DMEM (Invitrogen) with 10% fetal bovine serum. All cultures were maintained in a 5% CO2/20% O2-humidified incubator (Forma Scientific).

Acoustic Overexposure

Four-week-old mice were exposed free field, awake and unrestrained, in a small reverberant chamber (Wang et al., 2002). Acoustic trauma was produced by a 2 hr exposure to an 8-16 kHz octave band noise presented at 116 dB SPL. The exposure stimulus was generated by a custom white noise source, filtered (Brickwall Filter with a 60 dB/octave slope), amplified (Crown power amplifier), and delivered (JBL compression driver) through an exponential horn fitted securely to a hole in the top of a reverberant box. Sound exposure levels were measured at four positions within each cage using a 0.25 inch Bruel and Kjor condenser microphone: sound pressure was found to vary by <0.5 dB across these measurement positions.

Systemic or Round Window Administration of Target Agent (e.g. LY411575)

Four-week-old mice weighing 12-16 g were used. Before surgery, the animals were anesthetized with ketamine (20 mg/kg, intraperitoneally [i.p.]) and xylazine (100 mg/kg, i.p.), and an incision was madeposterior to the pinna near the external meatus after local administration of lidocaine (1%). The otic bulla was opened to approach the round window niche. The end of a piece of PE 10 tubing (Becton Dickinson) was drawn to a fine tip in a flame and gently inserted into the round window niche. LY411575 was dissolved in DMSO and diluted 10-fold in polyethylene glycol 400 (Sigma) to a final concentration of 4 mM. This solution (total volume 1 μl) was injected into the round window niche of the left ear. Polyethylene glycol 400 with 10% DMSO was injected into the right ear as a control. The solution was administered for 2 min. This approach is widely used clinically and has the advantage of sparing the inner ear but still taking advantage of the local route provided by the round window membrane for delivery of drug into the inner ear (Mikulec et al., 2008). Gelatin was placed on the niche to maintain the solution, and the wound was closed.

For the systemic administration, LY411575 (50 mg/kg) dissolved in 0.5% (w/v) methylcellulose (WAKO) was injected orally once daily for 5 consecutive days. Hearing was measured by ABR at 1 day before, 2 days, 1 week, 2 weeks, and 1, 2, and 3 months after noise exposure.

qRT-PCR

The organs of Corti were dissected in HBSS (Invitrogen) and stored in RNAlater (Ambion) at −80° C. until further use. Total RNA was extracted using the RNeasy Mini Kit (QIAGEN) according to the manufacturer's instructions. For reverse transcription, SuperScript II (Invitrogen) was used with random hexamers. The reverse transcription conditions were 25° C. for 10 min followed by 37° C. for 60 min. The reaction was terminated at 95° C. for 5 min. cDNAs were mixed with Taqman Gene Expression Mastermix (Applied Biosystems) and Hes5, Atoh1, or 18S primers (Applied Biosystems) according to the manufacturer's instructions. Samples were analyzed in 96 wells in triplicate by qPCR (Applied Biosystems 7900HT), and PCR thermal cycling conditions were as follows: initial denaturation at 95° C. for 2 min, denaturation at 95° C. for 15 s, and annealing and extension at 60° C. for 1 min for 45 cycles. Conditions were kept constant for each primer. Each PCR reaction was carried out in triplicate. Relative gene expression was analyzed by using the ΔΔCT method. Gene expression was calculated relative to 18S RNA, and the amount of cDNA applied was adjusted so that the Ct value for 18S RNA was between 8 and 11.

Immunohistochemistry

For spheres, cells were fixed for 10 min with 4% paraformaldehyde in PBS. Immunostaining was initiated by blocking for 1 hr with 0.1% Triton X-100 in PBS supplemented with 1% BSA and 5% goat serum (PBT1). Fixed and permeabilized cells were incubated overnight in PBT1 with polyclonal antibody to myosin VIIa (Proteus Biosciences). Samples were washed three times for 20 min with PBS. Primary antibodies were detected with secondary antibodies conjugated with Alexa 488 (Molecular Probes), with secondary antibody alone used as a negative control. The samples were counterstained with DAPI (Vector Laboratories) or Hoechst 33258 (Invitrogen) for 10 min and viewed by epifluorescence microscopy (Axioskop 2 Mot Axiocam, Zeiss).

For explants, the organs of Corti were fixed for 15 min with 4% paraformaldehyde in PBS. Immunostaining was initiated by blocking the tissues for 1 hr with 0.1% Triton X-100 in PBS supplemented with 5% donkey serum (PBT1). Fixed and permeabilized pieces were incubated overnight in PBT1 with antibodies to myosin VIIa (Proteus Biosciences), Sox2 (Santa Cruz), GFP (Invitrogen), prestin (Santa Cruz), neurofilament H (Chemicon), and CtBP2 (BD Biosciences). Samples were washed three times for 20 min with PBS. Primary antibodies were detected with secondary antibodies conjugated with Alexa 488 and 647 (Molecular Probes). The samples were stained with rhodamine phalloidin (Invitrogen) for 15 min and viewed by confocalfluorescence microscopy (TCS SP5, Leica).

For collection of the mature cochlea, deeply anesthetized mice were transcardially perfused with 0.01 M phosphate buffer (pH 7.4) containing 8.6% sucrose, followed by fixative consisting of freshly depolymerized 4% paraformaldehyde in 0.1 M phosphate buffer (pH 7.4). After decapitation, the temporal bones were removed and immediately placed in the same fixative at 4° C. Small openings were made at the round window, oval window, and apex of the cochlea. After immersion in the fixative overnight at 4° C., temporal bones were decalcified in 0.1 M EDTA (pH 7.4) containing 5% sucrose with stirring at 4° C. for 2 days. After decalcification, the cochlea was microdissected into four pieces for whole-mount preparation. Immunostaining was initiated by blocking the tissues for 1 hr with 0.1% Triton X-100 in PBS supplemented with 5% donkey serum (PBT1). Fixed and permeabilized pieces were incubated overnight in PBT1 with antibodies to myosin VIIa (Proteus Biosciences), Sox2 (Santa Cruz), and GFP (Invitrogen). Samples were washed three times for 20 min with PBS. Primary antibodies were detected with secondary antibodies conjugated with Alexa 488, 568, and 647 (Molecular Probes) and viewed by confocal fluorescence microscopy (TCS SP5, Leica). Cochlear lengths were obtained for each case, and a cochlear frequency map computed to precisely localize inner hair cells from the 5.6, 8.0, 11.3, 16.0, 22.6, 32, and 45.2 kHz regions. For cross-sectioning, fixed temporal bones were sunk in 30% sucrose in PBS at 4° C., incubated in OCT at room temperature for 1 hr, and frozen in liquid nitrogen. The staining protocol was the same as described above except for counterstaining with DAPI (Vector Laboratories). Specimens were viewed by epifluorescence microscopy (Axioskop 2 Mot Axiocam, Zeiss).

Cell Counts

Cell counting for spheres was performed with MetaMorph software. The cell number was determined from DAPI- or Hoechst-positive nuclei. Repeat cell counting gave a test variation of <1%. For explants, inner hair cells, outer hair cells, and supporting cells in the outer hair cell region were counted on cochlear whole mounts. Hair cells were identified with myosin VIIa antibodies or endogenous GFP in Atoh1-nGFP mice. High-power images of the full-length cochlea or cochlear explant cultures were assembled and analyzed in PhotoShop CS4 (Adobe). ImageJ software (NIH) was used to measure the total length of cochlear whole mounts and the length of individual counted segments. The total number of inner hair cells, outer hair cells, and supporting cells in the outer hair cell region was counted in each of four cochlear segments of 1,200-1,400 m (apical, midapical, midbasal, and basal). Density (cells per 100 m) was then calculated for each segment. For mature cochleae, high-power images of frequency-specific regions (5.6, 8.0, 11.3, and 16.0 kHz) according to the computed frequency map were assembled and analyzed. The number of inner hair cells, outer hair cells, and supporting cells in the outer hair cell region in 100 m was counted in each of the four frequency-specific regions of the cochlea. The number of Sox2 lineage-positive cells identified by GFP was counted by the same method.

ABR Measurements

Auditory brain stem responses (Kujawa and Liberman, 1997; Maison et al., 2003) were measured in each animal at seven log-spaced frequencies (half-octave steps from 5.6 to 45.2 kHz) before and 1 day after noise exposure, and 1 week, 1 month, and 3 months after surgery. Mice were anesthetized with ketamine (100 mg/kg, i.p.) and xylazine (20 mg/kg, i.p.). Needle electrodes were inserted at vertex and pinna, with a ground near the tail. ABRs were evoked with 5 ms tone pips (0.5 ms rise-fall with a cos 2 onset envelope delivered at 35/s). The response was amplified, filtered, and averaged in a LabVIEW-driven data acquisition system. Sound level was raised in 5 dB steps from >10 dB below threshold to <80 dB SPL. At each sound level, 1,024 responses were averaged (with stimulus polarity alternated), using an "artifact reject," whereby response waveforms were discarded when peak-to-peak response amplitude exceeded 15 V. On visual inspection of stacked waveforms, "ABR threshold" was defined as the lowest SPL level at which any wave could be detected, usually corresponding to the level step just below that at which the peak-to-peak response amplitude rose significantly above the noise floor (approximately 0.25 µV). When no response was observed at the highest sound level available, the threshold was designated as being 5 dB greater than that level so that statistical tests could be done. For amplitude versus level functions, the wave I peak was identified by visual inspection at each sound level and the peak-to-peak amplitude was computed.

Quantification and Statistical Analysis

The two-tailed Mann-Whitney U test was used to compare differences among treatment groups. Changes before and after treatment of the same animal were analyzed by two-tailed Wilcoxon t test. Repeated-measures ANOVA was used to compare time-dependent differences among groups. Data are presented in the text and in figures as mean SEM. p values less than 0.05 were considered significant.

Genotyping Primers

We used the following genotyping primers: LacZ F: 5'-ttcactggccgtcgttttacaacgtcgtga-3' (SEQ ID NO: 1) and LacZ R: 5'-atgtgagcgagtaacaacccgtcggattct-3' (SEQ ID NO: 2) for the Mos-iCsp3 mice; Cre F: 5'-tgggcggcatggtgcaagtt-3' (SEQ ID NO: 3) and Cre R: 5'-cggtgctaaccagcgttttc-3' (SEQ ID NO: 4) for the Pou4f3Cre and Sox2CreER mice; and oIMR7318 wild-type F: 5'-ctctgctgcctcctggcttct-3' (SEQ ID NO: 5), oIMR7319 wild-type R: 5'-cgaggcggatcacaagcaata-3' (SEQ ID NO: 6), and oIMR7320 mutant R: 5'-tcaatgggcggggtcgtt-3' (SEQ ID NO: 7) for the mT/mG mice.

REFERENCES

1. Balak K J, Corwin J T, Jones J E. Regenerated hair cells can originate from supporting cell progeny: evidence from phototoxicity and laser ablation experiments in the lateral line system. The Journal of neuroscience: the official journal of the Society for Neuroscience 1990; 10:2502-12.
2. Stone J S, Cotanche D A. Identification of the timing of S phase and the patterns of cell proliferation during hair cell regeneration in the chick cochlea. The Journal of comparative neurology 1994; 341:50-67.
3. Stone J S, Rubel E W. Temporal, spatial, and morphologic features of hair cell regeneration in the avian basilar papilla. The Journal of comparative neurology 2000; 417:1-16.
4. Warchol M E, Corwin J T. Regenerative proliferation in organ cultures of the avian cochlea: identification of the initial progenitors and determination of the latency of the proliferative response. The Journal of neuroscience: the official journal of the Society for Neuroscience 1996; 16:5466-77.
5. Mizutari K, Fujioka M, Hosoya M, et al. Notch inhibition induces cochlear hair cell regeneration and recovery of hearing after acoustic trauma. Neuron 2013; 77:58-69.
6. Ryals B M, Dent M L, Dooling R J. Return of function after hair cell regeneration. Hearing research 2013; 297:113-20.
7. Raphael Y. Evidence for supporting cell mitosis in response to acoustic trauma in the avian inner ear. Journal of neurocytology 1992; 21:663-71.
8. Salt A N, Hartsock J, Plontke S, LeBel C, Piu F. Distribution of dexamethasone and preservation of inner ear function following intratympanic delivery of a gel-based formulation. Audiology & neuro-otology 2011; 16:323-35.
9. Salt A N, Gill R M, Plontke S K. Dependence of hearing changes on the dose of intratympanically applied gentamicin: a meta-analysis using mathematical simulations of clinical drug delivery protocols. The Laryngoscope 2008; 118:1793-800.
10. Plontke S K, Biegner T, Kammerer B, Delabar U, Salt A N. Dexamethasone concentration gradients along scala tympani after application to the round window membrane. Otology & neurotology: official publication of the American Otological Society, American Neurotology Society [and] European Academy of Otology and Neurotology 2008; 29:401-6.
11. Plontke S K, Salt A N. Simulation of application strategies for local drug delivery to the inner ear. ORL; journal for oto-rhino-laryngology and its related specialties 2006; 68:386-92.
12. Plontke S K, Lowenheim H, Mertens J, et al. Randomized, double blind, placebo controlled trial on the safety and efficacy of continuous intratympanic dexamethasone delivered via a round window catheter for severe to profound sudden idiopathic sensorineural hearing loss after failure of systemic therapy. The Laryngoscope 2009; 119:359-69.
13. Van Tomme S R, Storm G, Hennink W E. In situ gelling hydrogels for pharmaceutical and biomedical applications. International journal of pharmaceutics 2008; 355:1-18.
14. Mundada A S, Avari J G. In situ gelling polymers in ocular drug delivery systems: a review. Critical reviews in therapeutic drug carrier systems 2009; 26:85-118.
15. Almeida H, Amaral M H, Lobao P, Lobo J M. In situ gelling systems: a strategy to improve the bioavailability of ophthalmic pharmaceutical formulations. Drug discovery today 2014; 19:400-12.
16. Shoichet M S, Tator C H, Poon P, Kang C, Baumann M D. Intrathecal drug delivery strategy is safe and efficacious for localized delivery to the spinal cord. Progress in brain research 2007; 161:385-92.
17. Gupta D, Tator C H, Shoichet M S. Fast-gelling injectable blend of hyaluronan and methylcellulose for intrathecal, localized delivery to the injured spinal cord. Biomaterials 2006; 27:2370-9.
18. Wise A K, Gillespie L N. Drug delivery to the inner ear. Journal of neural engineering 2012; 9:065002.
19. Swan E E, Mescher M J, Sewell W F, Tao S L, Borenstein J T. Inner ear drug delivery for auditory applications. Advanced drug delivery reviews 2008; 60:1583-99.
20. Surovtseva E V, Johnston A H, Zhang W, et al. Prestin binding peptides as ligands for targeted polymersome mediated drug delivery to outer hair cells in the inner ear. International journal of pharmaceutics 2012; 424:121-7.
21. Staecker H, Brough D E, Praetorius M, Baker K. Drug delivery to the inner ear using gene therapy. Otolaryngologic clinics of North America 2004; 37:1091-108.
22. Seidman M D. Glutamate Antagonists, Steroids, and Antioxidants as Therapeutic Options for Hearing Loss and Tinnitus and the Use of an Inner Ear Drug Delivery System. The international tinnitus journal 1998; 4:148-54.
23. Salt A N, Plontke S K. Principles of local drug delivery to the inner ear. Audiology & neuro-otology 2009; 14:350-60.
24. Salt A N, Plontke S K. Local inner-ear drug delivery and pharmacokinetics. Drug discovery today 2005; 10:1299-306.
25. Salt A. Guest editorial: drug delivery for treatment of inner ear disease: current state of knowledge. Ear and hearing 2010; 31:155.
26. Sakamoto T, Nakagawa T, Horie R T, et al. Inner ear drug delivery system from the clinical point of view. Acta oto-laryngologica Supplementum 2010:101-4.
27. Roy S, Johnston A H, Newman T A, et al. Cell-specific targeting in the mouse inner ear using nanoparticles conjugated with a neurotrophin-derived peptide ligand: potential tool for drug delivery. International journal of pharmaceutics 2010; 390:214-24.
28. Roy S, Glueckert R, Johnston A H, et al. Strategies for drug delivery to the human inner ear by multifunctional nanoparticles. Nanomedicine 2012; 7:55-63.
29. Rivera T, Sanz L, Camarero G, Varela-Nieto I. Drug delivery to the inner ear: strategies and their therapeutic implications for sensorineural hearing loss. Current drug delivery 2012; 9:231-42.
30. Richardson R T, Wise A K, Andrew J K, O'Leary S J. Novel drug delivery systems for inner ear protection and regeneration after hearing loss. Expert opinion on drug delivery 2008; 5:1059-76.
31. Plontke S K, Zimmermann R, Zenner H P, Lowenheim H. Technical note on microcatheter implantation for local inner ear drug delivery: surgical technique and safety aspects. Otology & neurotology: official publication of the American Otological Society, American Neurotology Society [and] European Academy of Otology and Neurotology 2006; 27:912-7.
32. Plontke S K, Siedow N, Wegener R, Zenner H P, Salt A N. Cochlear pharmacokinetics with local inner ear drug delivery using a three-dimensional finite-element computer model. Audiology & neuro-otology 2007; 12:37-48.
33. Plontke S K, Plinkert P K, Plinkert B, Koitschev A, Zenner H P, Lowenheim H. Transtympanic endoscopy for drug delivery to the inner ear using a new microendoscope. Advances in oto-rhino-laryngology 2002; 59:149-55.
34. Plontke S K. Evaluation of the round window niche before local drug delivery to the inner ear using a new mini-otoscope. Otology & neurotology: official publication of the American Otological Society, American Neurotology Society [and] European Academy of Otology and Neurotology 2011; 32:183-5.
35. Plontke S, Zenner H P. Pharmacokinetic considerations in intratympanic drug delivery to the inner ear. Acta oto-rhino-laryngologica Belgica 2002; 56:369-70.
36. Plontke S, Siedow N, Hahn H, Wegener R, Zenner H P, Salt A N. [1D- and 3D-computer simulation for experimental planning and interpretation of pharmacokinetic studies in the inner ear after local drug delivery]. Altex 2004; 21 Suppl 3:77-85.

37. Paulson D P, Abuzeid W, Jiang H, Oe T, O'Malley B W, Li D. A novel controlled local drug delivery system for inner ear disease. The Laryngoscope 2008; 118:706-11.

38. Pararas E E, Chen Z, Fiering J, et al. Kinetics of reciprocating drug delivery to the inner ear. Journal of controlled release: official journal of the Controlled Release Society 2011; 152:270-7.

39. Pararas E E, Borkholder D A, Borenstein J T. Microsystems technologies for drug delivery to the inner ear. Advanced drug delivery reviews 2012; 64:1650-60.

40. Paasche G, Gibson P, Averbeck T, Becker H, Lenarz T, Stover T. Technical report: modification of a cochlear implant electrode for drug delivery to the inner ear. Otology & neurotology: official publication of the American Otological Society, American Neurotology Society [and] European Academy of Otology and Neurotology 2003; 24:222-7.

41. Nakagawa T, Ito J. Local drug delivery to the inner ear using biodegradable materials. Therapeutic delivery 2011; 2:807-14.

42. Mimura T, Funatsu H, Usui T, Yamagami S, Noma H, Amano S. Topical ocular drug delivery to inner ear disease and sinusitis. Southern medical journal 2006; 99:1287-9.

43. McCall A A, Swan E E, Borenstein J T, Sewell W F, Kujawa S G, McKenna M J. Drug delivery for treatment of inner ear disease: current state of knowledge. Ear and hearing 2010; 31:156-65.

44. Li M L, Lee L C, Cheng Y R, et al. A novel aerosol-mediated drug delivery system for inner ear therapy: intratympanic aerosol methylprednisolone can attenuate acoustic trauma. IEEE transactions on bio-medical engineering 2013; 60:2450-60.

45. Lehner R, Brugger H, Maassen M M, Zenner H P. A totally implantable drug delivery system for local therapy of the middle and inner ear. Ear, nose, & throat journal 1997; 76:567-70.

46. Lajud S A, Han Z, Chi F L, et al. A regulated delivery system for inner ear drug application. Journal of controlled release: official journal of the Controlled Release Society 2013; 166:268-76.

47. Kim D K, Park S N, Park K H, et al. Development of a drug delivery system for the inner ear using poly(amino acid)-based nanoparticles. Drug delivery 2014.

48. Kanzaki S, Fujioka M, Yasuda A, et al. Novel in vivo imaging analysis of an inner ear drug delivery system in mice: comparison of inner ear drug concentrations over time after transtympanic and systemic injections. PloS one 2012; 7:e48480.

49. Herraiz C, Miguel Aparicio J, Plaza G. [Intratympanic drug delivery for the treatment of inner ear diseases]. Acta otorrinolaringologica espanola 2010; 61:225-32.

50. Engleder E, Honeder C, Klobasa J, Wirth M, Arnoldner C, Gabor F. Preclinical evaluation of thermoreversible triamcinolone acetonide hydrogels for drug delivery to the inner ear. International journal of pharmaceutics 2014; 471:297-302.

51. Chen Z, Kujawa S G, McKenna M J, et al. Inner ear drug delivery via a reciprocating perfusion system in the guinea pig. Journal of controlled release: official journal of the Controlled Release Society 2005; 110:1-19.

52. Chen G, Hou S X, Hu P, Jin M Z, Liu J. [Preliminary study on brain-targeted drug delivery via inner ear]. Yao xue xue bao=Acta pharmaceutica *Sinica* 2007; 42:1102-6.

53. Bohl A, Rohm H W, Ceschi P, et al. Development of a specially tailored local drug delivery system for the prevention of fibrosis after insertion of cochlear implants into the inner ear. Journal of materials science Materials in medicine 2012; 23:2151-62.

54. Hoskison E, Daniel M, Al-Zahid S, Shakesheff K M, Bayston R, Birchall J P. Drug delivery to the ear. Therapeutic delivery 2013; 4:115-24.

55. Staecker H, Rodgers B. Developments in delivery of medications for inner ear disease. Expert opinion on drug delivery 2013; 10:639-50.

56. Borenstein J T. Intracochlear drug delivery systems. Expert opinion on drug delivery 2011; 8:1161-74.

57. Pritz C O, Dudas J, Rask-Andersen H, Schrott-Fischer A, Glueckert R. Nanomedicine strategies for drug delivery to the ear. Nanomedicine 2013; 8:1155-72.

58. Peer D, Karp J M, Hong S, Farokhzad O C, Margalit R, Langer R. Nanocarriers as an emerging platform for cancer therapy. Nature nanotechnology 2007; 2:751-60.

59. Zahnert T. The differential diagnosis of hearing loss. Deutsches Arzteblatt international 2011; 108:433-43; quiz 44.

60. Sataloff R T, Sataloff J. Differential diagnosis of occupational hearing loss. Occupational health & safety 2001; 70:126-9.

61. Mills D M. Determining the cause of hearing loss: differential diagnosis using a comparison of audiometric and otoacoustic emission responses. Ear and hearing 2006; 27:508-25.

62. Isaacson J E, Vora N M. Differential diagnosis and treatment of hearing loss. American family physician 2003; 68:1125-32.

63. Lasak J M, Allen P, McVay T, Lewis D. Hearing loss: diagnosis and management. Primary care 2014; 41:19-31.

64. Brazilian Association of O, Brazilian College of R. Sensorineural hearing loss: radiologic diagnosis. Revista da Associacao Medica Brasileira 2012; 58:519-29.

65. Alford R L, Arnos K S, Fox M, et al. American College of Medical Genetics and Genomics guideline for the clinical evaluation and etiologic diagnosis of hearing loss. Genetics in medicine: official journal of the American College of Medical Genetics 2014; 16:347-55.

66. Shi F, Cheng Y F, Wang X L, Edge A S. Beta-catenin up-regulates Atoh1 expression in neural progenitor cells by interaction with an Atoh1 3' enhancer. The Journal of biological chemistry 2010; 285:392-400.

67. Jeon S J, Fujioka M, Kim S C, Edge A S. Notch signaling alters sensory or neuronal cell fate specification of inner ear stem cells. The Journal of neuroscience: the official journal of the Society for Neuroscience 2011; 31:8351-8.

68. Bramhall N F, Shi F, Arnold K, Hochedlinger K, Edge A S. Lgr5-positive supporting cells generate new hair cells in the postnatal cochlea. Stem cell reports 2014; 2:311-22.

69. Purow B. Notch inhibition as a promising new approach to cancer therapy. Advances in experimental medicine and biology 2012; 727:305-19.

70. Wu L, Griffin J D. Modulation of Notch signaling by mastermind-like (MAML) transcriptional co-activators and their involvement in tumorigenesis. Seminars in cancer biology 2004; 14:348-56.

71. Shih Ie M, Wang T L. Notch signaling, gamma-secretase inhibitors, and cancer therapy. Cancer research 2007; 67:1879-82.

72. Olsauskas-Kuprys R, Zlobin A, Osipo C. Gamma secretase inhibitors of Notch signaling. OncoTargets and therapy 2013; 6:943-55.

73. Meng R D, Shelton C C, Li Y M, et al. gamma-Secretase inhibitors abrogate oxaliplatin-induced activation of the Notch-1 signaling pathway in colon cancer cells resulting in enhanced chemosensitivity. Cancer research 2009; 69:573-82.

EXEMPLIFICATION

Example 1

Cell culture: Heterozygous Lgr5-EGFP-IRES-CreERT2 mice were obtained from Jackson Labs, and neonatal P2-P5 mice were used for cell isolation. Organ of Corti was isolated from Lgr5-GFP mice and further dissociated into single cells using trypsin. Cells were then cultured as previously described (Yin et al, 2014). Briefly, cells were entrapped in Matrigel and plated at the center of wells in a 24-well plate. Following polymerization of Matrigel, 500 µl of culture media (Advanced DMEM/F12 with N2 and B27) was added, containing growth factors including EGF (50 ng/ml) (epidermal growth factor), bFGF (20 ng/ml) (fibroblast growth factor), and IGF1 (50 ng/ml) (insulin-like growth factor 1), and small molecules including CHIR99021 (5 µM), valproic acid (1 mM), 2-phospho-L-ascorbic acid (280 µM), and 616452 (2 µM). Y-27632 (10 µM) was added for the first 2 days. In some experiments, bFGF was used at 50 ng/ml.

For single cell isolation, the organs of Corti were then treated with Cell Recovery Solution (Corning) for 1 h to separate cochlear epithelium from the underlying mesenchyme. Epithelia were then collected and treated with Trypsin (Life Technologies) for 15-20 minutes at 37° C. Single cells obtained by mechanical trituration were filtered by cell strainer (40 µm) and washed with cell culture media. For FACS sorting of Lgr5-high and Lgr5-Low cells, FACS ARIA (BD) was used and Lgr5-GFP was used as indicator of Lgr5 level. Sorted single cells were cultured in Matrigel in inner ear cell culture media with supplement growth factors and small molecules. Y-27632 was added in the first 2 days.

FACS analysis: Cell culture media was removed and Trypsin was added. After incubation at 37° C. for 10-20 min, colonies were dissociated into single cells. Live-cell number were counted using a hemocytometer and trypan blue staining. The cells were then stained with propidium iodide (PI) and analyzed with flow cytometry. The number of GFP-positive cells was calculated by multiplying the total number of cells by the percentage of GFP-positive cells.

Results

Figure 1B:
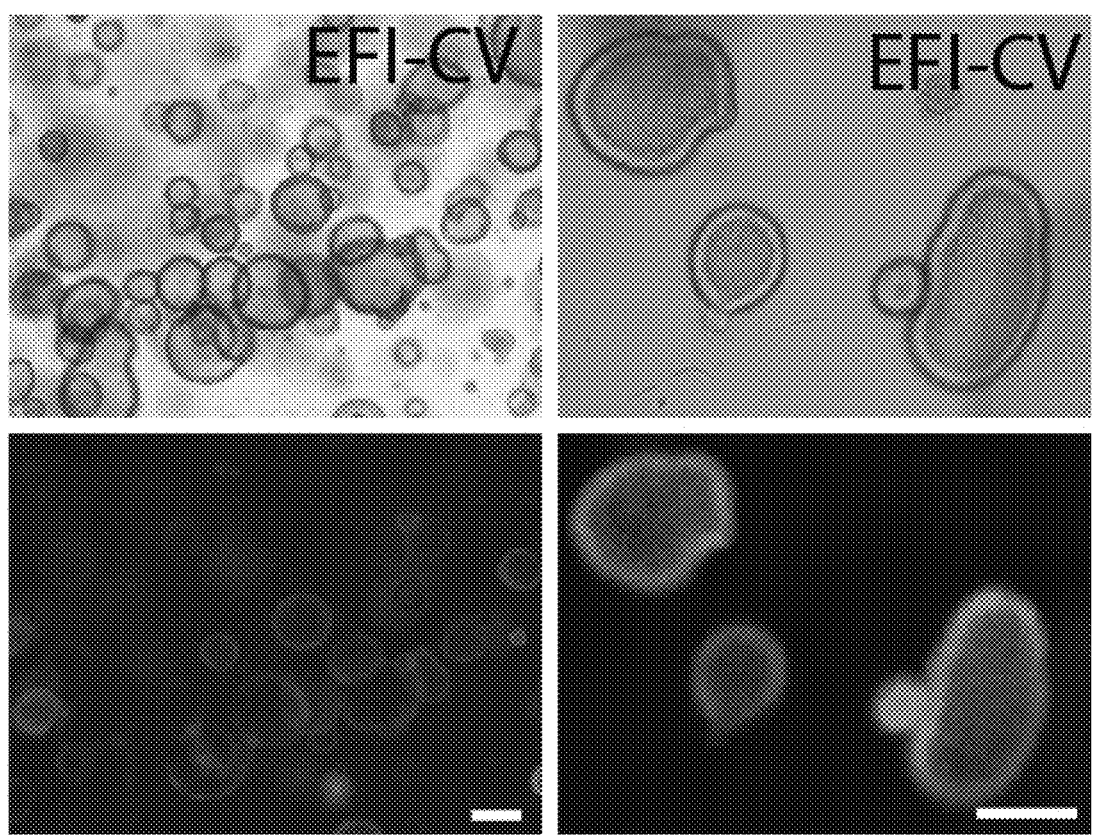
Figure 2A:
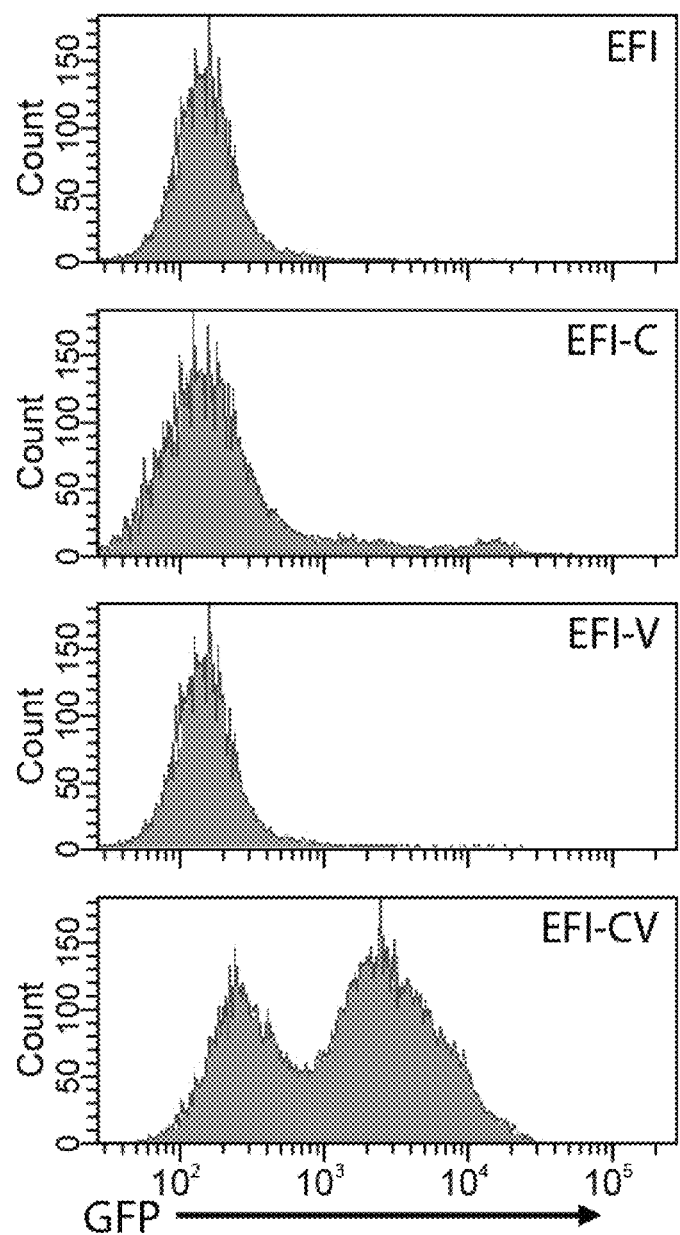
FIGS. 2A-C: Small molecules (CHIR99021 and VPA) promote the expansion of inner ear progenitor cells.
Figure 2B:
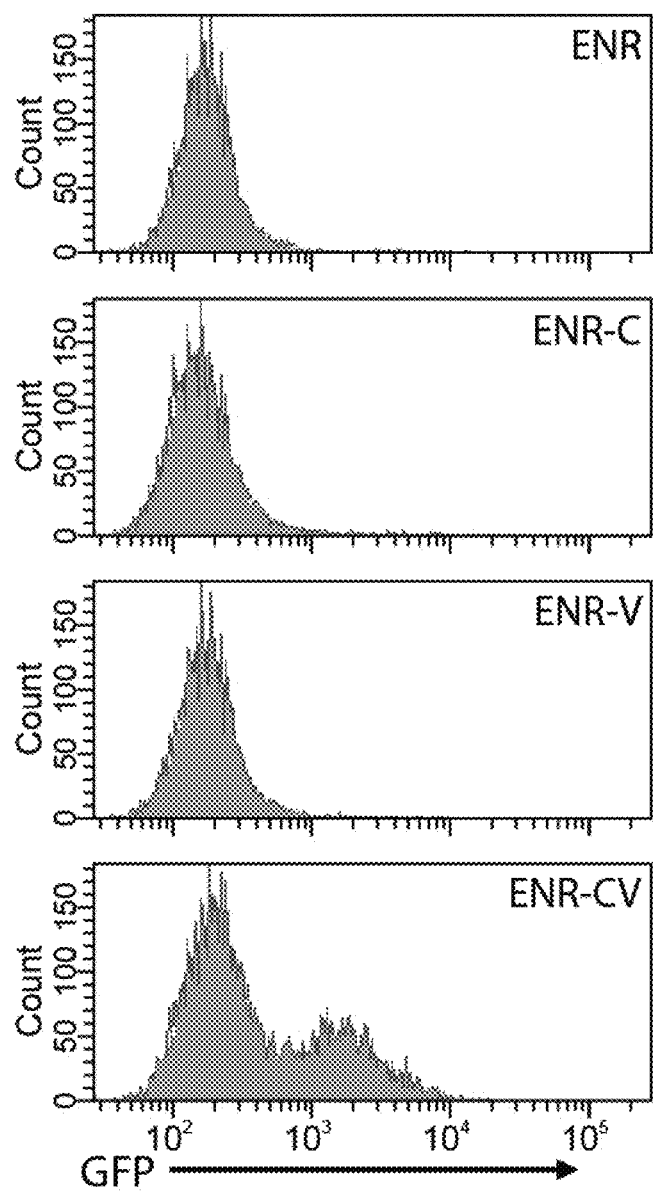
Figure 2C:
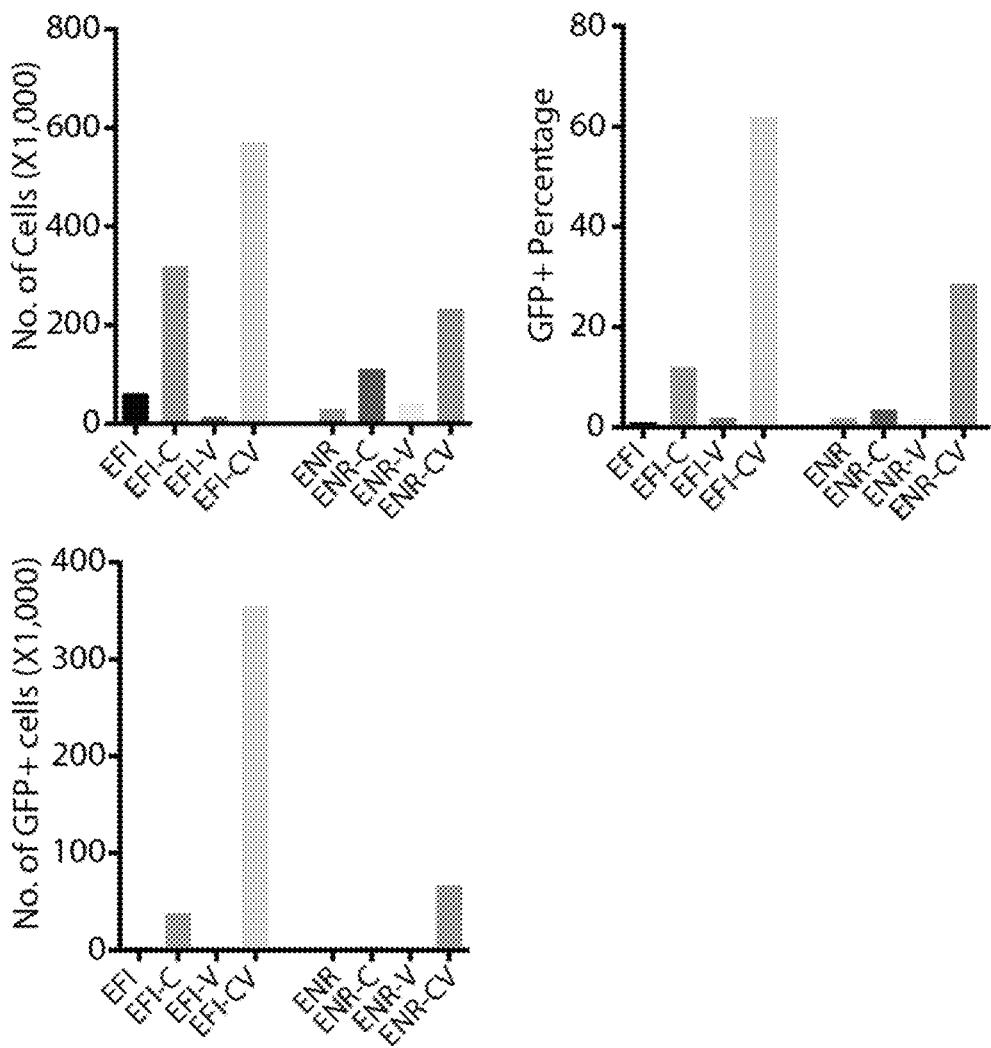

Lgr5 cells are present within a subset of supporting cells within the cochlear epithelium. Using an Lgr5-GFP mouse line, we tested the activation or inhibition of multiple pathways to expand single Lgr5$^+$ supporting cells isolated from the cochlea in a Matrigel based 3D culture system. Inner ear epithelial cells have been shown to be able to be cultured as neuro-spheres in the presence of growth factors including epidermal growth factor (EGF or E), basic fibroblast growth factor (bFGF or F), and insulin like growth factor 1 (IGF-1 or I) (Li et al., 2003). However, in this condition, no Lgr5-GFP cell growth was observed (FIG. 1A). We initially tested a combination of small molecules including the glycogen synthase kinase 30 (GSK30) inhibitor, CHIR99021 (CHIR or C) and the histone deacetylase (HDAC) inhibitor, valproic acid (VPA or V) with the growth factor cocktail. We found CHIR and VPA greatly promoted the expansion of Lgr5-GFP cells, and large colonies of Lgr5-GFP+ cells were observed in the culture (FIG. 1). Flow cytometry analysis revealed the combination of CHIR and VPA greatly increased GFP+ cell percentage (FIG. 2A). Similar phenotype was also observed when the inner ear Lgr5 cells were cultured using culture condition that was previously used for intestinal LGR5+ cells (Yin et al., 2014), although to a less extend (FIG. 2B). Cell number quantification revealed that the addition of CHIR and VPA significantly increased cell proliferation and Lgr5-GFP expression of the cells, resulting in a ~500 fold increase in Lgr5-GFP cells (FIG. 2C).

Figure 3:
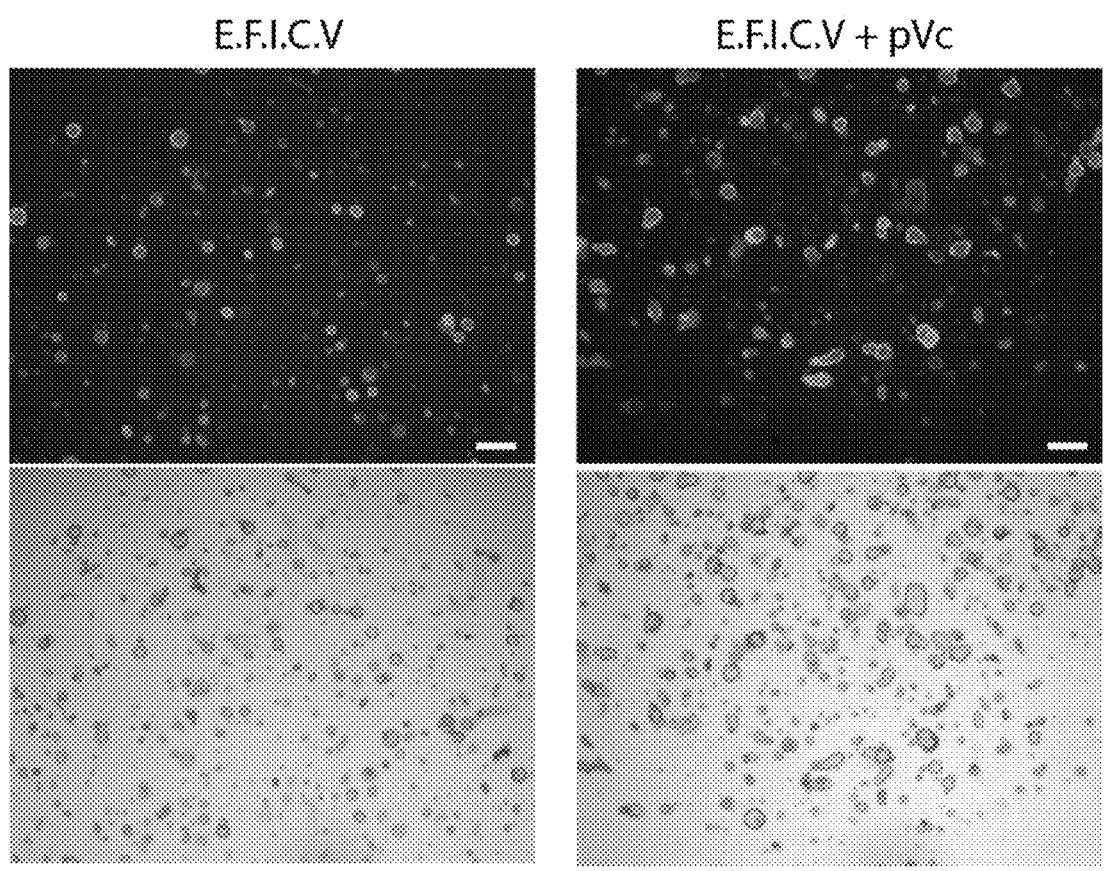
FIG. 3: Addition of pVc increases cell proliferation of Lgr5 inner ear progenitor cells. Scale bars: 400 µm.
Figure 4:
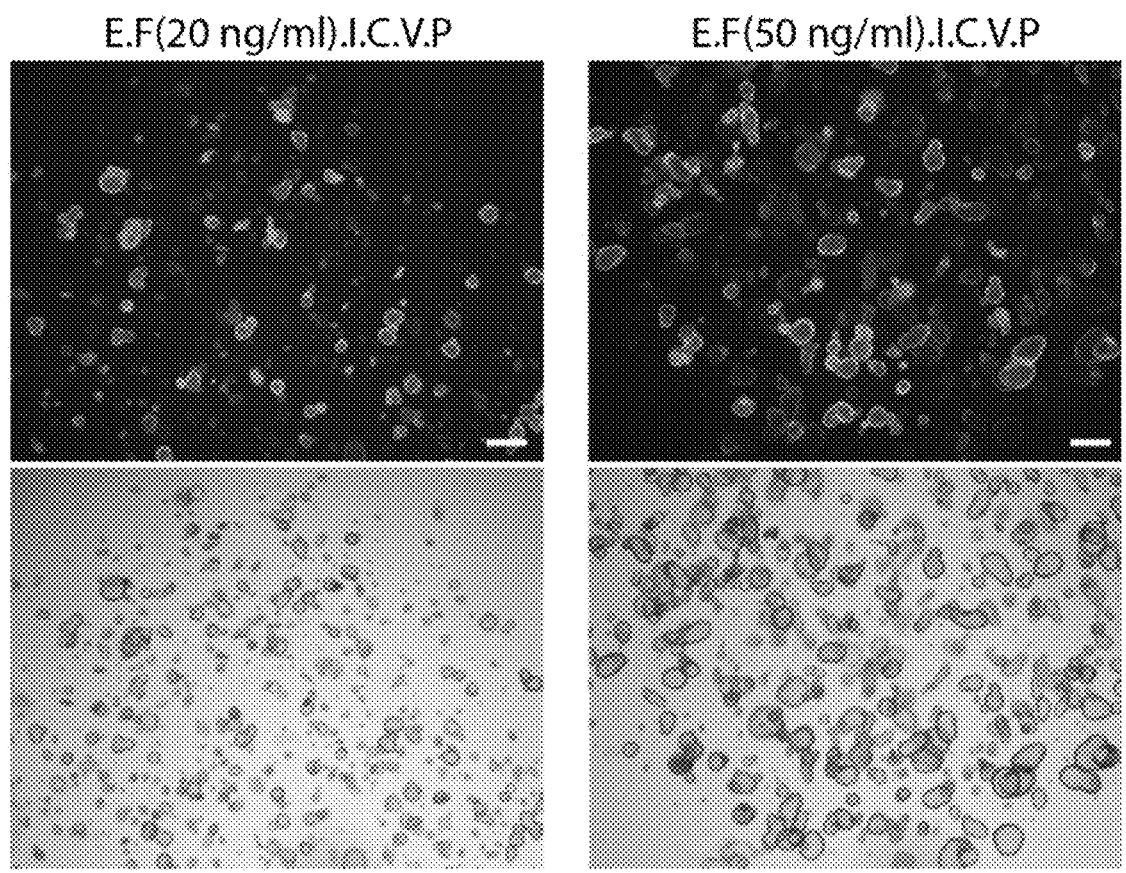
FIG. 4: Increasing bFGF concentration promotes the proliferation of Lgr5 inner ear progenitor cells. Scale bars: 400 µm.
Figure 5A:
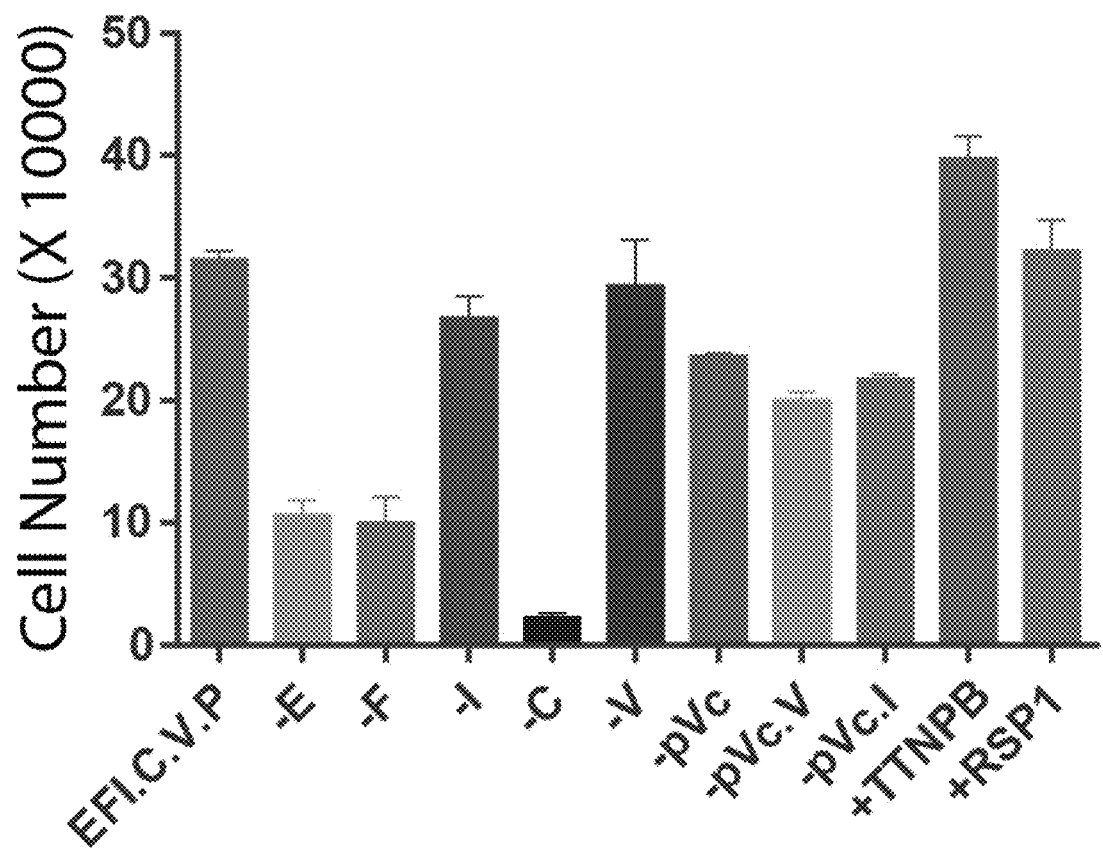
FIGS. 5A-B: Further screening of supportive factors for Lgr5 inner ear progenitor cells. TTNPB increased cell proliferation but didn't increase GFP expression. In the presence of pVc, CHIR is critical for cell proliferation and GFP expression, EGF, bFGF is important for cell proliferation but less important for GFP expression. VPA is important for GFP expression. IGF shows a marginal beneficial effect in promoting cell proliferation and GFP expression.
Figure 5B:
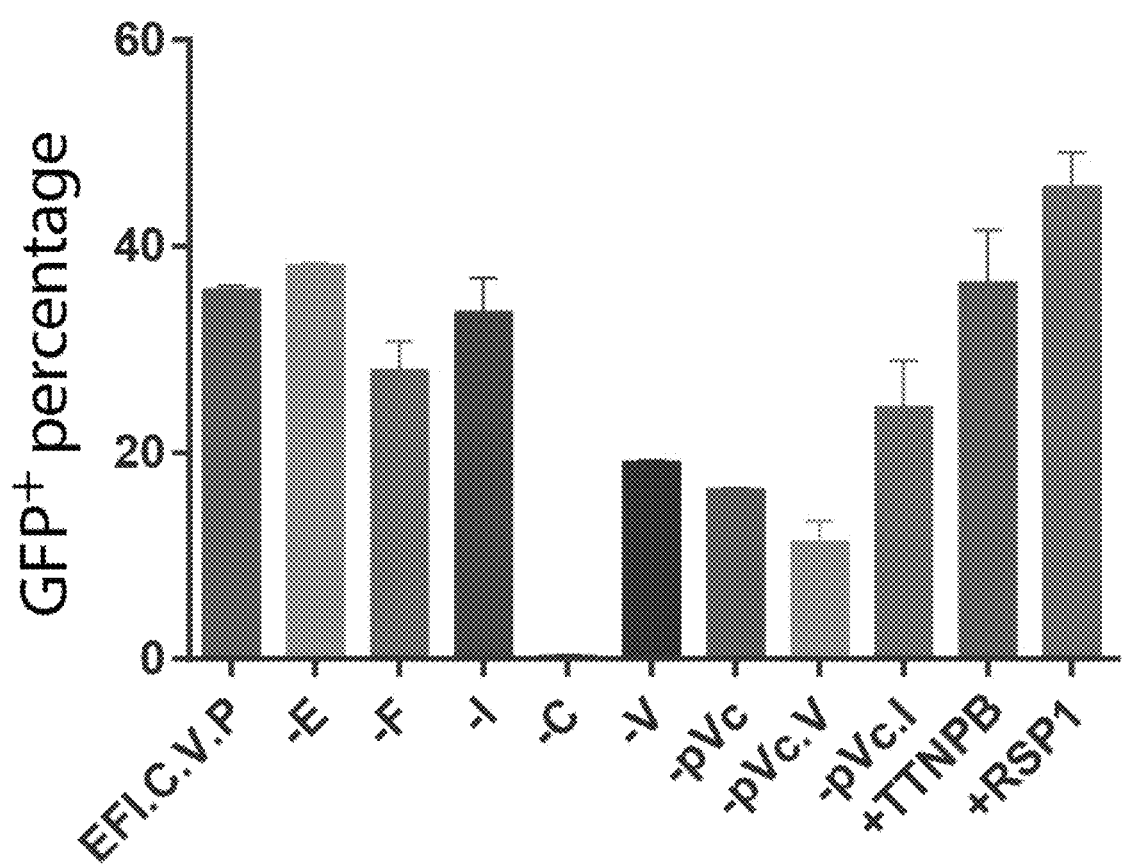
Figure 6:
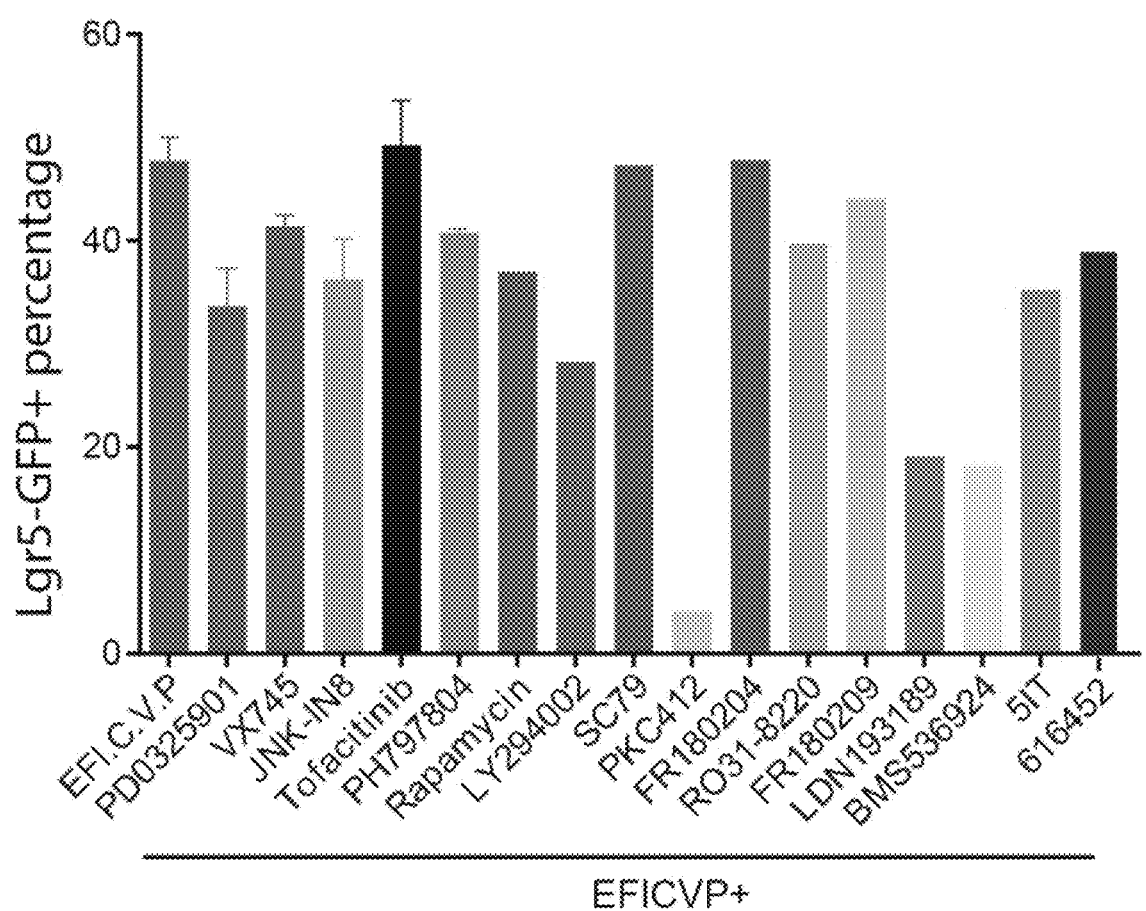
FIG. 6: Further screening of supportive factors for Lgr5 inner ear progenitor cells. Additional screening with major signaling pathway modulators demonstrates the manipulation of these singling pathways does not promote the expression of Lgr5-GFP. Small molecules used in screening include: PD0325901 (MEK inhibitor), VX745 (p38 inhibitor), JNK-IN8 (JNK inhibitor), Tofacitinib (JAK inhibitor), PH797804 (p38 inhibitor), Rapamycin (mTor inhibitor), LY294002 (PI3K inhibitor), SC79 (AKT activator), PKC412 (PKC inhibitor), FR180209 (Insulin Receptor inhibitor), LDN193189 (BMP inhibitor), BMS536924 (Insulin and insulin-like growth factor-1 receptor inhibitor), 5IT (Increase beta cell proliferation) and 616452 (Tgfb, ALK5 inhibitor).
Figure 7:
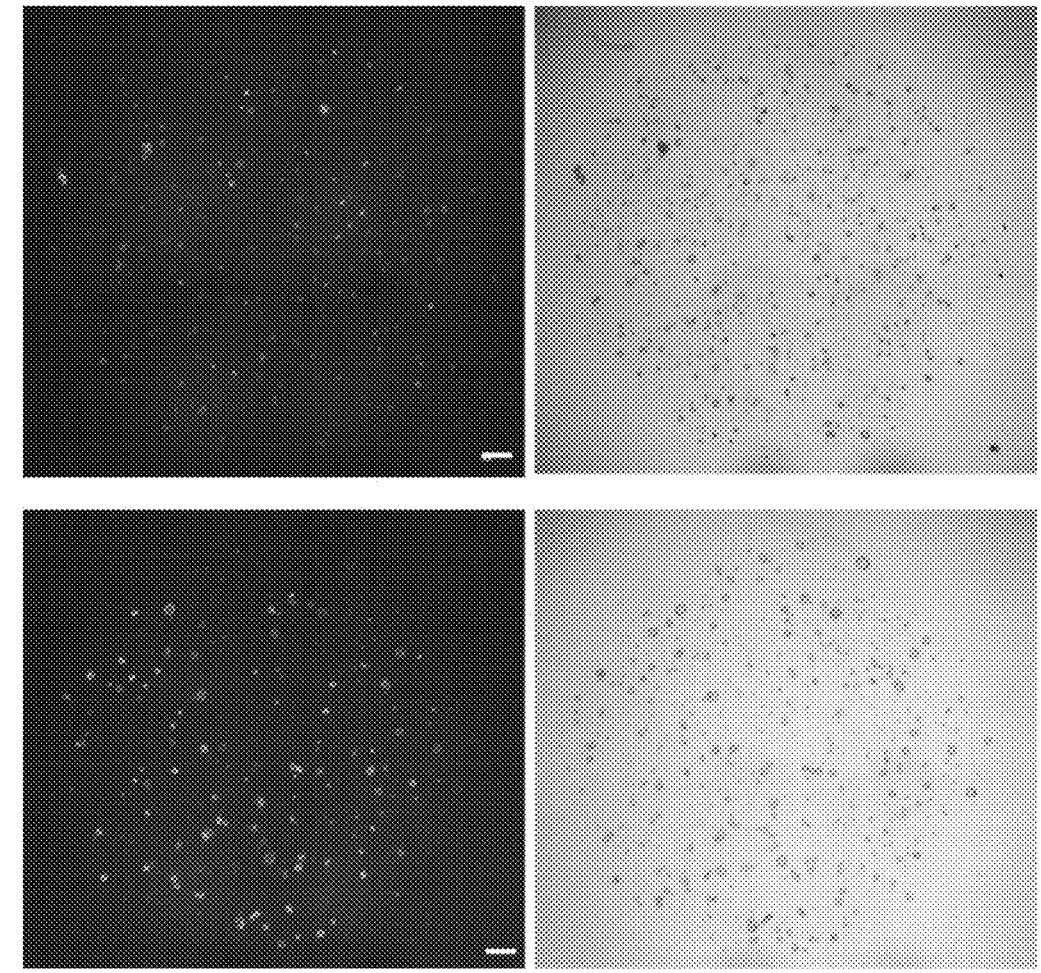
FIG. 7: The addition of 616452 on EFICVP increases the intensity of Lgr5-GFP and the size of colonies. Scale bars: 400 µm.
Figure 8A:
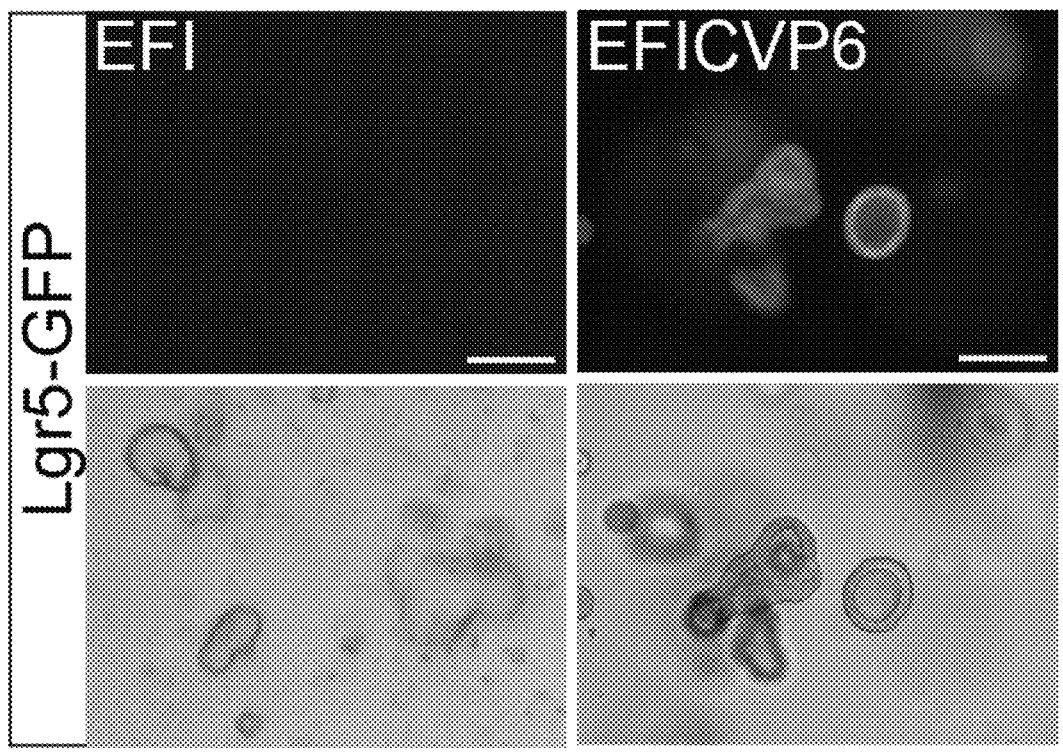
FIGS. 8A-C depict characterization of culture conditions to promote proliferation of inner ear progenitor cells.
Figure 8B:
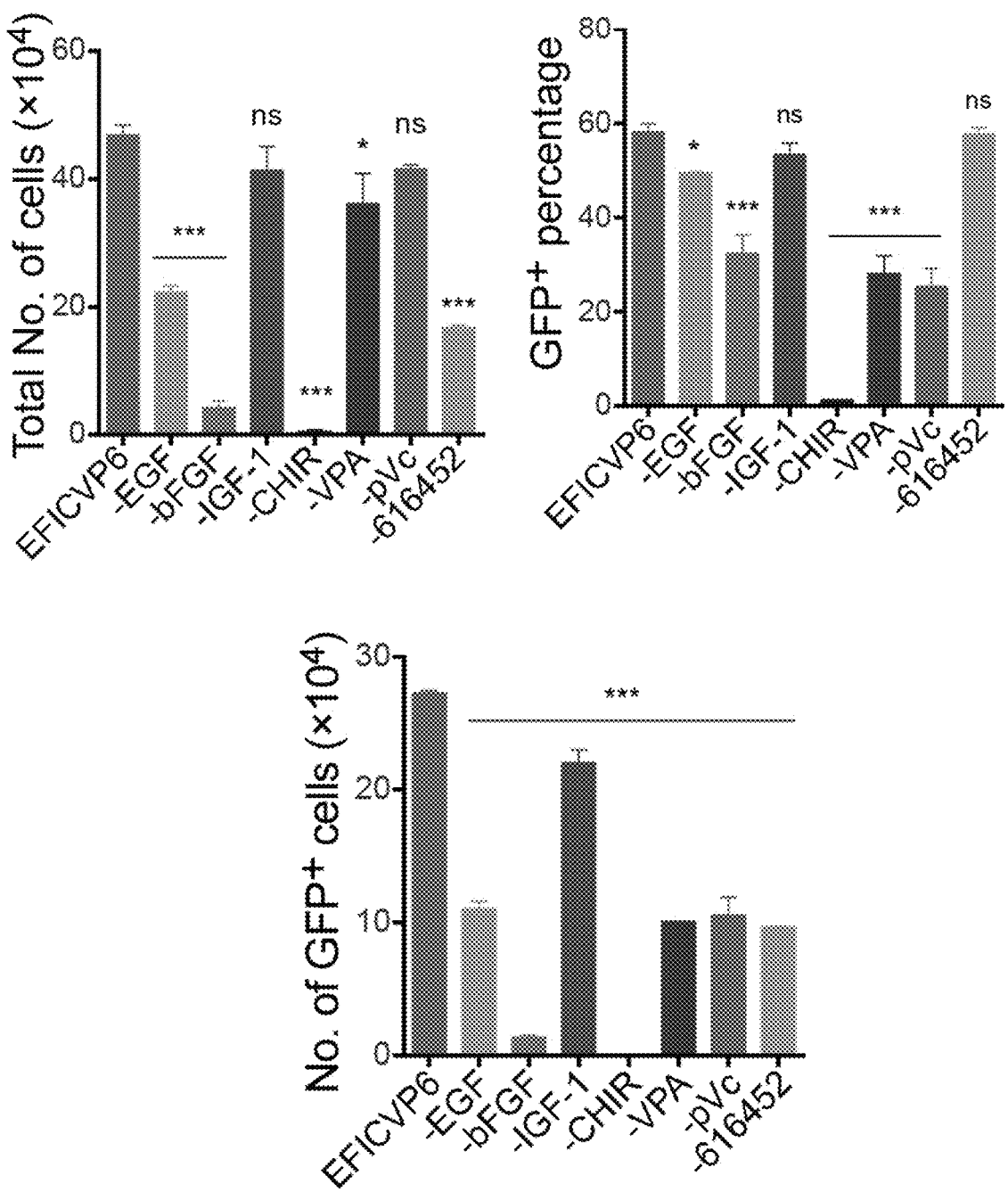
Figure 8C:
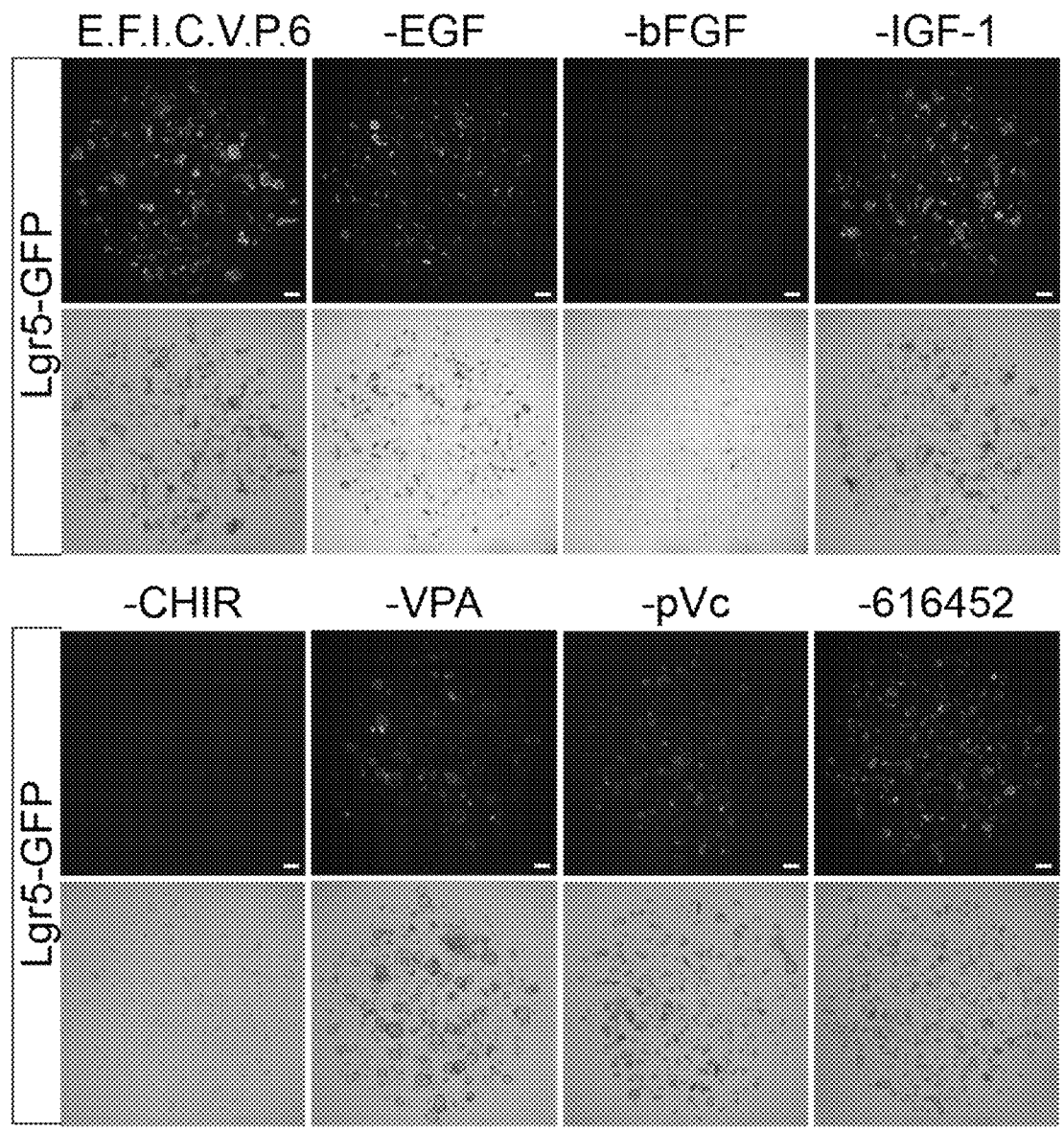
Figure 9A:
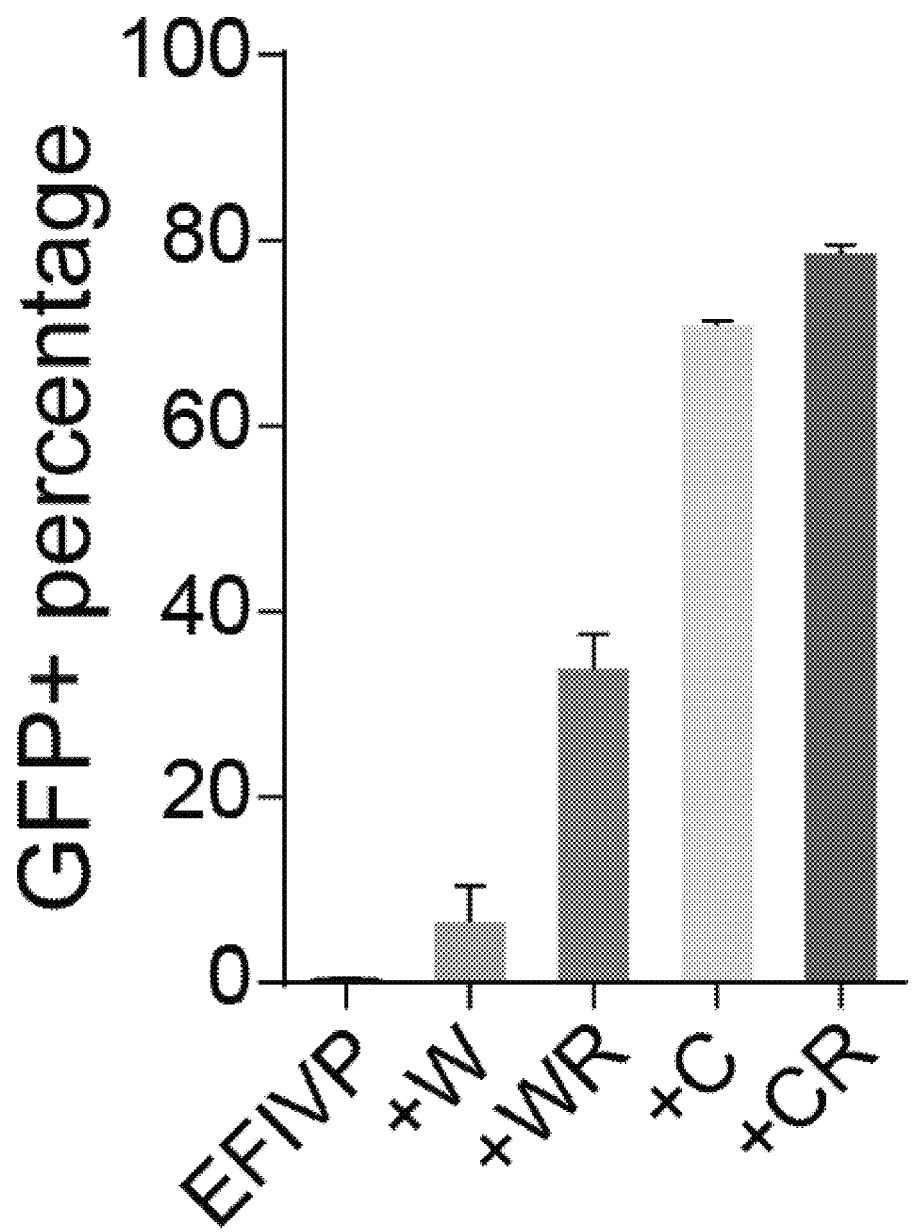
FIGS. 9A-F demonstrate how small molecules promote the maintenance of inner ear progenitor cells.
Figure 9B:
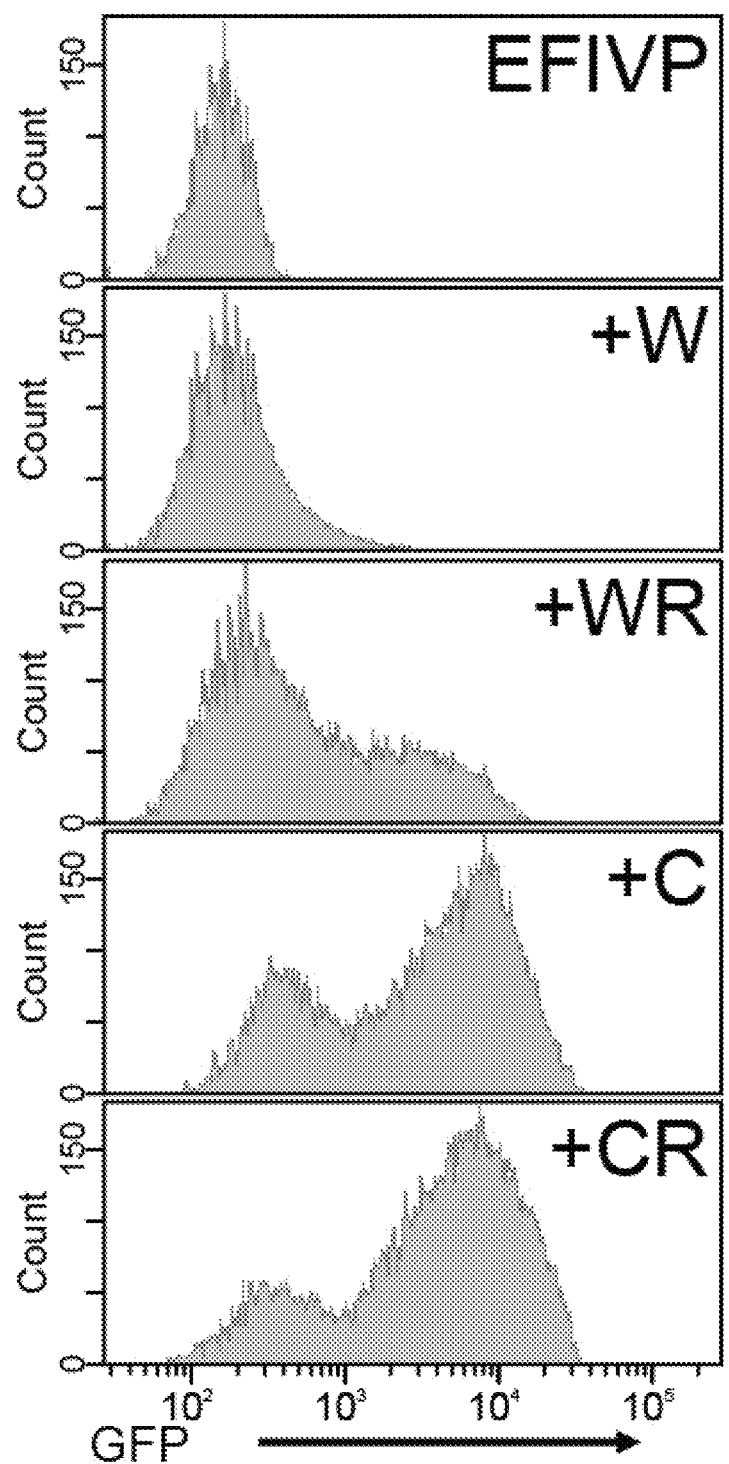
Figure 9C:
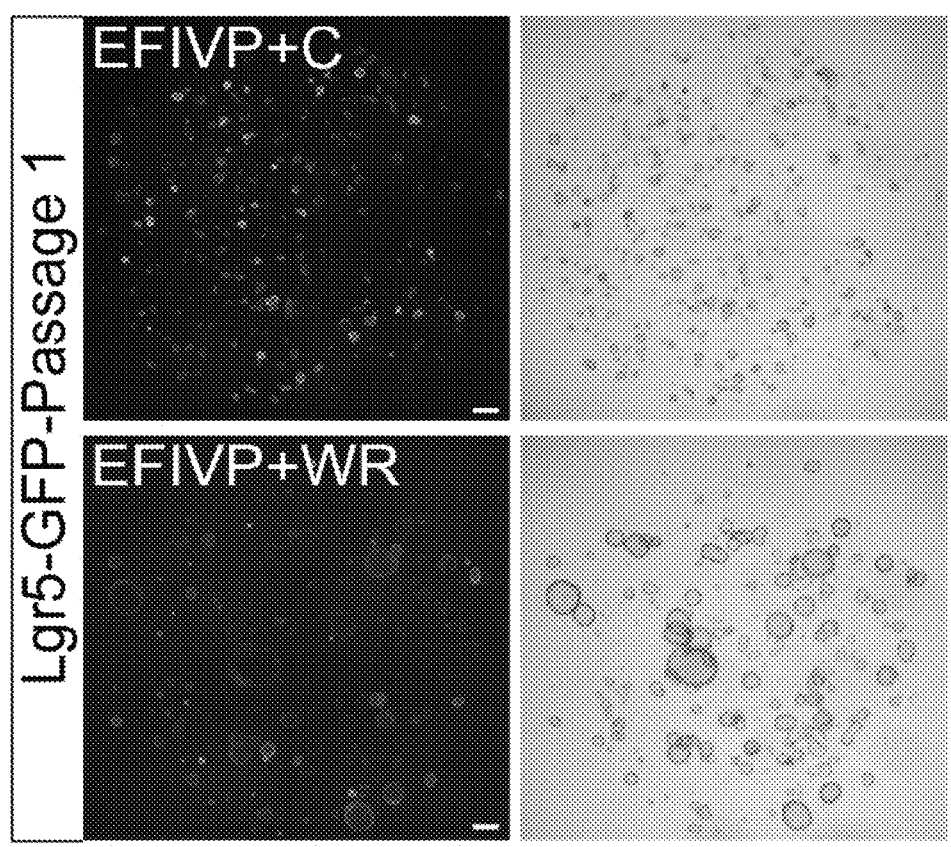
Figure 9D:
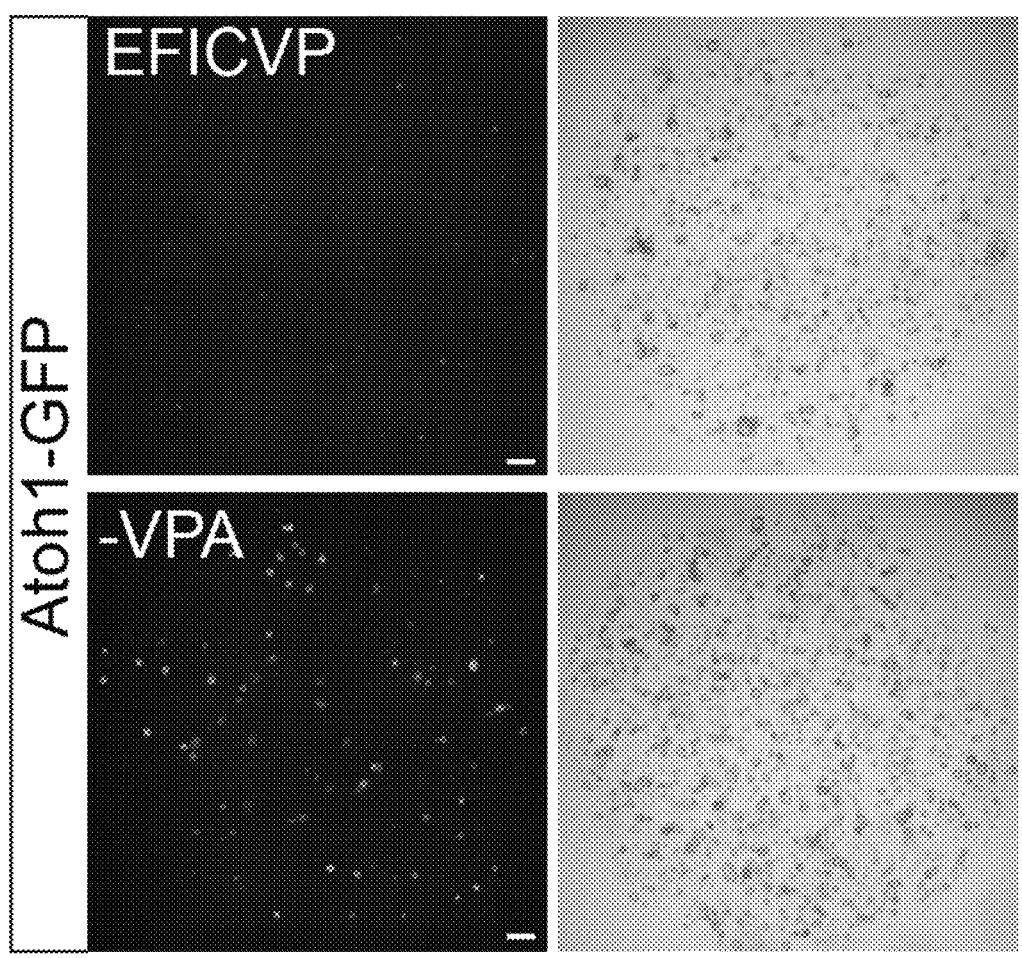
Figure 9E:
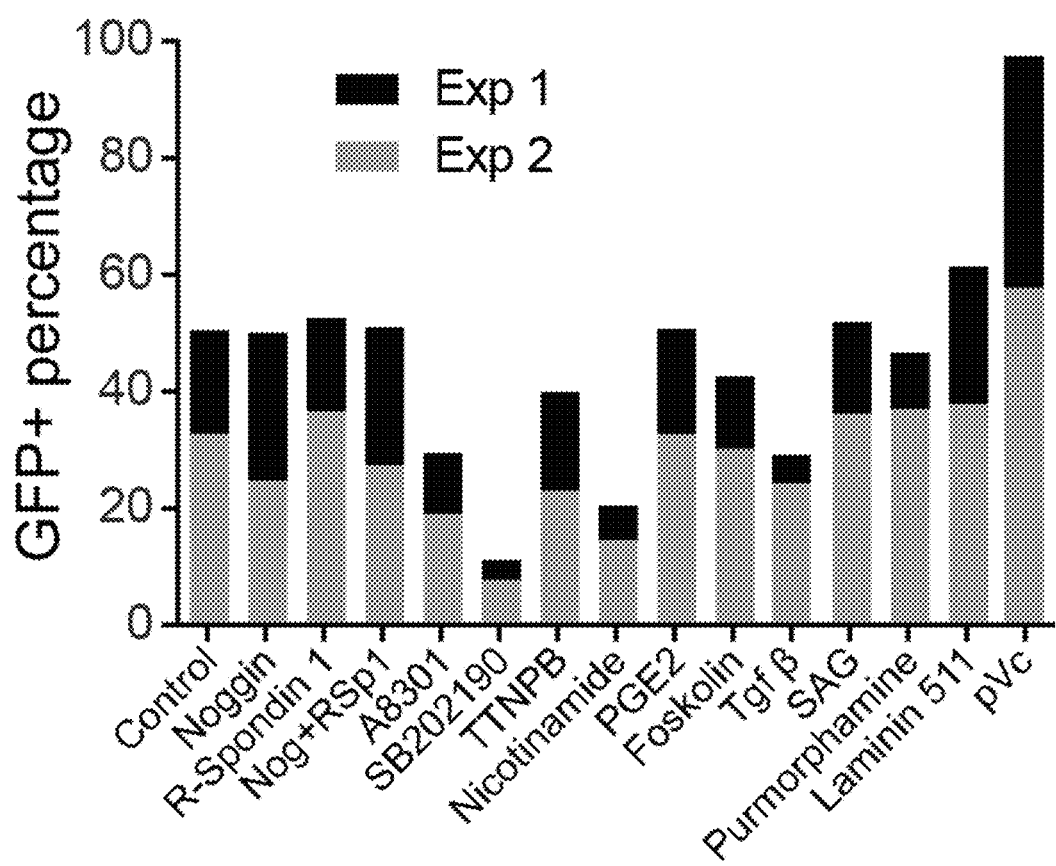
Figure 9F:
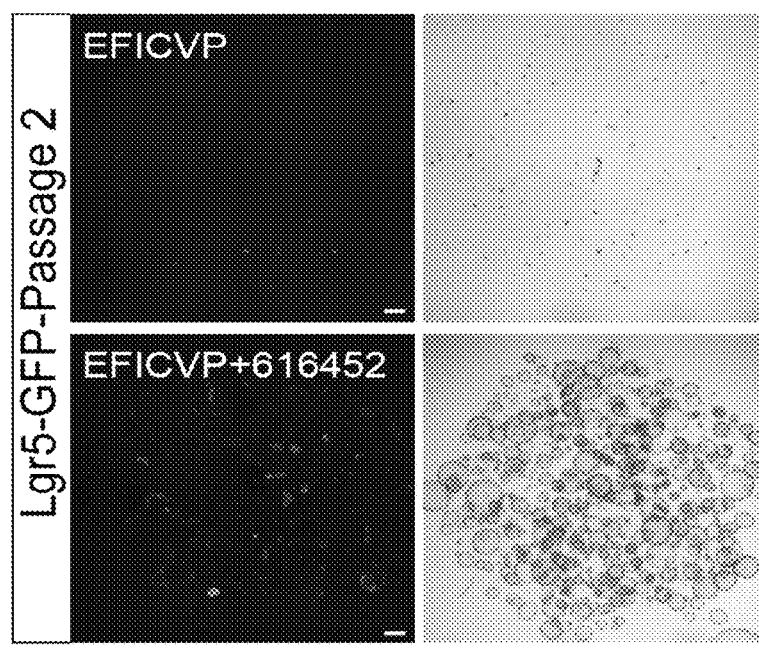

Unlike the intestinal colonies, cells from the inner ear epithelium lost the capacity for proliferation after passage. We reasoned that other factors were needed for prolonged culture of the cells and performed screening to identify additional factors. Addition of 2-phospho-L-ascorbic acid (pVc, Sigma), a stable form of vitamin C, increased Lgr5+ cell expansion by an additional 2-3 fold (FIG. 3 and FIG. 8B), which was further included in the culture media (EFI.C.V.P). We also found increased bFGF concentration (from 20 ng/ml to 50 ng/ml) increased cell proliferation (FIG. 4) thus bFGF was used at 50 ng/ml in the future experiments. Adding TTNPB, an RAR agonist, slightly increased cell proliferation but not GFP expression (FIGS. 5A-B), thus we didn't include TTNPB in the culture condition for neonatal cells. Further screen of small molecule modulators of major signaling pathways demonstrated these signaling pathway modulators didn't increase Lgr5-GFP expression (FIG. 6). Interestingly, we found that unlike the role of BMP inhibition in the small intestinal stem cells, where it's essential to promote the expression of Lgr5, the addition of BMP inhibitor LDN193189 greatly decreased Lgr5-GFP expression (FIG. 6). In addition, although the Tgf-β receptor (ALK5) inhibitor 616452 (Calbiochem, 6, also known as Repsox) didn't increase Lgr5-GFP expression, we observed that the colonies in conditions with 616452 tend to grow larger and possess brighter GFP expression than that in control conditions (FIG. 7). Further validation showed that the addition of 616452, also increased cell expansion (by 2-3 fold) before and after passage, and enabled the passage of colonies for up to 5 generations (FIG. 8B and FIG. 9F). Collectively, the addition of small molecules (CVP6) increased Lgr5+ cell number by >2000 fold compared to growth factors alone (EFI) (FIGS. 8A-C and FIGS. 9A-F).

To examine the relative importance of individual factors in our culture system (without passaging), we separately removed each factor from the medium and quantified cell proliferation and Lgr5 expression of inner ear epithelial cells following 10 days of culture (FIG. 8B). Removal of CHIR or bFGF had the greatest effect on proliferation, while removal of CHIR had the greatest effect on Lgr5 expression. Removing EGF or 616452 caused a significant reduction in proliferation, while removing VPA or pVc greatly reduced Lgr5 expression. The presence of IGF1 had a marginal beneficial effect on cell proliferation and Lgr5 expression. The treatment with the combined agents (EFICVP6) yielded the highest number of total cells, Lgr5+ cells and percentage of Lgr5+ cells following 10 days of culture. These results suggest that bFGF and CHIR were most critical while the other factors promoted maximal proliferation and Lgr5 expression. Similar results were obtained by direct visualization of GFP expression and cell growth (FIG. 8C).

We further examined the potential function of individual factors. The effects of CHIR in promoting cell proliferation and Lgr5 expression could be partially replicated with Wnt3a in combination with R-spondin1 (FIG. 9A), suggesting a role of CHIR in activating the Wnt pathway. Using an Atoh1-nGFP mouse line, we found that VPA suppressed spontaneous differentiation of hair cells (FIG. 9D), which is consistent with the role of VPA in maintaining Notch activation in intestinal stem cells (Yin et al., 2014).

Figure 10:
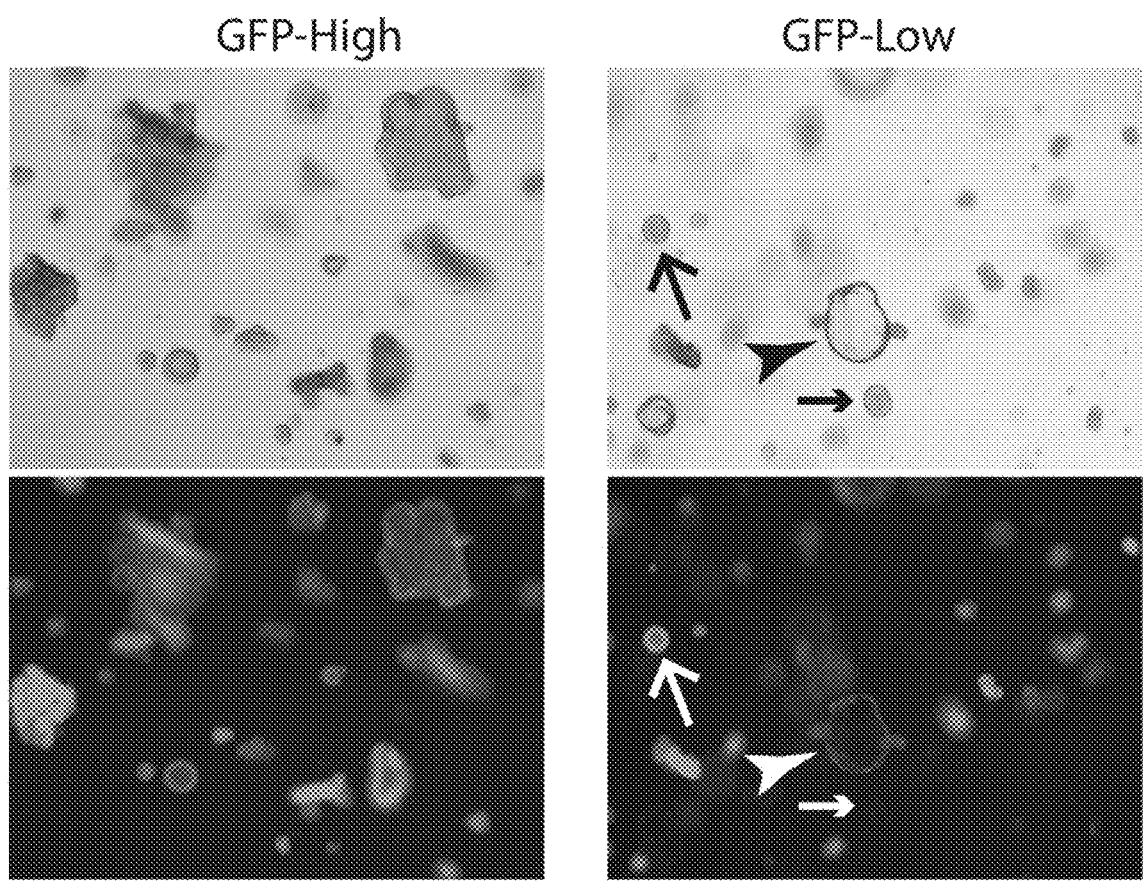
FIG. 10 demonstrates the expansion of single sorted Lgr5-GFP cells. Left, sorted GFP-High cells grow into large colonies uniformly express high level of GFP. Right, GFP-Low cells grow into colonies containing GFP-high (large arrow), GFP-low (arrow head) and GFP negative (small arrow) colonies.

To demonstrate that single sorted Lgr5-GFP cells can grow into GFP+ colonies in our expansion condition (EFICVP6), we sorted single Lgr5-GFP cells from inner ear epithelial into GFP-high and GFP-low fractions. Following 14 days of expansion in EFICVP6 condition, cultures initiated from single GFP-high cells contained high purity of colonies which highly express Lgr5-GFP. Whereas cultures initiated from GFP-low cells contained both GFP-high and GFP-low and GFP negative colonies (FIG. 10). This experiment demonstrated single sorted Lgr5-GFP cells can be expanded in EFICVP6 condition.

Example 2: Differentiation of Expanded Lgr5-Positive Cells to Hair Cells

Materials and Methods

Differentiation protocol: For differentiation of expanded Lgr5-positive cells, following 10 days of culture in the cell expansion condition (EFICVP6), the cell colonies were transferred to fresh Matrigel and further cultured in differentiation media. Differentiation media contains Notch pathway inhibitor (e.g. DAPT, D, 5 µM, or LY411575, LY, 5 µM), with or without Gsk3β inhibitor (e.g. CHIR99021). Media were changed every other day. Following another 6-10 days of incubation with differentiation media, the colonies were harvested for qPCR analysis or fixed with 4% PFA and immunostained with hair cell markers Myo7a and Prestin.

RNA extraction and quantitative real-time PCR (qPCR): RNA was isolated from cultured cells (RNeasy Mini Kit; Qiagen) according to the manufacturer's protocol. Quantitative real-time PCR was performed with QuantiTect Probe PCR kit (Qiagen) using commercially available primers and TaqMan probes (Myo7a and Hprt Life Technologies).

Immunocytochemistry staining: Colonies were fixed at room temperature in 4% paraformaldehyde/PBS for 15-20 min and then washed twice with PBS containing 0.1% BSA. Cells were then permeabilized with 0.25% Triton X-100 in PBS in 4° C. for 30 minutes. Following 2 washes with PBS containing 0.1% BSA, the cells were incubated with blocking solution (Power Block, Biogenex) for 1 h. Diluted primary antibodies (in Power Block solution) was applied for 4 h at room temperature or overnight at 4° C. Primary antibodies used were Myosin VIIA (1:500, Rabbit polyclonal from Proteus Biosciences) and Prestin (1:400, Goat polyclonal from Santa Cruz). After 3 washes for 5 minutes each, secondary antibodies (Alexafluor 594 and 647-conjugated; Invitrogen) were added at 1:500 dilution and incubated at room temperature for 30 minutes. Nuclei were visualized with 4,6-diamidino-2-phenylindole (DAPI, Vector Laboratories). Staining was visualized with inverted fluorescence microscope (EVOS; Advanced Microscopy Group).

Results

As an important function proof that the expanded Lgr5-positive cells are stem cells, we tested the differentiation ability of the expanded cells in vitro. Notch inhibition was shown to promote the differentiation of Lgr5 supporting cells to hair cells in vivo (Jeon et al., 2011). In addition, Wnt pathway activation achieved by β-catenin expression has also been shown to promote Atoh1 expression and hair cell differentiation (Shi et al., 2013). Thus, we tested these conditions in inducing hair cell differentiation of expanded Lgr5 cells.

Figure 11:
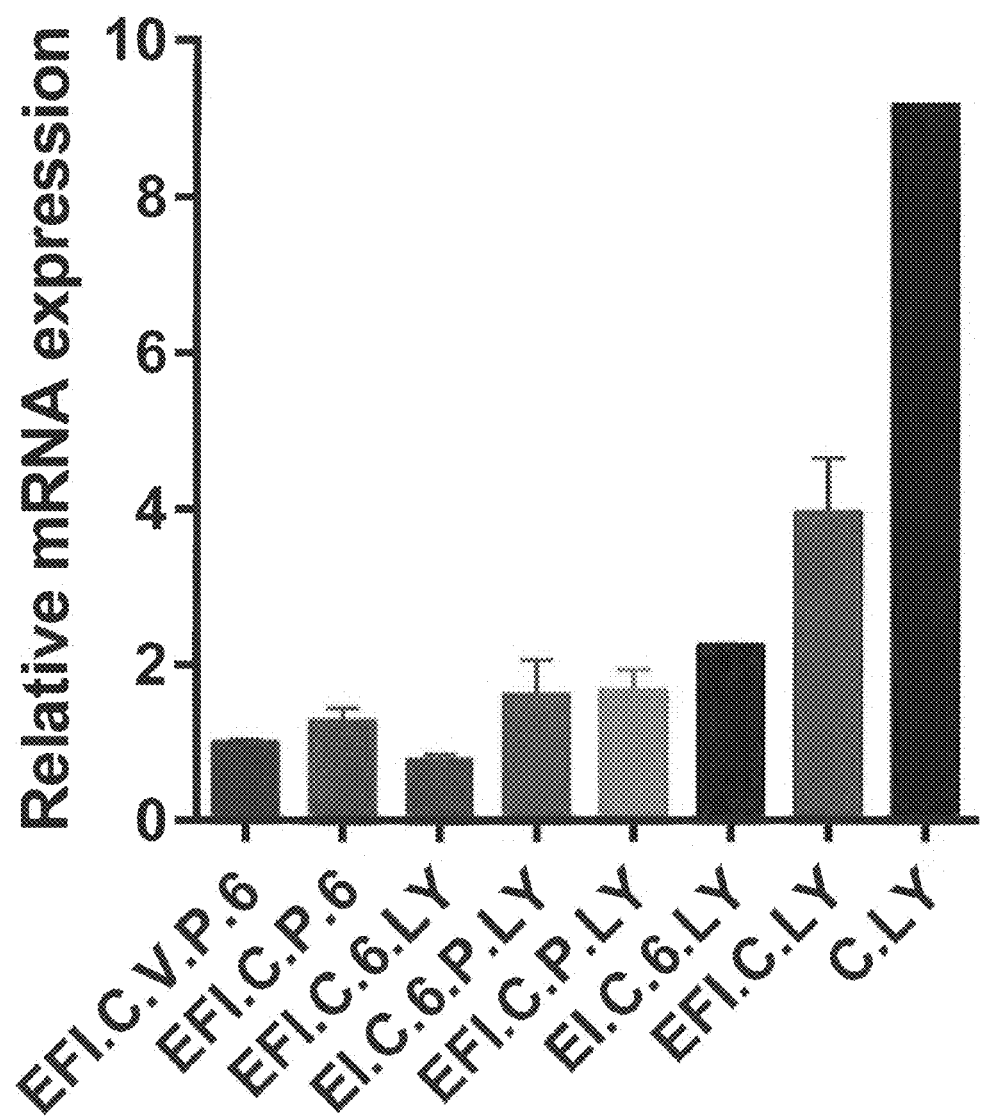
FIG. 11 depicts differentiation of expanded inner ear progenitors in multiple conditions. qPCR was performed to measure Myo7a expression following 6 days of differentiation. The condition without growth factors (EGF, bFGF, IGF) or small molecules (616452, pVC and VPA) gives highest Myo7a expression.

We first tested multiple conditions with different combination of growth factors (EGF, bFGF, IGF1) or small molecules (CHIR, VPA, 616452, pVc) and Notch inhibitor (e.g. LY411575) for the expression of hair cell marker Myo7a. The condition without growth factors or small molecules but with CHIR and Notch inhibitor gave the highest increase of Myo7a expression (FIG. 11), suggesting growth factors (EGF, bFGF, IGF1) or small molecules (VPA, 616452 and pVc) inhibit the differentiation of hair cells and should be removed in the differentiation media.

Figure 12A:
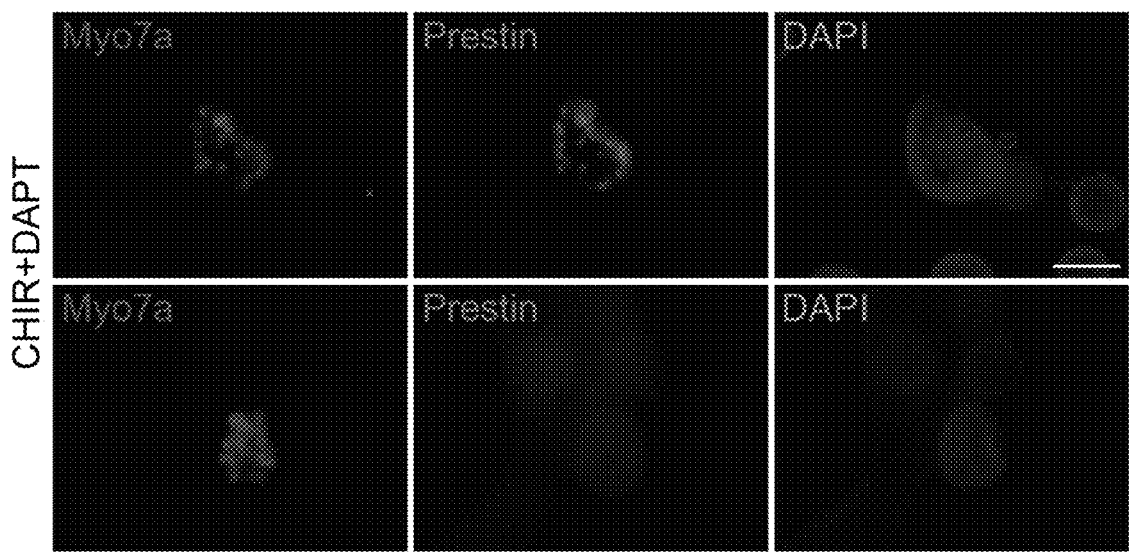
FIGS. 12A-B demonstrate that cultured inner ear progenitor cells generate hair cells in vitro.
Figure 12B:

We treated Lgr5-GFP cells, expanded by the above procedures with DAPT, a γ-secretase inhibitor and CHIR, the GSK3Beta inhibitor. Following 10 days of differentiation, the generation of hair cells were visualized by staining with hair cell markers including Myosin VIIA and Prestin. The combination of DAPT with CHIR induced hair cell generation indicated by Myosin VIIA and Prestin positive colonies (outer hair cells) (FIG. 12A upper panels) and Myosin VIIA positive but Prestin negative colonies (inner hair cells) (FIG. 12A, lower panels). Without the activation of Wnt signaling by GSK3Beta inhibitor, or with the inhibition of Wnt signaling by small molecule Wnt pathway inhibitor (IWP-2, 2 µM), hair cell generation is rarely observed (FIG. 12B).

Example 3: Expansion and Hair Cell Differentiation of Lgr5-Expressing Cells from Adult Inner Ear Tissue Materials and Methods For adult tissue, the stria vascularis was removed but the epithelium was not removed from the underlying mesenchyme due to the limited amount of intact cochlea that could be extracted. For adult cells, additional small molecule TTNPB (2 µM, Tocris) was added and the complete media contain EGF, bFGF, IGF-1, CHIR99021, VPA, pVc, 616452 and TTNPB.

Results

Figure 13A:
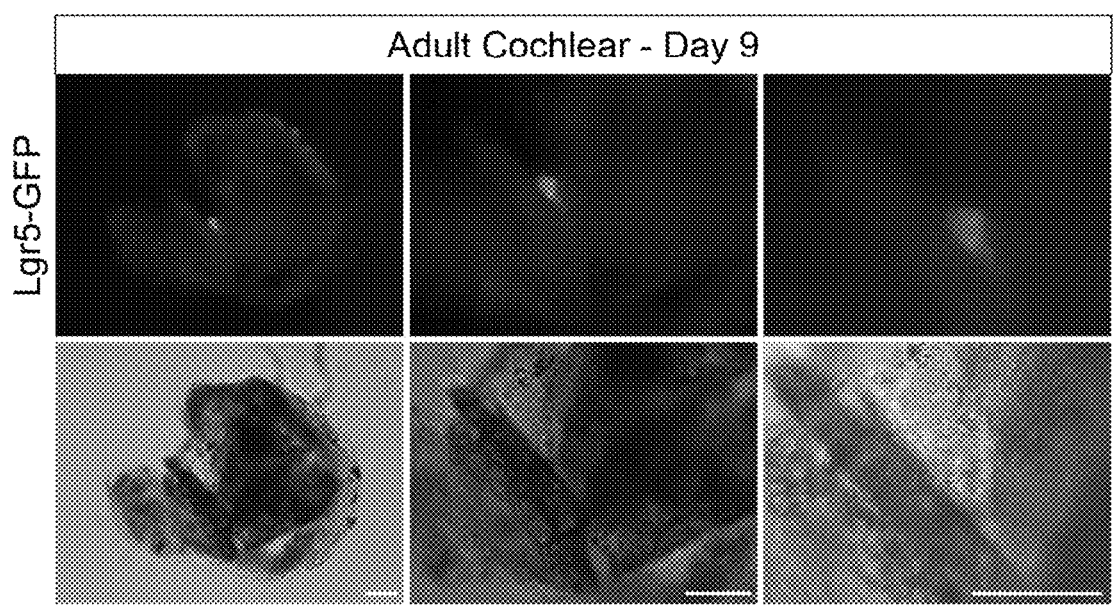
FIGS. 13A-C depict In vitro culture of Lgr5-GFP inner ear progenitor cells from adult mouse.
Figure 13B:
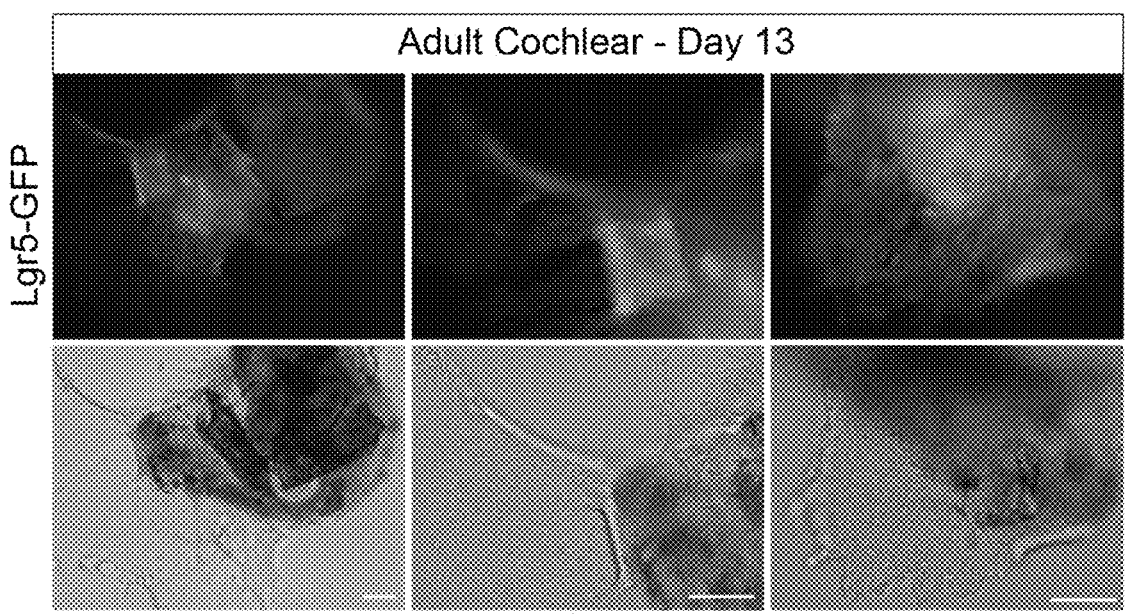
Figure 13C:
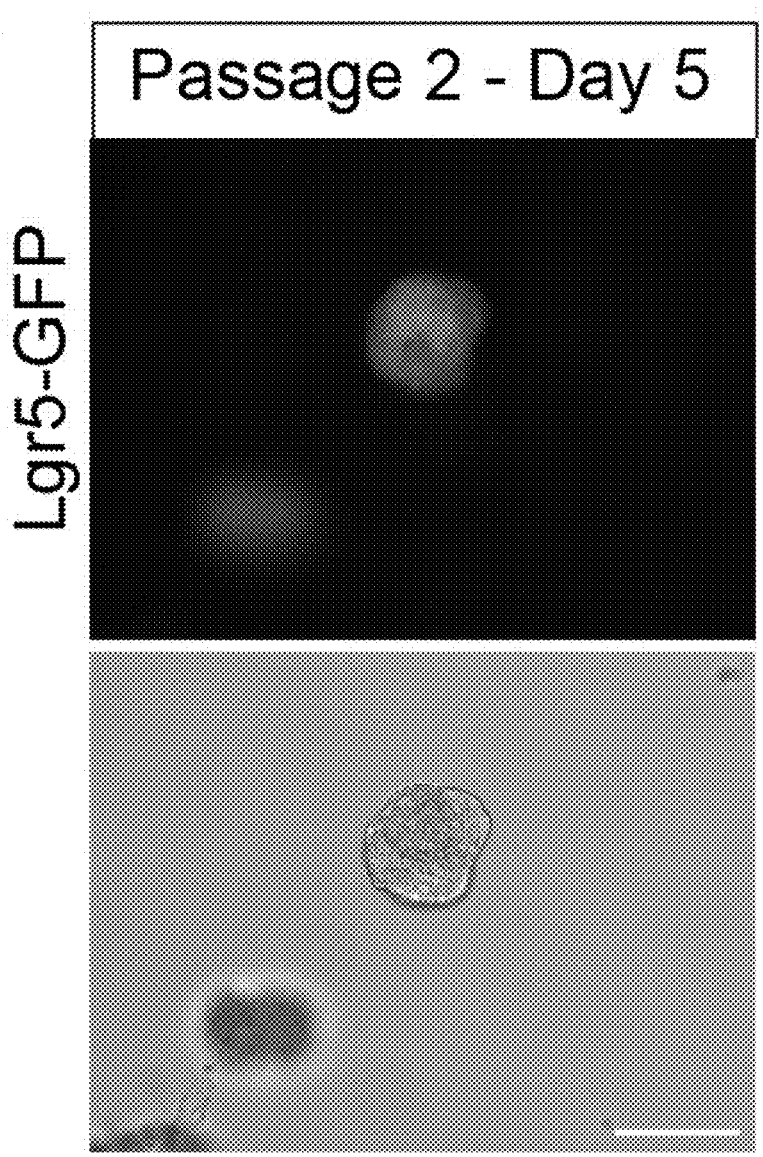
Figure 14:
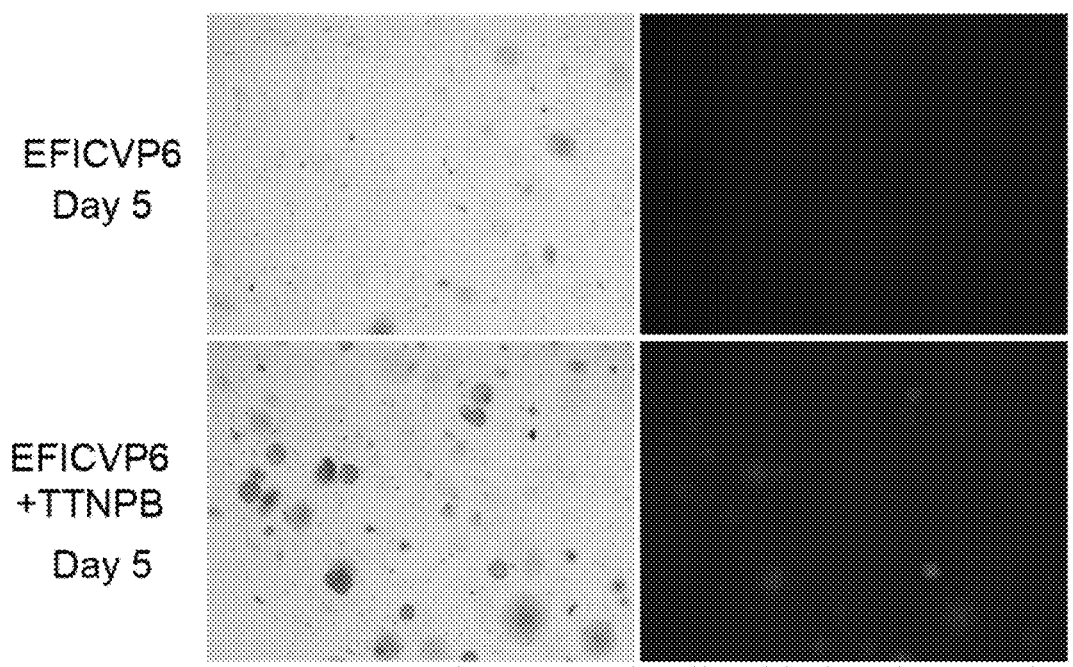
FIG. 14. Expansion of Lgr5-GFP inner ear cells from adult mice. In EFICVP6 condition, cell grow slowly. The addition of TTNPB increase cell proliferation and formation of GFP$^+$ colonies.

We found that although the condition EFICVP6 support the survival and growth of Lgr5 inner ear cells from adult mice (FIGS. 13A-C), the proliferation was very slow. We thus performed addition screening for addition factors that can promote the proliferation of Lgr5 cells from adult mice. We found that a small molecule RA signaling pathway agonist, TTNPB, significantly promoted the proliferation of cultured cells (FIG. 14). Thus it was further incorporated in the expansion media for Lgr5 inner ear cells.

Figure 15:
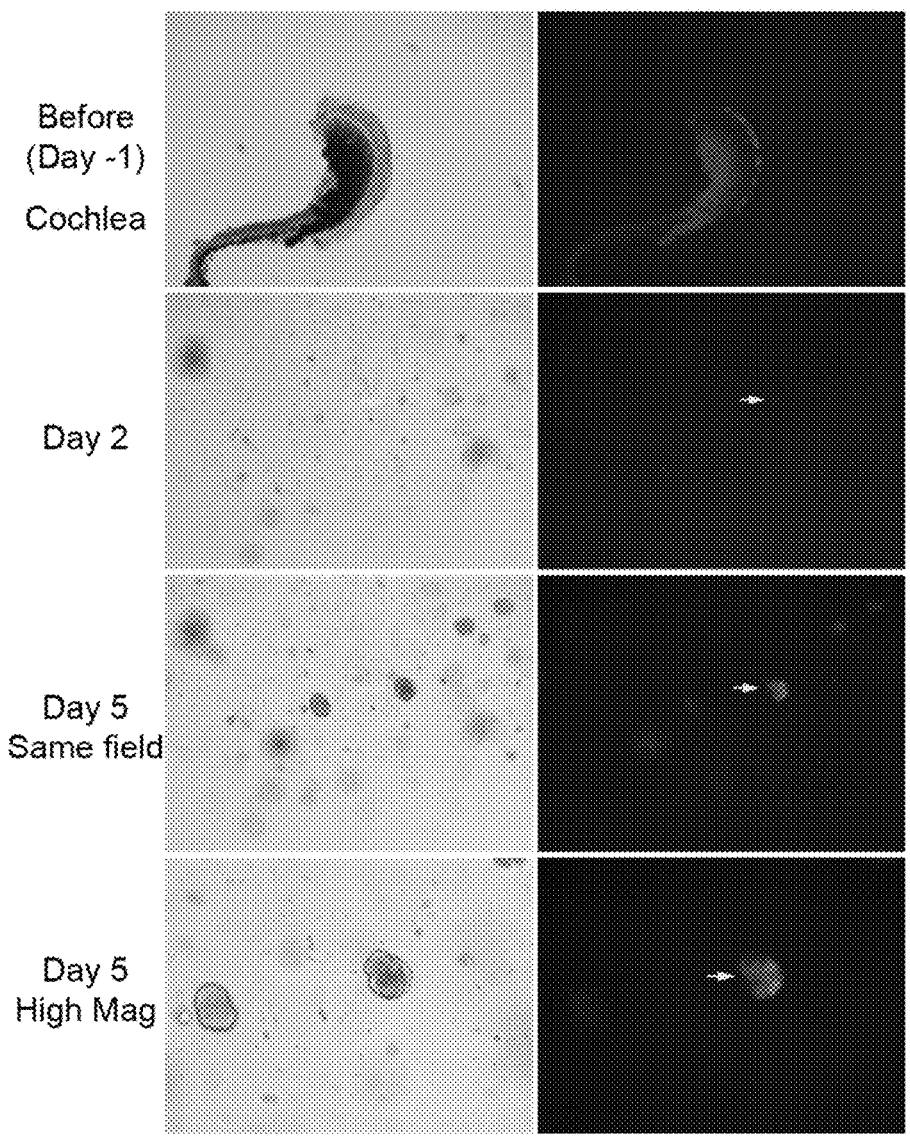
FIG. 15. Expansion of Lgr5-GFP+ inner ear cells from adult mice. Cells were cultured in conditions containing EGF, bFGF, IGF1, CHIR, VPA, pVc, 616452 and TTNPB. Images were taken at the same field on day 2 and day 5 in culture. Brightfield and GFP fluorescence images were shown.
Figure 16:
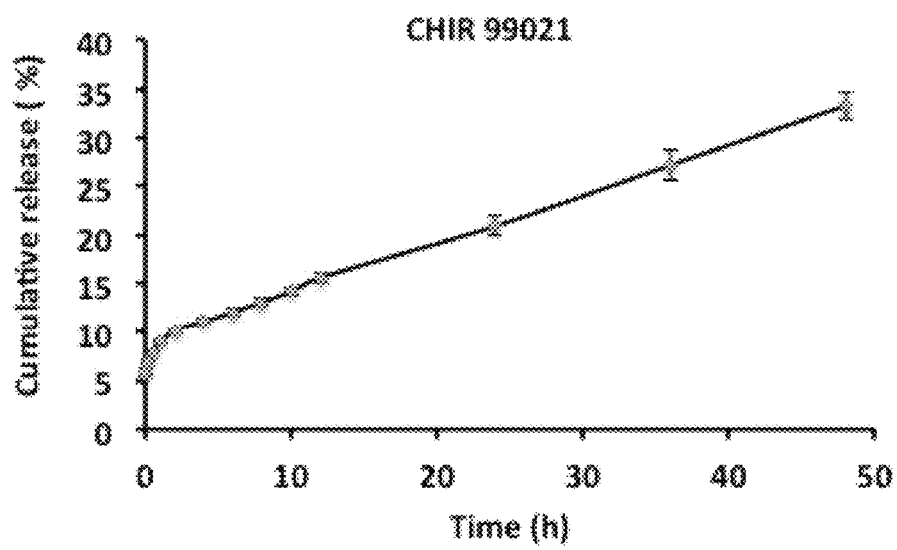
FIG. 16A: Percentage cumulative release of CHIR from poloxamer 407 based hydrogel formulation in a dialysis bag set up.
FIG. 16B: Percentage cumulative release of VPA from poloxamer 407 based hydrogel formulation in a dialysis bag set up.
Figure 16B:
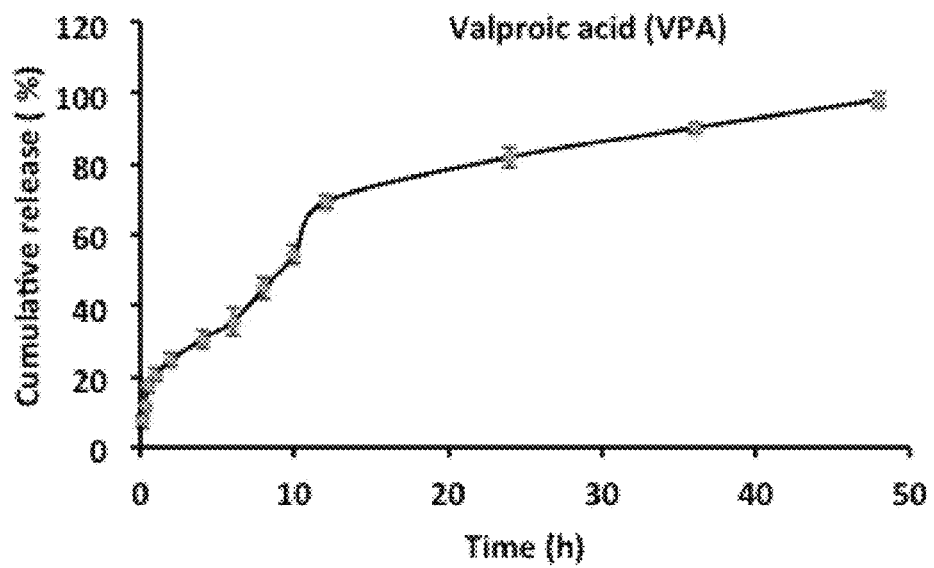
Figure 17A:
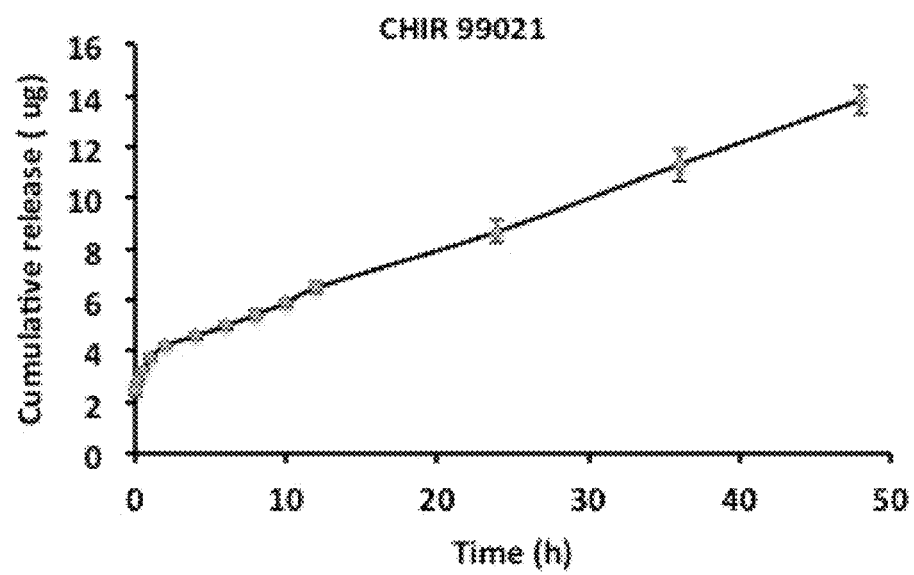
FIG. 17A: Cumulative release of CHIR from poloxamer 407 based hydrogel formulation in a dialysis bag set up. Initial loadings of CHIR and VPA were 41.7 μg and 2.63 mg per 30 ul, respectively.
Figure 17B:
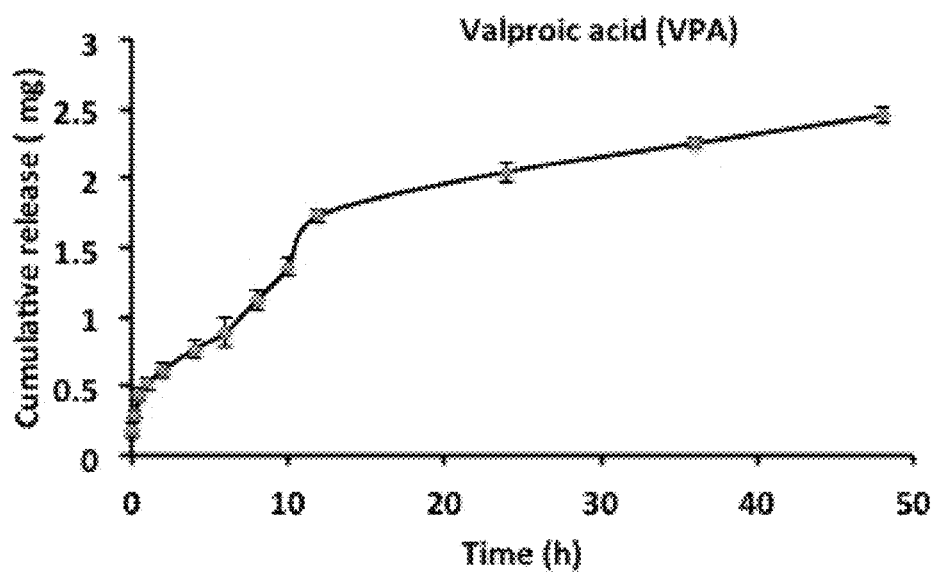
FIG. 17B: Cumulative release of VPA from poloxamer 407 based hydrogel formulation in a dialysis bag set up. Initial loadings of CHIR and VPA were 41.7 μg and 2.63 mg per 30 ul, respectively.

We tracked cell colonies formation of cells isolated from a 6-week old adult mouse. After 5 days of culture in EFICVP6+TTNPB condition, single cells form large GFP+ colonies confirming the proliferation of adult Lgr5 cells in this condition (FIG. 15). From a single cochlea, a large number of GFP+ colonies can be expanded (FIG. 14).

Discussion of Examples 1-3

The experiments illustrated in FIGS. 1A-B, 2A-C, 3, 4, 5A-B, 6, 7, 8A-C, 9A-F, 10, 11 12A-B, 13A-C, and 14 show the following:

FIGS. 1A-B and FIGS. 2A-C

Cocktail containing growth factors and small molecules including CHIR and VPA promote the proliferation and GFP expression of Lgr5 inner ear progenitor cells in vitro, and permit the expansion of these cells.

FIG. 3.

The addition of pVc (2-phospho-L-ascorbic acid) increases cell proliferation of Lgr5 inner ear progenitor cells

FIG. 4.

Increasing bFGF concentration promotes the proliferation of Lgr5 inner ear progenitor cells. FIGS. 5A-B, 6, 7

Additional small molecule (616452) promotes the proliferation of Lgr5 inner ear progenitor cells.

FIGS. 8A-C.

1. Cocktail containing growth factors and small molecules maintains Lgr5+ inner ear progenitors in vitro.

2. Cocktail containing all the factors (EGF, bFGF, IGF1, CHIR99021, VPA, pVc, 616452 (EFICVP6)) shows the best result in supporting cell proliferation and GFP expression, with $4.7 \times 10^5$ total number of cells, 58% GFP+ cells and $2.7 \times 10^5$ GFP+ cells.

3. Most of the factors in the cocktail are important:

CHIR is important to promote cell proliferation and GFP expression:

Removing CHIR results in ~100 fold decrease of total cell numbers ($4.7 \times 10^5$ v.s. $5.0 \times 10^3$) and ~50 fold decrease of GFP+ cells. (58% v.s. 1.3%). With ~4000 fold decrease of GFP+ cells ($2.7 \times 10^5$ v.s. ~65). bFGF is important to promote cell proliferation and important for GFP expression: Removing bFGF results in 10 fold decrease of cell numbers. ($4.2 \times 10^4$ total number of cells) and ~2 fold decrease of GFP+ percentage (58% v.s. 32%) as well as 20 fold decrease of GFP+ cell number ($2.7 \times 10^5$ v.s. $1.4 \times 10^4$ GFP+ cells).

4. EGF, 616452 are important to promote cell proliferation. Removing EGF results in ~2 fold decrease of total cell number ($2.2 \times 10^5$) and GFP+ cell number ($1.1 \times 10^5$). Removing 616452 results in ~3 fold decrease of total cell number ($1.7 \times 10^5$) and GFP+ cell number ($9.8 \times 10^4$).

5. VPA and pVc are important to promote GFP maintenance. Removing VPA results in 2 fold decrease of GFP percentage 28% and GFP+ cell number ($1.1 \times 10^5$). Removing pVc results in 2 fold decrease of GFP percentage 25% and GFP+ cell number ($1.1 \times 10^5$).

6. IGF-1 has marginal effect to promote cell proliferation ($4.1 \times 10^5$ total cells) or GFP maintenance (58% v.s. 53% GFP percentage).

FIGS. 9A-F

1. CHIR functions through Wnt pathway.

2. Combine with R-spondin1, Wnt3a may replace CHIR but not as effective.

3. VPA functions through suppressing differentiation (likely by activating/maintain Notch activation).

4. HDAC6 inhibitor does not work when HDAC6 inhibitor is used in place of VPA (Data not shown, trying Tubastatin A, ACY1215 and CAY10603).

5. pVc promotes GFP expression.

6. Laminin 511 promotes GFP expression.

7. Tgfp type I receptor (Tgf R1, ALK5) inhibitor 616452 enables extended culture of the cells.

8. CHIR can promote differentiation to Atoh-1+ cells.

FIG. 10.

Single sorted Lgr5-GFP cells can be expanded in cocktails containing growth factors and small molecules.

FIG. 11

1. The presence of Wnt pathway/CHIR increases the differentiation efficiency of a Notch inhibitor.

2. Cultured Lgr5 progenitor cells can generate both inner hair cells and outer hair cells.

In some in vivo embodiments the growth factors are not required.

FIGS. 13A-C

1. The expansion protocol for LGR5+ cells works on adult cochlea from mice and the cells can be passaged without loosing Lgr5 expression.

FIGS. 14-15

Small molecule TTNPB promote the proliferation of adult Lgr5 inner ear progenitor cells.

Example 4: Poloxamer-407 Hydrogel for Delivery of Small Molecules to Inner Ear for Regeneration of Hair Cells 1. Methods 1.1 Preparation of Formulation Poloxamer-407 hydrogels were prepared using the "cold-method". Briefly, a weighed amount of poloxamer-407 was added to 40 ml cold ultra pure water or cold PBS (pH 7.4), and stirred overnight at 4° C. on a magnetic stir plate to effect complete solubilization. Multiple concentrations of poloxamer-407 solution ranging from 18% (w/w) to 25% (w/w) were prepared. Hydrophilic drugs, including valproic acid (VPA) and phosphorylated ascorbic acid (PAC) were added to the 5 ml poloxamer-407 solution and dissolved at 4° C. on a magnetic stir plate. Weight ratio of poloxamer-407 to the drug was varied to understand the effects of drugs on the gelation properties of poloxamer-407, and to determine the optimal formulation that gels at 37° C. with maximum possible loading of the hydrophilic drugs. The gelation temperatures of the formulations were determined by the "visual tube inversion method". Briefly, glass vials containing poloxamer 407 solutions, with or without the hydrophilic drugs were placed in a water bath. The temperature was slowly increased and the temperature at which the solution stopped flowing on tilting the glass vial was noted as the gelation temperature.

To encapsulate hydrophobic drugs, including CHIR 99021 (CHIR), Repsox and TTNPB, appropriate volumes from their stock solutions in DMSO were added into the poloxamer-407 solutions containing the hydrophilic drugs, and mixed by pipetting at 4° C. Maximum DMSO concentration to be added with the hydrophobic drugs was limited to 5-6% (v/v) with respect to the total volume of the gel. Higher concentration of DMSO reduced the gelation temperature of the gel. Gelation temperature of the formulation was determined by the "visual tube inversion method", as described before.

1.2 In Vitro Drug Release

To understand the release kinetics of encapsulated drugs from poloxamer-407 hydrogels, in vitro release studies were performed using dialysis bag method at pH 7.4 and 37° C. temperature conditions. Briefly, sealed dialysis bag (3.5-5 kDa cutoff) containing 30 µL gel suspended in 1 ml PBS was placed in 10 mL of the release medium (PBS). The release medium was stirred at 100 rpm to prevent the formation of a stagnant layer at the membrane and outer solution interface. 1 mL aliquots were taken from the medium at predetermined intervals for the analysis of drugs using HPLC, and replaced with an equal volume of fresh medium.

Results 2.1 Formulation and Gelation:

The thermal gelation behavior of different formulations was investigated to determine the optimal formulation that would provide a rapid and reproducible liquid-gel transition between room and body temperatures while loaded with all the drugs. For poloxamer 407 solutions, without drug, the gelation temperature decreased with increasing the concentration of poloxamer 407. Addition of hydrophilic drugs, including VPA and pVc, at concentrations greater than 88 mg/ml and 14 mg/ml, respectively, inhibited gelation of poloxamer-407 solution. Therefore, gels were prepared using 18% (w/w) poloxamer solutions with concentrations of VPA and pVc to be equal to or less than 88 mg/ml and 14 mg/ml, respectively. Hydrophobic drugs, including CHIR, Repsox and TTNPB, appropriate volumes from their stock solutions in DMSO were added into the poloxamer-407 solutions containing the hydrophilic drugs, and mixed by pipetting at 4° C. Concentrations of drugs in stock solutions were maintained at 55.6-69.5 mg/ml, 23-28.75 mg/ml and 35 mg/ml for CHIR, Repsox and TTNPB, respectively to ensure total DMSO concentration in final formulation to be less than 5-6%. Higher concentration of DMSO significantly lowered the gelation temperature of the formulations. The final formulation was a viscous liquid at storage temperature (4° C.), and formed a semisolid gel above its liquid-gel transition temperature (37° C.).

2.2 In Vitro Drug Release:

In vitro release of encapsulated drugs from hydrogel formulation was studied using dialysis bag method. Both CHIR and VPA showed an initial burst release of 10% in 2 h and 17% in 0.5 h, respectively, followed by a sustained release over next 48 h. Also, the release kinetics of VPA was found to be significantly faster as compared to that of CHIR. Quantitatively, 33% cumulative release was observed for CHIR in 48 h, while 98% cumulative release was observed for VPA in 48 h. The detailed release profiles are shown in FIGS. 16A-B and 17A-B.

Example 5: Hearing Recovery in Mice

A 17% (w/w) stock solution of poloxamer 407 gel (Sigma-Aldrich) was prepared by slowly adding it to cold 1× phosphate-buffered saline at pH 7.4. This solution is liquid when refrigerated or at room temperature but solidifies at body temperature. The gel was tinted blue with Evans blue dye (50 ppm) for visualization during administration.

A formulation was prepared as described in Example 4 with 527 mM VPA and 2.975 mM CHIR in 17% Poloxamer 407 with 5% DMSO ("VPA/CHIR"). For comparison, a Notch inhibitor, LY411575, was prepared at 4 mM in 17% Poloxamer 407 with 5% DMSO ("LY411575"). Additionally, a vehicle-only control of 17% Poloxamer 407 with 5% DMSO was prepared ("Control").

Figure 18:
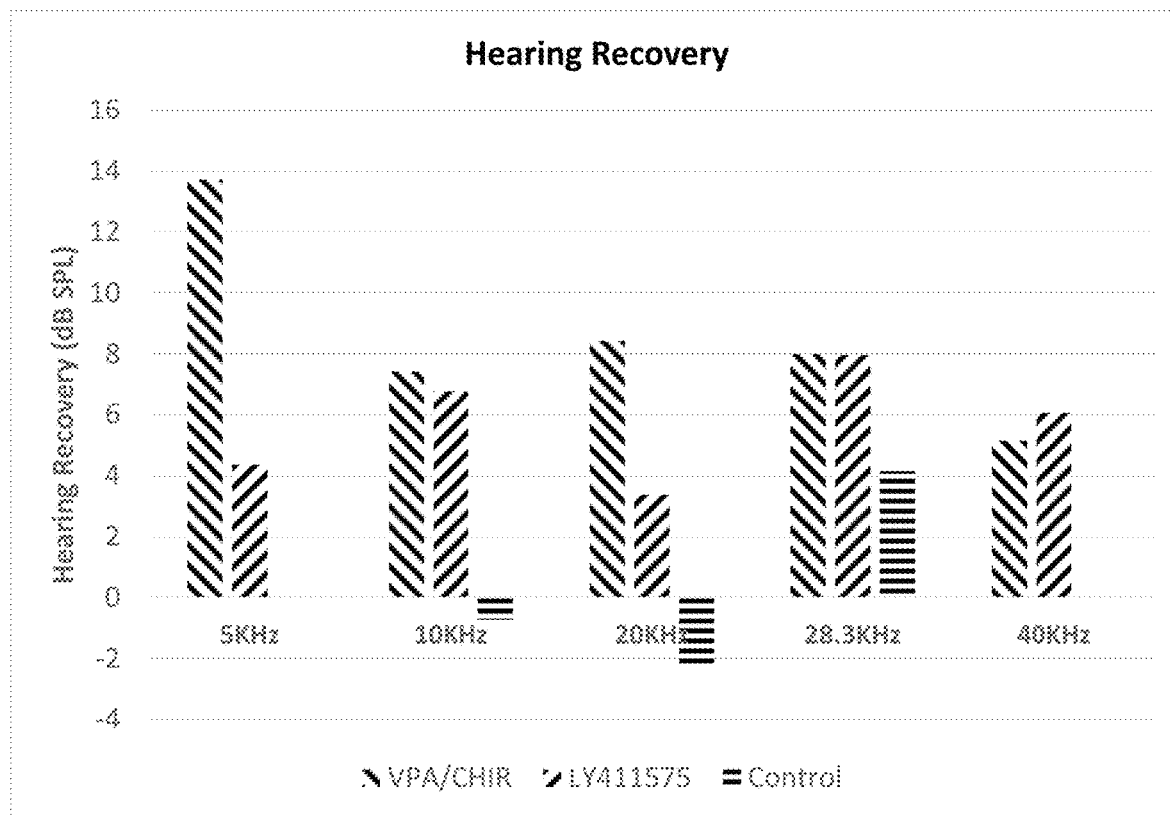
FIG. 18: Hearing recovery in CBA/CaJ mice. Animals treated with VPA/CHIR (n=7) showed significant recovery across all tested frequencies. Animals treated with LY411575 (n=8) showed significant recovery at 10 kHz, 28.3 KHz, and 40 kHz. Recovery did not occur in animals treated with control vehicle injections (n=8). [*=p<0.05]

CBA/CaJ mice were deafened in a noise chamber by exposure to an 8-16 kHz octave band noise band for 2 hours at 120 dB SPL. 24 hours after noise exposure, their hearing was assessed by measuring auditory brainstem responses (ABRs). The minimum sound pressure level (SPL) required for visual detection of ABR Wave I was determined at 5, 10, 20, 28.3, and 40 kHz. Following ABR measurements, a trans-tympanic injection of a Poloxamer gel drug mixture (described above as "VPA/CHIR", "LY411575", or "Control") was delivered to fill the middle ear cavity. After 30 days, ABR was assessed and the improvement in hearing threshold from 24 hrs to 30 days after noise exposure was determined. The results are shown in FIG. 18.

A 10 dB improvement in threshold creates a doubling in loudness for a given sound and is considered to be clinically meaningful. The "VPA/CHIR" formulation achieved a 10 dB recovery. Statistically significant improvements are shown with a star (*means $p<0.05$).

From the foregoing description, it will be apparent that variations and modifications may be made to the invention described herein to adopt it to various usages and conditions. Methods and materials are described herein for use in the present invention; other, suitable methods and materials known in the art can also be used. The materials, methods, and examples are illustrative only and not intended to be limiting. Such embodiments are also within the scope of the following claims. The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof. The teachings of all patents, published applications and references cited herein are incorporated by reference in their entirety. While this invention has been particularly shown and described with references to example embodiments thereof, it will be understood by those skilled in the art that various changes in form and details may be made therein without departing from the scope of the invention encompassed by the appended claims.

What is claimed is:

1. A method for expanding a population of cochlear cells in a cochlear tissue, the method comprising administering intratympanically or transtympanically to a subject a composition comprising:
   i) a biocompatible matrix having dispersed therein:
      a) a GSK3β inhibitor or Wnt agonist, or a pharmaceutically acceptable salt thereof; and
      b) a Notch agonist or HDAC inhibitor, or a pharmaceutically acceptable salt thereof.

2. The method of claim 1, wherein the GSK3β inhibitor or Wnt agonist, or pharmaceutically acceptable salt thereof, is selected from CHIR99021, LY2090314, lithium, A1070722, BML-284 and SKL2001, or a pharmaceutically acceptable salt thereof.

3. The method of claim 1, wherein the GSK3β inhibitor or Wnt agonist, or pharmaceutically acceptable salt thereof, is:

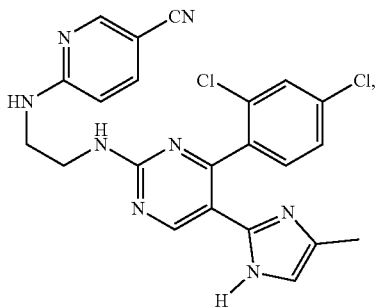 [SMILES: Cc1c[nH]c(-c2cnc(NCCNc3ccc(C#N)cn3)nc2-c2ccc(Cl)cc2Cl)n1]

or a pharmaceutically acceptable-salt thereof.

4. The method of claim 1, wherein the GSK3β inhibitor or Wnt agonist is LY2090314, or a pharmaceutically acceptable salt thereof.

5. The method of claim 1, wherein the GSK3β inhibitor or Wnt agonist is lithium, or a pharmaceutically acceptable salt thereof.

6. The method of claim 1, wherein the GSK3β inhibitor or Wnt agonist is A1070722, or a pharmaceutically acceptable salt thereof.

7. The method of claim 1, wherein the GSK3β inhibitor or Wnt agonist is BML-284, or a pharmaceutically acceptable salt thereof.

8. The method of claim 1, wherein the GSK3β inhibitor or Wnt agonist is SKL2001, or a pharmaceutically acceptable salt thereof.

9. The method of claim 1, wherein the Notch agonist or HDAC inhibitor, or pharmaceutically acceptable salt thereof, is selected from valproic acid, SAHA and Tubastatin A, or a pharmaceutically acceptable salt thereof.

10. The method of claim 1, wherein the Notch agonist or HDAC inhibitor, or pharmaceutically acceptable salt thereof, is:

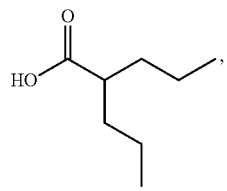

or a pharmaceutically acceptable salt thereof.

11. The method of claim 1, wherein:
   the GSK3β inhibitor or Wnt agonist, or pharmaceutically acceptable salt thereof, is selected from CHIR99021, LY2090314, lithium, A1070722, BML-284 and SKL2001, or a pharmaceutically acceptable salt thereof; and
   the Notch agonist or HDAC inhibitor, or pharmaceutically acceptable salt thereof, is selected from valproic acid, SAHA and Tubastatin A, or a pharmaceutically acceptable salt thereof.

12. The method of claim 1, wherein:
   the GSK3β inhibitor or Wnt agonist, or pharmaceutically acceptable salt thereof, is CHIR99021, or a pharmaceutically acceptable salt thereof; and
   the Notch agonist or HDAC inhibitor, or pharmaceutically acceptable salt thereof, is valproic acid, or a pharmaceutically acceptable salt thereof.

13. The method of claim 1, wherein:
   the GSK3β inhibitor or Wnt agonist, or pharmaceutically acceptable salt thereof, is between about 0.01 wt % and about 50 wt % of the composition; and
   the Notch agonist or HDAC inhibitor, or pharmaceutically acceptable salt thereof, is between about 0.01 wt % and about 50 wt % of the composition.

14. The method of claim 1, wherein:
   the GSK3β inhibitor or Wnt agonist, or pharmaceutically acceptable salt thereof, is between about 0.1 wt % and about 50 wt % of the composition; and
   the Notch agonist or HDAC inhibitor, or pharmaceutically acceptable salt thereof, is between about 0.1 wt % and about 50 wt % of the composition.

15. The method of claim 1, wherein:
   the GSK3β inhibitor or Wnt agonist, or pharmaceutically acceptable salt thereof, is between about 0.1 wt % and about 40 wt % of the composition; and
   the Notch agonist or HDAC inhibitor, or pharmaceutically acceptable salt thereof, is between about 0.1 wt % to about 40 wt % of the composition.

16. The method of claim 1, wherein:
   the GSK3β inhibitor or Wnt agonist, or pharmaceutically acceptable salt thereof, is between about 0.1 wt % and about 30 wt % of the composition; and
   the Notch agonist or HDAC inhibitor, or pharmaceutically acceptable salt thereof, is between about 0.1 wt % to about 30 wt % of the composition.

17. The method of claim 1, wherein:
   the GSK3β inhibitor or Wnt agonist, or pharmaceutically acceptable salt thereof, is between about 0.1 wt % and about 20 wt % of the composition; and
   the Notch agonist or HDAC inhibitor, or pharmaceutically acceptable salt thereof, is between about 0.1 wt % and about 20 wt % of the composition.

18. The method of claim 1, wherein:
   the GSK3β inhibitor or Wnt agonist, or pharmaceutically acceptable salt thereof, is between about 0.1 wt % and about 10 wt % of the composition; and
   the Notch agonist or HDAC inhibitor, or pharmaceutically acceptable salt thereof, is between about 0.1 wt % and about 10 wt % of the composition.

19. The method of claim 1, wherein:
   the GSK3β inhibitor or Wnt agonist, or pharmaceutically acceptable salt thereof, is between about 0.1 mg/mL to about 70 mg/mL of the composition; and
   the Notch agonist or HDAC inhibitor, or pharmaceutically acceptable salt thereof, is between about 0.01% to about 50% the composition.

20. The method of claim 1, wherein the GSK3β inhibitor or Wnt agonist, or pharmaceutically acceptable salt thereof, and the Notch agonist or HDAC inhibitor, or pharmaceutically acceptable salt thereof, are in lyophilized form.

21. The method of claim 1, wherein the GSK3β inhibitor or Wnt agonist, or pharmaceutically acceptable salt thereof, and the Notch agonist or HDAC inhibitor, or pharmaceutically acceptable salt thereof, are in hydrated form.

22. The method of claim 1, wherein the biocompatible matrix comprises one or more of hyaluronic acid, hyaluronates, lecithin gels, pluronics, poly(ethyleneglycol), poloxamers, chitosans, xyloglucans, collagens, fibrins, polyesters, poly(lactides), poly(glycolide), poly(lactic-co-glycolic acid (PLGA), sucrose acetate isobutyrate, glycerol monooleate, poly anhydrides, poly caprolactone sucrose, or glycerol monooleate or a combination thereof.

23. The method of claim 1, wherein the biocompatible matrix comprises a poloxamer.

24. The method of claim 23, wherein the poloxamer is Poloxamer 407.

25. The method of claim 1, wherein the biocompatible matrix comprises hyaluronic acid.

26. The method of claim 1, wherein the biocompatible matrix is a hydrogel.

27. The method of claim 1, wherein the biocompatible matrix is a biocompatible gel or foam.

28. The method of claim 1, wherein the composition is a controlled release formulation.

29. The method of claim 28, wherein the controlled release formulation when administered to a subject intratympanically or transtympanically imparts an immediate release, a delayed release, a sustained release, an extended release, a variable release, a pulsatile release, or a bi-modal release of one or more of a) the GSK3β inhibitor or Wnt agonist, or a pharmaceutically acceptable salt thereof; and b) the Notch agonist or HDAC inhibitor, or a pharmaceutically acceptable salt thereof.

30. The method of claim 1, wherein the method produces a population of Lgr5+ cells that are in s-phase.

31. The method of claim 1, wherein administering intratympanically or transtympanically the composition to a subject results in improved auditory functioning of the subject.

32. The method of claim 1, wherein administering is intratympanically.

33. The method of claim 1, wherein administering is transtympanically.

34. A method for expanding a population of cochlear cells in a cochlear tissue, the method comprising administering intratympanically or transtympanically to a subject a composition comprising:
i) a biocompatible matrix having dispersed therein:
a) a first compound selected from CHIR99021, LY2090314, lithium, A1070722, BML-284 and SKL2001, or a pharmaceutically acceptable salt thereof; and
b) a second compound selected from valproic acid, SAHA and Tubastatin A, or a pharmaceutically acceptable salt thereof.

35. The method of claim 34, wherein the first compound is CHIR99021, or a pharmaceutically acceptable salt thereof.

36. The method of claim 34, wherein the first compound is LY2090314, or a pharmaceutically acceptable salt thereof.

37. The method of claim 34, wherein the first compound is lithium, or a pharmaceutically acceptable salt thereof.

38. The method of claim 34, wherein the first compound is A1070722, or a pharmaceutically acceptable salt thereof.

39. The method of claim 34, wherein the first compound is BML-284, or a pharmaceutically acceptable salt thereof.

40. The method of claim 34, wherein the first compound is SKL2001, or a pharmaceutically acceptable salt thereof.

41. The method of claim 34, wherein the second compound is valproic acid, or a pharmaceutically acceptable salt thereof.

42. The method of claim 34, wherein:
the first compound is CHIR99021, or a pharmaceutically acceptable salt thereof; and
the second compound is valproic acid, or a pharmaceutically acceptable salt thereof.

43. The method of claim 34, wherein:
the first compound is between about 0.01 wt % and about 50 wt % of the composition; and
the second compound is between about 0.01 wt % and about 50 wt % of the composition.

44. The method of claim 34, wherein:
the first compound is between about 0.1 wt % and about 50 wt % of the composition; and
the second compound is between about 0.1 wt % and about 50 wt % of the composition.

45. The method of claim 34, wherein:
the first compound is between about 0.1 wt % and about 40 wt % of the composition; and
the second compound is between about 0.1 wt % to about 40 wt % of the composition.

46. The method of claim 34, wherein:
the first compound is between about 0.1 wt % and about 30 wt % of the composition; and
the second compound is between about 0.1 wt % to about 30 wt % of the composition.

47. The method of claim 34, wherein:
the first compound is between about 0.1 wt % and about 20 wt % of the composition; and
the second compound is between about 0.1 wt % and about 20 wt % of the composition.

48. The method of claim 34, wherein:
the first compound is between about 0.1 wt % and about 10 wt % of the composition; and
the second compound is between about 0.1 wt % and about 10 wt % of the composition.

49. The method of claim 34, wherein:
the first compound is between about 0.1 mg/mL to about 70 mg/mL of the composition; and
the second compound is between about 0.01% to about 50% the composition.

50. The method of claim 34, wherein the first compound and the second compound are in lyophilized form.

51. The method of claim 34, wherein the first compound and the second compound are in hydrated form.

52. The method of claim 34, wherein the biocompatible matrix comprises one or more of hyaluronic acid, hyaluronates, lecithin gels, pluronics, poly(ethyleneglycol), poloxamers, chitosans, xyloglucans, collagens, fibrins, polyesters, poly(lactides), poly(glycolide), poly(lactic-co-glycolic acid (PLGA), sucrose acetate isobutyrate, glycerol monooleate, poly anhydrides, poly caprolactone sucrose, or glycerol monooleate or a combination thereof.

53. The method of claim 34, wherein the biocompatible matrix comprises a poloxamer.

54. The method of claim 34, wherein the poloxamer is Poloxamer 407.

55. The method of claim 34, wherein the biocompatible matrix comprises hyaluronic acid.

56. The method of claim 34, wherein the biocompatible matrix is a hydrogel.

57. The method of claim 34, wherein the biocompatible matrix is a biocompatible gel or foam.

58. The method of claim 34, wherein the composition is a controlled release formulation.

59. The method of claim 58, wherein the controlled release formulation when administered to a subject intratympanically or transtympanically imparts an immediate release, a delayed release, a sustained release, an extended release, a variable release, a pulsatile release, or a bi-modal release of one or more of a) the GSK3β inhibitor or Wnt agonist, or a pharmaceutically acceptable salt thereof; and b) the Notch agonist or HDAC inhibitor, or a pharmaceutically acceptable salt thereof.

60. The method of claim 34, wherein the method produces a population of Lgr5$^+$ cells that are in s-phase.

61. The method of claim 34, wherein administering intratympanically or transtympanically the composition to a subject results in improved auditory functioning of the subject.

62. The method of claim 34, wherein administering is intratympanically.

63. The method of claim 34, wherein administering is transtympanically.

* * * * *

UNITED STATES PATENT AND TRADEMARK OFFICE
CERTIFICATE OF CORRECTION

PATENT NO. : 11,369,607 B2
APPLICATION NO. : 16/752256
DATED : June 28, 2022
INVENTOR(S) : Jeffrey M. Karp et al.

It is certified that error appears in the above-identified patent and that said Letters Patent is hereby corrected as shown below:

In the Claims

In Claim 2, Column 133, Line 11, please delete "GSK313" and insert --GSK3$\beta$--.
In Claim 8, Column 133, Line 47, please delete "GSK313" and insert --GSK3$\beta$--.
In Claim 54, Column 136, Line 64, please delete "34" and insert --53--.

Signed and Sealed this
Thirtieth Day of August, 2022

Katherine Kelly Vidal
*Director of the United States Patent and Trademark Office*